United States Patent
Campbell et al.

(10) Patent No.: US 11,505,528 B2
(45) Date of Patent: Nov. 22, 2022

(54) INHIBITORS OF MICROBIALLY INDUCED AMYLOID

(71) Applicant: Axial Therapeutics, Inc., Woburn, MA (US)

(72) Inventors: Anthony Stewart Campbell, Framingham, MA (US); Bridget Cole, Quincy, MA (US); Alessandra Bartolozzi, Norwalk, CT (US)

(73) Assignee: Axial Therapeutics, Inc., Woburn, MA (US)

( * ) Notice: Subject to any disclaimer, the term of this patent is extended or adjusted under 35 U.S.C. 154(b) by 0 days.

(21) Appl. No.: 16/636,511

(22) PCT Filed: Aug. 6, 2018

(86) PCT No.: PCT/US2018/045360
§ 371 (c)(1),
(2) Date: Feb. 4, 2020

(87) PCT Pub. No.: WO2019/028456
PCT Pub. Date: Feb. 7, 2019

(65) Prior Publication Data
US 2020/0290970 A1 Sep. 17, 2020

Related U.S. Application Data

(60) Provisional application No. 62/541,536, filed on Aug. 4, 2017.

(51) Int. Cl.
*C07D 215/56* (2006.01)
*C07D 333/68* (2006.01)
*A61K 9/00* (2006.01)

(52) U.S. Cl.
CPC ......... *C07D 215/56* (2013.01); *C07D 333/68* (2013.01); *A61K 9/0019* (2013.01); *A61K 9/0053* (2013.01)

(58) Field of Classification Search
CPC .................................................. C07D 215/56
See application file for complete search history.

(56) References Cited

U.S. PATENT DOCUMENTS

| 6,310,107 B1 | 10/2001 | Kato et al. |
| 2005/0032832 A1 | 2/2005 | Kuo et al. |
| 2006/0079578 A1 | 4/2006 | Laurin et al. |

FOREIGN PATENT DOCUMENTS

| EP | 0 070 767 A1 | 1/1983 |
| WO | WO 01/98290 A2 | 12/2001 |
| WO | WO 2004/110352 A2 | 12/2004 |
| WO | WO 2005/033102 A2 | 4/2005 |
| WO | WO 2006/002421 A2 | 1/2006 |
| WO | WO 2007/044565 A2 | 4/2007 |
| WO | WO 2009/023509 | * 2/2009 | ........... A61K 31/137 |
| WO | WO 2010/073078 A2 | 7/2010 |
| WO | WO 2011/072241 A1 | 6/2011 |
| WO | WO 2012/154888 A1 | 11/2012 |
| WO | WO 2015/116663 A1 | 8/2015 |

OTHER PUBLICATIONS

National Center for Biotechnology Information (2021). PubChem Compound Summary for CID 89283271. Retrieved Mar. 13, 2021 from https://pubchem.ncbi.nlm.nih.gov/compound/89283271.*
STN Registry database entry for CAS RN 2019151-53-0, Accessed Mar. 26, 2022, Entry Date Oct. 25, 2016.*
STN Registry database entry for CAS RN 190774-18-6, Accessed Mar. 26, 2022, Entry Date Jul. 4, 1997.*
Partial Supplementary European Search Report for Application No. EP 18841861.0 dated Jan. 26, 2021.
International Search Report and Written Opinion dated Dec. 7, 2018 in connection with Application No. PCT/US2018/045360.
International Preliminary Report on Patentability dated Feb. 13, 2020 in connection with Application No. PCT/US2018/045360.
Abdalha et al., Synthesis of some new tetrahydrobenzo[b] thiophene derivatives and tetrahydrobenzo-thienopyrimidine derivatives under microwave irradiation. Synthetic Communications. 2011; 41:2811-2821.
Amr et al., Antiarrhythmic, serotonin antagonist and antianxiety activities of novel substituted thiophene derivatives synthesized from 2-amino-4,5,6,7-tetrahydro-N-phenylbenzo[b]thiophene-3-carboxamide. Eur J Med Chem. Dec. 2010;45(12):5935-42. doi: 10.1016/j.ejmech.2010.09.059. Epub Oct. 14, 2010.
Huber et al., Effect of levofloxacin and 3-carboethoxy-4-quinolone on the β-amyloid fibrils formation. J Chem and Pharma Research. 2015; 7(8):993-1000.
Kar et al., Quantifying the structural requirements for designing newer FLT3 inhibitors. Med Chem. Sep. 2012;8(5):913-27. doi: 10.2174/157340612802084153.
Kumar et al., Crystal structure of 2-amino-N-(2-fluorophenyl)-4,5,6,7-tetrahydro-1-benzothiophene-3-carboxamide. Acta Cryst. 2015; 71(ll):o807-808. Supplemental Information 6 pages.
Massari et al., Structural investigation of cycloheptathiophene-3-carboxamide derivatives targeting influenza virus polymerase assembly. J Med Chem. Dec. 27, 2013;56(24):10118-31. doi: 10.1021/jm401560v. Epub Dec. 13, 2013.
Patch et al., Identification of 2-acylaminothiophene-3-carboxamides as potent inhibitors of FLT3. Bioorg Med Chem Lett. Jun. 15, 2006;16(12):3282-6. doi: 10.1016/j.bmcl.2006.03.032. Epub Mar. 31, 2006.
Pinkerton et al., Synthesis and SAR of thiophene containing kinesin spindle protein (KSP) inhibitors. Bioorg Med Chem Lett. Jul. 1, 2007;17(13):3562-9. doi: 10.1016/j.bmcl.2007.04.076. Epub Apr. 29, 2007.
Takasawa et al., Discovery of a new type inhibitor of human glyoxalase I by myricetin-based 4-point pharmacophore. Bioorg Med Chem Lett. Jul. 15, 2011;21(14):4337-42. doi: 10.1016/j.bmcl.2011.05.046. Epub May 23, 2011.

(Continued)

Primary Examiner — Alicia L Otton
(74) Attorney, Agent, or Firm — Wolf, Greenfield & Sacks, P.C.

(57) ABSTRACT

The present disclosure provides compounds useful for the prevention of amyloid formation and the treatment of amyloid related disorders, including synucleopathies such as Parkinson's Disease.

7 Claims, 36 Drawing Sheets

(56) References Cited

OTHER PUBLICATIONS

Truong et al., Substituted 2-Acylaminocycloalkylthiophene-3-carboxylic Acid Arylamides as Inhibitors of the Calcium-Activated Chloride Channel Transmembrane Protein 16A (TMEM16A). J Med Chem. Jun. 8, 2017;60(11):4626-4635. doi: 10.1021/acs.jmedchem.7b00020. Epub May 24, 2017.

Yang et al., Viral infectivity factor: a novel therapeutic strategy to block HIV-1 replication. Mini Rev Med Chem. Jun. 2013;13(7):1047-55. doi: 10.2174/1389557511313070008.

Yarahmadi et al., Barium Aluminate nano-powders efficient catalyst for the synthesis of novel benzo[b]thiophene, thieno[2,3-c]thiopyran and thieno[2,3-c]pyridine derivatives. Phosphorus, Sulfur, and Silicon and the Related Elements. Jun. 6, 2017; 192(8):945-49.

Zohdi et al., Convenient Heterocyclization Reactions with Ethyl 2-Amino-4,5,6,7-tetrahydrobenzo(b)thiophene-3-carboxylate: Synthesis of Thiazole, Isoxazole, Pyrazole, Pyrimidine and Pyridazine Derivatives. J Chem Research. 1996: 440-441.

Extended European Search Report for EP Application No. 18841861.0 dated Jun. 7, 2021.

Forezi et al., Synthesis, cytotoxicity and mechanistic evaluation of 4-oxoquinoline-3-carboxamide derivatives: finding new potential anticancer drugs. Molecules. May 22, 2014;19(5):6651-70. doi: 10.3390/molecules19056651.

Hsu et al., 2-(3-Fluorophenyl)-6-methoxyl-4-oxo-1,4-dihydroquinoline-3-carboxylic acid (YJC-1) induces mitotic phase arrest in A549 cells. Eur J Pharmacol. Mar. 15, 2007;559(1):14-20. doi: 10.1016/j.ejphar.2006.12.001. Epub Dec. 2006.

Jung et al., Synthesis and antibacterial activity of 2-substituted 6-fluoro-1,4-dihydro-4-oxo-3-quinolinecarboxylic acids. Farmaco. Sep. 2001;56(9):665-75. doi: 10.1016/s0014-827x(01)01112-0.

Rao et al., Synthesis of fluorinated 2-phenyl-4-quinolones from pyrrole-2,3-diones. J Chem Soc Perkins Trans. 2002;1:1232-5.

Stern et al., Novel 4-oxo-1,4-dihydroquinoline-3-carboxamide derivatives as new CB2 cannabinoid receptors agonists: synthesis, pharmacological properties and molecular modeling. J Med Chem. Jan. 12, 2006;49(1):70-9. doi: 10.1021/jm050467q.

\* cited by examiner

Veh.

ECGC

Str

Mid.

Str.

Str.

Mid.

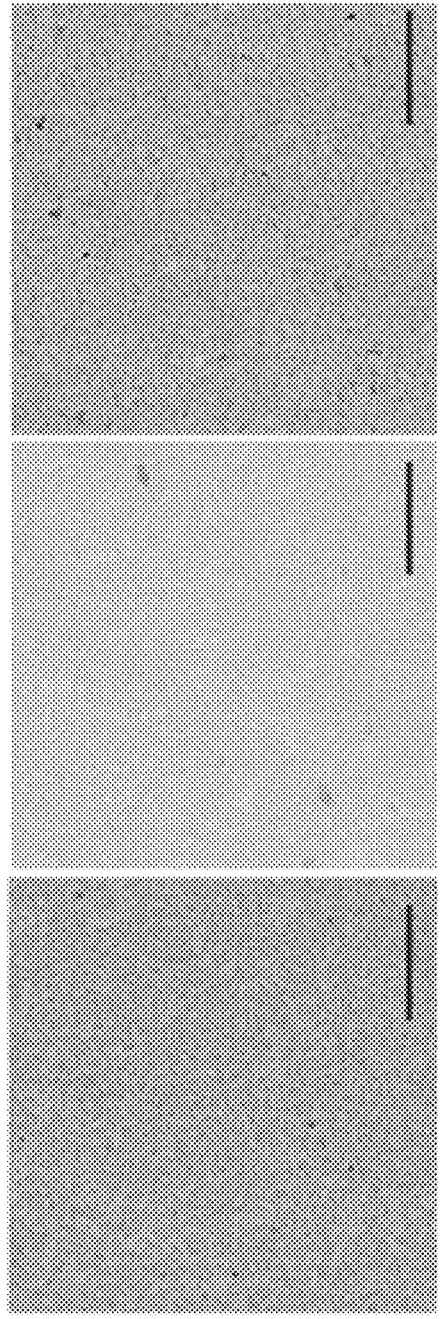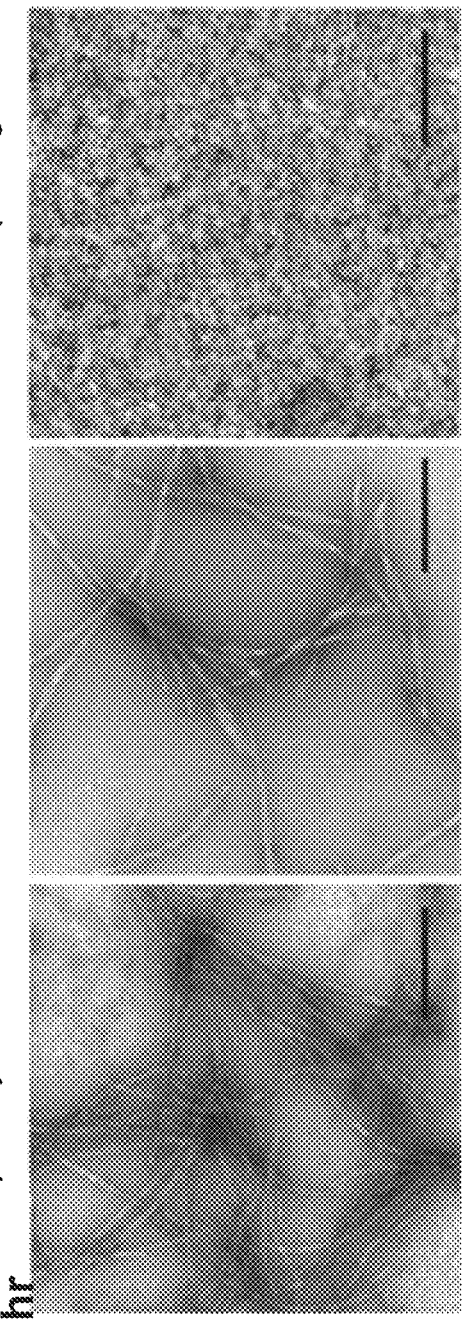
FIG. 6C 50 μM α-Synuclein
FIG. 6D 25:1 α-syn:CsgA
FIG. 6E 2 μM CsgA
0 hr
FIG. 6F 50μM α-synuclein
FIG. 6G 25:1 α-syn:CsgA
FIG. 6H 2 μM CsgA
60 hr 60 hr   50μM α-synuclein +5% CsgA seeds +5% α-synuclein seeds FIG. 7E
5% α-Synuclein seeds
FIG. 7F
5% CsgA seeds
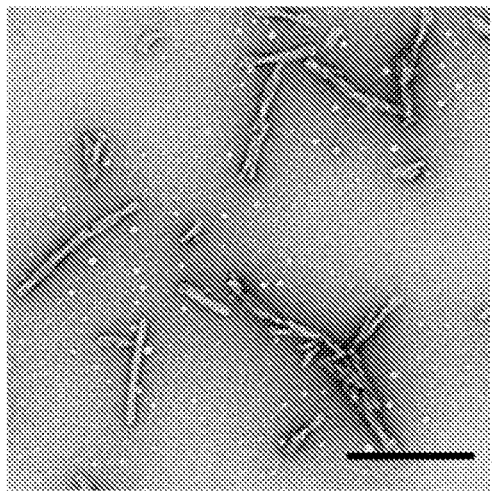
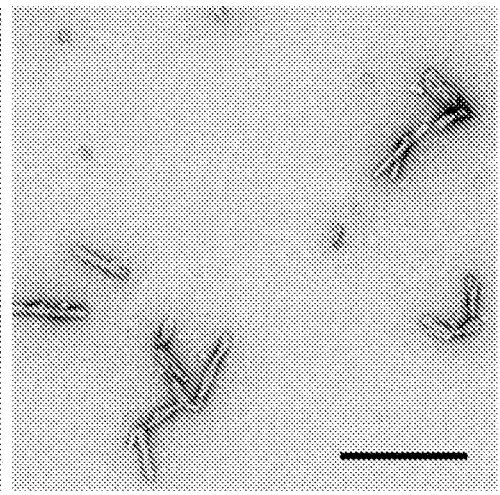

Enteroendocrine cells (STC-1 cell line)

INHIBITORS OF MICROBIALLY INDUCED AMYLOID

RELATED APPLICATIONS

This application is a national stage filing under 35 U.S.C. § 371 of international PCT application, PCT/US2018/045360, filed Aug. 6, 2018, which claims priority under 35 U.S.C. § 119(e) to U.S. provisional patent application, U.S. Ser. No. 62/541,536, filed Aug. 4, 2017, the entire contents of which is incorporated herein by reference.

GOVERNMENT SUPPORT

This invention was made with government support under R01NS085910 awarded by the National Institutes of Health. The government has certain rights in the invention.

TECHNICAL FIELD

The present disclosure relates to inhibitors of amyloid formation, and particularly inhibitors of microbially-induced amyloid formation, as well as methods of using such inhibitors to treat or inhibit neurological disorders and other disorders associated with amyloid accumulation. Methods of identifying compositions that inhibit or promote amyloid formation are also provided.

BACKGROUND

Many neurodegenerative diseases are associated with atypical aggregation of proteins in the brain, which leads to cell death and a resulting manifestation of many neuropathies. It is believed that disease specificity is a consequence of (i) the specific proteins involved in aggregation, (ii) the specific regions of the brain affected, and (iii) the specific neuronal cell types affected. In the case of the natural human protein α-synuclein, aberrant aggregation of this protein leads to any of over 50 "α-synucleinopathies," of which Parkinson's Disease is the most common and most widely studied. In Parkinson's Disease, α-synuclein aggregation leads to the accumulation of large precipitated aggregates, called Lewy bodies, within certain neuronal cell types, most typically those that produce the neurotransmitter dopamine. When enough α-synuclein aggregate is present, neuronal death occurs and dopamine production declines. Dopamine is required for proper control of movement, and once dopaminergic neurons are killed they are not replaced. Over time the dopamine pool declines irreversibly to a point where motor symptoms progress and become debilitating.

The most pathogenic form of α-synuclein is still unclear, e.g., whether full intact Lewy bodies or smaller oligomeric α-synuclein fibrils are most relevant to disease progression and pathology. Traditional pharmaceutical and biotech approaches to inhibiting α-synuclein aggregation have focused on attacking the aggregation process in the neurons and brain regions most associated with disease symptoms. Small molecule approaches, antibody approaches and a vaccine approach all have been attempted and continue to be evaluated as interventions for Parkinson's Disease and other α-synucleinopathies. Importantly, all of these strategies presently rely on the therapeutic entity crossing the blood-brain barrier and reaching the target neuronal tissue. Traversing the blood-brain barrier remains one of the most significant pharmacokinetic challenges that hinders drug development for neurodegenerative diseases. Accordingly, there is a need for inhibitors of amyloid formation, and especially α-synuclein aggregation inhibitors, that have the potential for providing therapeutic effects without having to cross the blood-brain barrier.

SUMMARY

In some embodiments, the composition is formulated for delivery outside of the systemic circulation of a subject. Said composition may be formulated for enteric or intranasal delivery, for example, and/or said compositions may further be formulated for controlled release within the lower intestine or colon. The aforementioned compositions may comprise an enteric-coated capsule, tablet, soft-gel, spray dried powder, polymer matrix, hydrogel, enteric-coated solid, crystalline solid, amorphous solid, glassy solid, coated micronized particle, liquid, nebulized liquid, aerosol, or microcapsule.

The present disclosure further provides a method of disrupting the formation of amyloid aggregates, comprising contacting an amyloid or a precursor of an amyloid with a composition comprising one or more compounds of the invention.

The present disclosure further provides a method of disrupting the formation of amyloid aggregates in a subject, comprising administering to said subject a composition comprising one or more polyphenols or polyphenol-like compounds, such as a composition comprising a compound of the invention. Optionally, said subject is additionally selected or identified as one that would receive the benefit of a molecule that disrupts the formation of amyloid aggregates prior to administration of said composition. Such selection or identification can be made by clinical or diagnostic evaluation, prior to administering said composition. Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof. Optionally, prior to, during or after administration of the composition, the disruption or inhibition of the formation of amyloid aggregates in said subject is measured or evaluated.

The present disclosure further provides a method of inhibiting, ameliorating, reducing the likelihood, delaying the onset of, treating, or preventing an amyloid disorder in a subject. The method can comprise administering to the subject a composition comprising a compound of the invention, as described herein. Optionally, the subject is additionally selected or identified as one that would receive the benefit of a molecule that inhibits or disrupts the formation of amyloid aggregates prior to administration of said composition, for example by detecting a presence or level of a bacterial protein (such as CsgA), or a presence or level of a microbial organism that makes the bacterial protein in an intestinal sample of the subject. Such selection or identification can be made by clinical or diagnostic evaluation, prior to administering said composition. Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof. Optionally, prior to, during or after administration of the composition, the disruption or inhibition of the formation of amyloid aggregates in said subject is measured or evaluated.

In some embodiments according to the methods and compositions as described herein, said amyloid aggregates may comprise one or more mammalian amyloid or mammalian amyloid precursors such as proteins, and/or one or more bacterial or fungal proteins (e.g., a composition comprising CsgA). In some embodiments according to the methods and compositions disclosed herein, said amyloid aggregates may be present within the gastrointestinal tract, the enteric nervous tissue, cranial sinus, or nasal cavity (e.g., the olfactory bulb).

In some embodiments, the methods of the present disclosure further comprise measuring or evaluating a change in the subject's nervous system, such as a neurological symptom, motor behavior, or other behavior of the subject, which may comprise, e.g., one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and/or visual, auditory, olfactory, and/or tactile hallucinations, vertigo, cognitive dysfunction, altered dopamine levels, altered serotonin levels, altered kynurenine levels, or any combination thereof.

In some embodiments, the methods of the present disclosure further comprise measuring or evaluating a change in the gastrointestinal system, such as a gastrointestinal symptom or behavior of the subject, which may comprise, e.g., one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, leaky gut, intestinal dysbiosis, hypersalivation (sialorrhea), anorectal dysfunction, dyssynergic defecation, or any combinations thereof. As used herein, the terms IBS and IBD have their customary and ordinary meaning as understood by one of skill in the art in view of this disclosure. Such hyperpermeability may result from inflammation of the intestinal lining and/or failure of the tight junctions between cells of the intestinal epithelium, which allows the passage of substances from the lumen into the surrounding tissues where some may enter the peritoneal cavity and/or systemic circulation. Because of this leakage of substances from the gut or intestinal lumen, intestinal hyperpermeability may be referred to as "leaky gut" or "leaky gut syndrome."

In some embodiments, the compositions of the present disclosure may be administered to a subject prior to, or following, the appearance of a neurological symptom or condition. In some embodiments, the compositions of the present disclosure may be administered to a subject prior to, or following, the appearance of a gastrointestinal symptom or condition associated with an amyloid disorder. In some embodiments, said subject is selected as one that has been identified as being at risk for developing or already having Lewy Body Dementia, incidental Lewy body disease, Lewy body variant of Alzheimer's disease, multiple system atrophy, pure autonomic failure, or any combination thereof, such as by clinical or diagnostic evaluation. In some embodiments, said subject is under the age of 18, 18-30, 30-50, 50-60, 60-70, or over the age of 70. In some embodiments, said subject is one that has been identified or selected as being at risk for developing or already having Parkinson's disease, such as by clinical or diagnostic evaluation or family history analysis.

In some embodiments according to the compositions and methods disclosed herein said composition may be coadministered with caffeine, nicotine, theophylline, theobromine, xanthine, methylxanthine, or derivatives thereof. In some embodiments, the methods as disclosed herein further comprise administering to said subject an inhibitor of α-synuclein aggregation. In some embodiments, the methods as disclosed herein further comprise administering to said subject L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like, or any combination thereof. In some embodiments, the methods as disclosed herein comprise administering to said subject an inhibitor of α-synuclein aggregation, and further comprise administering to said subject L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like, or any combination thereof. In some embodiments, the inhibitor of α-synuclein aggregation and the L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like are administered in the same composition. In some embodiments, the inhibitor of α-synuclein aggregation and the L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like are administered in separate compositions. In some embodiments, the separate compositions are administered at the same time. In some embodiments, the separate compositions are administered at the different times.

In some embodiments, the composition according to any of the compositions and methods disclosed herein is for medical use. In some embodiments, the composition according to any of the compositions and methods disclosed herein is for use in treating an amyloid disorder as described herein (such as an amyloid disorder of Table 3). In some embodiments, the amyloid disorder is selected from the group consisting of Parkinson's Disease, Lewy Body Dementia, incidental Lewy body disease, Lewy body variant of Alzheimer's disease, multiple system atrophy, or pure autonomic failure, or any combination of two or more of these. In some embodiments the composition according to the compositions and methods disclosed herein is for use in preparing a medicament for the treatment for an amyloid disorder as described herein (such as an amyloid disorder of Table 3). In some embodiments, the amyloid disorder is selected from the group consisting of Parkinson's Disease, Lewy Body Dementia, incidental Lewy body disease, Lewy body variant of Alzheimer's disease, multiple system atrophy, or pure autonomic failure, or any combination of two or more of these. In some embodiments, the composition comprises one or more compounds of the invention, as described herein. In some embodiments, the composition is formulated for delivery to the gastrointestinal tract, for example via oral or rectal delivery, or formulated with an enteric coating. In some embodiments, the composition is formulated for delivery to the central nervous system, for example via intraspinal or intracranial delivery, or formulated to cross the blood brain barrier. In some embodiments, the composition is formulated to bypass the blood brain barrier. Such formulations may be administered, for example, intranasally. Such formulations may also be administered via the olfactory route.

The present disclosure provides methods of identifying compositions that affect the formation of microbially-induced amyloid. In some approaches, the methods comprise contacting a plurality of concentrations of a microbial amyloid or a microbial amyloid precursor with a plurality of concentrations of α-synuclein and/or other mammalian amyloid or mammalian amyloid precursor in the presence of a composition, analyzing or measuring the formation of amyloid after the reaction set forth above; and comparing said analysis or measurement to an analysis or measurement of a control, wherein said control comprises analyzing or measuring the formation of amyloid after the reaction set forth above in the absence of said composition. In some methods and compositions disclosed herein, said microbial amyloid or microbial amyloid precursor comprises CsgA. In some embodiments, the methods according to the present disclosure also comprise agitation during the contacting step and/or prior to measurement.

In certain embodiments, said contacting of a plurality of concentrations of a microbial amyloid or a microbial amyloid precursor (e.g., a composition comprising CsgA) with a plurality of concentrations of α-synuclein and/or other mammalian amyloid or mammalian amyloid precursor is conducted in the presence of an indicator of amyloid formation. In some further embodiments, said indicator is a fluorescent indicator, a spin-labeled indicator, an enzyme, an antibody, or a colorimetric indicator. In some further embodiments, said indicator is Thioflavin T (ThT). Where said indicator of amyloid formation is an antibody, the methods of the present disclosure provide that said antibody may have specificity for aggregated α-synuclein and/or another mammalian amyloid or mammalian amyloid precursor, and optionally may be conjugated to a fluorescent label, an enzyme, a colorimetric label, a spin label, a metal ion binding moiety, a nucleic acid, a polysaccharide, or a polypeptide. In some embodiments according to the methods of the present disclosure, CsgA and said α-synuclein and/or other such bacterial amyloid precursor and/or mammalian amyloid/mammalian amyloid precursor are each separately labeled.

In some embodiments according to the methods of the present disclosure, said contacting a plurality of concentrations of a microbial amyloid or a microbial amyloid precursor (e.g., a composition comprising CsgA) with a plurality of concentrations of α-Synuclein and/or other mammalian amyloid or mammalian amyloid precursor in the presence of a composition, analyzing or measuring the formation of amyloid after the reaction set forth above; and comparing said analysis or measurement to an analysis or measurement of a control, further comprises identifying or selecting a composition that alters or modulates or is suspected of altering or modulating amyloid formation. In some embodiments, the methods described herein further comprise identifying or selecting compositions that reduce or enhance amyloid formation. In some embodiments, the methods described herein further comprise identifying or selecting compositions that reduce or enhance amyloid formation that also do not cross the blood brain barrier. The compounds identified by these methods, can be administered to subjects identified or selected as a population that would benefit from receiving a compound that alters amyloid formation (e.g., a compound that reduces amyloid formation, preferably without crossing the blood brain barrier). Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof.

The methods according to the present disclosure further contemplate a method of making microbially-induced amyloid, comprising contacting a plurality of concentrations of a microbial amyloid or a microbial amyloid precursor with a plurality of concentrations of α-Synuclein and/or other mammalian amyloid or mammalian amyloid precursor in the presence or absence of a composition; generating microbially-induced amyloid; and analyzing or quantifying the microbially-induced amyloid. In some further embodiments, said microbial amyloid or microbial amyloid precursor comprises CsgA. In some further embodiments, the methods according to the present disclosure further comprise agitation during said contacting or prior to measurement. In some further embodiments, said method is conducted in the presence of an indicator of amyloid formation. In some further embodiments, said indicator of amyloid formation may comprise a fluorescent indicator, a spin-labeled indicator, or a colorimetric indicator. In some embodiments, said indicator said indicator is Thioflavin T (ThT). In some embodiments, CsgA and α-Synuclein, or other such bacterial amyloid/bacterial amyloid precursor and mammalian amyloid/mammalian amyloid precursor are each separately labeled. In some embodiments, said amyloid formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.

In some embodiments according to the methods of the present disclosure, said composition to be present during said contacting of a plurality of concentrations of a microbial amyloid or a microbial amyloid precursor (e.g., a composition comprising CsgA) with a plurality of concentrations of α-Synuclein and/or other mammalian amyloid or mammalian amyloid precursor comprises a mixture of compounds. The composition may comprise tissue, bodily fluid or an extract thereof. In some embodiments, said composition comprises feces, urine, blood, spinal fluid, or saliva, or a component thereof. In some embodiments, the composition comprises an extract from a natural product. In some further embodiments, the natural product is an herb, a botanical substance, or foodstuff. In some embodiments, said natural product is a fungal tissue, legume, seed, berry, leaf, fruit, flower, plant root, plant stem, or plant bark. In some embodiments, the composition may comprise one or more bacteria, bacterial extracts, lysates, conditioned culture media, lyophilized bacteria, lyophilized lysates, lyophilized culture media, or any combination thereof. In some embodiments, the composition may comprise one or more microbes, microbial extracts, lysates, conditioned culture media, lyophilized microbes, lyophized lysates, lyophilized culture media, or any combination thereof. In some embodiments, the methods above further comprise identifying or selecting compositions that increase or reduce amyloid formation, preferably compounds that also do not cross the blood brain barrier. The compounds identified by these methods, can be administered to subjects identified or selected as a population that would benefit from receiving a compound that alters amyloid formation (e.g., a compound that reduces amyloid formation, preferably without crossing the blood brain barrier). Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof.

In some embodiments, the inhibitors of amyloid formation may be intended for administration systemically or locally to the enteric of central nervous system. For example, inhibitors which are effective against mammalian amyloid or mammalian amyloid precursor protein aggregation may be useful in treatment of one or more of the amyloid disorders described herein (e.g., one or more of the disorders of Table 3). Therefore, for such embodiments, the compositions comprising the inhibitors of amyloid formation may be formulated for parenteral administration, including systemic administration (e.g., intravenous, subcutaneous, intramuscular, intraperitoneal) or local administration (e.g., local injection near the vagus nerve, intraspinal injection, or intracranial injection). For delivery into the CNS, it is necessary for the inhibitors to pass through the blood brain barrier. Therefore, in such embodiments, the inhibitors are preferably lipid soluble molecules, or may be modified to increase lipid solubility, or may be co-administered with compounds that enhance passage through the blood brain barrier (see, e.g., WO2014076655A1, WO2012159052A2, WO1992018529A1).

The present disclosure also contemplates a kit comprising a microbial amyloid or a microbial amyloid precursor and α-Synuclein and/or other mammalian amyloid or mammalian amyloid precursor, being present in one or more containers within said kit whereby the methods of the present disclosure may be practiced. In some embodiments, said microbial amyloid or microbial amyloid precursor comprises CsgA.

The present disclosure provides a method of inhibiting amyloid formation in a subject in need thereof, comprising administering to the subject a compound of the invention, as described herein, or a pharmaceutically acceptable salt thereof, or a pharmaceutical composition thereof.

The present disclosure provides a method of preventing or treating a disorder associated with amyloid formation in a subject in need thereof, comprising administering to the subject a compound of the invention, as described herein, or a pharmaceutically acceptable salt thereof, or a pharmaceutical composition thereof.

The present disclosure provides a method of preventing or treating an amyloid disorder in a subject in need thereof, comprising administering to the subject a compound of the invention, as described herein, or a pharmaceutically acceptable salt thereof, or a pharmaceutical composition thereof.

In the methods of the present disclosure, the amyloid disorder or the disorder associated with amyloid formation may be a neurological disorder. The disorder may be Parkinson's disease (PD), Lewy body dementia, multiple system atrophy, α-synucleinopathy, PD-associated constipation, PD-associated hyposmia, Huntington's Disease, Alexander's Disease, amyotrophic lateral sclerosis (ALS), or Alzheimer's Disease. The disorder may be intestinal dysbiosis, intestinal hyperpermeability, irritable bowel syndrome (IBS), inflammatory bowel disease (IBD), ulcerative colitis or Crohn's disease.

The subject may suffer from gastrointestinal symptoms including one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, hypersalivation (sialorrhea), anorectal dysfunction, dyssynergic defacation, and nausea. The gastrointestinal symptoms may be associated with Parkinson's Disease or Parkinsonism.

In certain embodiments, the amyloid disorder can be diagnosed by detecting the presence or level of intestinal bacterial amyloid aggregates. the aggregates may comprise a bacterial CsgA protein. In certain embodiments, the disorder can be diagnosed by detecting the presence or level of intestinal bacterial genes and gene transcripts.

The methods of the present disclosure may further comprise detecting the presence or level of a bacterial protein, such as CsgA, or a microorganism that produces the bacterial protein, in an intestinal sample of the subject. In certain embodiments, the subject is selected as in need of said prevention or treatment if the presence of the bacterial protein or the microorganism that produces the bacterial protein is detected in the intestinal sample, or if the level of the bacterial protein or the microorganism that produces the bacterial protein in the intestinal sample is greater than a predetermined level or control.

The methods of the present disclosure may further comprise determining a decrease or absence of the intestinal amyloid aggregates following the administration, or identifying the subject as displaying a gastrointestinal symptom.

The methods of the present disclosure further provide a method of treating or inhibiting an amyloid disorder (e.g., a neurological disorder such as Parkinson's Disease, Lewy Body Dementia, incidental Lewy body disease, Lewy body variant of Alzheimer's disease, multiple system atrophy, or pure autonomic failure, or any combination thereof) in a tested subject comprising contacting a plurality of concentrations of a microbial amyloid or a microbial amyloid precursor with a plurality of concentrations of α-Synuclein and/or other mammalian amyloid or mammalian amyloid precursor, which may be obtained from a biological sample from said tested subject, in the presence or absence of a composition; analyzing or measuring the formation of amyloid; and comparing the analysis or measurement made with an analysis or measurement of a control, wherein said control may comprise analyzing or measuring the formation of amyloid in the absence of said composition or comparison to a standard such as the amount or rate or formation of amyloid from a healthy subject or a subject having amyloidosis (e.g., a subject suffering from Parkinson's Disease, Lewy Body Dementia, incidental Lewy body disease, Lewy body variant of Alzheimer's disease, multiple system atrophy, or pure autonomic failure, or any combination thereof); and if the formation of amyloid in the presence of said composition is increased relative to the formation of amyloid in the absence of said composition or if the amount or rate or formation of amyloid is the same or greater in the sample from the tested subject, for example, than the amount, rate, or formation of amyloid from the healthy subject control or the control subject having amyloidosis, administering to said tested subject an effective amount of a pharmaceutical composition suitable for inhibiting or treating said amyloid disorder. In some further embodiments of these methods, said microbial amyloid or microbial amyloid precursor comprises, consists essentially of, or consists of CsgA.

In some embodiments, the methods as described herein further comprise identifying or selecting said tested subject as one that would benefit from a treatment or inhibition of an amyloid disorder, and may further comprise identifying or selecting said subject as one at risk of or showing symptoms of one or more of Parkinson's Disease, Lewy Body Dementia, incidental Lewy body disease, Lewy body variant of Alzheimer's disease, multiple system atrophy, pure autonomic failure, or any combination thereof.

BRIEF DESCRIPTION OF THE DRAWINGS

FIG. 1A is a graph showing Crystal violet staining of biofilm growth by wild-type E. coli following 4 days in static culture, with indicated concentrations of epigallocatechin gallate (EGCG); data assessed by optical density (OD). FIG. 1C is a graph showing RNA was extracted from fecal pellets and csgA expression quantified by qRT-PCR, relative to the E. coli reference gene rrsA. FIGS. 1D-H show assessment of motor function was assessed at 15-16 weeks of age by quantifying beam traversal time (FIG. 1D), pole descent time (FIG. 1E), nasal adhesive removal time (FIG. 1F), hindlimb clasping score (FIG. 1G), and wirehang tests (FIG. 1H). FIG. 1I is a graph showing principal component analysis of compiled motor scores from tests in (FIGS. 1D-H). FIGS. 1J-K are a series of graphs showing Proteinase K resistant αSyn aggregates (annotated with white arrows) in the substantia nigra imaged via immunofluorescence microscopy. Shown are vehicle-treated (FIG. 1J) and EGCG-treated mice (FIG. 1K). Fewer proteinase K resistant αSyn aggregates were observed in the mouse treated with EGCG (FIG. 1K) than in the vehicle-treated control (FIG. 1J). FIGS. 1L-M show quantification of insoluble αSyn fibrils in the striatum (FIG. 1L) and ventral midbrain (FIG. 1M) by dot blot assay.

FIGS. 1N-O are a series of graphs showing thin sections of brain were stained for Iba1 (microglia), βD cellular reconstructions generated, and morphological characteristics quantified from microglia resident in the striatum (FIG. 1N) and substantia nigra (FIG. 1O). n=3 (FIGS. 1A, 1B, 1N, 1O), n=8 (FIG. 1C), n=10-11 (FIGS. 1D-I), n=4 (FIGS. 1L-M). Points represent individuals, bars represent the mean and standard error. Data analyzed by one-way ANOVA with Tukey post-hoc test for FIG. 1A, two-tailed Mann-Whitney for FIGs. C-K, or two-tailed t-test for FIG. 1L. For FIGS. 1A-1L *p≤0.05; p≤0.01; *p≤0.001. Motor data are compiled from 2 independent cohorts.

FIG. 2A is a graph showing total αSyn in whole brain lysates quantified by ELISA. FIG. 2B is a graph showing quantification of insoluble αSyn fibrils in the striatum by dot blot assay. FIGS. 2C-D show quantification of TNFα (FIG. 2C) and IL-6 (FIG. 2D) by ELISA from the striatum. FIGS. 2E-G show the results of staining thin sections of brains derived from ASO mice. Sections were stained for Iba1 (microglia), 3D cellular reconstructions generated, and morphological characteristics quantified of microglia resident in the striatum. n=3 (FIGS. 2A-B), n=6-7 (FIG. 2C, 2D), n=4 (FIGS. 2E-G) (averaged from 20-40 cells for diameters, or 5-7 cells for branching). Points represent individuals, bars represent the mean and standard error. Data analyzed by one-way ANOVA with Tukey post-hoc test for FIGS. 2A-D, or two-tailed t-test for FIGS. 2E and 2F. *p≤0.05; p≤0.01; *p≤0.001; ****p≤0.0001.

FIG. 3G is a graph depicting principal component analysis of compiled motor scores of FIGS. 3A-F. FIGS. 3H-I depict quantification of insoluble αSyn fibrils in the striatum (FIG. 3H) and ventral midbrain (FIG. 3I) by dot blot assay. n=8 (FIGS. 3A-G), n=4 (FIG. 3H). Points represent individuals, bars represent the mean and standard error. Time courses analyzed by two-way ANOVA, with Sidak post-hoc test for between group comparisons indicated above individual time points, and brackets indicating significance between treatments. Data in (FIG. 3H) analyzed by two-tailed Mann-Whitney test. For FIGS. 3A-I, *p≤0.05; p≤0.01; *p≤0.001; ****p≤0.0001.

FIG. 5F depicts principal component analysis of compiled motor scores from FIGS. 5A-D. Thin sections of brain were stained for Iba1 (microglia) and morphological characteristics quantified of microglia resident in the striatum (FIGS. 5G-H) and substantia nigra (FIGS. 5I-J). N=10-11 (FIGS. 5A-F), n=3 (FIGS. 5G-J) (averaged from 5-7 cells for branching). Bars represent the mean and standard error.

Time courses analyzed by two-way ANOVA, with Sidak post-hoc test for between group comparisons indicated above individual time points, and brackets indicating significance between treatments. Data in (FIGS. 5G-J) analyzed by two-tailed t-test. *p≤0.05; p≤0.01; **p≤0.0001.

Figure 6A:
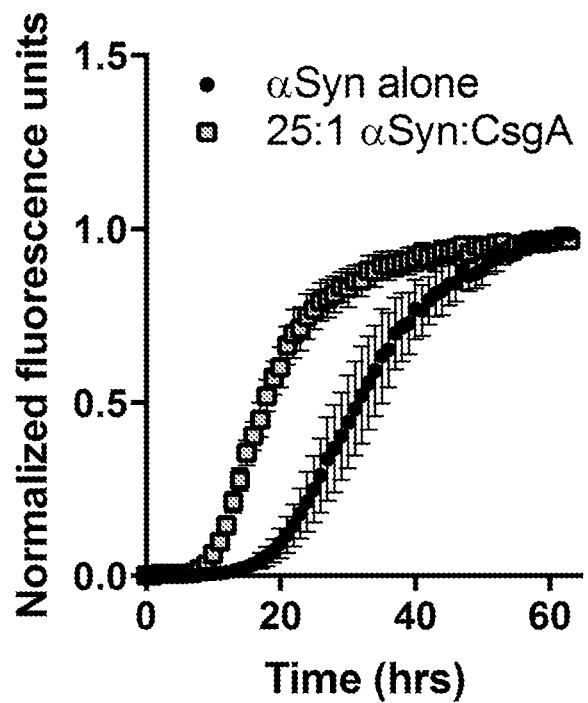
Figure 6B:
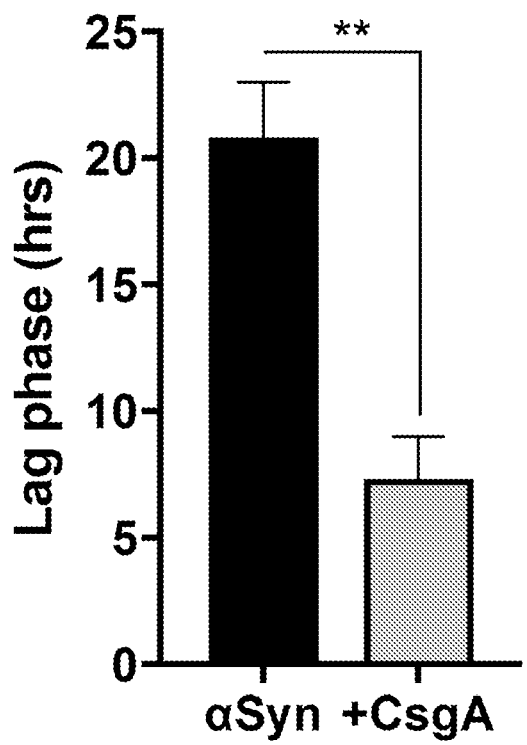
Figure 6I:
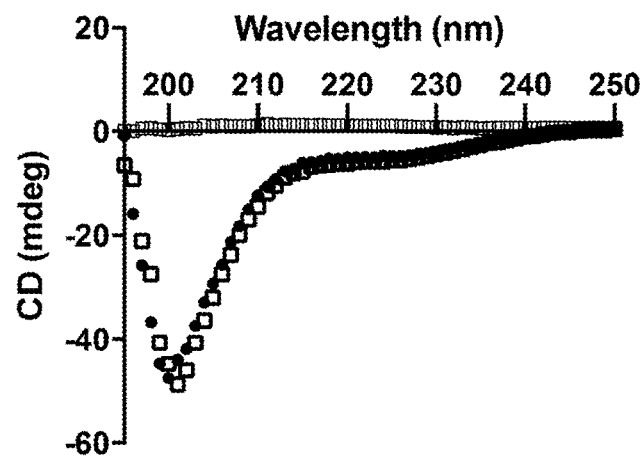
Figure 6J:
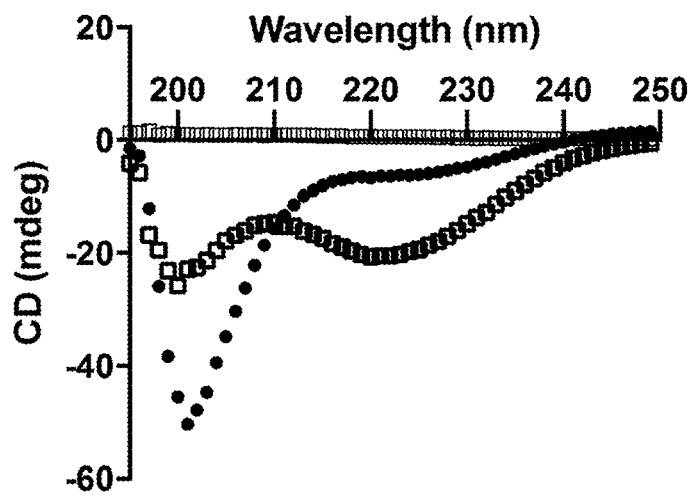
Figure 6K:
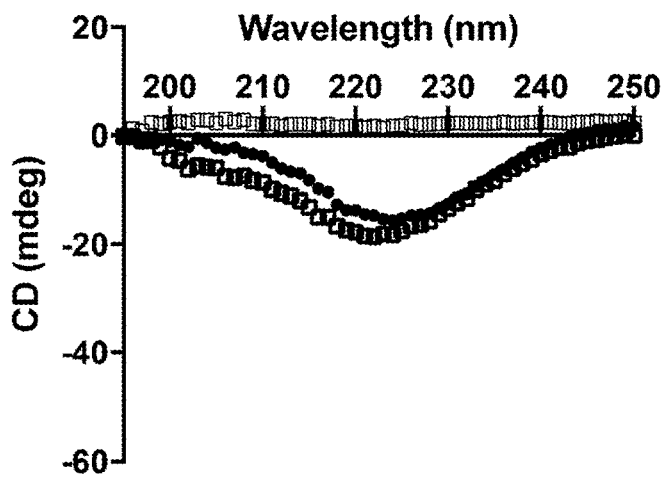

FIGS. 6A-6K are a series of graphs illustrating that the bacterial amyloid protein, CsgA, in accordance with some embodiments herein seeds αSyn fibrilization. In vitro biophysical analysis was conducted with purified αSyn and CsgA proteins. FIG. 6A shows aggregation as measured by Thioflavin T fluorescence over time during αSyn amyloid formation alone or in the presence of CsgA monomers (25:1 molar ratio, yellow). FIG. 6B shows time to reach exponential fibrilization, lag phase. FIGS. 6C-H are a series of representative transmission electron micrographs of αSyn alone (FIGS. 6C, 6F) or CsgA alone (FIGS. 6E, 6H), or in combination (FIGS. 6D, 6G), at 0 hours (FIGS. 6C-E) and 60 hours (FIGS. 6F-H) post-aggregation. FIGS. 6I-K are a series of graphs illustrating circular dichroism spectroscopic analysis of αSyn fibrilization alone or in the presence of CsgA at 0, 12.5, and 60 hours post-aggregation. For FIG. 6A and FIG. 6B, n=3. Bars represent the mean and standard error. Data are analyzed by two-tailed, t-test. **p≤0.01. Data are representative of 2 independent trials.

Figure 7A:
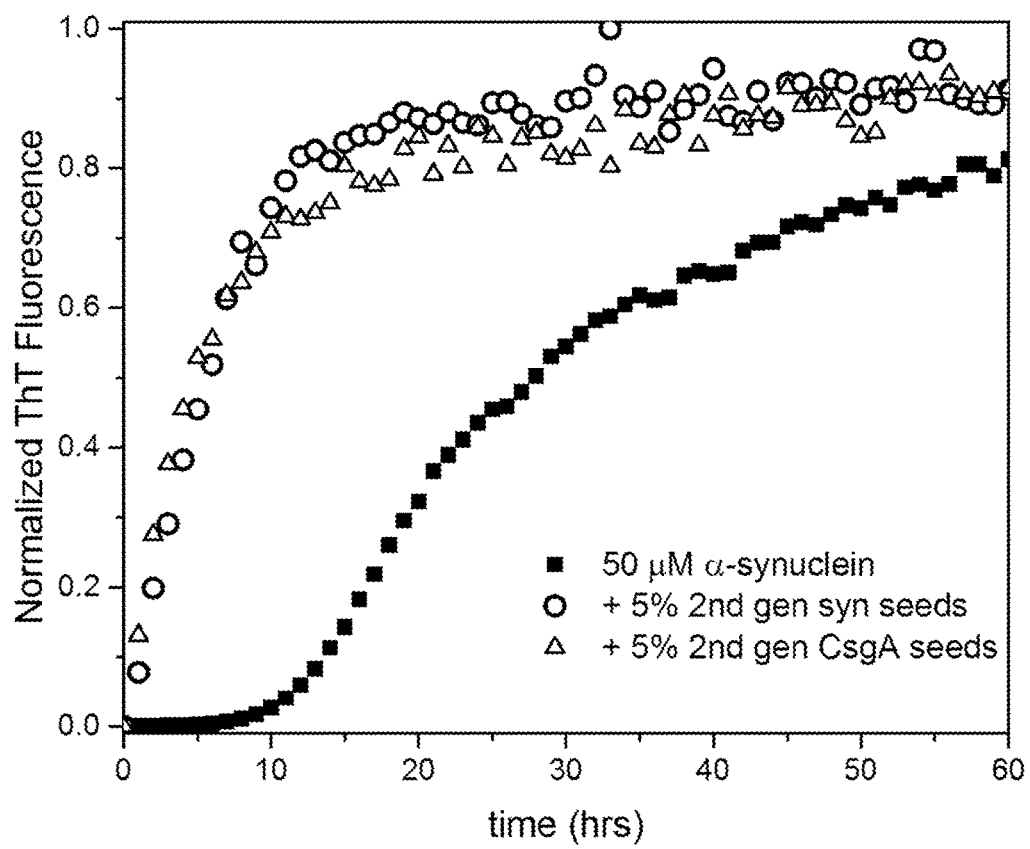
Figure 7B:
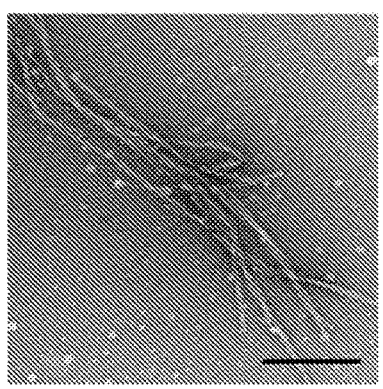
Figure 7C:
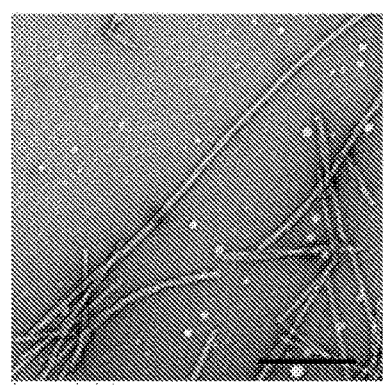
Figure 7D:
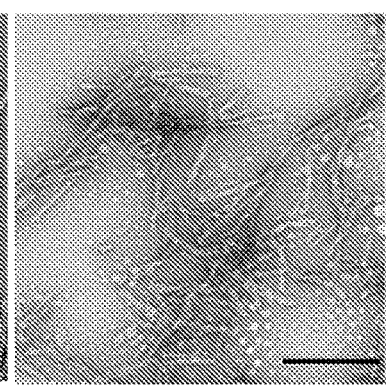
Figure 7G:
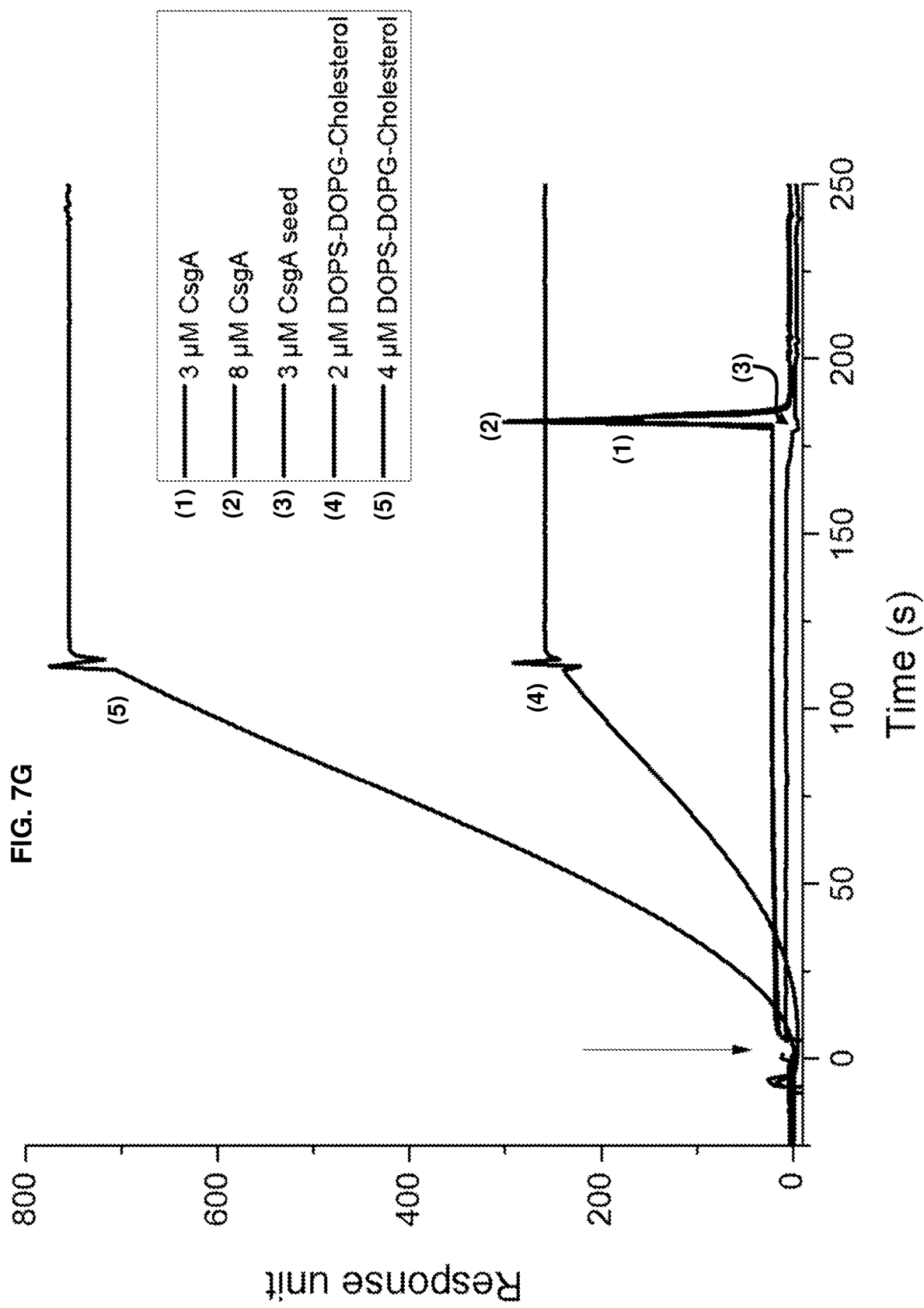

FIGS. 7A-F are a series of graphs and transmission electron microscope images illustrating that CsgA seeds synuclein aggregation and propagation through transient interactions. FIG. 7A is a graph showing Thioflavin T fluorescence during αSyn amyloid formation alone or in the presence of 5% seeds previously generated by addition of CsgA monomer to αSyn (as in FIG. 6A) or αSyn alone. FIGS. 7B-F are a series of transmission electron micrograph of fibril structures generated by the addition of above seeds and of seeds themselves. FIG. 7G is a graph showing surface plasmon resonance measurements of surface immobilized αSyn with additions of either CsgA monomer or seeds, or DOPS-DOPG cholesterol as positive control.

Figure 8:
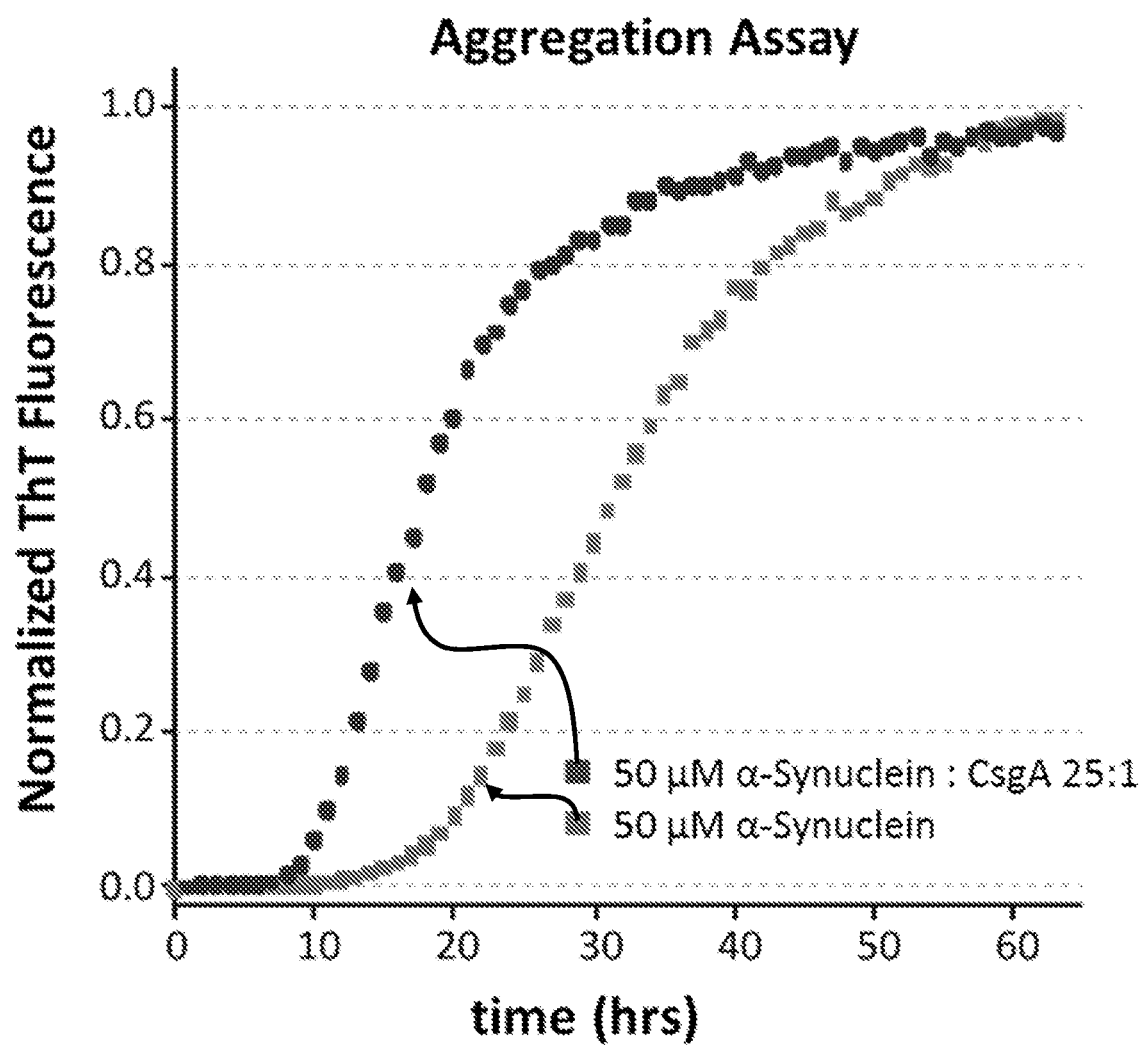

FIG. 8 is a graph illustrating an amyloid aggregation assay according to some embodiments. Shown is the aggregation of α-Synuclein over time is measured by Thioflavin T (ThT) fluorescence, in the presence and absence of CsgA.

Figure 9:
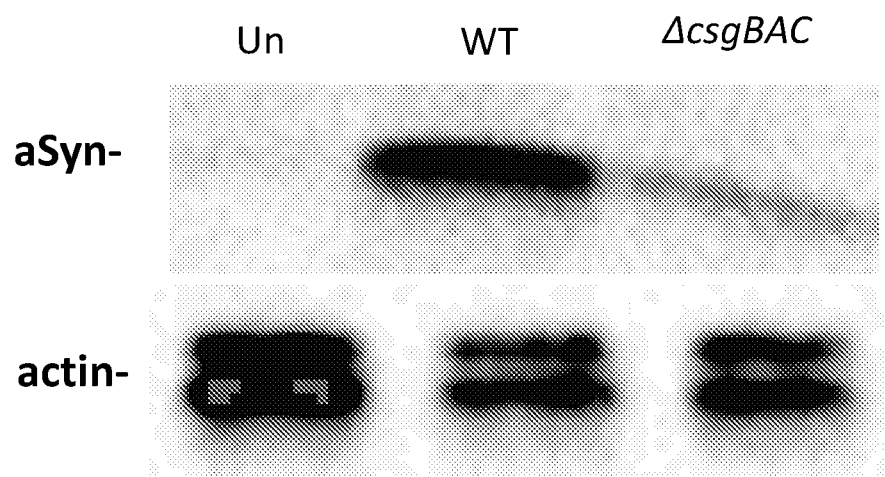

FIG. 9 is a western blot for α-Synuclein in enteroendocrine (STC-1 cell line) cells treated with E. coli K12 or the ΔcsgBAC, curli-deficient strain at an MOI of 10:1 for 4 hours.

Figure 10:
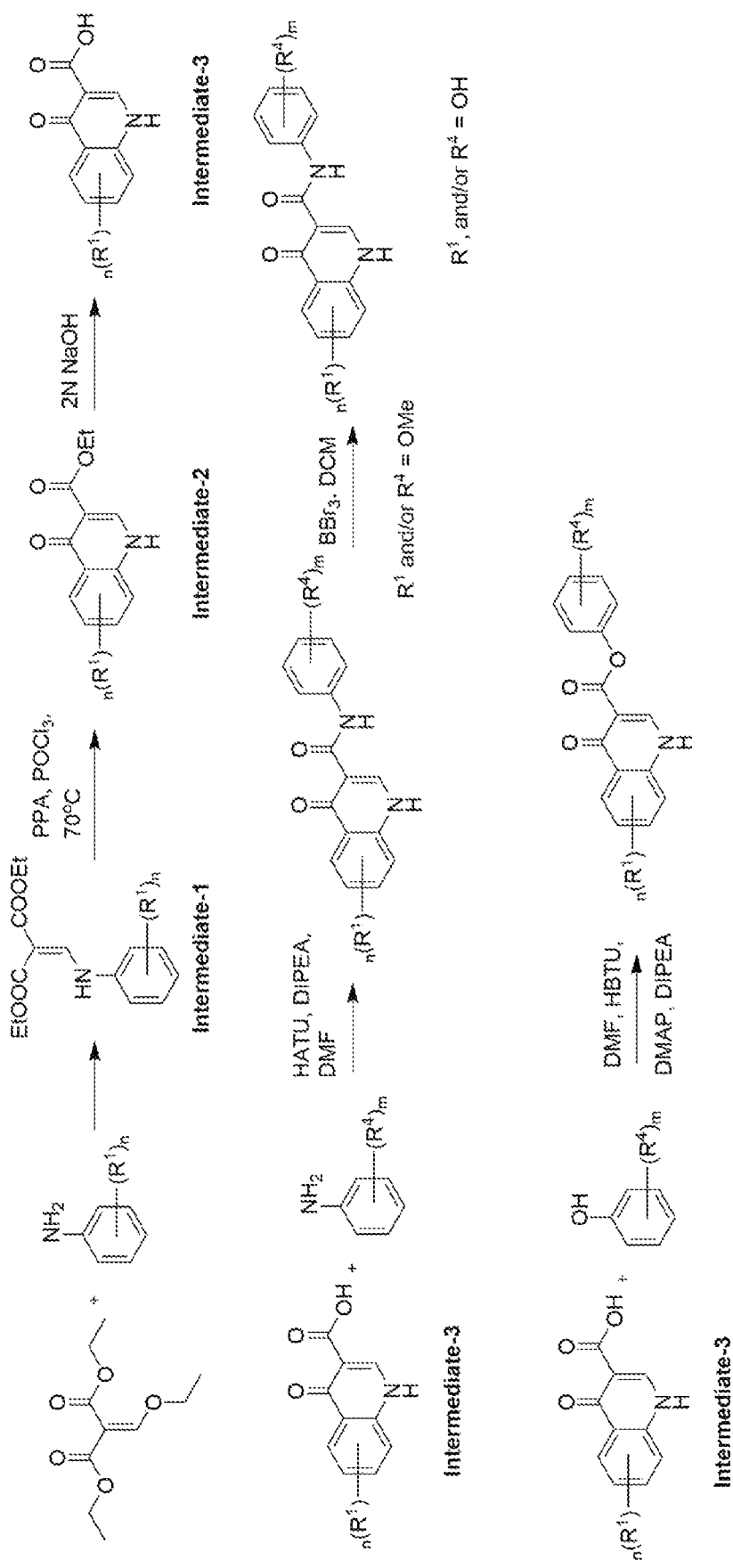

FIG. 10 shows a method of synthesizing a compound of Formula (II).

Figure 11:
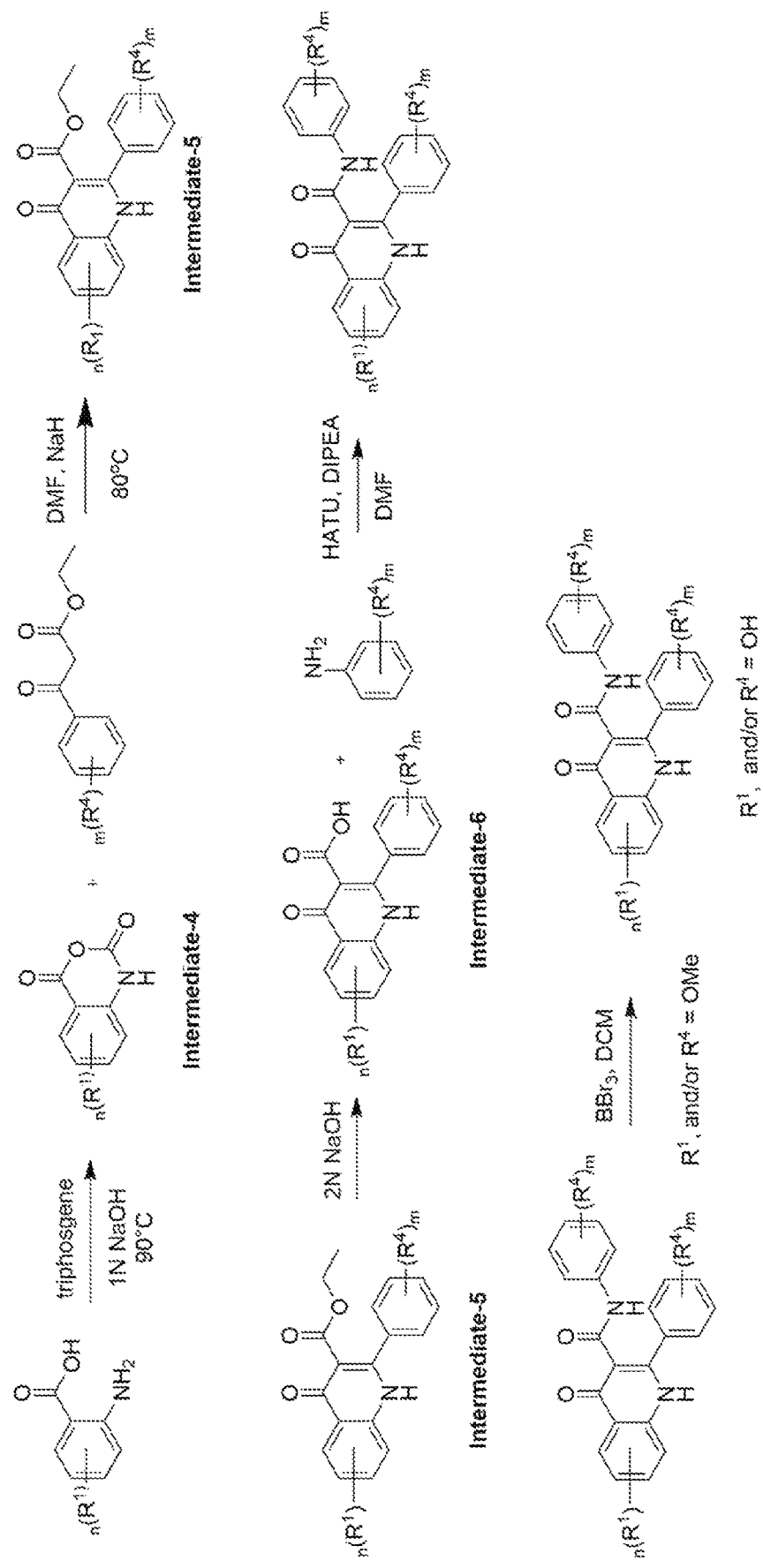

FIG. 11 shows a method of synthesizing a compound of Formula (II).

Figure 12:
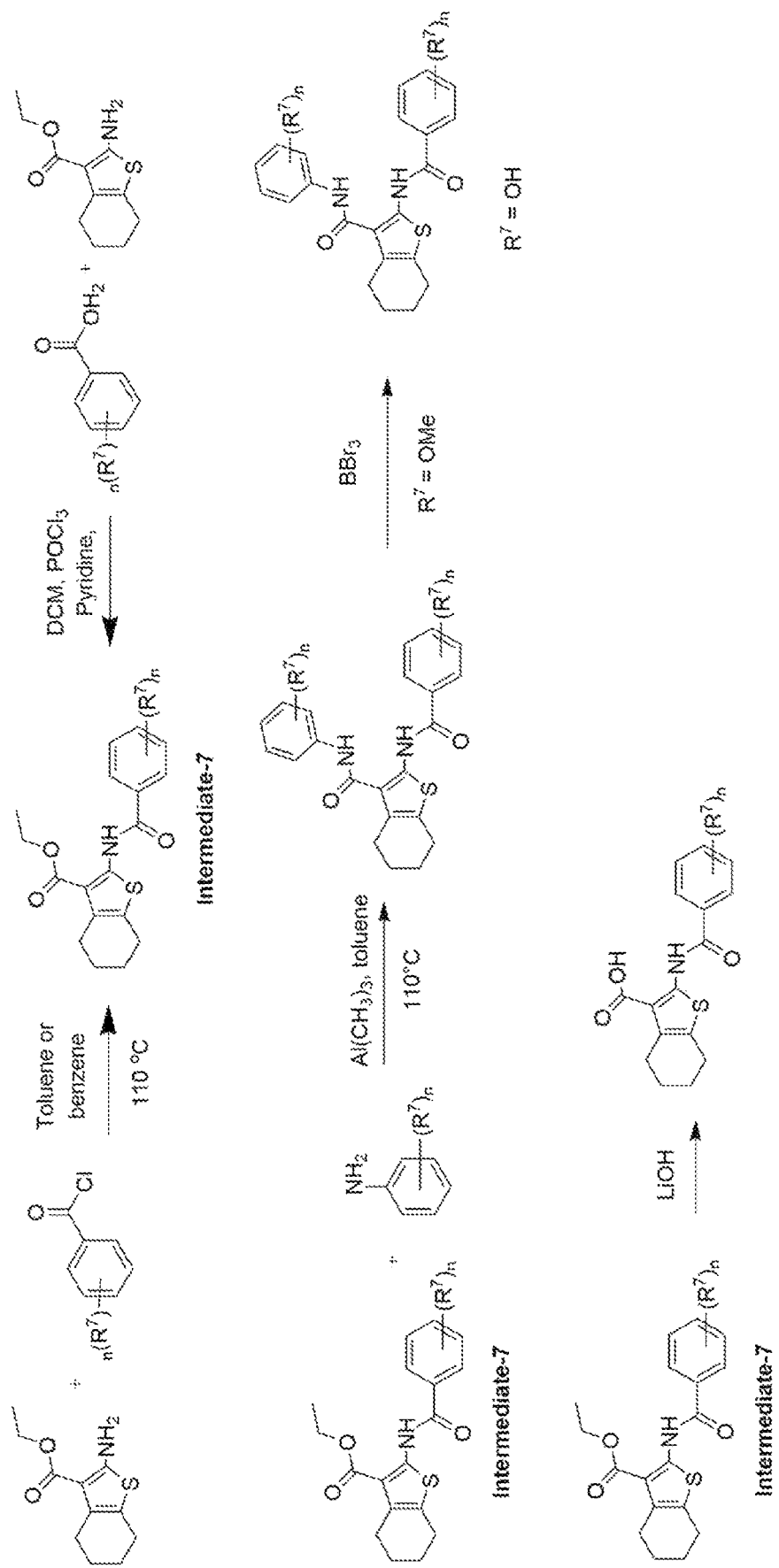

FIG. 12 shows a method of synthesizing a compound of Formula (I).

Figure 13:
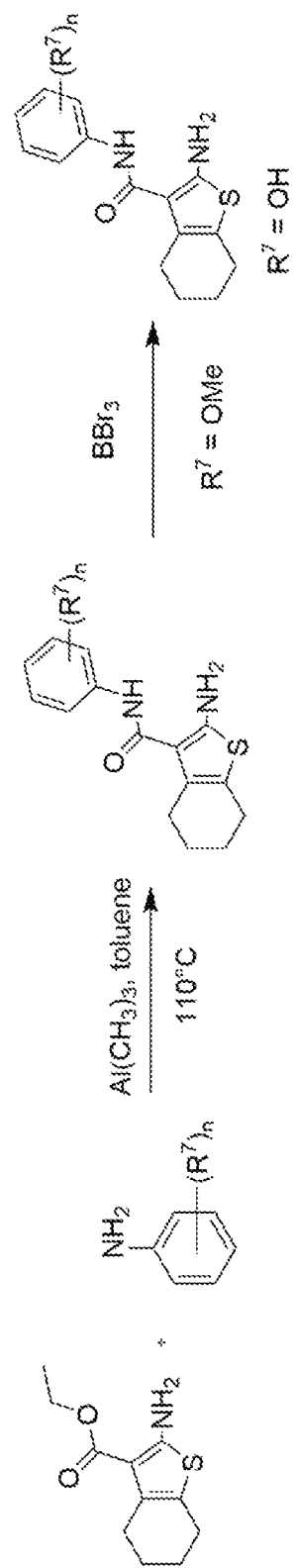

FIG. 13 shows a method of synthesizing a compound of Formula (I).

DETAILED DESCRIPTION

The majority of cases of neurodegenerative diseases are idiopathic, which, conventionally, has made it difficult to identify the etiology of most such diseases. An emerging theory is that many neurodegenerative diseases start not in the brain or central nervous system (CNS), but in the periphery and gradually migrate to the brain over the course of many years in a slow, progressive process. Still, the molecular etiology in the periphery has been the subject of study. In the case of Parkinson's Disease, it is known that constipation and hyposmia occur in many patients often decades before the emergence of the stereotypical motor symptoms that currently define Parkinson's Disease. Without being limited by theory, it is therefore contemplated that α-synuclein aggregation begins in the gastrointestinal (GI) tract and in the olfactory bulb, and that aggregated α-synuclein gradually progresses to the brain in a prion-like propagative process. In this scenario, known more generally as Braak's Hypothesis, it is contemplated that analysis of the molecular mechanisms involved in these peripheral tissues can lead to non-intuitive, non-conventional approaches for preventing and/or treating amyloid disorders, such as α-synucleinopathies, such as Parkinson's Disease.

Without being limited by theory, one molecular mechanism contemplated herein implicates bacterial amyloid as the seeding factor that nucleates or otherwise leads to α-synuclein aggregation thereby initiating the pathological process that leads ultimately to Lewy body deposition and clinical manifestation of Parkinson's Disease and other α-synucleinopathies. Bacterial amyloids are aggregated forms of secreted bacterial proteins and are thought to play a role in both bacterial adhesion to host cells and biofilm formation. In the right environment and in the presence of host proteins prone to aggregation, it is believed, without being limited by theory, that bacterial amyloids themselves serve as a direct structural template for host protein aggregation in a prion-like fashion. The bacterial chaperone machinery responsible for driving bacterial amyloid aggregation may also use the host protein as a substrate and thereby facilitate host protein aggregation into amyloid structures. Once aggregated, the host protein aggregation is perpetuated in a prion-like fashion through the enteric nervous system over the course of many years. Ultimately, these aggregates spread into brain tissue and result in the stereotypical clinical symptoms of Parkinson's Disease. This effect may also result in the development of other amyloid-driven diseases such as Alzheimer's disease, in which aggregation of the host proteins A-beta and/or tau are implicated. Consistent with this, analysis of current publicly-available human microbiome datasets reveals increased representation of the curli-associated csgA gene from E. coli in persons with Parkinson's Disease, and transplantation of fecal microbes from PD patients into germ-free (GF) wild-type or ASO mice results in greater csgA abundance compared to microbiomes from healthy controls, based on PICRUSt imputed analysis of 16s rRNA sequences (See Example 7). It is shown herein that intestinal amyloid aggregates can lead to symptoms associated with Parkinson's Disease and other amyloid disorders (See Examples 6-8), and that treating these animals with compounds that inhibit and/or disrupt amyloid aggregates can ameliorate these symptoms associated with Parkinson's Disease and other amyloid disorders (See Example 10). In some embodiments, a method for inhibiting, ameliorating, reducing the likelihood, delaying the onset of, treating, and/or preventing the amyloid disorder comprising administering a composition (e.g., a pharmaceutical composition) comprising a compound of the invention, for example any of the compounds of Tables 1 and 2 or Table 4 (infra). In some embodiments, the composition comprises or consists essentially of one or more compounds selected from the group consisting of the compounds identified by a compound activity range of "+++" in any column of Table 4. In some embodiments, the composition comprises or consists essentially of one or more compounds selected from the group consisting of the set of compounds identified by a compound activity range of "++" or "+++" in any column of Table 4. In some embodiments, the composition comprises or consists essentially of one or more compounds selected from the group consisting of the set of compounds identified by a compound activity range of "+", "++," or "+++" in any column of Table 4. In some embodiments, the composition comprises or consists essentially of one or more compounds selected from the group consisting of the compounds identified by a compound activity range of "+++" in the "αSyn" column of Table 4. In some embodiments, the composition comprises or consists essentially of one or more compounds selected from the group consisting of the set of compounds identified by a compound activity range of "++" or "+++" in the "αSyn" column of Table 4. In some embodiments, the composition comprises or consists essentially of one or more compounds selected from the group consisting of the set of compounds identified by a compound activity range of "+", "++," or "+++" in the "αSyn" column of Table 4. In some embodiments, the composition comprises or consists essentially of one or more compounds selected from the group consisting of the compounds identified by a compound activity range of "+++" in the "CsgA-seeded αSyn" column of Table 4. In some embodiments, the composition comprises or consists essentially of one or more compounds selected from the group consisting of the set of compounds identified by a compound activity range of "++" or "+++" in the "CsgA-seeded αSyn" column of Table 4. In some embodiments, the composition comprises or consists essentially of one or more compounds selected from the group consisting of the set of compounds identified by a compound activity range of "+", "++," or "+++" in the "CsgA-seeded αSyn" column of Table 4. In some embodiments, the composition comprises or consists essentially of one or more compounds selected from the group consisting of the compounds identified by a compound activity range of "+++" in the "CsgA" column of Table 4. In some embodiments, the composition comprises or consists essentially of one or more compounds selected from the group consisting of the set of compounds identified by a compound activity range of "++" or "+++" in the "CsgA" column of Table 4. In some embodiments, the composition comprises or consists essentially of one or more compounds selected from the group consisting of the set of compounds identified by a compound activity range of "+", "++" or "+++" in the "CsgA" column of Table 4. In some embodiments, the subject is selected as in need of the composition by detecting a presence and/or level of aggregates in an intestinal sample of the subject, such as a fecal sample. A presence or level of intestinal aggregates greater than a negative control (for example, fecal sample of a healthy control subject, or control subject known not to have an amyloid disorder) can indicate that the subject is in need of the composition.

In some embodiments, detecting the presence and/or level of intestinal aggregates in a sample of the subject comprises detecting a presence and/or level of a bacterial protein in the sample, for example a curli-associated protein, such as CsgA. In some embodiments, detecting the presence and/or level of intestinal aggregates in a sample of the subject comprises detecting a level of a bacteria that produces an amyloid in the sample, for example a curli-associated protein, such as CsgA. For example, a bacterial amyloid can be detected directly, or a nucleic acid encoding the amyloid can be detected in the sample, thus indicating a presence of amyloid-producing bacteria in the subject's gastrointestinal tract. Examples of amyloid-producing bacteria can include CsgA-producing Enterobacteraceae such as *E. coli*.

Amyloids are produced in the gastrointestinal tract by members of the gastrointestinal microbiota, such as *E. coli* and some other Proteobacteria. These microbial amyloids may interact with cells with which they are in contact in the gastrointestinal tract and affect α-synuclein expression and/or α-synuclein aggregation. The STC-1 cell line was derived from tumors of the mouse small intestine and possesses many features of native gastrointestinal enteroendocrine cells (McCarthy et al. (2015), STC-1 Cells. In: Verhoeckx K. et al. (eds) *The Impact of Food Bioactives on Health*. Springer, Cham.). In an in vitro assay wherein α-synuclein expression by STC-1 cells was determined by Western blot, exposure to an *E. coli* strain expressing wild-type CsgA resulted in a notable increase in α-synuclein expression, while exposure to an isogenic mutant in which csgA was deleted had little effect on α-synuclein levels (See FIG. 9 and Example 33). Thus, while the exact mechanisms by which CsgA affected α-synuclein expression are unclear, CsgA can interact with enteroendocrine-like cells of the gastrointestinal tract and cause α-synuclein over-expression in vitro, suggesting that similar effects may take place in vivo when pathogenic microbial amyloids contact enteroendocrine cells or other cells in the gastrointestinal tract. While mouse α-synuclein is generally not observed to aggregate, over-expression of human α-synuclein may lead to aggregation that in turn impairs cell function, propagates in a prion-like fashion to adjacent cells in the gastrointestinal tract and enteric nervous system, and has detrimental effects on gastrointestinal function. These negative effects can include one or more of intestinal dysbiosis, intestinal hyperpermeability, irritable bowel syndrome (IBS), inflammatory bowel disease (IBD), ulcerative colitis and/or Crohn's disease. These disorders can be associated with one or more symptoms, including dysphagia, reduced gut motility, gastroparesis, constipation (including chronic constipation and chronic idiopathic constipation), small intestinal bacterial overgrowth (SIBO), diarrhea (including chronic diarrhea), abdominal pain and/or cramping, bloating, flatulence, and nausea. In some cases, neurological and gastrointestinal symptoms of amyloid disorders can be linked. For example, in Parkinson's Disease and Parkinsonism (a clinical syndrome characterized by tremor, bradykinesia, rigidity, and postural instability) decreased levels of dopamine can lead to the neurological symptom of dyskinesia and the gastrointestinal symptom of chronic idiopathic constipation. Thus, treatments which improve gut motility, including the methods of the invention, can improve dopamine absorption in the gut and, thereby, reduce dyskinesia. Therefore, treatments that manage constipation (or, more generally, intestinal dysbiosis or intestinal hyperpermeability) can slow the progression of motor symptoms of Parkinson's Disease as well as increasing "on-time" periods of adequate control of Parkinson's Disease symptoms.

Consistent with the ability of STC-1 cells to respond to *E. coli* CsgA in vitro, gastrointestinal cells have been observed to sense and respond to microbial amyloids. For example, *Salmonella enterica* CsgA has been shown to modulate gastrointestinal permeability in mice via activation of the TLR2/PI3K pathway. Additionally, Tukel discloses in U.S. Pat. No. 9,814,756 a method for modulating gastrointestinal permeability via administration of variants of CsgA and/or CsgB. Tukel discloses in U.S. Pat. No. 9,814,756 decreasing permeability of epithelium of the small intestine or large intestine by administering a composition comprising, inter alia, an isolated curli fibril having epithelium permeability-reducing activity such as (i) a CsgA polypeptide variant which differs from a naturally occurring CsgA polypeptide in that from 1 to 5 amino acids have been substituted, deleted or added; (ii) a CsgB polypeptide variant which differs from a naturally occurring CsgB polypeptide in that from 1 to 5 amino acids have been substituted, deleted or added; or (iii)

a combination of said CsgA polypeptide variant and said CsgB polypeptide variant. Thus, while there may be additional mechanisms by which microbial amyloids interact with gastrointestinal cells, at least one such mechanism is contemplated herein.

The present disclosure relates to methods and compositions for the treatment, amelioration, or prevention of amyloid disorders. Disclosed herein are compositions and methods, which alter the ability of bacterial amyloid to promote aggregation and amyloid formation of the eukaryotic protein α-synuclein. Said alterations may include alterations in the extent, rate of formation, stability, and/or rate of disaggregation of microbially induced amyloid, or any combination thereof. Further disclosed herein are compositions (e.g., comprising compounds of the invention) and methods useful for the treatment or inhibition of neurodegenerative diseases, as well as, compositions and methods useful for the prevention or amelioration of the progression of neurodegenerative diseases. Further disclosed herein are compositions and methods useful for the treatment or inhibition of gastrointestinal dysfunction related to neurodegenerative diseases. Additionally disclosed herein are methods for studying the molecular etiology of mammalian amyloid diseases and the molecular link between bacterial amyloid production and mammalian amyloid production. According to the methods of the present disclosure, said neurodegenerative diseases and/or mammalian amyloid diseases may comprise one or more of Parkinson's disease (PD), Lewy body dementia, multiple system atrophy, and all other α-synucleinopathies, PD-associated constipation, PD-associated hyposmia, Huntington's Disease, Alexander's Disease, amyotrophic lateral sclerosis (ALS), Alzheimer's Disease and other diseases in which amyloids are implicated. In some embodiments, the composition comprises, consists essentially of, or consists of a compound of the invention as described herein. The present disclosure further relates to methods that facilitate the evaluation of aggregation and dis-aggregation of both host and bacterial amyloid proteins. Methods of the present disclosure are also useful for identifying drug candidates that affect these processes.

It is contemplated that in some embodiments, a composition comprising, consisting essentially of, or consisting of a compound of the invention as described herein is useful in preventing α-synuclein aggregation, the seeding of α-synuclein aggregation by CsgA or other microbial amyloids, and the formation of microbial amyloids that may seed α-synuclein aggregation in vivo, and these compounds may thus be useful in preventing or treating Parkinson's Disease and/or other α-synucleinopathies (See, e.g., Example 32 and Table 3).

It is contemplated that in some embodiments, a composition comprising, consisting essentially of, or consisting of a compound of the invention as described herein may be useful in preventing α-synuclein aggregation with or without seeding by microbial amyloids and thereby may have benefit in preventing or treating α-synucleinopathies independent of microbial amyloids (See, e.g., Example 32 and Table 3).

It is contemplated that in some embodiments, a composition comprising, consisting essentially of, or consisting of a compound of the invention as described herein may be useful in preventing α-synuclein aggregation seeded by microbial amyloids and thereby have therapeutic benefit, for example if dosed at sites where microbial amyloids may be abundant, such as the gastrointestinal tract (See, e.g., Example 32 and Table 3).

It is contemplated that in some embodiments, a composition comprising, consisting essentially of, or consisting of a compound of the invention as described herein may have therapeutic benefit in Parkinson's Disease and other α-synucleinopathies. Without being limited by theory, this benefit may be due to these compounds' inhibition of aggregation of α-synuclein and/or microbial amyloids. It is further contemplated that for compounds in which more than one type of aggregation is inhibited, these inhibitory effects may be additive or synergistic. (See, e.g., Example 32 and Table 3).

Accordingly, provided herein are compounds (i.e., compounds of the invention) that are useful in inhibiting, ameliorating, reducing the likelihood, delaying the onset of, treating, and/or preventing an amyloid disorders for example, any of the amyloid disorders of Table 4 (infra), such as an α-synucleinopathy, Parkinson's Disease, Lewy Body Dementia, incidental Lewy body disease, Lewy body variant of Alzheimer's disease, multiple system atrophy, pure autonomic failure, or a combination of two or more of the listed items.

Compounds of the Invention

In one aspect, provided herein is a compound of Formula (I):

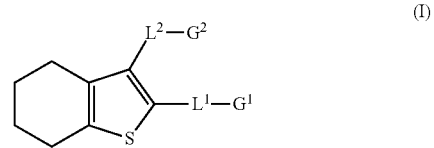

or a pharmaceutically acceptable salt thereof.

Formula (I), embodiments of Formula (I) provided herein, and pharmaceutically acceptable salts thereof, are defined as follows:

$L^1$ is a divalent moiety selected from a bond and —N($R^5$)(C=O)—.

$L^2$ is a divalent moiety selected from —(C=O)— and —(C=O)O—.

$G^1$ is a monovalent moiety selected from —N($R^5$)$_2$ and $R^6$. In certain embodiments, $G^1$ is —NH$_2$. In certain embodiments, $G^1$ is —NHR$^5$. In certain embodiments, $G^1$ is —N($R^5$)$_2$. In certain embodiments, $G^1$ is $R^6$.

$G^2$ is a monovalent moiety selected from —H, —N($R^5$)$_2$, and —N($R^5$)($R^6$). In certain embodiments, $G^2$ is —H. In certain embodiments, $G^2$ is —NH$_2$. In certain embodiments, $G^2$ is —NHR$^5$. In certain embodiments, $G^2$ is —N($R^5$)$_2$. In certain embodiments, $G^2$ is —NHR$^6$. In certain embodiments, $G^2$ is —N($R^5$)($R^6$).

Each $R^5$ is a monovalent moiety independently selected from —H and alkyl. In certain embodiments, $R^5$ is substituted $C_{1-6}$ alkyl. In certain embodiments, $R^5$ is unsubstituted $C_{1-6}$ alkyl. In certain embodiments, $R^5$ is methyl. In certain embodiments, $R^5$ is —H.

Each $R^6$ is aryl substituted with n instances of $R^7$. For each $R^6$, n is 0, 1, 2, 3, or 4. In certain embodiments, n is 0. In certain embodiments, n is 1. In certain embodiments, n is 2. In certain embodiments, n is 3. In certain embodiments, n is 4.

Each $R^7$ is independently selected from —F, —OH, and —O(alkyl). In certain embodiments, each $R^7$ is independently selected from —F, —OH, and —OCH$_3$. In certain embodiments, each $R^7$ is independently selected from —OH and —OCH$_3$. In certain embodiments, each R$^7$ is —OH. In certain embodiments, each R$^7$ is —OCH$_3$.

In certain embodiments, Formula (I) is of Formula (I-a):

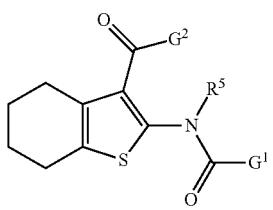

(I-a)

or a pharmaceutically acceptable salt thereof.

In certain embodiments of Formula (I-a):
G$^1$ is R$^6$;
G$^2$ is —NH$_2$ or —N(R$^5$)(R$^6$);
R$^5$ is —H or —CH$_3$;
R$^6$ is phenyl substituted with n instances of R$^7$;
R$^7$ is independently, for each occurrence, —F, —OH or —OCH$_3$; and
n is 0, 1, 2, 3, or 4.

In certain embodiments, Formula (I) is of Formula (I-b):

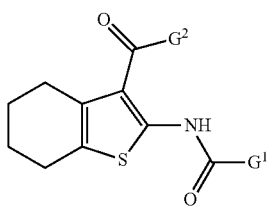

(I-b)

or a pharmaceutically acceptable salt thereof.

In certain embodiments, Formula (I-b) is of Formula (I-b-1) or Formula (I-b-2):

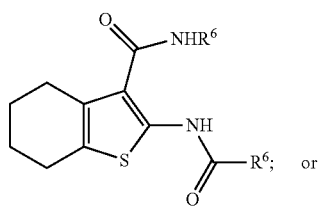

(I-b-1)

(I-b-2)

or a pharmaceutically acceptable salt thereof.

In certain embodiments, the compound of Formula (I), (I-a), (I-b), (I-b-1), or (I-b-2), or a pharmaceutically acceptable salt thereof, has 0-6 instances of R$^7$. In certain embodiments, the compound has 1-6 instances of R$^7$. In certain embodiments, the compound has 2-6 instances of R$^7$. In certain embodiments, the compound has 3-6 instances of R$^7$. In certain embodiments, the compound has 1-3 instances of R$^7$. In certain embodiments, the compound has 2-4 instances of R$^7$. In certain embodiments, the compound has 2 instances of R$^7$. In certain embodiments, the compound has 3 instances of R$^7$. In certain embodiments, the compound has 4 instances of R$^7$. In certain embodiments, the compound has 5 instances of R$^7$. In certain embodiments, the compound has 6 instances of R$^7$.

In certain embodiments of the compound of Formula (I), (I-a), (I-b), (I-b-1), or (I-b-2), or a pharmaceutically acceptable salt thereof, each R$^6$ is independently selected from:

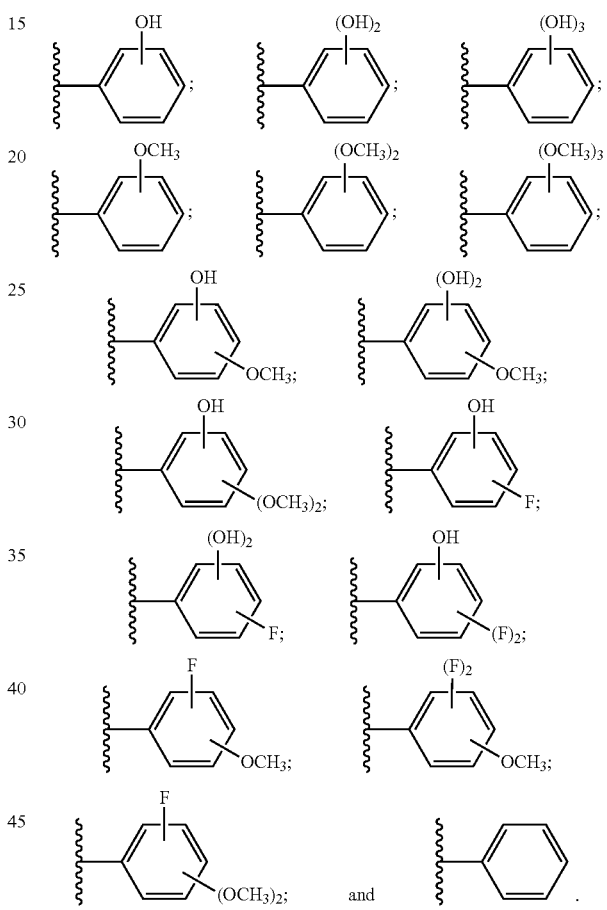

In certain embodiments of the compound of Formula (I), (I-a), (I-b), (I-b-1), or (I-b-2), or a pharmaceutically acceptable salt thereof, each R$^6$ is independently selected from:

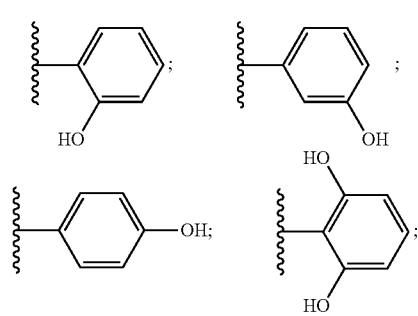

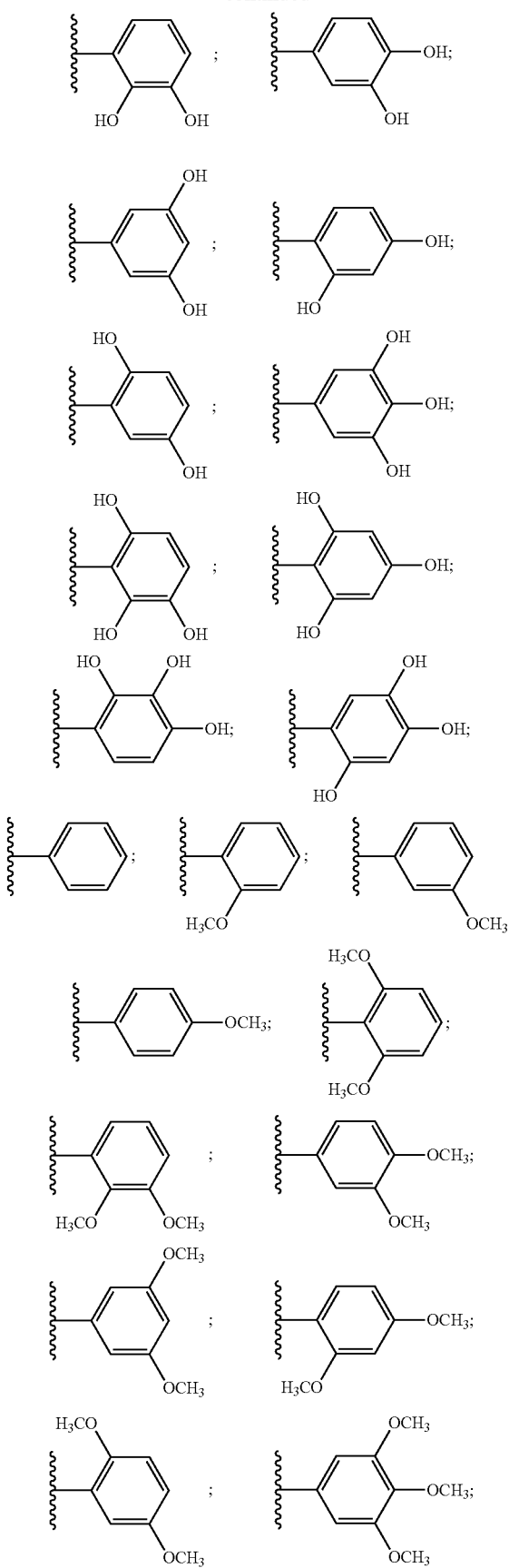
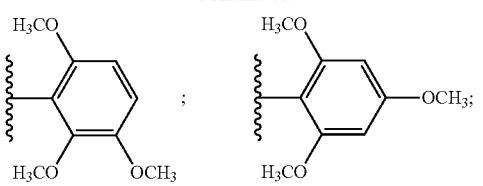
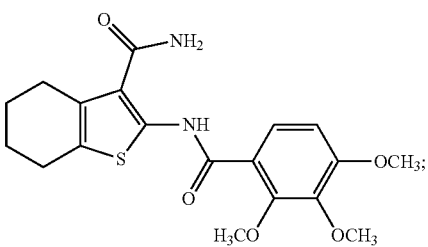
In certain embodiments, it is provided that the compound of Formula (I), (I-a), (I-b), (I-b-1), or (I-b-2):
(a) comprises at least one instance of $R^6$; and/or
(b) comprises at least three instances of $R^7$; and/or
(c) is not one of the following compounds:
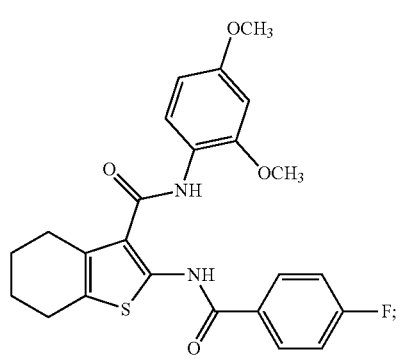
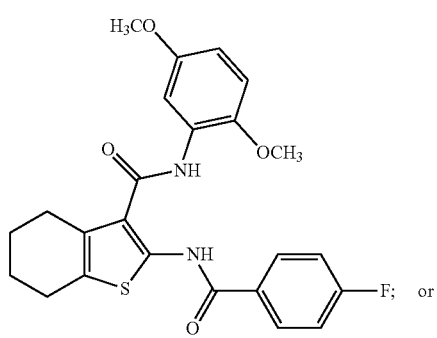

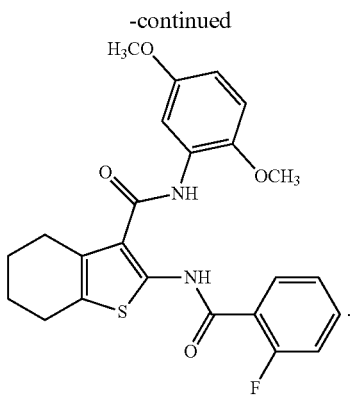
In certain embodiments, the compound of Formula (I), (I-a), (I-b), (I-b-1), or (I-b-2) is selected from the compounds of Table 1, and pharmaceutically acceptable salts thereof.
TABLE 1
1
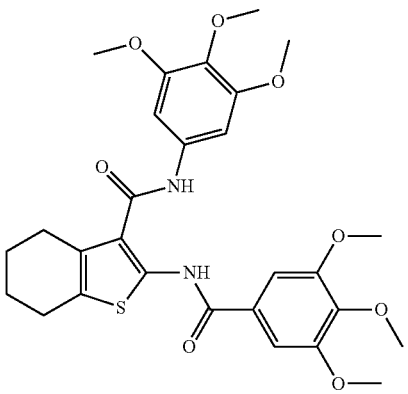 [SMILES: COc1cc(NC(=O)c2c(NC(=O)c3cc(OC)c(OC)c(OC)c3)sc3c2CCCC3)cc(OC)c1OC]
2
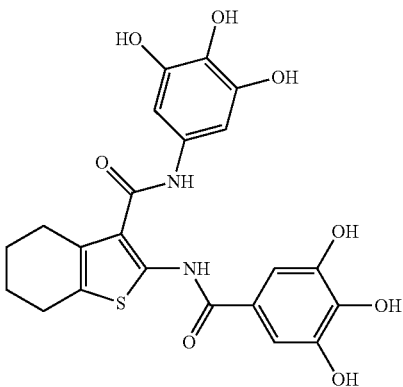 [SMILES: O=C(Nc1sc2c(c1C(=O)Nc1cc(O)c(O)c(O)c1)CCCC2)c1cc(O)c(O)c(O)c1]
TABLE 1-continued
3
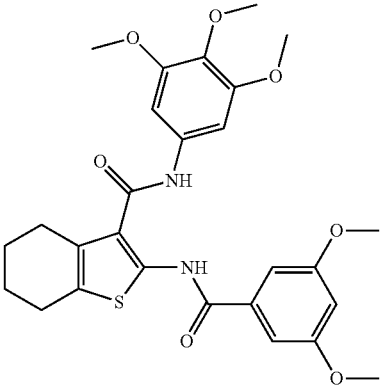 [SMILES: COc1cc(OC)cc(C(=O)Nc2sc3c(c2C(=O)Nc2cc(OC)c(OC)c(OC)c2)CCCC3)c1]
4
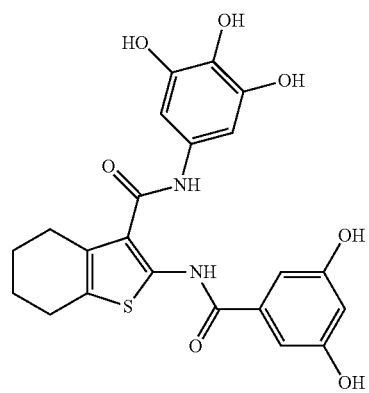 [SMILES: O=C(Nc1sc2c(c1C(=O)Nc1cc(O)c(O)c(O)c1)CCCC2)c1cc(O)cc(O)c1]
5
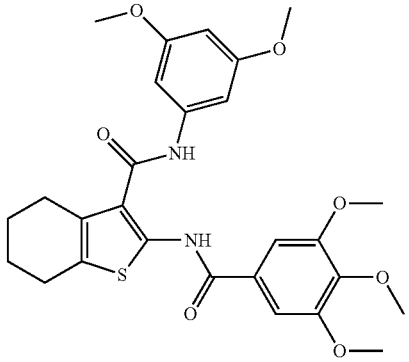 [SMILES: COc1cc(NC(=O)c2c(NC(=O)c3cc(OC)c(OC)c(OC)c3)sc3c2CCCC3)cc(OC)c1]
6
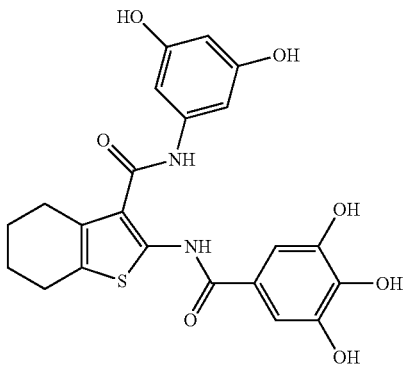 [SMILES: O=C(Nc1sc2c(c1C(=O)Nc1cc(O)cc(O)c1)CCCC2)c1cc(O)c(O)c(O)c1]

TABLE 1-continued
| | |
|---|---|
| 7 | 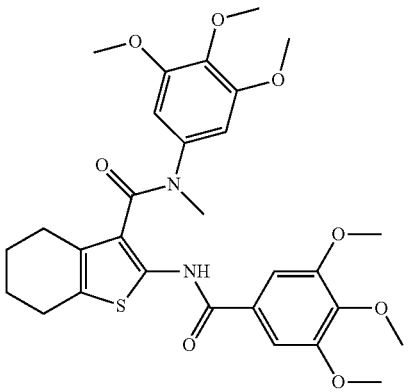 [SMILES: COc1cc(C(=O)Nc2sc3c(c2C(=O)N(C)c2cc(OC)c(OC)c(OC)c2)CCCC3)cc(OC)c1OC] |
| 8 | 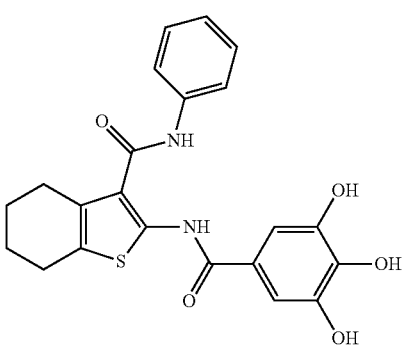 [SMILES: O=C(Nc1sc2c(c1C(=O)Nc1ccccc1)CCCC2)c1cc(O)c(O)c(O)c1] |
| 9 | 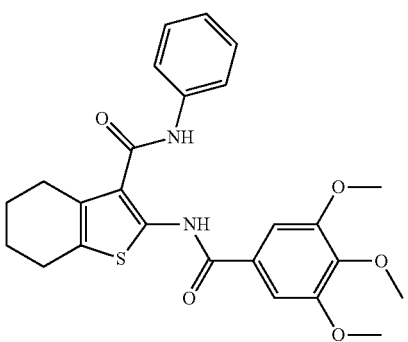 [SMILES: COc1cc(C(=O)Nc2sc3c(c2C(=O)Nc2ccccc2)CCCC3)cc(OC)c1OC] |
| 10 | 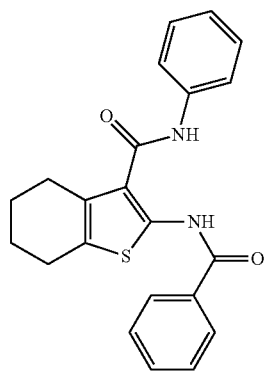 [SMILES: O=C(Nc1sc2c(c1C(=O)Nc1ccccc1)CCCC2)c1ccccc1] |
| 11 | 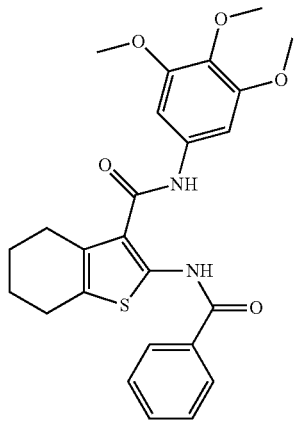 [SMILES: COc1cc(NC(=O)c2c(NC(=O)c3ccccc3)sc3c2CCCC3)cc(OC)c1OC] |
| 12 | 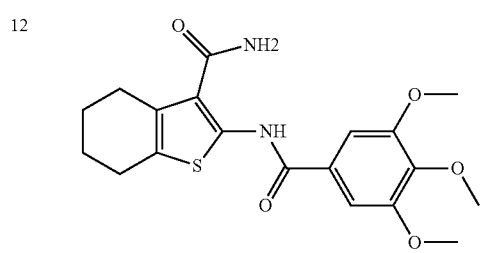 |
| 13 | 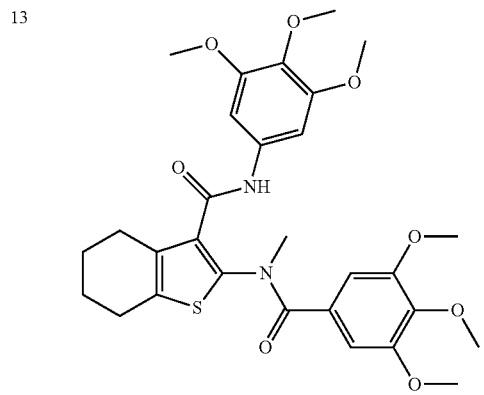 |
| 14 | 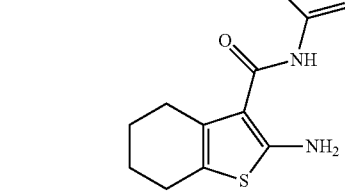 |
| 15 | 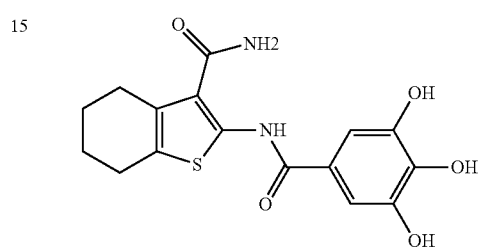 |
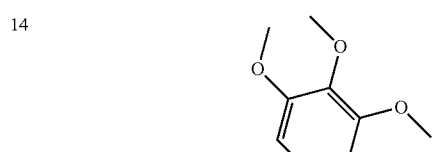

TABLE 1-continued

16
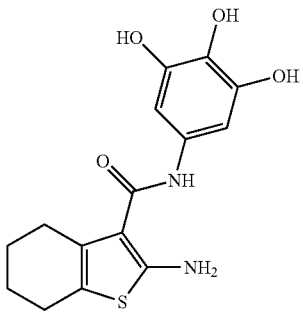

17
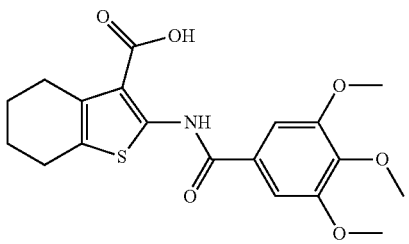

18
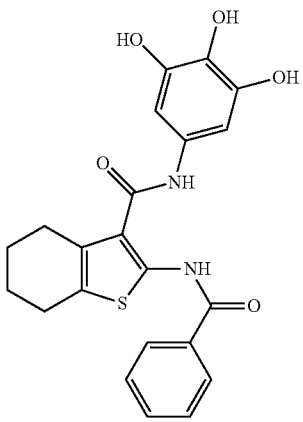

In another aspect, provided herein is a compound of Formula (II):

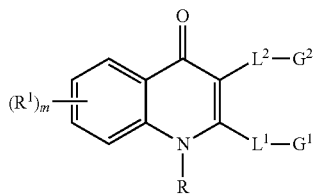

(II)

or a pharmaceutically acceptable salt thereof.

Formula (II), embodiments of Formula (II) provided herein, and pharmaceutically acceptable salts thereof, are defined as follows.

$L^1$ is a bond.

$L^2$ is a divalent moiety selected from a bond, —$CH_2$—, —(C=O)—, —(C=O)O—, and —$NR^2$(C=O)—.

$G^1$ is a monovalent moiety selected from —H and $R^3$. In certain embodiments, $G^1$ is —H. In certain embodiments, $G^1$ is $R^3$.

$G^2$ is a monovalent moiety selected from —H, —N($R^2$)$_2$, —N($R^2$)($R^3$), and $R^3$. In certain embodiments, $G^2$ is —H. In certain embodiments, $G^2$ is —N($R^2$)$_2$. In certain embodiments, $G^2$ is —$NH_2$. In certain embodiments, $G^2$ is —N($C_{1-6}$ alkyl)$_2$. In certain embodiments, $G^2$ is —N($R^2$)($R^3$). In certain embodiments, $G^2$ is $R^3$.

R is a monovalent moiety selected from —H and alkyl. In certain embodiments, R is substituted $C_{1-6}$ alkyl. In certain embodiments, R is unsubstituted $C_{1-6}$ alkyl. In certain embodiments, R is methyl. In certain embodiments, R is —H.

Each $R^1$ is independently selected from —F, —OH, and —O(alkyl). In certain embodiments, each $R^1$ is independently selected from —F, —OH, and —$OCH_3$. In certain embodiments, each $R^1$ is independently selected from —OH and —$OCH_3$. In certain embodiments, each $R^1$ is —OH. In certain embodiments, each $R^1$ is —$OCH_3$.

Each $R^2$ is a monovalent moiety independently selected from —H and alkyl. In certain embodiments, $R^2$ is substituted $C_{1-6}$ alkyl. In certain embodiments, $R^2$ is unsubstituted $C_{1-6}$ alkyl. In certain embodiments, $R^2$ is methyl. In certain embodiments, $R^2$ is —H.

Each $R^3$ is aryl substituted with n instances of $R^4$. For each $R^3$, n is 0, 1, 2, 3, or 4. In certain embodiments, n is 0. In certain embodiments, n is 1. In certain embodiments, n is 2. In certain embodiments, n is 3. In certain embodiments, n is 4.

Each $R^4$ is independently selected from —F, —OH, and —O(alkyl). In certain embodiments, each $R^4$ is independently selected from —F, —OH, and —$OCH_3$. In certain embodiments, each $R^4$ is independently selected from —OH and —$OCH_3$. In certain embodiments, each $R^4$ is —OH. In certain embodiments, each $R^7$ is —$OCH_3$.

m is 0, 1, 2, 3, or 4. In certain embodiments, m is 0. In certain embodiments, m is 1. In certain embodiments, m is 2. In certain embodiments, m is 3. In certain embodiments, m is 4.

In certain embodiments, $L^1$ is a bond;

$L^2$ is a bond, —$CH_2$—, —(C=O)—, —(C=O)O—, or —$NR^2$(C=O)—;

$G^1$ is —H or $R^3$;

$G^2$ is —N($R^2$)($R^3$) or $R^3$;

R is H or —$CH_3$;

$R^1$ is —OH or —$OCH_3$;

$R^2$ is —H or —$CH_3$;

$R^3$ is phenyl substituted with m instances of $R^4$;

$R^4$ is independently, for each occurrence, —F, —OH or —$OCH_3$;

n is, for each occurrence 0, 1, 2, 3, or 4; and m is 0, 1, 2, 3, or 4.

In certain embodiments, Formula (II) is of Formula (II-a) or Formula (II-b):

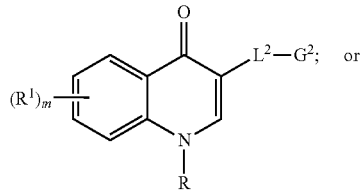

(II-a)

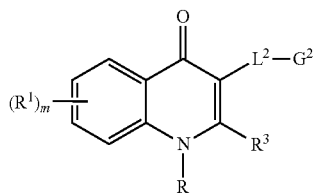

or a pharmaceutically acceptable salt thereof.

In certain embodiments, Formula (II-a) is of Formula (II-a-1) or Formula (II-a-2):

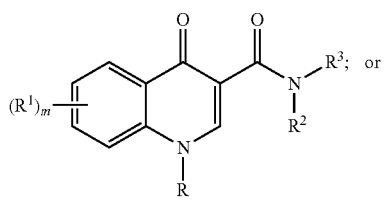

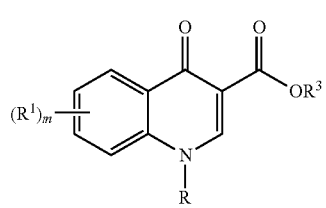

or a pharmaceutically acceptable salt thereof.

In certain embodiments, Formula (II-b) is of Formula (II-b-1) or Formula (II-b-2):

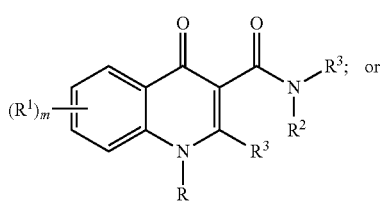

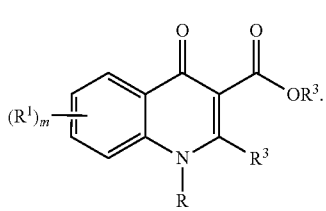

or a pharmaceutically acceptable salt thereof.

In certain embodiments, the compound of Formula (II), (II-a), (II-a-1), (II-a-2), (II-b), (II-b-1), (II-b-2), or a pharmaceutically acceptable salt thereof, has 0-6 instances of $R^4$. In certain embodiments, the compound has 1-6 instances of $R^4$. In certain embodiments, the compound has 2-6 instances of $R^4$. In certain embodiments, the compound has 3-6 instances of $R^4$. In certain embodiments, the compound has 1-3 instances of $R^4$. In certain embodiments, the compound has 2-4 instances of $R^4$. In certain embodiments, the compound has 2 instances of $R^4$. In certain embodiments, the compound has 3 instances of $R^4$. In certain embodiments, the compound has 4 instances of $R^4$. In certain embodiments, the compound has 5 instances of $R^4$. In certain embodiments, the compound has 6 instances of $R^4$.

In certain embodiments of the compound of Formula (II), (II-a), (II-a-1), (II-a-2), (II-b), (II-b-1), (II-b-2), or a pharmaceutically acceptable salt thereof, the sum of all instances of m and n is 0-9. In certain embodiments, the sum is 1-9. In certain embodiments, the sum is 2-9. In certain embodiments, the sum is 3-9. In certain embodiments, the sum is 4-9. In certain embodiments, the sum is 5-9. In certain embodiments, the sum is 6-9. In certain embodiments, the sum is 1-6. In certain embodiments, the sum is 2-6. In certain embodiments, the sum is 3-6. In certain embodiments, the sum is 1-3. In certain embodiments, the sum is 2. In certain embodiments, the sum is 3. In certain embodiments, the sum is 4. In certain embodiments, the sum is 5. In certain embodiments, the sum is 6. In certain embodiments, the sum is 7. In certain embodiments, the sum is 8. In certain embodiments, the sum is 9.

In certain embodiments of the compound of Formula (II), (II-a), (II-a-1), (II-a-2), (II-b), (II-b-1), (II-b-2), or a pharmaceutically acceptable salt thereof, each $R^3$ is independently selected from:

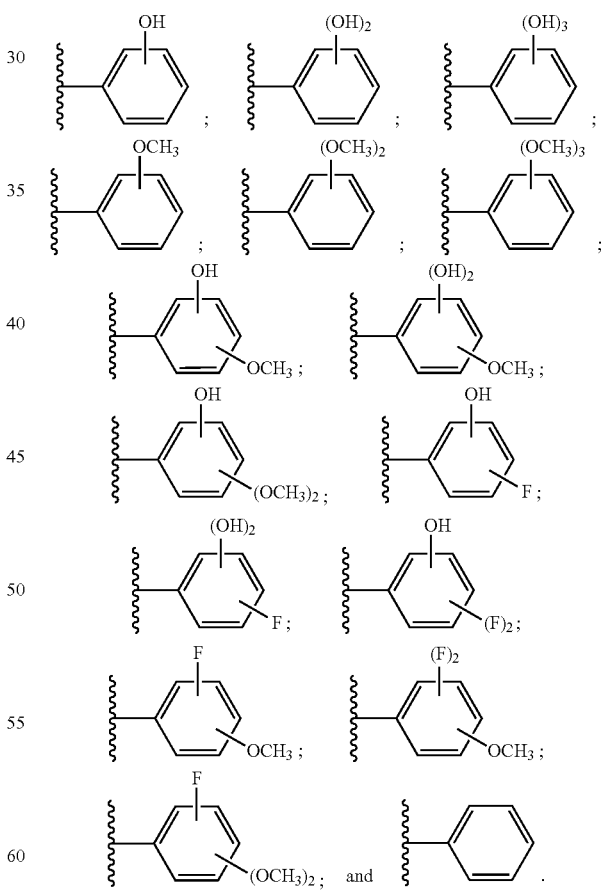

In certain embodiments of the compound of Formula (II), (II-a), (II-a-1), (II-a-2), (II-b), (II-b-1), (II-b-2), or a pharmaceutically acceptable salt thereof, each $R^3$ is independently selected from:

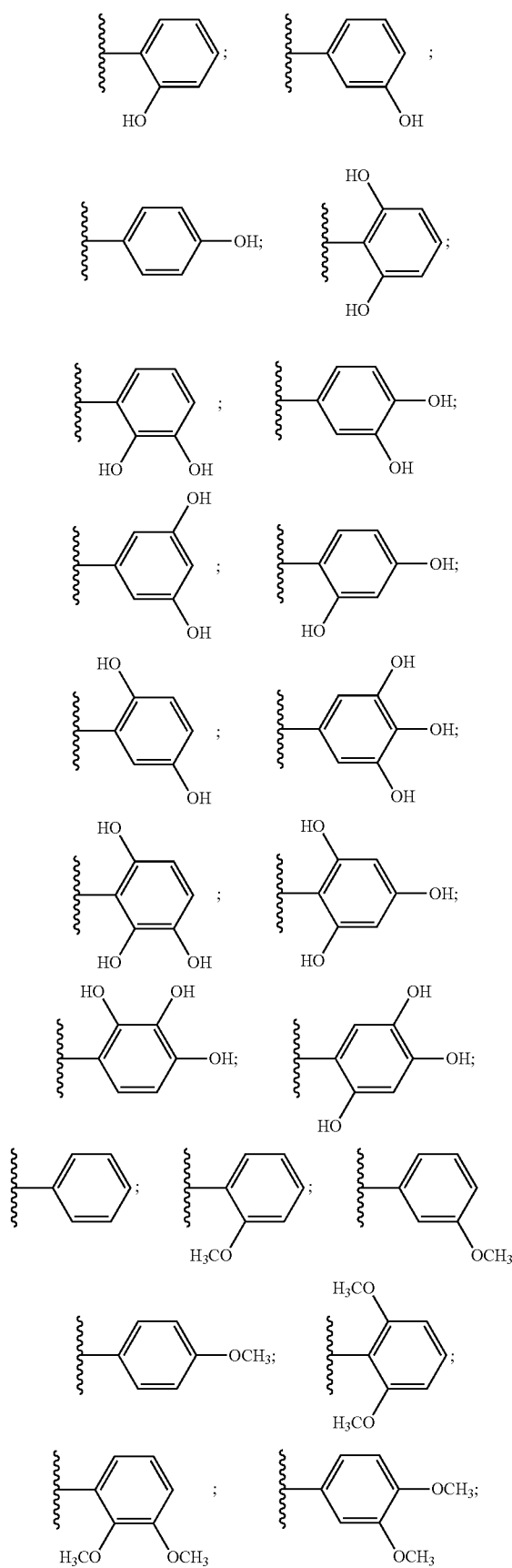
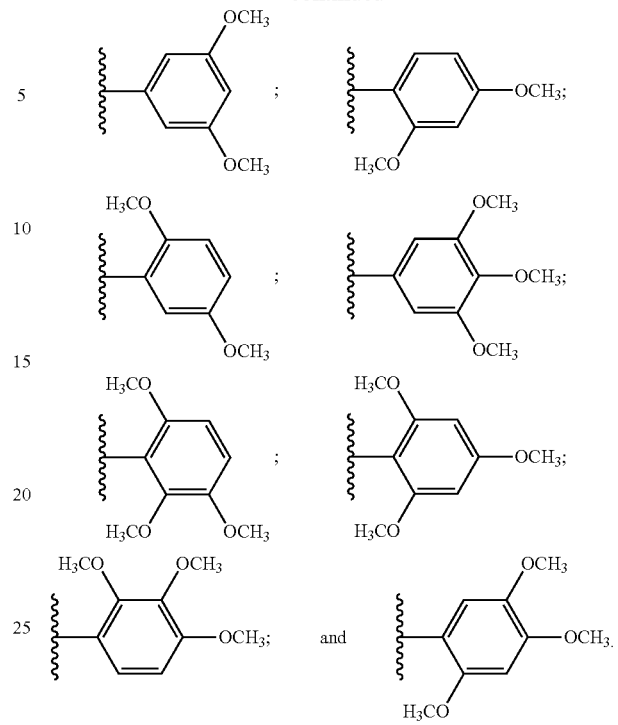
In certain embodiments of the compound of Formula (II), (II-a), (II-a-1), (II-a-2), (II-b), (II-b-1), or (II-b-2), it is provided that:
(a) the compound comprises at least one instance of $R^3$; and/or
(b) the sum of all instances of m and n is at least three; and/or
(c) the compound does not have the structure:
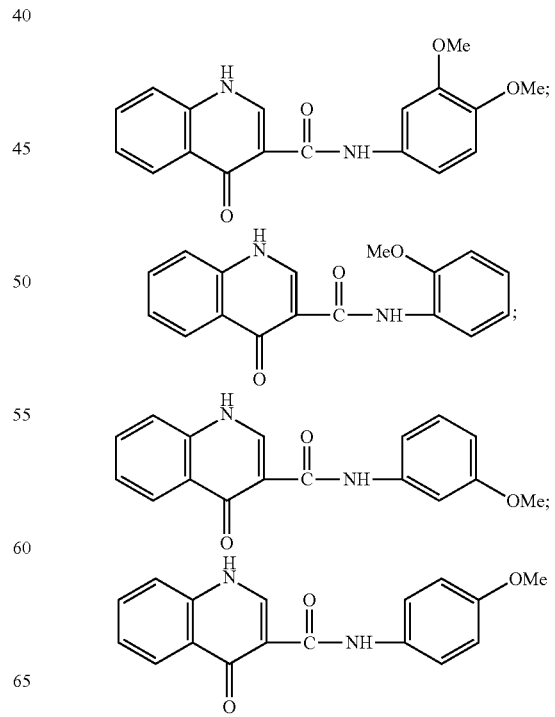

-continued
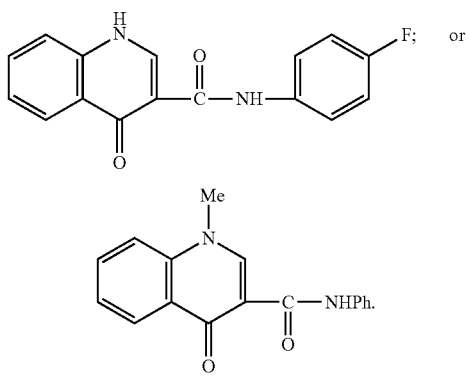
In certain embodiments, the compound of Formula (II), (II-a), (II-a-1), (II-a-2), (II-b), (II-b-1), or (II-b-2) is selected from the compounds of Table 2, and pharmaceutically acceptable salts thereof.
TABLE 2

TABLE 2-continued
30
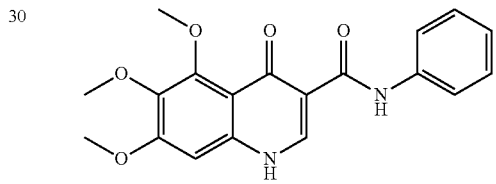
31
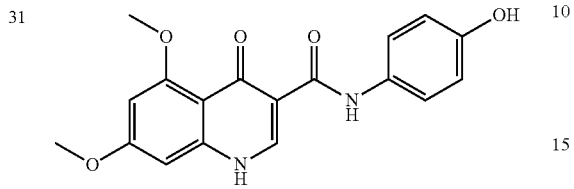
32
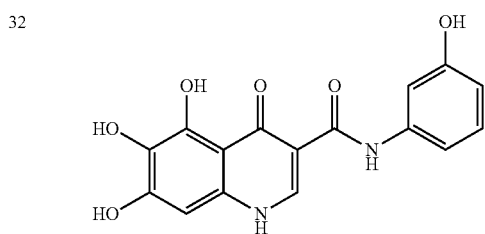
33
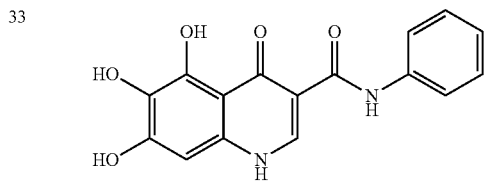
34
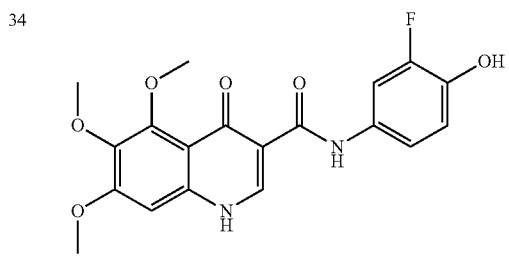
35
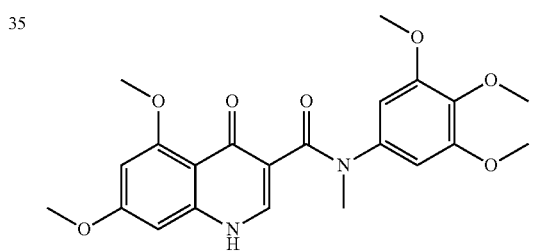
36
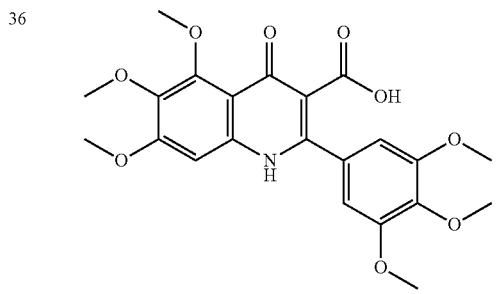
TABLE 2-continued
37
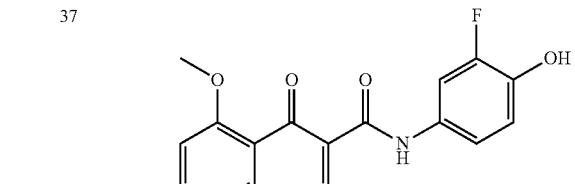
38
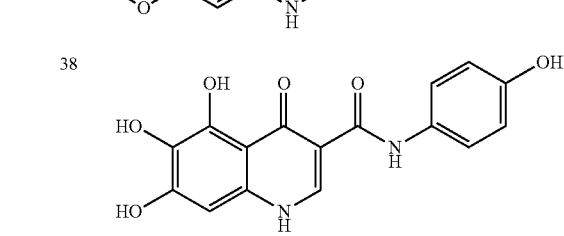
39
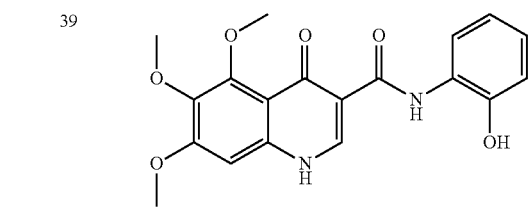
40
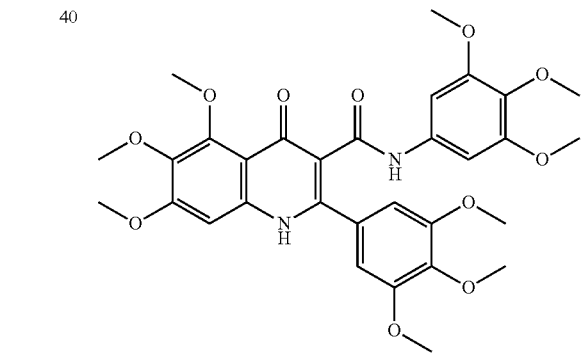
41
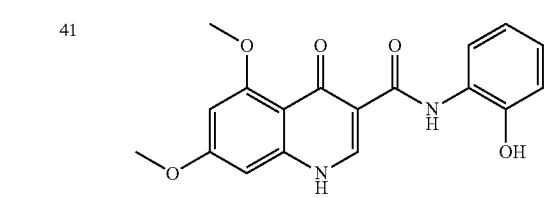
42
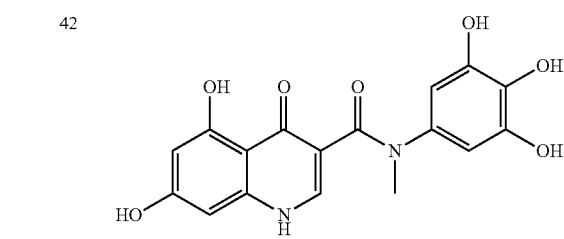
43
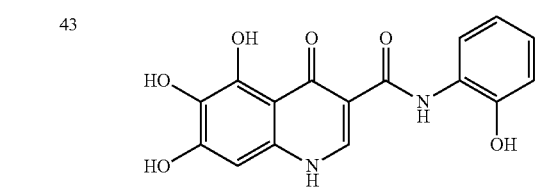

TABLE 2-continued

| | |
|---|---|
| 44 | 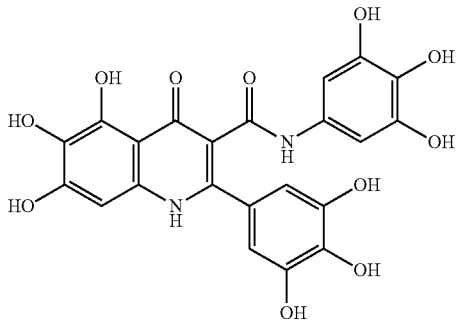 |
| 45 | 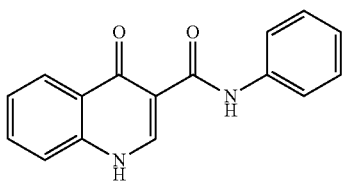 |
| 46 | 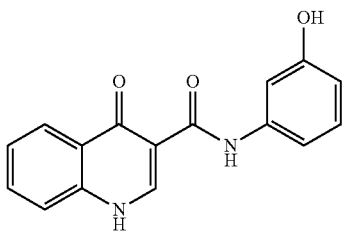 |
| 47 | 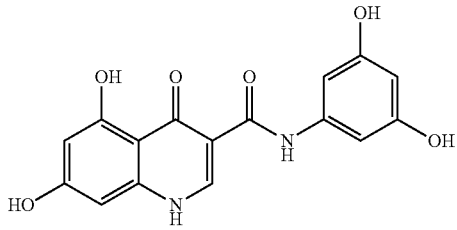 |
| 48 | 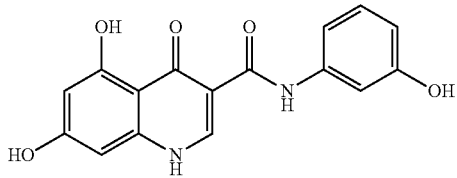 |
| 49 | 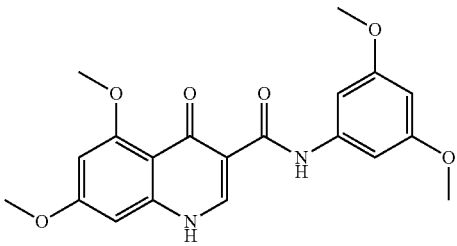 |

The compounds described above, and pharmaceutically acceptable salts thereof, may be referred to collectively as compounds of the invention.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)). An alkyl group may be branched or unbranched.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents (e.g., —F, —OH or —O($C_{1-6}$ alkyl). In certain embodiments, the aryl group is an unsubstituted $C_{6-14}$ aryl. In certain embodiments, the aryl group is a substituted $C_{6-14}$ aryl.

"Solvate" has its customary and ordinary meaning as understood by one of skill in the art in view of this disclosure. It refers to the compound formed by the interaction of a solvent and an active pharmaceutical ingredient (or API), a metabolite, or salt thereof. Suitable solvates are pharmaceutically acceptable solvates including hydrates.

The terms "decrease", "reduced", "reduction", "inhibit" or "disrupt" are all used herein to mean a decrease by a statistically significant amount. In some embodiments, "reduce," "reduction", "decrease", "inhibit" or "disrupt" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

An "effective amount" or "effective dose" of a compound (e.g., a compound of the invention) or composition containing such compound, refers to the amount sufficient to achieve a desired biological and/or pharmacological effect, e.g., when delivered to a cell or organism according to a selected administration form, route, and/or schedule. The phrases "effective amount" and "therapeutically effective amount" are used interchangeably. As will be appreciated by those of ordinary skill in this art, the absolute amount of a particular compound or composition that is effective may vary depending on such factors as the desired biological or pharmacological endpoint, the agent to be delivered, the target tissue, etc. Those of ordinary skill in the art will further understand that an "effective amount" may be administered to a subject in a single dose, or through use of multiple doses, in various embodiments.

Pharmaceutical Compositions, Formulation, Administration and Dosing

In another aspect, provided herein is a pharmaceutical composition comprising a compound of the invention and a pharmaceutically acceptable carrier. Pharmaceutical compositions described herein are useful for inhibiting amyloid formation.

In certain embodiments, the pharmaceutical composition is formulated for delivery outside of the systemic circulation of a subject. In certain embodiments, the pharmaceutical composition is formulated for delivery to the central nervous system of a subject. Said composition may be formulated for enteric or intranasal delivery, for example, and/or said compositions may further be formulated for controlled release within the lower intestine or colon. The aforementioned compositions may comprise an enteric-coated capsule, tablet, soft-gel, spray dried powder, polymer matrix, hydrogel, enteric-coated solid, crystalline solid, amorphous solid, glassy solid, coated micronized particle, liquid, nebulized liquid, aerosol, or microcapsule.

In certain embodiments, the pharmaceutical composition is formulated for oral administration. In certain embodiments, the pharmaceutical composition is formulated for administration by injection. The injection may be intravenous, subcutaneous, intramuscular, intraperitoneal, intraspinal or intracranial.

The pharmaceutical composition an effective amount of one or more compounds of the invention. The effective amount is sufficient to achieve one or more desired biological and/or pharmacological effects, e.g., the disruption or inhibition of the formation of amyloid aggregates, the treatment or prevention of a neurological disorder, or symptoms of a neurological disorder, or the treatment or prevention of a gastrointestinal disorders, or symptoms of a gastrointestinal disorder.

"Administering" has its customary and ordinary meaning as understood by one of skill in the art in view of this disclosure. It refers to providing a pharmaceutical agent, dietary supplement, or composition to a subject, and includes, but is not limited to, administering by a medical professional and self-administration. Administration of the compounds disclosed herein or the pharmaceutically acceptable salts thereof can be via any of the accepted modes of administration for agents that serve similar utilities including, but not limited to, orally, intraperitoneally, or rectally. Oral administrations are customary in administering the compositions that are the subject of the preferred embodiments. However, in some embodiments, the compositions to be administered according to the methods of the present disclosure are administered rectally, such as by enema or suppository. In some embodiments, administration of the compounds may occur outside the body, for example, by apheresis or dialysis.

The term "agent" has its customary and ordinary meaning as understood by one of skill in the art in view of this disclosure. It includes any substance, molecule, element, compound, entity, or a combination thereof. It includes, but is not limited to, e.g., protein, polypeptide, peptide or mimetic, small organic molecule, polysaccharide, polynucleotide, polymer, resin, organic or inorganic microparticle, organic or inorganic nanoparticle, and the like. It can be a natural product, a synthetic compound, or a chemical compound, or a combination of two or more substances.

In some embodiments, the methods of the present disclosure contemplate the administration of one or more compositions useful for the amelioration or treatment of one or more neurological disorders associated with amyloid formation. Said compositions can be formulated into pharmaceutical compositions and/or dietary supplements for use in treating, inhibiting, or ameliorating a neurological disease or neurological disorder associated with amyloid formation such as Parkinson's disease (PD), Lewy body dementia, multiple system atrophy, and all other α-synucleinopathies, PD-associated constipation, PD-associated hyposmia, Huntington's Disease, Alexander's Disease, amyotrophic lateral sclerosis (ALS), and/or Alzheimer' s Disease and/or other diseases in which amyloids are implicated. Standard pharmaceutical and/or dietary supplement formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical and/or dietary supplement compositions comprising: (a) a safe and therapeutically effective amount of one or more compounds described herein, or pharmaceutically acceptable salts thereof; and (b) a pharmaceutically acceptable carrier, diluent, excipient or combination thereof.

The term "pharmaceutically acceptable carrier" or "pharmaceutically acceptable excipient" has its customary and ordinary meaning as understood by one of skill in the art in view of this disclosure. It includes any and all solvents, diluents, emulsifiers, binders, buffers, dispersion media, coatings, antibacterial and antifungal agents, isotonic and absorption delaying agents and the like, or any other such compound as is known by those of skill in the art to be useful in preparing pharmaceutical formulations. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

Some examples of substances, which can serve as pharmaceutically-acceptable carriers or components thereof in accordance with methods and compositions of some embodiments herein, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and/or phosphate buffer solutions, or any combination thereof.

The choice of a pharmaceutically-acceptable carrier to be used in conjunction with the one or more compounds for administration as described herein can be determined by the way the compound is to be administered.

In addition, the present disclosure includes compositions comprising various salts, esters, hydrates, prodrugs, fluorinated analogs, or isotopically substituted analogs, including deuterated forms, of the compounds described herein.

As used herein, "systemic circulation" has its customary and ordinary meaning as understood by one of skill in the art in view of this disclosure. It refers to circulation within the blood or circulatory system of a subject.

As used herein, "enteric coating" has its customary and ordinary meaning as understood by one of skill in the art in view of this disclosure. It refers to a pharmaceutical excipient coating or placed around a particle which, by control of its solubility or timing of dissolution, increases the likelihood that said particle will be protected from solvent until its arrival in a desired portion of the gastrointestinal tract, for example, by conferring resistance to stomach acid or by having higher solubility at neutral or basic pH. Representative enteric coatings include, for example, those described in Remington's The Science and Practice of Pharmacy, 21st Ed., Lippincott Williams & Wilkins (2005). Exemplary enteric coatings include but are not limited to, shellac, sodium alginate, zein, cellulose acetate trimellitate, methyl methacrylate-methacrylic acid copolymer, polyvinyl acetate phthalate, polylactic acid, polylactic-co-glycolic acid, hypromellose acetate, hypromellose acetate succinate, Hydroxypropyl methyl cellulose phthalate, Cellulose acetate succinate, Cellulose acetate phthalate, Methyl acrylate-methacrylic acid copolymer, polyvinyl acetate phthalate, Opadry®, and others as are known in the art of drug delivery and formulation. In accordance with method and compositions of some embodiments, the composition comprising a compound as described herein further comprises an enteric coating.

The term "gut selective" as used herein has its customary and ordinary meaning as understood by one of skill in the art in view of this disclosure. It refers to a composition or formulation that is released in the gut of a subject, and preferably is not absorbed, or if absorption occurs, does not enter the systemic circulation.

The term "intrinsically enteric" as used herein has its customary and ordinary meaning as understood by one of skill in the art in view of this disclosure. With reference to a pharmaceutical formulation refers to a composition which innately has the ability to prevent disintegration or release in the gastric environment.

A composition for administration to a subject as described herein is preferably provided in a unit dosage form. As used herein, a "unit dosage form" has its customary and ordinary meaning as understood by one of skill in the art in view of this disclosure. It refers to a composition containing an amount of a compound that is suitable for administration to a subject, in a single dose, according to good medical practice. The preparation of a single or unit dosage form however, does not imply that the dosage form is administered once per day or once per course of therapy. A unit dosage form may comprise a single daily dose or a fractional sub-dose wherein several unit dosage forms are to be administered over the course of a day in order to complete a daily dose. According to the present disclosure, a unit dosage form may be given more or less often that once daily, and may be administered more than once during a course of therapy. Such dosage forms may be administered in any manner consistent with their formulation, including orally, rectally, nasally, and/or parenterally. While single administrations are specifically contemplated, the compositions administered according to the methods described herein may also be administered as a continuous infusion or via an implantable infusion pump.

The methods as described herein may utilize any of a variety of suitable forms for a variety of routes for administration, for example, for oral, nasal, rectal, or parenteral routes of administration. Depending upon the particular route of administration desired, a variety of pharmaceutically-acceptable carriers well-known in the art may be used. Pharmaceutically-acceptable carriers include, for example, solid or liquid fillers, diluents, hydrotropes, surface-active agents, and encapsulating substances. Optional pharmaceutically-active materials may be included, which do not substantially interfere with the activity of the one or more compounds in the formulation. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and/or bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and/or melting agents. Further solid dosage forms may comprise milled powders, spray-dried powders, crystalline forms, amorphous forms, and glassy forms, which may be administered as tablets or may be administered as aerosols or airborne particles, for example for nasal or pulmonary delivery. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and/or flavoring agents, or any combination thereof. Further liquid dosage forms may comprise forms for intranasal or pulmonary delivery. Such dosage forms may comprise liquids for intranasal injection, nasal lavage, pulmonary lavage, nebulization or aerosol delivery.

The pharmaceutically-acceptable carriers suitable for the preparation of unit dosage forms for peroral administration in accordance with methods and compositions of some embodiments herein are well-known in the art. Tablets typically comprise conventional pharmaceutically-compatible adjuvants as inert diluents, such as calcium carbonate, sodium carbonate, mannitol, lactose and/or cellulose; binders such as starch, gelatin and/or sucrose; disintegrants such as starch, alginic acid and/or croscarmelose; lubricants such as magnesium stearate, stearic acid, microcrystalline cellulose, carboxymethyl cellulose, and/or talc. Tablets may also comprise solubilizers or emulsifiers, such as poloxamers, cremophor/Kolliphor®/Lutrol®, or methylcellulose, hydroxypropylmethylcellulose, or others as are known in the art, or any combination thereof. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and/or fruit flavors, or any combination thereof, are useful adjuvants for chewable tablets. Capsules typically comprise one or more solid diluents disclosed above. The selection of carrier components depends on secondary considerations like taste, cost, and shelf stability, which can be readily made by a person skilled in the art.

Peroral (PO) compositions in accordance with methods and compositions of some embodiments herein also include liquid solutions, emulsions, or suspensions. The pharmaceutically-acceptable carriers suitable for preparation of such compositions are well known in the art. Typical components of carriers for syrups, elixirs, emulsions and/or suspensions include ethanol, glycerol, propylene glycol, polyethylene glycol, liquid sucrose, sorbitol and/or water. For a suspension, typical suspending agents include methyl cellulose, sodium carboxymethyl cellulose, AVICEL RC-591, tragacanth and/or sodium alginate; typical wetting agents include lecithin and/or polysorbate 80; and typical preservatives include methyl paraben and/or sodium benzoate, or any combination thereof. Peroral liquid compositions may also contain one or more components such as sweeteners, flavoring agents and/or colorants, as disclosed above.

Such compositions may also be coated by conventional methods, typically with pH or time-dependent coatings, such that the subject one or more compounds are released in the gastrointestinal tract in the vicinity of the desired application, or at various times to extend the desired action. Exemplary dosage forms for release in the gastrointestinal tract may incorporate one or more of cellulose acetate phthalate, polyvinyl acetate phthalate, hydroxypropyl methyl cellulose phthalate, ethyl cellulose, Eudragit coatings, waxes, alginate and/or shellac, or other excipients known to those of skill in the art, or any combination thereof. According to some embodiments, the compositions to be administered according to the methods described herein are formulated for release in the gastrointestinal tract. According to some embodiments, the compositions to be administered according to the methods described herein are formulated for release in the lower gastrointestinal tract. In some embodiments, the compositions are provided as enteric coated capsules, tablets, soft gels; or intrinsically enteric capsules.

The actual unit dose of the compositions in accordance with methods and compositions of some embodiments herein depends on the one or more compounds in the formulation. In some embodiments, the amount of each compound in the formulation may be from 0.01 mg/kg to 0.05 mg/kg of body weight per day, from 0.04 mg/kg to 0.1 mg/kg of body weight per day, from 0.09 mg/kg to 0.15 mg/kg of body weight per day, from 0.14 mg/kg to 0.2 mg/kg of body weight per day, from 0.2 mg/kg to 0.5 mg/kg of body weight per day, from 0.4 mg/kg to 1 mg/kg of body weight per day, from 1 mg/kg to 6 mg/kg of body weight per day, 5 mg/kg to 500 mg/kg or more of body weight per day, from 10 mg/kg or less to 70 mg/kg, from 50 mg/kg to 80 mg/kg of body weight per day, from 70 mg/kg to 120 mg/kg of body weight per day, from 100 mg/kg to 300 mg/kg of body weight per day, or from 250 mg/kg to 500 mg/kg of body weight per day. In some embodiments, the dose may be less than 100 mg/kg, 500 mg/kg, 300 mg/kg, 200 mg/kg, 150 mg/kg, 100 mg/kg, 50 mg/kg, 40 mg/kg, 30 mg/kg, 25 mg/kg, 20 mg/kg, 10 mg/kg, 7.5 mg/kg, 6 mg/kg, 5 mg/kg, 4 mg/kg, 3 mg/kg, 2.5 mg/kg, or 1 mg/kg of body weight per day or an amount that is within a range defined by any two of the aforementioned amounts. In some embodiments, the actual unit dose is 5, 10, 25, 50, 75, 100, 150, or 200 mg/kg of body weight per day or an amount that is within a range defined by any two of the aforementioned amounts. Thus, for administration to a 70 kg person, for example, the dosage range is from 0.1 mg to 1 mg, 0.9 mg to 2 mg, from 1.5 mg to 5 mg, from 4 mg to 10 mg, from 9 mg to 20 mg, from 15 mg to 50 mg, from 40 mg to 75 mg, from 50 mg to 100 mg, from 75 mg to 200 mg, from 100 mg to 300 mg, from 200 mg to 400 mg, 350 mg to 750 mg, from 500 mg to 1 g, from 750 mg to 2 g, from 1 g to 5 g, from 2.5 g to 6 g, from 4 g to 10 g, from 8 g to 20 g, from 15 g to 35 g, or from 1 g or less to 35 g or more, or an amount that is within a range defined by any two of the aforementioned amounts. In some embodiments, the actual unit dose is 6 g. In some embodiments, the actual unit dose is 10 g. In some embodiments, the actual unit dose is 35 g. In some embodiments, the actual unit dose is 1 g or less but not zero. In some embodiments, the actual unit dose is 10 g or less but not zero. In some embodiments, the actual unit dose is 35 mg or less but not zero.

"Loading dose," as used herein refers to an initial dose of a compound which is higher than subsequent doses.

"Maintenance dose," as used herein refers to a subsequent dose that follows a loading dose, and occurs later in time than a loading dose. One of ordinary skill in the art will be aware that the dosage form or mode of administration of a maintenance dose may be different from that used for the loading dose. In any of the embodiments disclosed herein, a maintenance dose may comprise administration of the unit dosage form on any dosing schedule contemplated herein, including but not limited to, monthly or multiple times per month, biweekly or multiple times each two weeks, weekly or multiple times per week, daily or multiple times per day. It is contemplated within the present disclosure that dosing holidays may be incorporated into the dosing period of the maintenance dose. Such dosing holidays may occur immediately after the administration of the loading dose or at any time during the period of administration of the maintenance dose. As used herein, the period of administration of the maintenance dose may be referred to as the "maintenance phase" of the treatment period.

"Mode of administration" as used herein refers to the avenue by which one or more compounds are administered to a subject. As used herein, "mode of administration"

comprises the dosage form (for example, a tablet, powder, dissolved liquid, suspension, emulsion, etc.) and mechanism by which the dosage form is applied to the subject (for example, by injection, topically, such as by cream, lotion, or patch; orally, such as by a pill, dissolved liquid, oral suspension, buccal film, or mouth rinse). As used herein, "mode of administration" also comprises the dose, dose amount, and dosing schedule by which a compound is administered to a subject.

In some embodiments, the compositions to be administered according to the methods of the present disclosure are provided with, or mixed into, a foodstuff, beverage, or other ingestible item. In some embodiments, said beverage, foodstuff, or other ingestible item may comprise one or more of a candy, an applesauce, a yogurt, a soft pudding, a gelatin foodstuff, a juice, milk, a soy or nut beverage, a thickened beverage, or a cheese, or any combination thereof. One of ordinary skill will readily recognize that the combination of the compositions to be administered according to the methods of the disclosure can be combined with any suitable food or beverage to facilitate ingestion of the compositions.

In some embodiments in accordance with methods and compositions of some embodiments herein, the mode of administration comprises administering a loading dose followed by a maintenance dose. In some embodiments, the loading dose is 20 g or less but not zero; 15 g or less but not zero; 10 g or less but not zero, 6 g or less but not zero, 4 g or less but not zero, 2 g or less but not zero, or 1 g or less but not zero or an amount that is within a range defined by any two of the aforementioned amounts. In some embodiments, the maintenance dose is 20 g or less but not zero; 10 g or less but not zero, 6 g or less but not zero, 4 g or less but not zero, 2 g or less but not zero, 1 g or less but not zero, 500 mg or less but not zero, or 250 mg or less but not zero or an amount that is within a range defined by any two of the aforementioned amounts.

In some embodiments in accordance with methods and compositions of some embodiments herein, the loading dose is administered over a period of one day or 24-hour period. In some embodiments the loading dose is administered in a single administration. In some embodiments, the loading dose is administered in multiple administrations. In some embodiments, the loading dose is administered in multiple administrations during a single day or 24-hour period. In some embodiments the loading dose is administered over a period of 2 days. In some embodiments the loading dose is administered over a period of 3 days. In some embodiments the loading dose is administered over a period of 4 days. In some embodiments the loading dose is administered over a period of 5, 6 or 7 days. In some embodiments, the loading dose is administered over a period of 8-14 days or fewer. In some embodiments, the loading dose is administered over a period of 14 days.

The methods according to the present disclosure contemplate varying or controlling the timing of administration of a composition described herein, in order to enhance the effectiveness of any treatment that is administered. In some embodiments, a composition to be administered according to the methods of the present disclosure may be administered with food, such as concurrently with a meal or other ingestion of a foodstuff. In some further embodiments, a composition to be administered according to the methods of the present disclosure may be administered immediately before or immediately after a meal or other ingestion of a foodstuff. In some further embodiments, a composition to be administered according to the methods of the present disclosure may be administered within 1-5 minutes, within 3-10 minutes, within 6-15 minutes, within 10-20 minutes, within 15-30 minutes, within 20-45 minutes, or within one hour before or after a meal or other ingestion of a foodstuff. In some embodiments, a composition to be administered according to the methods of the present disclosure may be administered without food, such as between 1-3 hours, between 2-5 hours, between 4-8 hours, between 6-12 hours, between 9-18 hours, between 12-24 hours, or more than 24 hours before or after a meal or other ingestion of a foodstuff.

As used herein, "duration of the treatment" refers to the time commencing with administration of the first dose and concluding with the administration of the final dose, such length of time being determined by one of ordinary skill in the art of treating neurological disorders or disorders implicating intestinal hyperpermeability or "leaky gut," with reference to the symptoms and health of the subject being treated therefor. Such duration may be determined with reference to periodic, sporadic, or ongoing monitoring of the levels of amyloid as disclosed herein or as known to one of skill in the art of treating neurological disorders.

As used herein, "dosing holiday" refers to a period of 24 hours or more during which either no dose is administered to the subject, or a reduced dose is administered to the subject. As used herein, "reduced dose" refers to a dose that is less than the total daily dose to be administered to a subject.

According to the present disclosure, the dosing schedule may be varied so as to attain the desired therapeutic effect. In each of the embodiments as disclosed herein, variations in dosing schedule may be repeated throughout the duration of the therapeutic protocol being administered. In each of the embodiments as disclosed herein, the first dosage may be higher, lower, or the same as the dosages following the first dosage. In each of the embodiments disclosed herein, a loading dose may precede the disclosed dosing regimen, and a dosing holiday may or may not follow the administration of the loading dose.

In some embodiments the methods of the present disclosure comprise administration of one or more compositions as provided herein daily or less frequently than daily, such as every second day, every third day, every fourth day, every fifth day, every sixth day, or every seventh day or for a time period that is within a range defined by any two of the aforementioned times. In some embodiments, the compositions as described herein are formulated for such administration.

According to the methods disclosed herein, a treatment or inhibition of a disorder implicating amyloid formation may be achieved by modulating the dosing schedule for the administration of a composition such that subjects experience periodic partial or full reductions in dosing for fixed amounts of time, followed by a resumption of dosing. In some embodiments, dosages are administered daily for between one and thirty days, followed by a dosing holiday lasting for between one and thirty days. In some embodiments, during the dosing holiday, no dose is administered. In some further embodiments, the composition of the present disclosure is allowed to clear completely from the subject's body prior to administration of the next dose. In some other embodiments, during the dosing holiday, a dose less than the usual daily dose is administered. In some further embodiments, an amount of the administered composition less than the therapeutically effective amount is allowed to remain within the subject during the dosing holiday. In some further embodiments, an amount of the administered composition sufficient to maintain therapeutic levels in the affected tissues is allowed to remain within the subject. In some embodiments, a composition is administered at any time following the onset of one or more of the aforementioned symptoms of a neurological disorder associated with amyloid formation. In some embodiments, a composition according to the methods described herein is administered prior to the onset of symptoms of said disorder or disorders. In some embodiments, a composition according to the methods described herein is administered concurrently with or after the onset of symptoms of said disorder or disorders.

Methods of Use

The present disclosure provides methods for inhibiting, ameliorating, reducing the likelihood, delaying the onset of, treating, and/or preventing the amyloid disorder, including methods that inhibit or disrupt one or more of the following: (1) bacterial amyloid aggregation on the bacterial surface or in the proximal extracellular space; (2) the interaction between bacterial amyloid and α-synuclein in the GI tract or olfactory system (including enteroendocrine cells and enteric neuronal cells); and/or (3) aggregation of α-synuclein in the GI tract (including enteroendocrine cells and enteric neuronal cells).

According to the methods of the present disclosure, α-synuclein should be viewed as a representative amyloid protein of the wider range of known host amyloid proteins, including one or more of Beta amyloid from Amyloid precursor protein, Medin, tau, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, superoxide dismutase 1 (SOD1) and/or Immunoglobulin light chain AL, and the compositions and methods as disclosed herein may be adapted by one of skill in the art to disrupt the aggregation of any amyloid protein in which one amyloid protein (bacterial or human) prompts aggregation of another amyloid protein.

Without being limited by theory, representative disorders that present amyloid formation and the proteins involved in these disorders, which may be inhibited or disrupted using the methods of the present disclosure, include but are not limited to those disclosed in Table 3.

TABLE 3

Amyloid Disorders

| Disease | Protein featured | Abbreviation |
| --- | --- | --- |
| Alzheimer's disease (AD) | Beta amyloid from Amyloid precursor protein | Aβ, APP |
| Aortic medial amyloid | Medin | AMed |
| Atherosclerosis | Apolipoprotein AI | AApoA1 |
| Cardiac arrhythmias, isolated atrial amyloidosis | Atrial natriuretic factor | AANF |
| Cerebral amyloid angiopathy | Beta amyloid | Aβ |
| Cerebral amyloid angiopathy (Icelandic type) | Cystatin | ACys |
| Diabetes mellitus type 2 | IAPP (Amylin) | AIAPP |
| Dialysis related amyloidosis | Beta-2 microglobulin | Aβ2M |
| Familial amyloid polyneuropathy | Transthyretin | ATTR |
| Fatal familial insomnia | PrP | APrP |
| Finnish amyloidosis | Gelsolin | AGel |
| Hereditary non-neuropathic systemic amyloidosis | Lysozyme | ALys |
| Huntington's disease (HD) | Huntingtin | HTT |
| Lattice corneal dystrophy | Keratoepithelin | AKer |
| Medullary carcinoma of the thyroid | Calcitonin | ACal |
| Parkinson's disease (PD) | α-synuclein | α-Syn |
| Prolactinomas | Prolactin | APro |
| Rheumatoid arthritis (RA) | Serum amyloid A | AA |

TABLE 3-continued

Amyloid Disorders

| Disease | Protein featured | Abbreviation |
| --- | --- | --- |
| Sporadic Inclusion body myositis (S-IBM) | various, including beta-amyloid | |
| Systemic AL amyloidosis | Immunoglobulin light chain AL | AL |
| Transmissible spongiform encephalopathy (e.g., bovine spongiform encephalopathy) | PrP | APrP |

The methods of the compositions and methods of the invention can also be used to treat amyloid-mediated disorders of the gastrointestinal tract including intestinal dysbiosis, intestinal hyperpermeability, irritable bowel syndrome (IBS), inflammatory bowel disease (IBD), ulcerative colitis and/or Crohn's disease. These disorders can be associated with one or more symptoms, including dysphagia, reduced gut motility, gastroparesis, constipation (including chronic constipation and chronic idiopathic constipation), small intestinal bacterial overgrowth (SIBO), diarrhea (including chronic diarrhea), abdominal pain and/or cramping, bloating, flatulence, and nausea.

As used herein, the term "intestinal dysbiosis" has its customary and ordinary meaning as understood by one of skill in the art in view of this disclosure and refers to an imbalance and/or maladaptation of the flora or microbiota within the gut or intestines, and particularly the small intestine. Such dysbiosis is characterized by a change in the composition of the intestinal or gut microbiome, in terms of the species/strains which are present and/or the relative abundance or proportion of the species/strains which are present, in which the change has a deleterious effect on the host organism. The deleterious effect on the host organism can result from microbiome-mediated changes in electrolyte balance, biofilm formation, integrity of the barrier formed by the intestinal epithelial lining, or the release from the microbiome of metabolites which are directly (e.g., as toxicity or effectors) or indirectly (e.g., as pre-cursors to toxins or effector) injurious to the health of the host.

As used herein, the term "intestinal hyperpermeability" has its customary and ordinary meaning as understood by one of skill in the art in view of this disclosure. It refers to abnormal increased permeability of the barrier formed by the intestinal epithelial lining between the intestinal lumen and the surrounding issues. Such hyperpermeability may result from inflammation of the intestinal lining and/or failure of the tight junctions between cells of the intestinal epithelium, which allows the passage of substances from the lumen into the surrounding tissues where some may enter the peritoneal cavity and/or systemic circulation. Because of this leakage of substances from the gut or intestinal lumen, intestinal hyperpermeability may be referred to as "leaky gut" or "leaky gut syndrome."

As used herein, the term "amyloid disorders," including variations of this root term, includes, but is not limited to any or all of the disorders of Table 3 as well as amyloid-mediated disorders of the gastrointestinal tract.

As used herein, the term "mammalian amyloid or mammalian amyloid precursor" includes, but is not limited to, one or more of tau, Beta amyloid from Amyloid precursor protein, Medin, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, and/or Immunoglobulin light chain AL. In certain methods and compositions disclosed herein, said microbial amyloid or microbial amyloid precursor comprises CsgA.

Some embodiments include a method of inhibiting, ameliorating, reducing the likelihood, delaying the onset of, treating, or preventing an amyloid disorder, the method comprising administering a composition as described herein to a subject in need thereof. The amyloid disorder can be selected from the group consisting of: α-synucleinopathy, Parkinson's Disease, Lewy Body Dementia, incidental Lewy body disease, Lewy body variant of Alzheimer's disease, multiple system atrophy, and pure autonomic failure, or any combination of any of these. The amyloid disorder can also be selected from the group consisting of: intestinal dysbiosis, intestinal hyperpermeability, irritable bowel syndrome (IBS), inflammatory bowel disease (IBD), ulcerative colitis and/or Crohn's disease. In some embodiments, the composition administered in the method comprises, consists essentially of, or consists of any of the molecules of Table 1 or Table 2. In some embodiments, the composition administered in the method comprises, consists essentially of, or consists of a compound of the invention as described herein. In some embodiments of the method, the amyloid disorder comprises intestinal amyloid aggregates. For example, the aggregates can comprise a bacterial protein, for example a curli-associated protein such as CsgA. Accordingly, in some embodiments, the method further comprises detecting a presence or level of such a bacterial protein in an intestinal sample of the subject, a presence or level of nucleic acids encoding the microbial (e.g., bacterial) protein, or a presence of level of a microbial organism that produces the bacterial protein (e.g., a curli-associated protein such as CsgA) in the intestinal sample of the subject, for example a fecal sample. For example, the protein can be detected by an immunoassay such as an ELISA, Western Blot, lateral flow assay, no-wash assay or the like. For example, the microbial organism that produces the microbial protein can be detected by nucleic acid analysis (such as qualitative or quantitative PCR, microarray analysis, or sequencing). For example, the nucleic acid that encodes the microbial protein can be detected by qualitative or quantitative PCR, microarray analysis, sequencing or branched DNA analysis. An intestinal presence of the bacterial protein or microbial organism that produces the protein, or a level of the bacterial protein (or microbial organism that produces the protein) greater than a control can identify the subject as being in need of the composition. By way of example, suitable controls can include subjects that are negative for the bacterial protein (or microbial organisms that make the bacterial protein), for example healthy individuals, or an individual identified as not having the bacterial protein (or microbial organisms that make the bacterial protein) in their intestines. In some embodiments, the method comprises detecting a presence or level of intestinal curli (or a curli-associated protein such as CsgA), or an intestinal level of a microorganism that produces intestinal curli-associated protein (such as CsgA) in a sample of the subject. In some embodiments, the subject is identified as a member of a subpopulation of subject having the amyloid disorder, and in need of the composition. In some embodiments, the method further comprises determining a decrease or absence of the intestinal amyloid aggregates following the administration.

The compositions of the present disclosure may, in some embodiments, inhibit the formation of α-synuclein aggregates (e.g., fibrils, Lewy bodies, or other aggregates) or other host amyloid at its point of initiation in the gut, thus depriving microbially induced amyloid aggregation thought to serve as a template or seed for α-synuclein or other host amyloid aggregation and doing so without having to cross the blood brain barrier. Targeting α-synuclein or other host amyloid aggregation in the gut obviates the need for the drug to cross the blood-brain barrier, providing efficacy at a lower dose, with fewer side-effects due to reduction in systemic exposure. Further, targeting α-synuclein or other host amyloid aggregation at its point of initiation allows intervention at an earlier stage in the pathogenic process, preventing or inhibiting disease progression before motor symptoms or other neurodegenerative symptoms develop. Targeting α-synuclein aggregation in the gut may also address gastrointestinal dysfunction and/or ameliorate gastrointestinal symptoms or behaviors of the subject, which may comprise, e.g., one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD, e.g., ulcerative colitis and Crohn's disease), intestinal hyperpermeability, hypersalivation (sialorrhea), anorectal dysfunction, dyssynergic defecation, or any combinations thereof, for example in accordance with compositions and methods of some embodiments herein.

In addition to targeting host amyloid aggregation in the brain as an approach to treating or inhibiting neurodegenerative diseases, targeting bacterial amyloid aggregation provides new therapies for infectious diseases, such as urinary tract infections (UTIs). In both cases, certain classes of compounds have been identified, largely represented as "polyphenols" or polyphenol equivalents, as having the ability to inhibit amyloid aggregation process in tissues of interest, such as in the brain for α-synuclein and the urinary mucosae for UTIs.

In some embodiments, the compositions and methods of the present disclosure contemplate the use of polyphenols and/or polyphenol equivalents as inhibitors of the interaction between a host amyloid, such as α-synuclein and a bacterial amyloid, such as curli or adhesive pili. In some embodiments, the compositions and methods of the present disclosure, contemplate the use of polyphenols and/or polyphenol equivalents as inhibitors of host amyloid aggregation and/or promoters of amyloid dis-aggregation in peripheral tissue, such as the gut or nasopharynx, rather than in the brain. The compositions and methods of the present disclosure further contemplate modified polyphenols or polyphenol equivalents, that act locally in the gut and are essentially not absorbed into peripheral tissues, such as, for example, non-orally bioavailable analogs of polyphenols that retain amyloid inhibiting activity, but do not traverse the gut epithelium or enter the primary circulation.

In some embodiments, the compositions and methods of the present disclosure contemplate formulations that enable delivery of said compositions to the site of action in the lower small intestine, the large intestine, and/or the colon. Said formulations may comprise enteric coated tablets, capsules, liquid-gels or powders, and the like, such that the formulation inhibits the release of the drug in the stomach or upper GI tract. Alternatively, said compositions may comprise intrinsically enteric capsules or similar solid dosage forms wherein the capsule composition comprises a polymer or material that dissolves at or near the site of action, such as, for example, EnTrinsic® intrinsically enteric capsules, preferably in the lower GI tract, and more especially the lower small intestine, the large intestine, or the colon. In some embodiments, said compositions are not absorbed and remain in the GI tract.

The compositions and methods of the present disclosure contemplate gut-restricted small molecule inhibitors that target one or more elements of amyloid formation. Exemplary compounds of the invention include polyphenol moieties, many of which are orally bioavailable. The compositions and methods of the present disclosure also contemplate gut-selective or gut-restricted, non-orally absorbed derivatives of non-polyphenol classes that are known to have the ability to inhibit amyloid formation. The compositions and methods according to the present disclosure further contemplate non-orally absorbed, gut-selective derivatives or formulations of said polyphenol or non-polyphenol compounds.

"Subject" as used herein, has its customary and ordinary meaning as understood by one of skill in the art in view of this disclosure. It refers to a human or a non-human mammal including but not limited to a dog, cat, horse, donkey, mule, cow, domestic buffalo, camel, llama, alpaca, bison, yak, goat, sheep, pig, elk, deer, domestic antelope, or a non-human primate selected or identified for a diagnosis, treatment, inhibition, amelioration of a neurological disease or neurological disorder associated with microbially induced amyloid, such as Parkinson's Disease, Lewy Body Dementia, incidental Lewy body disease, Lewy body variant of Alzheimer's disease, multiple system atrophy, pure autonomic failure, intestinal dysbiosis, intestinal hyperpermeability, irritable bowel syndrome (IBS), inflammatory bowel disease (IBD), ulcerative colitis, Crohn's disease, or any combination thereof.

"Diagnosing" has its customary and ordinary meaning as understood by one of skill in the art in view of this disclosure. It can refer to the act or process of determining whether a subject exhibits any symptom or indicator of a neurological disease or neurological disorder associated with microbially induced amyloid such as Parkinson's Disease, Lewy Body Dementia, incidental Lewy body disease, Lewy body variant of Alzheimer's disease, multiple system atrophy, pure autonomic failure, or any combination thereof. It can also refer to the act or process of determining whether a subject exhibits any symptom or indicator of a gastrointestinal disorder associated with microbially induced amyloid such as intestinal dysbiosis, intestinal hyperpermeability, irritable bowel syndrome (IBS), inflammatory bowel disease (IBD), ulcerative colitis and/or Crohn's disease. Diagnosing may further comprise the determination of whether the body of a subject or any tissue, fluid, component, organ, or compartment thereof contains microbially induced amyloid. Diagnosing may further comprise the determination of whether the body of a subject or any tissue, fluid, component, organ, or compartment thereof contains any factor capable of affecting the rate of aggregation or disaggregation of microbially induced amyloid.

"Subject suspected of having" has its customary and ordinary meaning as understood by one of skill in the art in view of this disclosure. It refers to a subject exhibiting one or more clinical indicators of a disease or condition. In certain embodiments, the disease or condition may comprise one or more of Parkinson's Disease, Lewy Body Dementia, incidental Lewy body disease, Lewy body variant of Alzheimer's disease, multiple system atrophy, pure autonomic failure, or any combination thereof. In some embodiments, the disorder can be selected from the group consisting of: intestinal dysbiosis, intestinal hyperpermeability, irritable bowel syndrome (IBS), inflammatory bowel disease (IBD), ulcerative colitis and/or Crohn's disease.

"Subject in need thereof" has its customary and ordinary meaning as understood by one of skill in the art in view of this disclosure. It refers to a subject selected or identified as one being in need of diagnosis of a disorder implicating amyloid formation, or one in need of a treatment, inhibition, amelioration of a neurological disease or neurological disorder associated with microbially induced amyloid such as Parkinson's Disease, Lewy Body Dementia, incidental Lewy body disease, Lewy body variant of Alzheimer's disease, multiple system atrophy, pure autonomic failure, or any combination thereof. In other embodiments, the disorder can be selected from the group consisting of: intestinal dysbiosis, intestinal hyperpermeability, irritable bowel syndrome (IBS), inflammatory bowel disease (IBD), ulcerative colitis and/or Crohn's disease.

"Microbially induced amyloid" as used herein has its customary and ordinary meaning as understood by one of skill in the art in view of this disclosure. It refers to amyloid fibrils or aggregates that are produced through the contact of a mammalian or microbial protein with one or more microbial proteins. Said microbial protein may comprise one or more proteins of bacterial or fungal origin, although the present disclosure contemplates amyloid produced by the interaction of proteins, whatever their origin, with proteins originating from bacteriophages, viruses, bacteria, archaea, fungi, and other eukaryotes.

A "therapeutic effect" has its customary and ordinary meaning as understood by one of skill in the art in view of this disclosure. It relieves, to some extent, one or more of the symptoms of a disease or disorder, and includes curing the disease or disorder. "Curing" means that the symptoms of active disease are eliminated. However, certain long-term or permanent effects of the disease may exist even after a cure is obtained (such as tissue damage).

"Amelioration" has its customary and ordinary meaning as understood by one of skill in the art in view of this disclosure. It refers to a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Modulation" has its customary and ordinary meaning as understood by one of skill in the art in view of this disclosure. It refers to an alteration in the presence, absolute level, relative level, function or activity of any factor within the body of a subject or any tissue, fluid, component, organ, or compartment thereof. In certain embodiments, modulation refers to an increase in gene expression. In certain embodiments, modulation refers to a decrease in gene expression. In certain embodiments, modulation refers to an increase or decrease in total serum levels of a specific protein. In certain embodiments, modulation refers to an increase or decrease in free serum levels of a specific protein. In certain embodiments, modulation refers to an increase or decrease in the aggregation state of a protein. In certain embodiments, modulation refers to increasing or decreasing the stability of amyloid fibrils. In certain embodiments modulation refers to increasing or decreasing the length, width, spacing, or density of amyloid fibrils. In certain embodiments, modulation refers to an increase or decrease in total serum levels of a specific non-protein factor, e.g., a metabolite. In certain embodiments, modulation refers to an increase or decrease in free serum levels of a specific non-protein factor. In certain embodiments, modulation refers to an increase or decrease in total bioavailability of a specific protein. In certain embodiments, modulation refers to an increase or decrease in total bioavailability of a specific non-protein factor. In certain embodiments, modulation refers to alterations in the aggregation state of a protein. In certain embodiments modulation refers to alterations in the rate or extent of aggregation or disaggregation of microbially induced amyloid.

In some compositions and methods of some embodiments in accordance with the present disclosure, a subject is selected or identified to receive the administration of the compositions described herein. In some embodiments, said subject is selected or identified as one having elevated levels of curli in the gut. Such a selection can be made by clinical or diagnostic evaluation. In some embodiments, said subject is selected or identified as one having elevated levels of microbially induced amyloid in the gut. Such a selection can also be made by clinical or diagnostic evaluation. In some embodiments, said subject is selected or identified as one having elevated levels of α-synuclein in the gut. Again, such a selection can be made by clinical or diagnostic evaluation. In some further embodiments, said subject is one showing one or more symptoms of a neurodegenerative disorder, such as a demonstration of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, and/or altered kynurenine levels, gastroparesis, anorectal dysfunction, dyssnergic defecation, or any combination thereof. In some embodiments, said subject has been diagnosed according to methods known in the art of diagnosis of neurological and amyloid disorders, as having an amyloid disorder. In some further embodiments, said subject has been diagnosed as having or as being at risk of having Lewy Body Dementia, incidental Lewy body disease, Lewy body variant of Alzheimer's disease, multiple system atrophy, pure autonomic failure, or any combination thereof. In some embodiments, said subject further displays gastrointestinal symptoms. In some further embodiments, said gastrointestinal symptoms may comprise one or more of constipation, diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof.

In compositions and methods according to some embodiments of the present disclosure, a subject selected for treatment may be under the age of 18 years. In some embodiments, a subject selected for treatment may be between 17 and 30 years of age. In some embodiments, a subject selected for treatment may be between 29 and 50 years of age. In some embodiments, a subject selected for treatment may be between 49 and 60 years of age. In some embodiments, a subject selected for treatment may be between 59 and 70 years of age. In some embodiments, a subject selected for treatment according to the compositions and methods described herein may be greater than 69 years of age.

In compositions and methods according to some embodiments of the present disclosure, administration of one or more of the compositions as described herein provides the effect of preventing the formation of, or promoting the disaggregation of, amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of inhibiting the further aggregation of amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of causing or enhancing the disaggregation of amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of causing or enhancing the disaggregation of preexisting amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of preventing the development of one or more symptoms of one or more neurological or neurodegenerative disorders. In some embodiments, administration of one or more of the compositions as described herein provides the effect of ameliorating one or more symptoms of one or more neurological or neurodegenerative disorders. In some embodiments, administration of one or more of the compositions as described herein provides the effect of reversing one or more symptoms of one or more neurological or neurodegenerative disorders. In some embodiments, said one or more symptoms of one or more neurological disorders may comprise one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, and/or altered kynurenine levels, gastroparesis, anorectal dysfunction, dyssnergic defecation, or any combination thereof. In some embodiments, said one or more neurological disorders may comprise an amyloid disorder. In some further embodiments, said one or more neurological disorders may comprise one or more of Lewy Body Dementia, incidental Lewy body disease, Lewy body variant of Alzheimer's disease, multiple system atrophy, and/or pure autonomic failure, or any combination thereof.

In other embodiments, the inhibitors of amyloid formation may be intended for administration systemically or locally to the enteric of central nervous system. For example, inhibitors which are effective against mammalian amyloid or mammalian amyloid precursor protein aggregation may be useful in treatment of one or more of the amyloid disorders described herein (Table 3). Therefore, for such embodiments, the compositions comprising the inhibitors of amyloid formation may be formulated for parenteral administration, including systemic administration (e.g., intravenous, subcutaneous, intramuscular, intraperitoneal) or local administration (e.g., local injection near the vagus nerve, intraspinal injection, or intracranial injection). For delivery into the CNS, it is necessary for the inhibitors to pass through the blood brain barrier. Therefore, in such embodiments, the inhibitors are preferably lipid soluble molecules, or may be modified to increase lipid solubility, or may be co-administered with compounds that enhance passage through the blood brain barrier (see, e.g., WO2014076655A1, WO2012159052A2, WO1992018-529A1).

In compositions and methods according to some embodiments of the present disclosure, levels of amyloid and/or microbially induced amyloid in the tissues, fluids, or feces of the subject are monitored or evaluated during the course of therapy. In some further embodiments, levels of amyloid and/or microbially induced amyloid are monitored before and/or after the course of therapy. In some embodiments, levels of α-synuclein in the tissues, fluids, or feces of the subject are monitored during the course of therapy. In some embodiments, levels of α-synuclein are monitored before and/or after the course of therapy. In some embodiments, measurement of amyloid, microbially induced amyloid, and/or α-synuclein are measured in a fecal sample from the subject. In some embodiments, measurement of amyloid, microbially induced amyloid, and/or α-synuclein are measured in a tissue sample from the subject. In some embodiments, said tissue sample comprises gut epithelium, peritoneum, enteric nervous tissue, olfactory tissue, nasal endothelium, sinus endothelium, brain, and/or nervous tissue. In some embodiments, said tissue sample comprises cerebrospinal fluid or synovial fluid. In some embodiments, said tissue sample comprises blood, lymph, or plasma.

Methods to Identify Compounds

Disclosed herein are methods to identify compounds, which alter the ability of bacterial amyloid to promote aggregation and amyloid formation of the eukaryotic protein α-synuclein. Further disclosed herein are methods of screening for entities useful for the treatment or inhibition of neurodegenerative diseases and screening for entities useful for the prevention or amelioration of the progression of neurodegenerative diseases. Further disclosed herein are methods of screening for entities useful for the treatment or inhibition of gastrointestinal dysfunction related to neurodegenerative diseases. Additionally disclosed herein are methods for studying the molecular etiology of mammalian amyloid diseases and the molecular link between bacterial amyloid production and mammalian amyloid production. According to the methods of the present disclosure, said neurodegenerative diseases and/or mammalian amyloid diseases may comprise one or more of Parkinson's disease (PD), Lewy body dementia, multiple system atrophy, and all other α-synucleinopathies, PD-associated constipation, PD-associated hyposmia, Huntington's Disease, Alexander's Disease, amyotrophic lateral sclerosis (ALS), Alzheimer's Disease and other diseases in which amyloids are implicated.

The methods as disclosed herein comprise a suite of in vitro assays that measure one or more of the following (1) bacterial amyloid aggregation on the bacterial surface or in the proximal extracellular space; (2) the interaction between bacterial amyloid and α-synuclein in the GI tract or olfactory system (including enteroendocrine cells and enteric neuronal cells); or (3) aggregation of α-synuclein in the GI tract (including enteroendocrine cells and enteric neuronal cells). According to the methods of the present disclosure, α-synuclein should be viewed as a representative amyloid protein of the wider range of known mammalian amyloid or mammalian amyloid precursor proteins, and the methods as disclosed herein may be adapted by one of skill in the art to evaluate the aggregation of any amyloid protein in which a one amyloid protein (bacterial or human) prompts aggregation of another amyloid protein. Representative disorders that present amyloid formation and the proteins involved in these disorders, which may be evaluated using the methods of the present disclosure, include but are not limited to those disclosed in Table 3. Accordingly, in some embodiments, the methods comprise contacting a plurality of concentrations of a microbial amyloid or a microbial amyloid precursor with a plurality of concentrations of α-Synuclein and/or other mammalian amyloid or mammalian amyloid precursor in the presence of a composition, analyzing or measuring the formation or disaggregation of amyloid after the reaction set forth above; and comparing said analysis or measurement to an analysis or measurement of a control, wherein said control comprises analyzing or measuring the formation of amyloid after the reaction set forth above in the absence of said composition. In certain methods and compositions disclosed herein, said microbial amyloid or microbial amyloid precursor comprises CsgA.

In some embodiments, the methods according to the present disclosure contemplate contacting a microbial amyloid or a microbial amyloid precursor (e.g., a composition comprising CsgA) with varying concentrations of a mammalian amyloid or mammalian amyloid precursor in the presence of a composition, said composition comprising a compound or mixture to be tested for its ability to inhibit amyloid formation or enhance amyloid disaggregation. In some further embodiments, said combination of microbial amyloid or microbial amyloid precursor, mammalian amyloid or mammalian amyloid precursor, and test composition are analyzed or measured for changes in the amount of amyloid present. In some further embodiments, the rate and/or extent of amyloid formation within said combination of microbial amyloid or microbial amyloid precursor, mammalian amyloid or mammalian amyloid precursor, and test composition is compared to the rate of amyloid formation within a control sample lacking said composition. In some embodiments, the rate of formation of amyloid is measured. In some further embodiments, the total amount of amyloid formation is measured. In some further embodiments, the temperature of the assay is varied, whereby the stability of the newly-formed amyloid fibrils is measured relative to those formed under native conditions. In some embodiments, the methods are carried out by placing said composition within the wells of a multi-well assay plate. In some further embodiments, the methods according to the present disclosure are carried out in the presence of a physical agitator. In some further embodiments, said physical agitator comprises glass, teflon, or polymer beads. In some further embodiments, said polymer beads may comprise polystyrene, polylactic acid, poly lactic-co-glycolic acid, polycarbonate, or polytetrafluoroethylene (Teflon®) beads. In some embodiments, the beads or objects used for agitation will be from 10-1000 μm in their longest dimension. In some embodiments, the beads or objects used for agitation are from 10-100 μm, from 80-200, from 180-300 μm, from 280-400 μm, from 380-500 μm, from 480-600 μm, from 580-700 μm, from 680-800 μm, from 780-900 μm, or from 880-1000 μm in their longest dimension. In some embodiments, the beads or objects used for agitation will be greater than 1 mm in their longest dimension. In some embodiments, the beads or objects used for agitation will be less than 10 mm in their longest dimension. In certain embodiments, the beads or objects are 1-3 mm, 1-5 mm, 2-5 mm, 3-5 mm, 4-5 mm, 5-6 mm, 5-7 mm, 5-8 mm, 5-9 mm, 5-10 mm, 2-10 mm, 4-10 mm, 6-10 mm, or 8-10 mm. In certain particular embodiments, the beads or objects are 1 mm, 2 mm, 3 mm, 4 mm, 5 mm, 6 mm, 7 mm, 8 mm, 9 mm, or 10 mm in their longest dimension.

In some embodiments, the microbial amyloid or microbial amyloid precursor comprises CsgA, the major protein constituent of curli, also known as adhesive pili, or any analogue or homologue thereof. In some embodiments, the microbial amyloid or microbial amyloid precursor comprises CsgB, which nucleates the conversion of CsgA to its amyloid form, or polypeptides derived therefrom. In some embodiments, said mammalian amyloid or mammalian amyloid precursor comprises α-synuclein.

In some embodiments, contacting microbial amyloid or a microbial amyloid precursor (e.g., a composition comprising CsgA) with varying concentrations of mammalian amyloid or mammalian amyloid precursor with a composition occurs in the presence of an indicator of amyloid formation. In some further embodiments, said indicator may comprise a fluorescent indicator, in which the fluorescence intensity of the indicator varies in a manner correlated with the amount of amyloid present in the sample. Said variation may occur due to changes in fluorescence related to changes in the molecular environment associated with interposition of the label into the assembling amyloid fibril. In some further embodiments, said indicator may comprise thioflavin T (ThT). In some embodiments, labels that are bound to amyloid precursor molecules may show changes in intensity or wavelength of emission due to intermolecular fluorescence quenching or fluorescence resonance energy transfer that is correlated with the formation of amyloid fibrils. Exemplary fluorescent labels are disclosed in The Molecular Probes Handbook (Invitrogen, Inc., 2010), which is hereby incorporated by reference for its teachings regarding FRET pairs, fluorescence quenching, and fluorescent probes conjugatable to proteins. Other exemplary fluorescent labels may comprise fluorescence proteins, including but not limited to the Green fluorescent protein (GFP), the Yellow Fluorescent Protein (YFP), AmCyan1, AsREd2, mBanana, mCherry, Dendra2, DsRed2, DsRed-express, DsRed-monomer, DsRed, E2-Crimson, GFP-UV, the Blue Fluorescent Protein (BFP), HcRed1, mOrange, PAmCherry, mPlum, mRaspberry, mStrawberry, tdTomato, ZsGreen1, ZsYellow1, or AcGFP1, or their derivatives, or others fluorescent proteins as are known in the art. In some further embodiments, the label attached to the mammalian amyloid precursor is different from the label that is attached to the bacterial amyloid or bacterial amyloid precursor. In some embodiments, the bacterial amyloid or bacterial amyloid precursor is unlabeled. In some embodiments, the mammalian amyloid, mammalian amyloid precursor, bacterial amyloid precursor, or bacterial amyloid contain more than one label. In some further embodiments, said indicator may comprise a colorimetric indicator, a spin label (such as, for example, 3H, 15N or 13C), a metal ion binding compound (such as, for example, a porphyrin, chelator, polyhistidine, or other metal binding polypeptide), an enzyme, or an amyloid-specific antibody. In some embodiments, the development of amyloid fibrils is observed directly by optical microscopy. In some embodiments, amyloid formation is observed by direct light transmission, or by reflectivity. In some embodiments, amyloid formation is observed by total internal reflection FTIR. In some embodiments, amyloid formation is observed by NMR, FTIR, SPIR, or SPR spectroscopy. In some embodiments, amyloid formation is observed and/or confirmed by optical birefringence. In some embodiments, samples are stained with congo red dye prior to visualization. In some embodiments, amyloid formation is observed by Raman scattering. In some embodiments, amyloid formation is observed by monitoring changes in the internal fluorescence of the sample, such as that due to internal tryptophan, tyrosine, phenylalanine, histidine, and arginine residues. In some embodiments, amyloid formation is observed by monitoring the binding of an amyloid-specific antibody, by means as are known in the art such as by conjugation of said antibody to a fluorescent label, a colorimetric label, a spin label, a radioisotope, and enzyme, a fluorescent protein, a metal binding domain or other methods known to those of ordinary skill in the art for the detection or visualization of antibodies. According to the methods as described herein, said antibody may comprise an antibody with binding activity that is selective for either amyloid, or amyloid precursor.

In some embodiments, the methods of the present disclosure may be carried out by monitoring the kinetics of fluorescence intensity of an amyloid specific dye in the presence of a mammalian amyloid precursor, and one or more bacterial amyloid precursors or aggregates. In some embodiments, said mammalian amyloid precursor is α-synuclein. In some embodiments, said bacterial amyloid precursor or aggregate is CsgA. In some embodiments, said amyloid specific dye is Thioflavin T.

In some embodiments, the present disclosure contemplates a kit for the practice of the methods described herein. In some embodiments, said kit comprises at least a mammalian amyloid or mammalian amyloid precursor, a bacterial amyloid or bacterial amyloid precursor, an indicator of amyloid formation as described herein, wherein such indicator may or may not be conjugated to said mammalian amyloid or mammalian amyloid precursor, a bacterial amyloid or bacterial amyloid precursor, and one or more reaction vessels. Said kit may comprise a multi-well plate. Said kit may further comprise instructions for the carrying out of the methods described herein.

The methods of the present disclosure provide methods of screening candidate compounds in order to identify compounds that modulate the aggregation and/or disaggregation of amyloid, especially microbially induced amyloid. In some embodiments, the methods of the present disclosure comprise the screening of a library of candidate compounds. In some further embodiments, the compositions contacted with mammalian amyloid or mammalian amyloid precursor, and bacterial amyloid precursor or bacterial amyloid, according to the methods disclosed herein, comprise one or more compounds, or combinations thereof, suspected in the art to inhibit amyloid formation or to destabilize or disaggregate existing amyloid. In certain embodiments the compositions contacted with mammalian amyloid or mammalian amyloid precursor, and bacterial amyloid precursor or bacterial amyloid, according to the methods disclosed herein, comprise a natural product or an extract from a natural product. In some embodiments the compositions contacted with mammalian amyloid or mammalian amyloid precursor, and bacterial amyloid precursor or bacterial amyloid, according to the methods disclosed herein, comprise an herb, herbal extract, or botanical substance. In some embodiments, said compositions may comprise tissue or fluid from an animal, plant, or fungus. In some further embodiments, said compositions may comprise tissue, fluid, or extracts of tissue or fluid, from a seed, fruit, flower, leaf, stem, cambium, or root of a plant, or combinations thereof. In some further embodiments, said compositions may comprise tissue, fluid, or extracts of a tissue or fluid, from the feces, urine, blood, lymphatic fluid, synovial fluid, cerebrospinal fluid, saliva, or any internal organ of an animal. In some embodiments, said composition may comprise one or more bacteria, or lysates, extracts, conditioned culture media, lyophilized bacteria, lyophilized lysates, lyophilized culture media thereof, or any combination thereof. In some embodiments said bacteria comprise one or more of *Bacteroides, Prevotella, Parabacteroides,*

*Faecalibacterium, Eubacterium, Roseburia, Blautia, Coprococcus*, and *Bifidobacterium*, or any combination thereof.

In some embodiments, the methods of the present disclosure can be used to diagnose or assess the risk for developing an amyloid disorder in a subject. The methods of the present disclosure may be used in the treatment, prevention, and/or amelioration of one or more neurological disorders including Parkinson's Disease, Lewy Body Dementia, incidental Lewy body disease, Lewy body variant of Alzheimer's disease, multiple system atrophy, pure autonomic failure, or any combination thereof. The disorders may include behavioral symptoms as are known in the art of clinical diagnosis and treatment of neurological disorders such as communicative symptoms, stereotyped behaviors, sensorimotor issues, and/or anxiety-like behaviors in addition to physical symptoms as are known in the art of diagnosis and treatment of neurological disorders such as tremors, paralysis, dyskinesia, and/or gastrointestinal symptoms such one or more of constipation, diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof. Accordingly, such clinical and/or diagnostic evaluations and determinations can be used to identify and/or select one or more subjects for receiving one or more compounds described herein in accordance with the one or more methods provided in this disclosure. The methods of the present disclosure may, in some embodiments, include monitoring of the behavioral, physical, and/or gastrointestinal symptoms as are known in the art of diagnosis and treatment of neurological disorders. In some embodiments, the methods according to the present disclosure incorporate monitoring changes in the behavior of a subject. In some further embodiments, the methods according to the present disclosure incorporate monitoring the subject for behavioral symptoms as are known to be related to Parkinson's Disease, Lewy Body Dementia, incidental Lewy body disease, Lewy body variant of Alzheimer's disease, multiple system atrophy, pure autonomic failure, or any combination thereof. In some further embodiments, the methods according to the present disclosure incorporate monitoring the subject for bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, or any combination thereof or any other symptom known to those in the art of neurological diagnosis or treatment to be useful in the diagnosis of amyloid disorders, and especially α-synucleinopathies. In some further embodiments, the methods according to the present disclosure incorporate monitoring the subject for gut motility, including gastroparesis, colonic motility, anorectal dysfunction and dyssynergic defecation. Again, such clinical and/or diagnostic evaluations and determinations can be used to identify and/or select one or more subjects for diagnosis and/or treatment according to the methods described herein. In some embodiments, the methods of the present disclosure may include monitoring of levels of bacterial, host-derived, and microbially-induced amyloid as disclosed herein in addition to the aforementioned clinical monitoring. According to the methods of the present disclosure, said amyloid may be monitored in the gut, feces, urine, blood, saliva, cerebrospinal fluid, and/or synovial fluid of a subject. The methods of the present disclosure contemplate the monitoring of said amyloid in any tissue or fluid obtainable from a subject during the course of treatment, and thereby identifying whether said sample contains factors which enhance or inhibit amyloid formation. In some embodiments, a subject from whom a tissue, fluid, or other sample is derived, for which sample the assays described herein indicate the presence of factors, which enhance or accelerate amyloid formation, may be considered to be at elevated risk of developing an amyloid disorder. In some embodiments, said subject may be administered a drug or treatment to ameliorate or prevent said amyloid disorder. Again, such clinical and/or diagnostic evaluations and determinations can be used to identify and/or select one or more subjects for receiving one or more compounds described herein in accordance with the one or more methods provided in this disclosure.

According to the methods disclosed herein, a treatment or inhibition of a disorder implicating amyloid formation may be achieved by modulating the dosing schedule for the administration of a composition such that subjects experience periodic partial or full reductions in dosing for fixed amounts of time, followed by a resumption of dosing. In some embodiments, dosages are administered daily for between one and thirty days, followed by a dosing holiday lasting for between one and thirty days. In some embodiments, during the dosing holiday, no dose is administered. In some further embodiments, the composition of the present disclosure is allowed to clear completely from the subject's body prior to administration of the next dose. In some other embodiments, during the dosing holiday, a dose less than the usual daily dose is administered. In some further embodiments, an amount of the administered composition less than the therapeutically effective amount is allowed to remain within the subject during the dosing holiday. In some further embodiments, an amount of the administered composition sufficient to maintain therapeutic levels in the affected tissues is allowed to remain within the subject. In some embodiments, a composition is administered at any time following the onset of one or more of the aforementioned symptoms of a neurological disorder associated with amyloid formation. In some embodiments, a composition according to the methods described herein is administered prior to the onset of symptoms of said disorder or disorders. In some embodiments, a composition according to the methods described herein is administered concurrently with or after the onset of symptoms of said disorder or disorders.

The following items are set forth in accordance with some embodiments herein.

1. A method of disrupting and/or inhibiting the formation of amyloid aggregates comprising contacting amyloid or a precursor of amyloid with a composition comprising a compound of the invention.

2. A method of inhibiting the formation of amyloid aggregates comprising contacting amyloid or a precursor of amyloid with a composition comprising a compound of the invention.

3. A method of disrupting the formation of amyloid aggregates in a subject comprising:
administering to said subject a composition comprising a compound of the invention; and optionally, selecting said subject to receive the benefit of a molecule that disrupts the formation of amyloid aggregates, such as by clinical or diagnostic evaluation, prior to administering said composition; and/or optionally, measuring a disruption or inhibition of the formation of amyloid aggregates in said subject after administration of said composition.

4. A method of disrupting the formation of amyloid aggregates comprising contacting amyloid or a precursor of amyloid with a composition comprising a compound of the invention.

5. A method of inhibiting, ameliorating, reducing the likelihood, delaying the onset of, treating, or preventing an amyloid disorder, the method comprising administering to a subject in need thereof a compound of the invention, or a pharmaceutical composition thereof.

6. The method of item 5, wherein the amyloid disorder is selected from the group consisting of: α-synucleinopathy, Parkinson's Disease, Lewy Body Dementia, incidental Lewy body disease, Lewy body variant of Alzheimer's disease, multiple system atrophy, or pure autonomic failure, or any combination thereof.

7. The method of any one of Items 5-6, wherein the amyloid disorder comprises intestinal amyloid aggregates, for example aggregates that comprise a bacterial protein such as CsgA.

8. The method of any one of Items 5-7, wherein the amyloid disorder is intestinal dysbiosis, intestinal hyperpermeability, irritable bowel syndrome (IBS), inflammatory bowel disease (IBD), ulcerative colitis and Crohn's disease.

9. The method of any one of Items 5-8, further comprising detecting a presence or level of a bacterial protein, such as CsgA, nucleic acids encoding the microbial protein, or a microorganism that produces the bacterial protein in an intestinal sample of the subject.

10. The method of Item 9, wherein the subject is selected as in need of the composition if a presence of the bacterial protein or the microorganism that produces the bacterial protein is detected in the intestinal sample, or if a level of the bacterial protein or the microorganism that produces the bacterial protein in the intestinal sample is greater than a predetermined level or control.

11. The method of any one of Items 7-10, further comprising determining a decrease or absence of the intestinal amyloid aggregates following the administration.

12. The method of any one of Items 7-11, further comprising identifying the subject as displaying a gastrointestinal symptom.

14. The method of any one of Items 5-12, wherein the subject suffers from gastrointestinal symptoms comprising one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, hypersalivation (sialorrhea), anorectal dysfunction, dyssynergic defecation, and nausea.

16. The method of any of Items 1-14, wherein said composition is formulated for enteric or intranasal delivery.

17. The method of any of Items 1-16, wherein said composition is formulated for controlled release within the lower intestine or colon.

18. The method of any of Items 1-17, wherein said composition is an enteric-coated capsule, tablet, soft-gel, spray dried powder, polymer matrix, hydrogel, enteric-coated solid, crystalline solid, amorphous solid, glassy solid, coated micronized particle, liquid, nebulized liquid, aerosol, or microcapsule.

19. The method of any of Items 1-18, wherein said amyloid aggregates comprise one or more mammalian proteins such as, any one or more of α-synuclein, tau, Beta amyloid from Amyloid precursor protein, Medin, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, SOD1, and/or Immunoglobulin light chain AL.

20. The method of any of Items 1-19, wherein said amyloid aggregates comprise one or more bacterial or fungal proteins, such as CsgA.

21. The method of any of Items 1-20, wherein said amyloid aggregates comprise a bacterial protein, such as CsgA.

22. The method of any of Items 1-21, wherein said amyloid aggregates are present within the gastrointestinal tract, cranial sinus, or nasal cavity.

23. The method of any of Items 1-22, wherein said amyloid aggregates are present within enteric nervous tissue or the olfactory bulb.

24. The method of any of Items 1-23, wherein the composition is administered daily.

25. The method of any of Items 1-24, wherein the composition is administered multiple times per day.

26. The method of any of Items 1-25, wherein the composition is administered less frequently than daily.

27. The method of any of Items 1-24 or 26, wherein the composition is administered every second day, every third day, every fourth day, every fifth day, every sixth day, or every seventh day.

28. The method of any of Items 1-27, further comprising measuring or evaluating enteric amyloid levels and/or amyloid aggregation during the course of administration.

29. The method of any of Items 1-28, further comprising measuring or evaluating enteric amyloid levels and/or amyloid aggregation following the course of administration.

30. The method of any of Items 1-29, further comprising measuring or evaluating a change in the nervous system, such as a neurological symptom or behavior of the subject.

31. The method of any of Items 1-30, wherein said subject is under the age of 18, 18-30, 30-50, 50-60, 60-70, or over the age of 70.

32. The method of any of Items 1-31, further comprising measuring or evaluating a change in the gastrointestinal system, such as a gastrointestinal symptom or behavior of the subject.

33. The method of Item 32, wherein said gastrointestinal symptom comprises constipation.

34. The method of any of Items 1-33, wherein said subject suffers from gastrointestinal symptoms comprising one or more of constipation, diarrhea, abdominal pain and/or cramping, bloating, flatulence, nausea, or any other symptoms of irritable bowel syndrome (IBS), inflammatory bowel disease (IBD, such as ulcerative colitis and Crohn disease), intestinal hyperpermeability, or any combinations thereof.

35. The method of any of Items 1-34, wherein the composition is administered following the appearance of a neurological symptom or condition.

36. The method of Item 35, wherein said neurological symptom or condition comprises one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, altered kynurenine levels, and/or any combination thereof.

37. The method of any of Items 1-36, wherein the composition is administered prior to the appearance of a neurological symptom or condition.

38. The method of any of Items 1-37, wherein the method is repeated.

39. The method of any of Items 1-38, wherein, for a given administration, the composition is different from a composition previously administered.

40. The method of any of Items 1-39, wherein, for a given administration, the dose administered is different from a dosage previously administered.

41. The method of any of Items 1-40, wherein the composition is co-administered with a caffeine, nicotine, theophylline, theobromine, xanthine, methylxanthine, or derivatives thereof.

42. The method of any of Items 1-41, further comprising administering to said subject an inhibitor of α-synuclein aggregation.

43. The method of any of Items 1-42, wherein said subject is one that has been identified or selected as being at risk for developing or already having Parkinson's disease, such as by clinical or diagnostic evaluation.

44. The method of any of Items 1-43, wherein said subject is one that has been identified or selected as being at risk for developing or already having Lewy Body Dementia, incidental Lewy body disease, Lewy body variant of Alzheimer's disease, multiple system atrophy, pure autonomic failure, or any combination thereof, such as by clinical or diagnostic evaluation.

45. The method of item 14, wherein the gastrointestinal symptoms are associated with Parkinson's Disease or Parkinsonism.

46. The method of any one of items 1-44, wherein the amyloid disorder can be diagnosed by detecting the presence or level of intestinal bacterial amyloid aggregates.

Additional Options

The following options are set forth in accordance with some embodiments herein.

1. A method of identifying a composition that affects the formation of microbially-induced amyloid, comprising:
(a) contacting a plurality of concentrations of a microbial amyloid or a microbial amyloid precursor (e.g., CsgA) with a plurality of concentrations of α-Synuclein in the presence of a composition comprising a compound of the invention;
(b) analyzing or measuring the formation of amyloid produced by the reaction set forth in (a); and
(c) comparing the analysis or measurement made in (b) with an analysis or measurement of a control, wherein said control comprises analyzing or measuring the formation of amyloid after the reaction set forth in (a) in the absence of said composition.

2. The method of Option 1, wherein said microbial amyloid or microbial amyloid precursor comprises CsgA.

3. The method of Options 1 or 2, further comprising agitation during (a).

4. The method of Options 1-3, wherein the contacting performed in (a) is conducted in the presence of an indicator of amyloid formation.

5. The method of Option 4, wherein said indicator is a fluorescent indicator, a spin-labeled indicator, an enzyme, an antibody, or a colorimetric indicator.

6. The method of Option 4, wherein said indicator is Thioflavin T.

7. The method of Option 4 wherein said antibody has specificity for aggregated α-Synuclein, and wherein said antibody optionally is conjugated to a fluorescent label, an enzyme, a colorimetric label, a spin label, a metal ion binding moiety, a nucleic acid, a polysaccharide, or a polypeptide.

8. The method of any of Options 1-7, wherein said CsgA and said α-Synuclein are each separately labeled.

9. The method of any of Options 1-8, wherein the formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.

10. The method of any of Options 1-9, wherein said composition comprises a mixture of compounds.

11. The method of any of Options 1-10, wherein said composition comprises tissue, bodily fluid or an extract thereof.

12. The method of any of Options 1-11, wherein said composition comprises feces, urine, blood, spinal fluid, or saliva, or a component thereof.

16. The method of any of Options 1-10 wherein said composition comprises one or more bacteria, bacterial extracts, lysates, conditioned culture media, lyophilized bacteria, lyophilized lysates, lyophilized culture media, or any combination thereof.

17. The method of any of Options 1-16, further comprising identifying or selecting compositions that alter amyloid formation.

18. The method of any of Options 1-17, further comprising identifying or selecting compositions that reduce amyloid formation.

19. The method of any of Options 1-18, wherein the rate of formation of amyloid is analyzed or measured in (b).

20. A method of making microbially-induced amyloid, comprising:
(a) contacting a plurality of concentrations of a microbial amyloid or a microbial amyloid precursor (e.g., CsgA) with a plurality of concentrations of α-Synuclein in the presence of a composition comprising a compound of the invention;
(b) providing conditions that allow for the formation of new microbially-induced amyloid; and
(c) analyzing or quantifying the microbially-induced amyloid formed in (b).

21. The method of Option 20, wherein said microbial amyloid or microbial amyloid precursor comprises CsgA.

22. The method of Options 20 or 21, further comprising agitation during (a).

23. The method of any of Options 20-22, wherein the contacting performed in (a) is conducted in the presence of an indicator of amyloid formation.

24. The method of Option 23, wherein said indicator is a fluorescent indicator, a spin-labeled indicator, or a colorimetric indicator.

25. The method of Options 23 or 24, wherein said indicator is Thioflavin T.

26. The method of any of Options 20-25, wherein said CsgA and said α-Synuclein are each separately labeled.

27. The method of any of Options 20-26, wherein the formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.

28. The method of any of Options 20-27, wherein said composition comprises a mixture of compounds.

29. The method of any of Options 20-28, wherein said composition comprises tissue, bodily fluid or an extract thereof.

30. The method of any of Options 20-29, wherein said composition comprises feces, urine, blood, spinal fluid, or saliva, or a component thereof.

31. The method of any of Options 28-30 wherein said composition comprises one or more bacteria, bacterial extracts, lysates, conditioned culture media, lyophilized bacteria, lyophilized lysates, lyophilized culture media, or any combination thereof.

35. The method of any of Options 20-34, further comprising identifying or selecting compositions that reduce amyloid formation.

36. The method of any of Options 20-35, wherein the rate of formation of amyloid is analyzed or quantified in (c).

37. A kit comprising a microbial amyloid or a microbial amyloid precursor and α-Synuclein, being present in one or more containers within said kit.

38. The kit of Option 37, wherein said microbial amyloid or microbial amyloid precursor comprises CsgA.

39. A method of treating or inhibiting an amyloid disorder in a subject comprising:
(a) contacting a plurality of concentrations of a microbial amyloid or a microbial amyloid precursor with a plurality of concentrations of α-Synuclein in the presence of a composition;
(b) analyzing or measuring the formation of new amyloid after the reaction set forth in (a);
(c) comparing the analysis or measurement made in (b) with an analysis or measurement of a control, wherein said control comprises analyzing or measuring the formation of amyloid after the reaction set forth in (a) in the absence of said composition; and
(d) if the formation of amyloid in the presence of said composition is increased relative to the formation of amyloid in the absence of said composition, administering to said subject an effective amount of a pharmaceutical composition suitable for inhibiting or treating said amyloid disorder.

40. The method of Option 39, wherein said microbial amyloid or microbial amyloid precursor comprises CsgA.

41. The method of any of Options 39-40, wherein said composition comprises tissue, bodily fluid or an extract thereof.

42. The method of any of Options 39-41, wherein said composition comprises feces, urine, blood, spinal fluid, or saliva, or a component thereof.

43. The method of Options 39-42, wherein said pharmaceutical composition comprises one or more probiotic bacteria.

44. The method of Options 39-43, wherein said pharmaceutical composition comprises one or more bacteria selected from the group consisting of *Bacteroides, Prevotella, Parabacteroides, Faecalibacterium, Eubacterium, Roseburia, Blautia, Coprococcus*, and *Bifidobacterium*, or any combination thereof.

45. The method of any of Options 39-44, wherein said pharmaceutical composition comprises one or more bacteria selected from the group consisting of *B. fragilis, B. vulgatus*, and *B. thetaiotaomicron*; or any combination thereof.

46. The method of any of Options 39-45, wherein the rate of formation of amyloid is analyzed or quantified in (b).

47. The method of any of Options 39-46, further comprising identifying or selecting said subject as one that would benefit from a treatment or inhibition of an amyloid disorder.

48. The method of any of Options 39-47, further comprising identifying or selecting said subject as one at risk of or showing symptoms of one or more of Parkinson's Disease, Lewy Body Dementia, incidental Lewy body disease, Lewy body variant of Alzheimer's disease, multiple system atrophy, pure autonomic failure, or any combination thereof.

EXAMPLES

Example 1

To a subject, one or more of the compounds described above (e.g., a composition comprising a compound of the invention) is administered orally or rectally on a regular basis, such as daily. Bacterial amyloid formation in the GI tract and/or α-synuclein aggregation levels within the GI tissue are monitored by fecal sampling or by biopsy. Therapy is continued to prevent bacterial amyloid (curli) formation and/or α-synuclein aggregation. Changes in the patient's GI function and motor symptoms are monitored. For subjects in which the administration of said one or more compounds results in reduced formation of microbially-induced amyloid in the gut, improvements in one or more GI symptoms, one or more motor symptoms and/or one or more neurological symptoms are observed.

Example 2

One or more of the compounds of the invention is obtained or synthesized and incorporated into an enteric or colon-selective formulations to release material at site of action and by-pass the stomach and most of the small intestine. This provides delivery of the composition at the site of curli production and/or α-synuclein aggregation, and minimizes absorption of the composition into systemic circulation.

Example 3

One or more of the compounds of the invention is obtained or synthesized and incorporated into a formulation for controlled release in the lower small intestine or in the colon. This provides for lower and/or less frequent dosing, and side effects are minimized. Controlled release in the lower small intestine or colon may be achieved by any of a variety of approaches known in the art and includes enteric coated capsules, tablets, soft gels, intrinsically enteric capsules, multi-layered formulations, coated micronized forms of the polymeric material, and the like.

Example 4

A subject is administered a combination of more than one of the compounds of the invention. Combining a curli inhibitor with an α-synuclein aggregation inhibitor blocks aggregation at two critical points simultaneously. For subjects in which the administration of said one or more compounds results in reduced formation of microbially-induced amyloid in the gut, improvements in one or more GI symptoms, one or more motor symptoms and/or one or more neurological symptoms are observed or measured.

Example 5

The Thy1-α-synuclein (α-synuclein-overexpressing [ASO]) mouse displays progressive deficits in fine and gross motor function, as well as, gut motility defects. Evidence has linked unregulated α-synuclein expression in humans to a higher risk of PD, providing an epidemiological foundation for the Thy1-α-synuclein mouse model. Defects in coordinated motor tasks become evident at 12 weeks of age. Motor function is measured via four tests: beam traversal, pole descent, nasal adhesive removal, and hind limb clasping reflexes, as previously validated in this model (described in Fleming et al., *J. Neurosci.* 24, 9434-9440 (2004), and Sampson et al., *Cell* 167(6):1469-1480 (2016) the content of which are hereby expressly incorporated by reference in its entirety). ASO mice require significantly more time to cross a challenging beam compared to wild-type littermates and also exhibit increased time to descend a pole, two measures of gross motor function. Removal of an adhesive from the nasal bridge, a test of fine motor control, is also impaired in SPF-ASO mice compared to SPF-WT mice, as is the hind limb clasping reflex, a measure of striatal dysfunction.

ASO neonates are divided into two groups. To one group is administered one or more compositions as described above, and the other is untreated or mock-treated. Compositions are administered daily for 12-13 weeks. At 13 weeks and thereafter, motor skills are evaluated. ASO mice treated with the compositions described above require less time to cross a challenging beam, decreased time to descend a pole, enhanced removal of an adhesive from the nasal bridge, and an enhanced hind limb clasping reflex relative to untreated ASO mice.

Fecal pellets are also obtained from test animals. Fecal pellets from treated ASO mice show lower levels of bacterial adhesive pili (curli), as well as, lower levels of aggregated α-synuclein relative to untreated ASO animals.

After 16 weeks, animals are sacrificed and their brain enteric nervous tissue is analyzed for the presence of α-synuclein aggregates. Utilizing an antibody that recognizes only conformation-specific α-synuclein aggregates and fibrils, immunofluorescence microscopy is performed to visualize α-synuclein inclusions. Notable aggregation of α-synuclein is observed in the caudoputamen (CP), substantia nigra (SN), and enteric neurons of untreated ASO animals relative to levels seen in treated animals. Western blots of brain extracts are also performed. Significantly less insoluble α-synuclein is found in brains and enteric nervous tissue of treated ASO animals.

Example 6

Figure 1A:
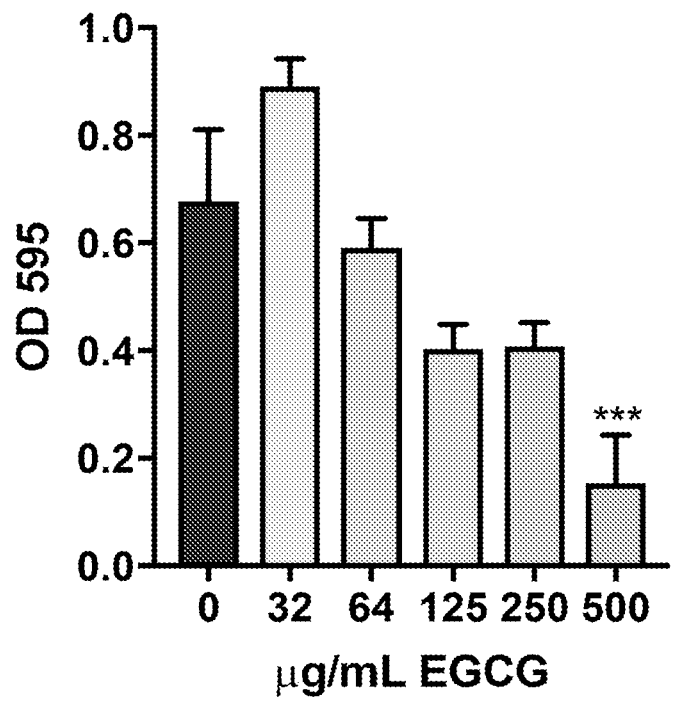
FIGS. 1A-O are a series of graphs and images depicting that curli-driven pathophysiology in mice requires functional amyloid formation.
Figure 1B:
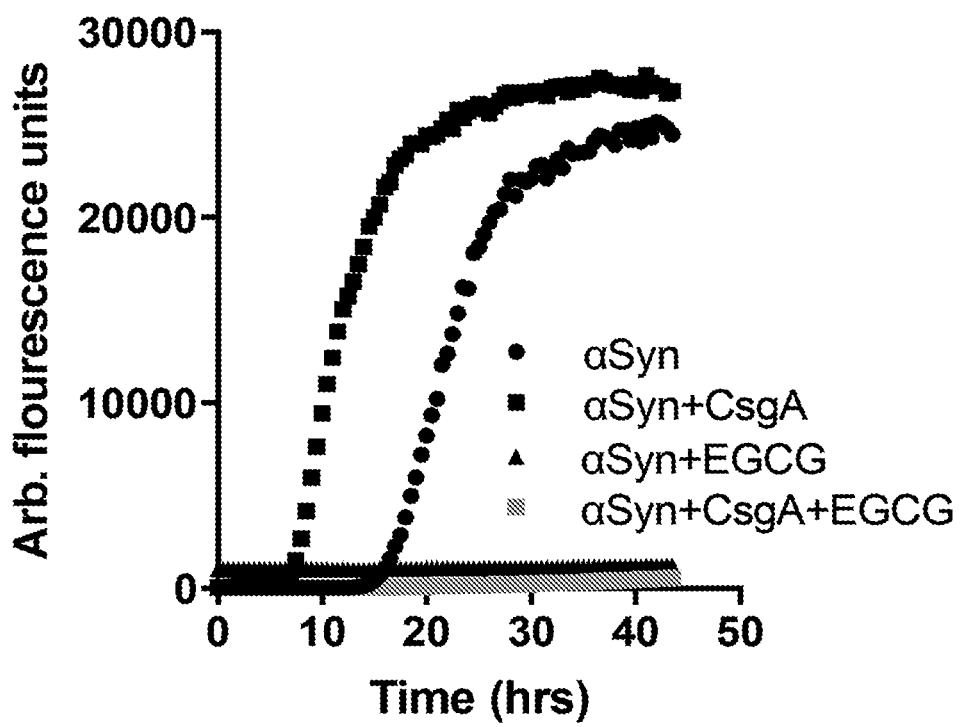
FIG. 1B is a graph showing in vitro αSyn aggregation measured by Thioflavin T fluorescence during αSyn amyloid formation alone or in the presence of CsgA (25:1 molar ratio), with and without EGCG (50 μM) treatment.

Roles of functional amyloid formation in curli-driven pathophysiology were examined in mice using techniques described in co-pending application PCT/US2018/032605, the entire content of which are herein incorporated by reference. As an initial matter, effects of epigallocatechin gallate (EGCG) on biofilm growth by wild-type *E. coli* were examined, along with effects of EGCG on αSyn amyloid formation in vitro. FIG. 1A is a graph showing Crystal violet staining of biofilm growth by wild-type *E. coli* following 4 days in static culture, with indicated concentrations of EGCG; data assessed by optical density (OD). FIG. 1B is a graph showing in vitro αSyn aggregation measured by Thioflavin T fluorescence during αSyn amyloid formation alone or in the presence of CsgA (25:1 molar ratio), with and without EGCG (50 µM) treatment.

Figure 1C:
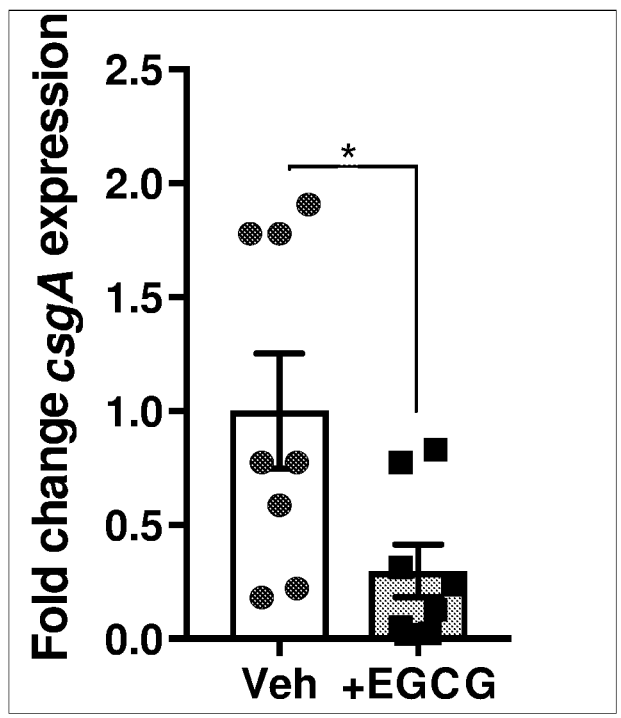
FIGS. 1C-L show results for germ-free Thy1-αSyn mice (ASO) mono-colonized with WT E. coli at 5-6 weeks of age, and given water alone (Vehicle: Veh) or treated with EGCG ad libitum in drinking water (+EGCG).
Figure 1D:
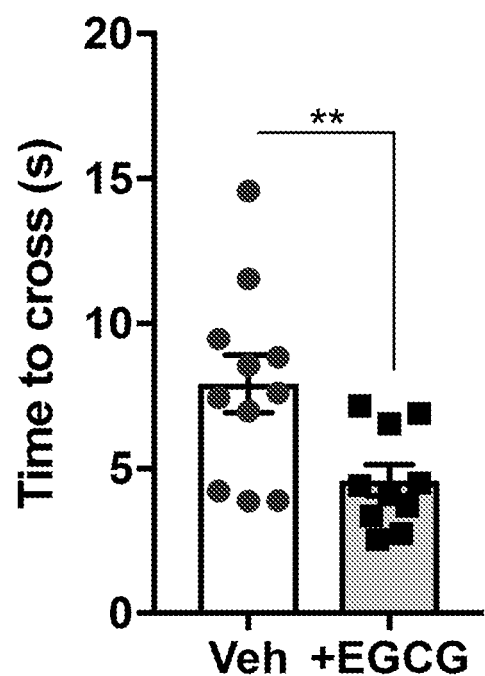
Figure 1E:
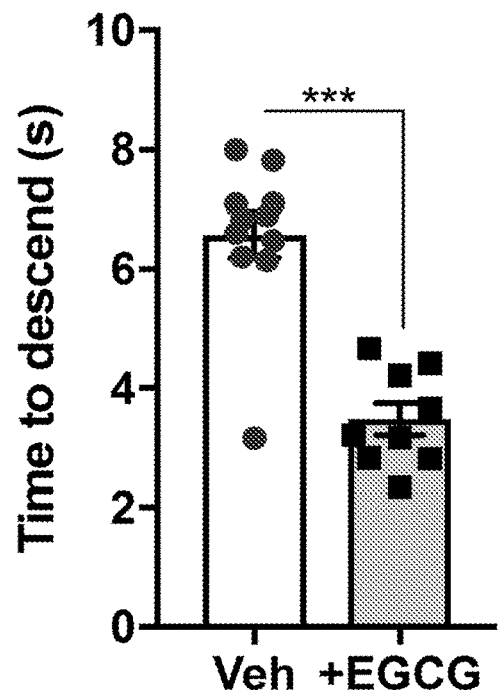
Figure 1F:
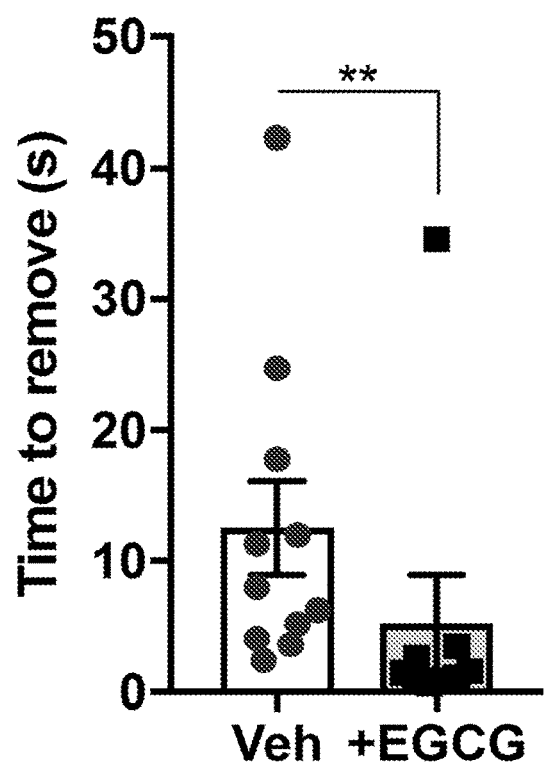
Figure 1G:
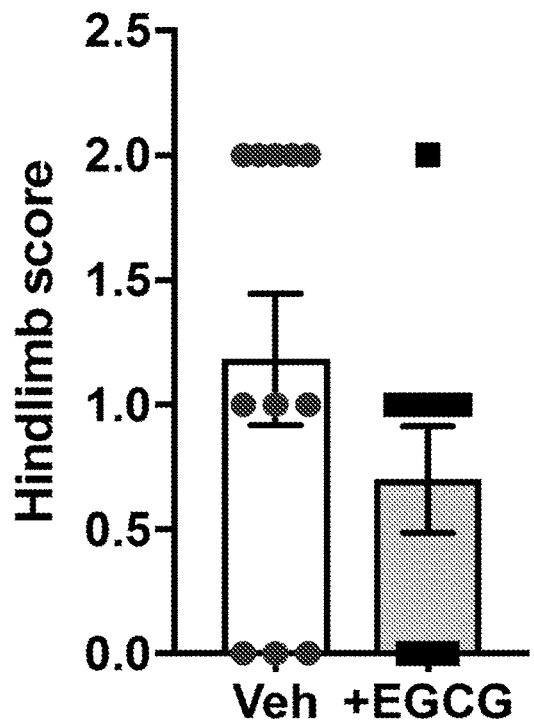
Figure 1H:
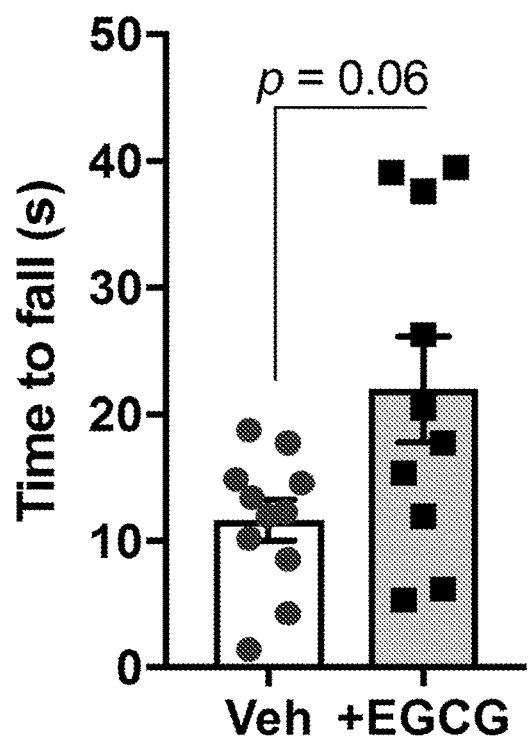

Germ-free Thy1-αSyn mice (ASO) mono-colonized with WT *E. coli* at 5-6 weeks of age, and given water alone (Vehicle: Veh) or treated with EGCG ad lib in drinking water (+EGCG). RNA was extracted from fecal pellets and csgA expression quantified by qRT-PCR, relative to rrsA. FIG. 1C is a graph showing fold-change in csgA expression. Motor function was assessed at 15-16 weeks of age by quantifying beam traversal time (FIG. 1D), pole descent time (FIG. 1E), nasal adhesive removal time (FIG. 1F), hindlimb clasping score (FIG. 1G), and wire hang tests (FIG. 1H). Time to cross, time to descent, time to remove, and hindlimb score were lower in the EGCG-treated mice, while time to fall was higher in the EGCG-treated mice compared to vehicle treated control.

Figure 1I:
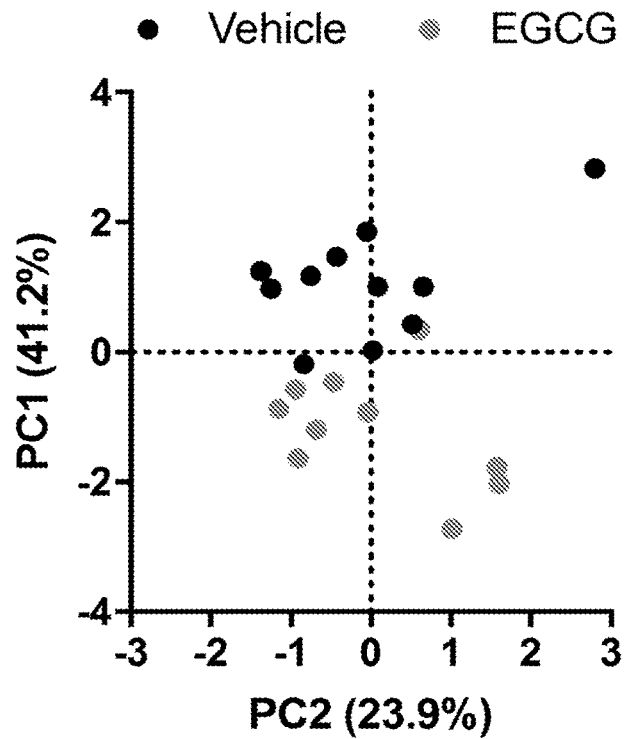
Figure 1J:
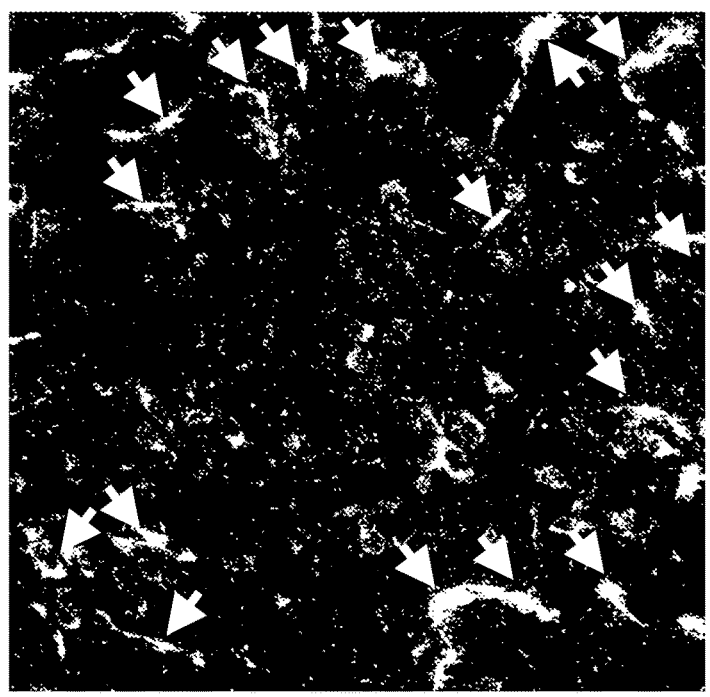
Figure 1K:
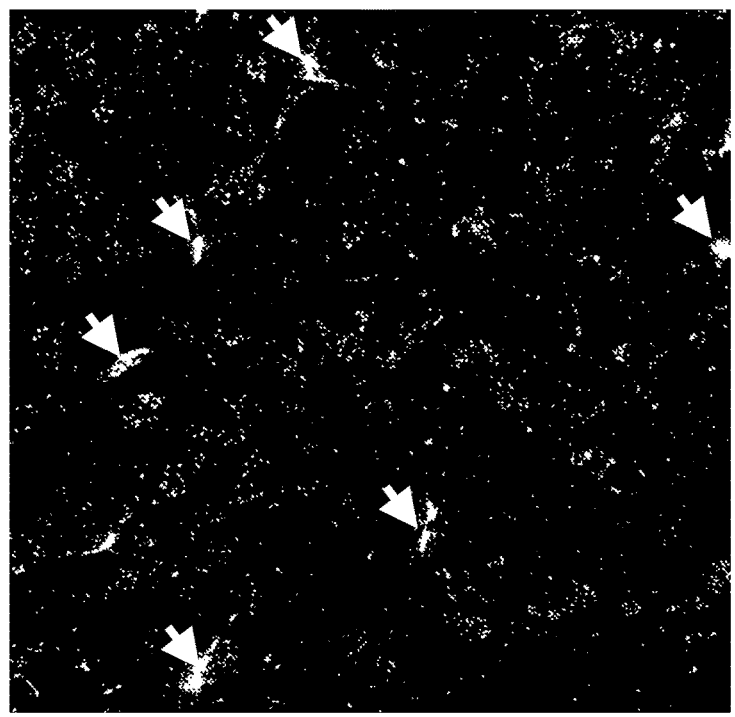

FIG. 1I is a graph showing principal component analysis of compiled motor scores from tests in (FIGS. 1D-H). FIGS. 1J-K are a series of graph showing Proteinase K resistant αSyn aggregates (indicated by white arrows) in the substantia nigra imaged via immunofluorescence microscopy. Shown are vehicle-treated (FIG. 1J) and EGCG-treated mice (FIG. 1K). Levels of Proteinase K resistant αSyn aggregates were lower in the EGCG-treated mice than in untreated controls. Thus, assessment of motor performance reveals that EGCG treatment in accordance with some embodiments herein successfully dampens progressive motor deficits exacerbated by *E. coli*, while also preventing αSyn aggregation in both the striatum and midbrain.

Figure 1L:
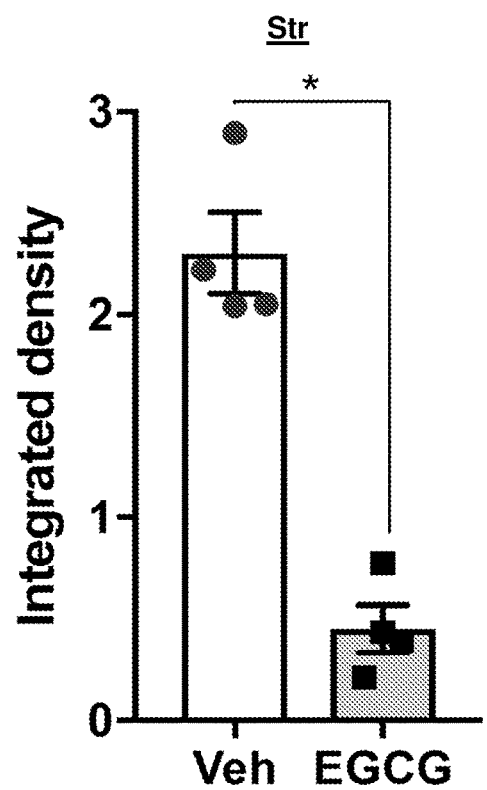
Figure 1M:
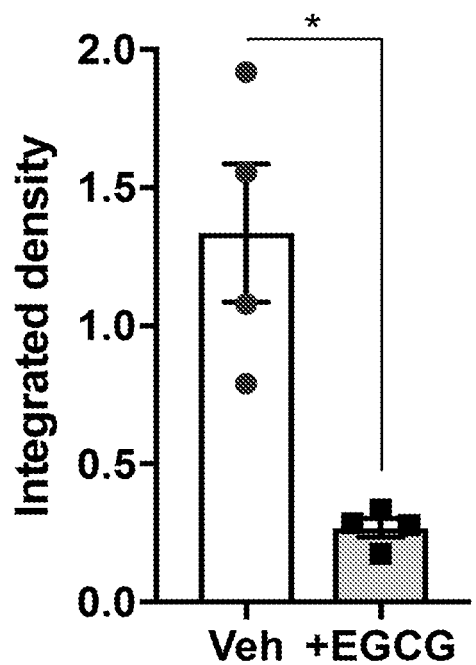
Figure 1N:
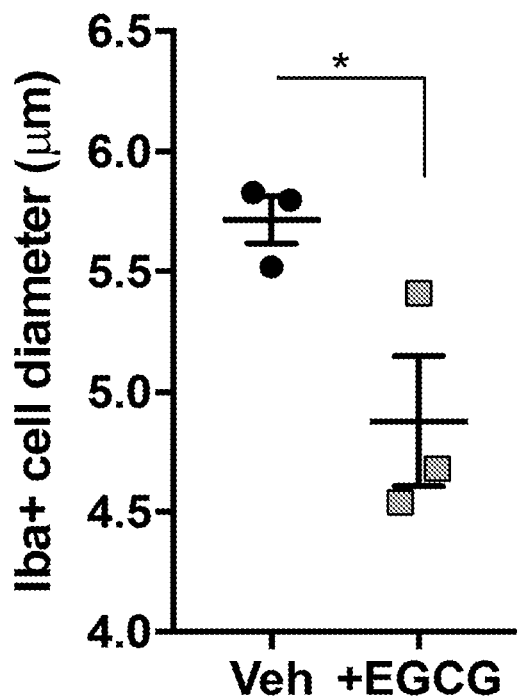
Figure 1O:
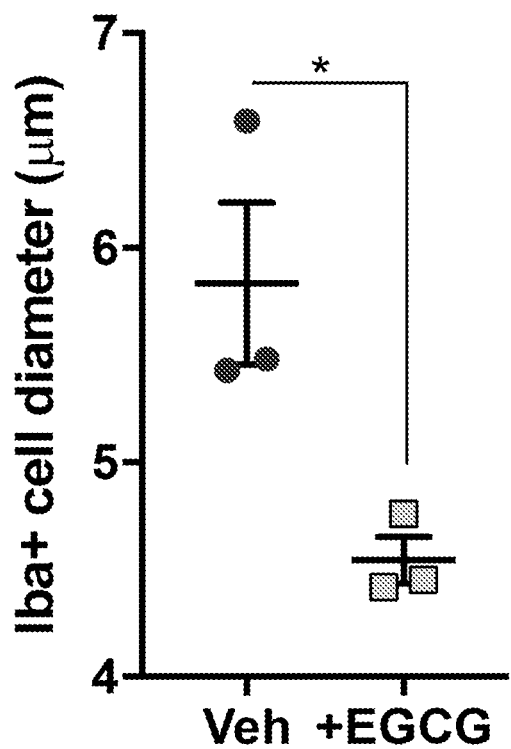

FIGS. 1L-M show quantification of insoluble αSyn fibrils in the striatum (FIG. 1L) and ventral midbrain (FIG. 1M) by dot blot assay. Thin sections of brain were stained for Iba1 (microglia), 3D cellular reconstructions generated, and morphological characteristics quantified from microglia resident in the striatum (FIG. 1N) and substantia nigra (FIG. 1O). n=3 (FIGS. 1A, 1B, 1N, 1O), n=8 (FIG. 1C), n=10-11 (FIGS. 1D-I), n=4 (FIGS. 1L-M). Points represent individuals, bars represent the mean and standard error. Data analyzed by one-way ANOVA with Tukey post-hoc test for FIG. 1A, two-tailed Mann-Whitney for FIGs. C-K, or two-tailed t-test for FIG. 1L. For FIGS. 1A-1L *p≤0.05; p≤0.01; *p≤0.001. Motor data are compiled from 2 independent cohorts.

Accordingly, it is shown that in vivo treatment with compounds in accordance with compositions and methods in accordance with some embodiments herein inhibit or reduce αSyn amyloid formation in vitro. Furthermore, these compounds improved motor scores, consistent with inhibition, amelioration, and alleviation of symptoms of aggregate-related diseases such as parkinsonism in accordance with some embodiments herein.

Example 7

Figure 2A:
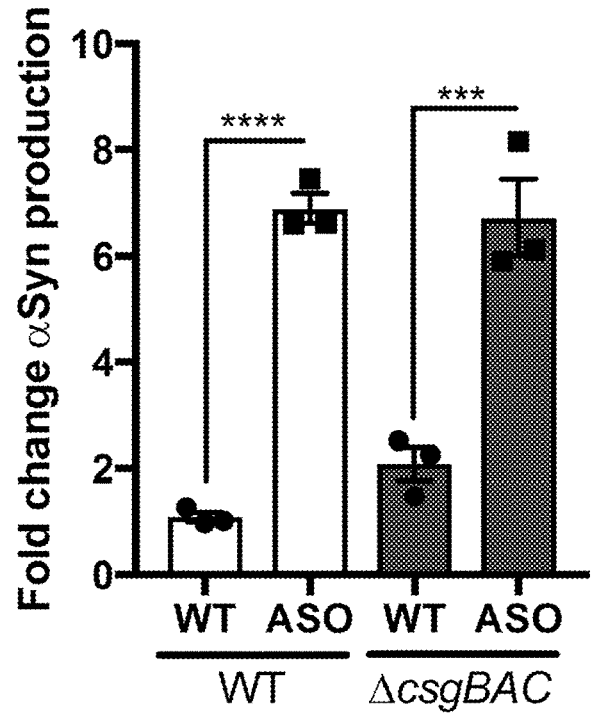
FIGS. 2A-G are a series of graphs and images depicting that mono-colonization with curli-sufficient bacteria induce increased αSyn-dependent pathology and inflammatory responses in the brain. Germ-free (GF) wild-type (WT) or Thy1-αSyn (ASO) animals were mono-colonized with either wild-type, curli-sufficient E. coli (WT) or curli-deficient E. coli (ΔcsgBAC).
Figure 2B:
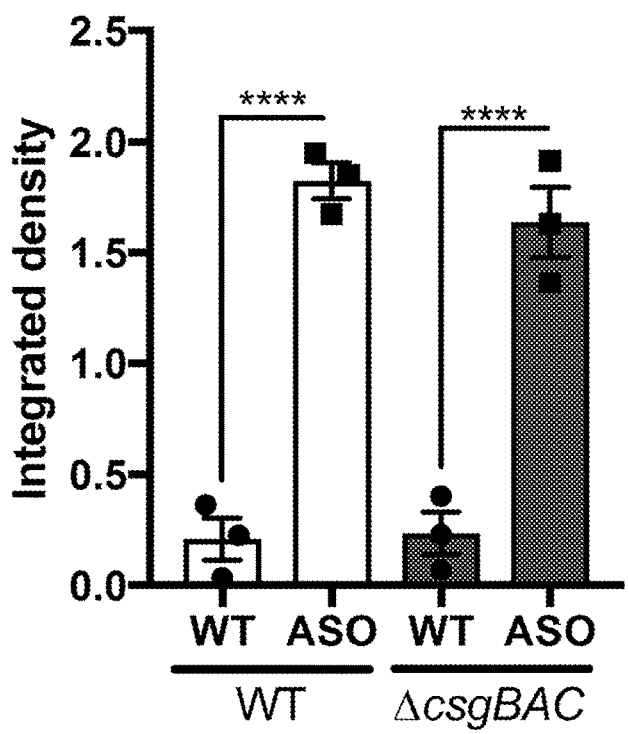
Figure 2C:
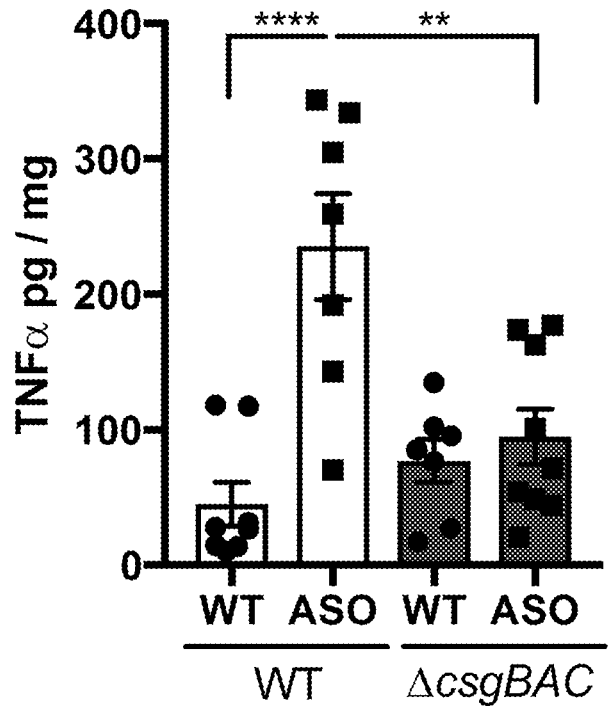
Figure 2D:
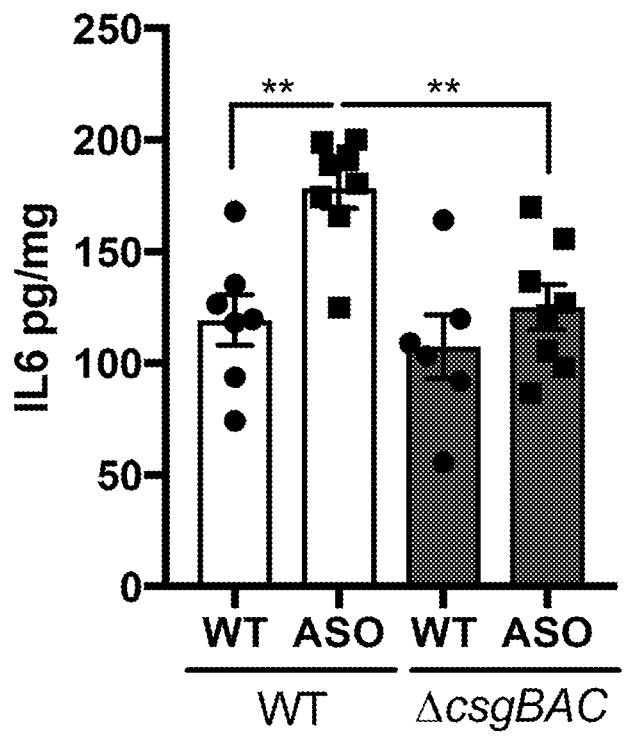
Figure 2E:
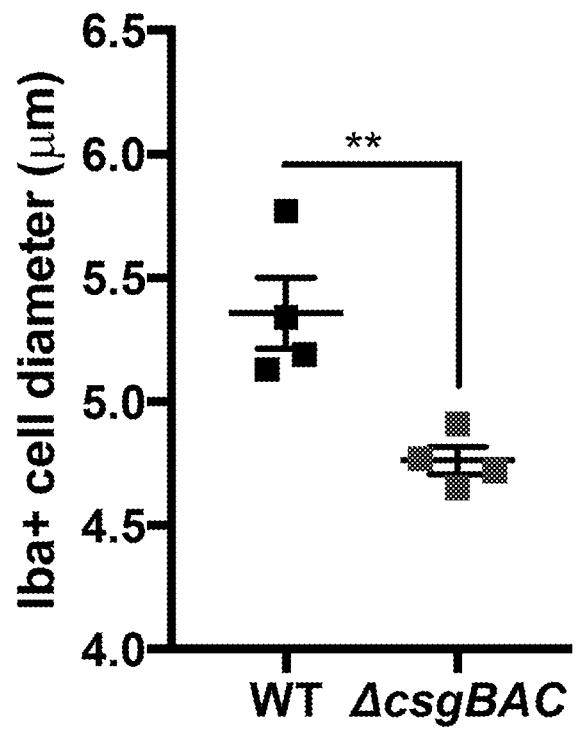
Figure 2F:
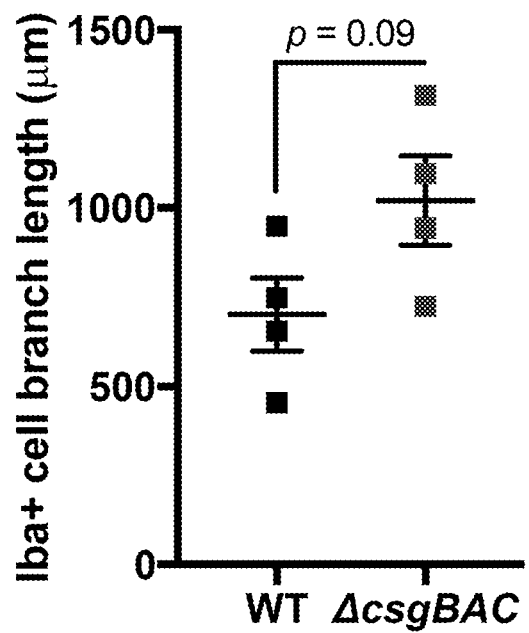
Figure 2G:
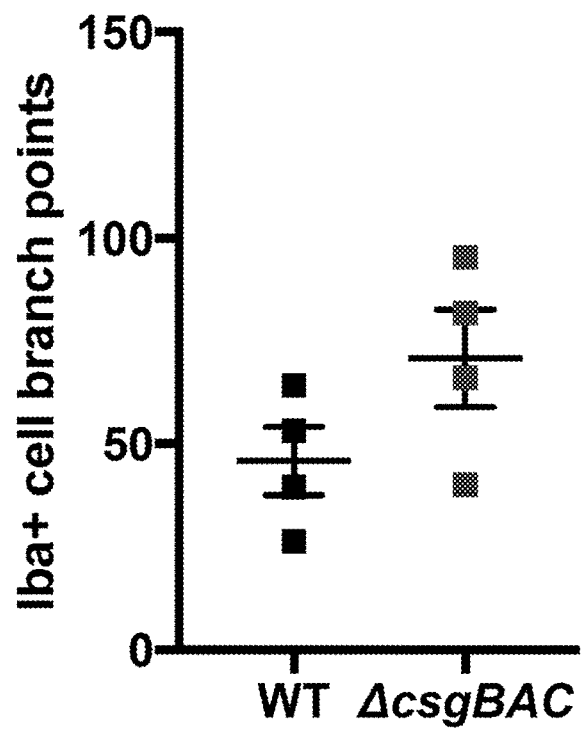
Figure 2H:
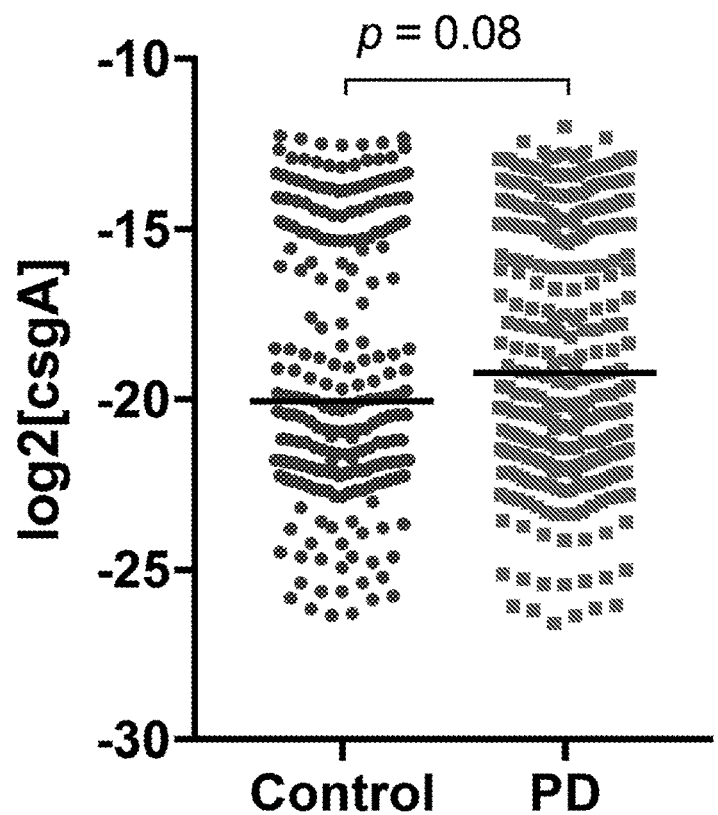
FIGS. 2H-J are a series of graphs showing levels of csgA in human fecal samples (FIG. 2H), in wild-type mice colonized with microbes derived from persons with PD or matched controls (FIG. 2I), or in Thy1-αSyn (ASO) mice colonized with microbes derived from persons with PD or matched controls (FIG. 2J). Consistent with these data, csgA is predicted to be enriched in microbes derived from persons with PD.
Figure 2I:
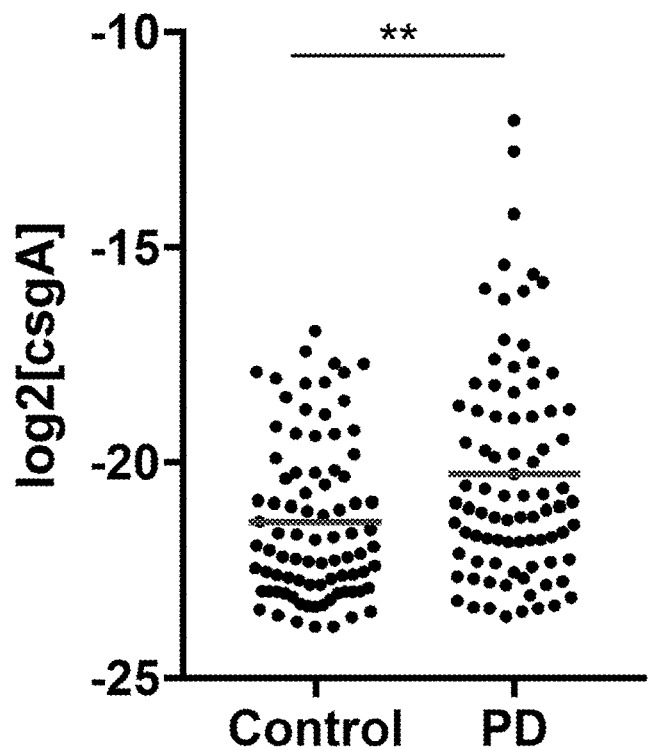
Figure 2J:
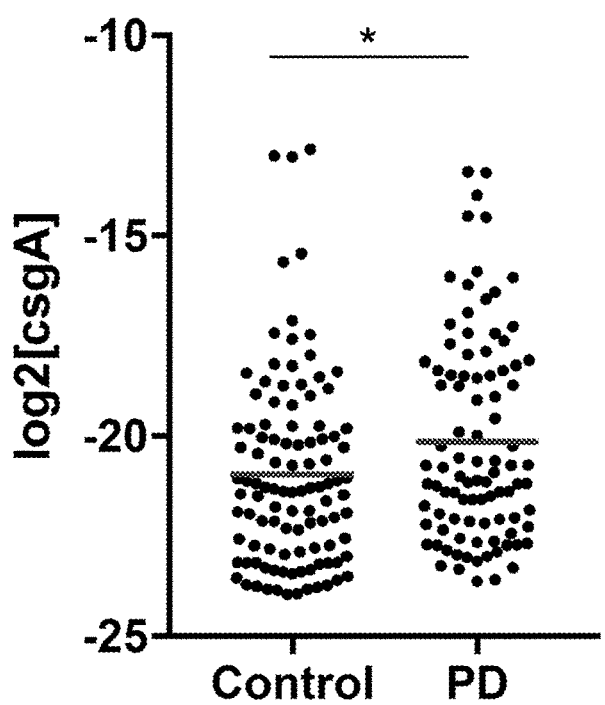

Additional experiments, using techniques described in co-pending application PCT/US2018/032605, the entire content of which are herein incorporated by reference, showed that mono-colonization with curli-sufficient bacteria induce increased αSyn-dependent pathology and inflammatory responses in the brain. Germ-free (GF) wild-type (WT) or Thy1-αSyn (ASO) mice were mono-colonized with either wild-type, curli-sufficient *E. coli* (WT) or curli-deficient *E. coli* (ΔcsgBAC). FIG. 2A is a graph showing total αSyn in whole brain lysates quantified by ELISA. FIG. 2B is a graph showing quantification of insoluble αSyn fibrils in the striatum by dot blot assay. FIGS. 2C-D show quantification of TNFα (FIG. 2C) and IL-6 (FIG. 2D) by ELISA from the striatum. FIGS. 2E-G show the results of staining thin sections of brains derived from ASO mice were stained for Iba1 (microglia), 3D cellular reconstructions generated, and morphological characteristics quantified of microglia resident in the striatum. n=3 (FIGS. 2A-B), n=6-7 (FIG. 2C, 2D), n=4 (FIGS. 2E-G) (averaged from 20-40 cells for diameters, or 5-7 cells for branching). Points represent individuals, bars represent the mean and standard error. Data analyzed by one-way ANOVA with Tukey post-hoc test for FIGS. 2A-D, or two-tailed t-test for FIGS. 2E and 2F *p≤0.05; p≤0.01; *p≤0.001; ****p≤0.0001. Consistent with this effect of curli-sufficient bacteria on mouse models, it is shown that the relative abundance of csgA is increased in the gut of human Parkinson's Disease (PD) patients. Relative abundance of csgA was determined by PICRUSt analysis of available 16S RNA data from human fecal samples (ENA Accessions: PRJNA268515, PRJEB4927, and PRJEB14674). Based on this analysis, it was observed that relative abundance of csgA was higher in the gut of the PD patients (FIG. 2H). Furthermore, wild-type (FIG. 2I) or Thy1-αSyn (ASO) (FIG. 2J) mice were colonized with microbes derived from persons with PD or matched controls (ENA Accession: PRJEB17694), and PICRUSt imputed analysis of 16s rRNA sequences indicated greater abundance in the PD-transplanted microbiomes compared to healthy controls (FIG. 2K). For FIGS. 2H-J, points represent individuals, bars represent the mean, data analyzed by two-tailed Mann-Whitney test. *p≤0.05; **p≤0.01. Thus, it is observed that the presence or elevated levels (compared to healthy controls) of bacterial proteins such as csgA in the gut correlates with amyloid disorders, including PD.

Example 8

Figure 3A:
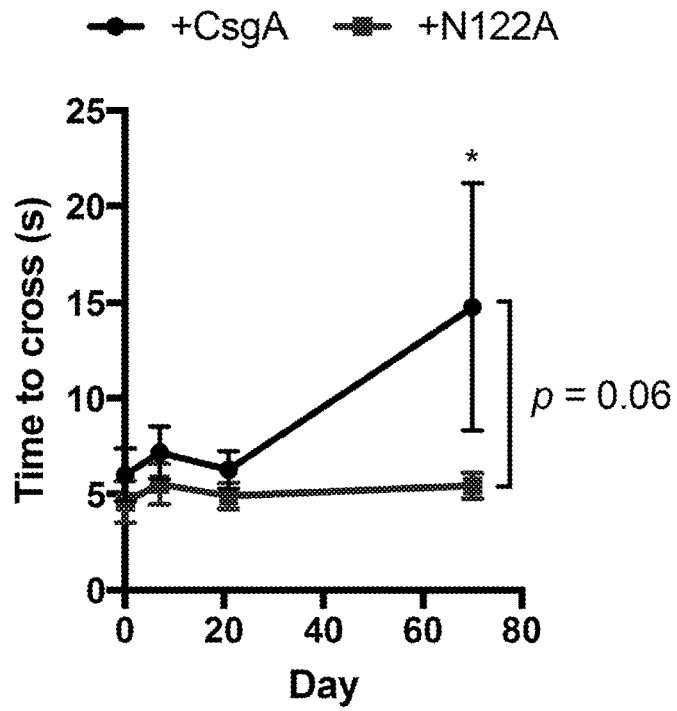
FIGS. 3A-I are a series of graphs depicting that intestinal curli promotes progressive synuclein-dependent pathophysiology. Conventionally-raised Thy1-αSyn (ASO) animals were injected intestinally with 30 μg of synthetic CsgA hexamer (CsgA; N-QYGGNN-C) or non-amyloidogenic peptide (N122A; N-QYGGNA-C). For FIGS. 3A-G, motor and GI function tested overtime at 0, 7, 21, and 70 days post-injection in the beam traversal (FIG. 3A), pole descent (FIG. 3B), adhesive removal (FIG. 3C), hindlimb clasping score (FIG. 3D), wirehang (FIG. 3E), fecal output (at day 70) (FIG. 3F).
Figure 3B:
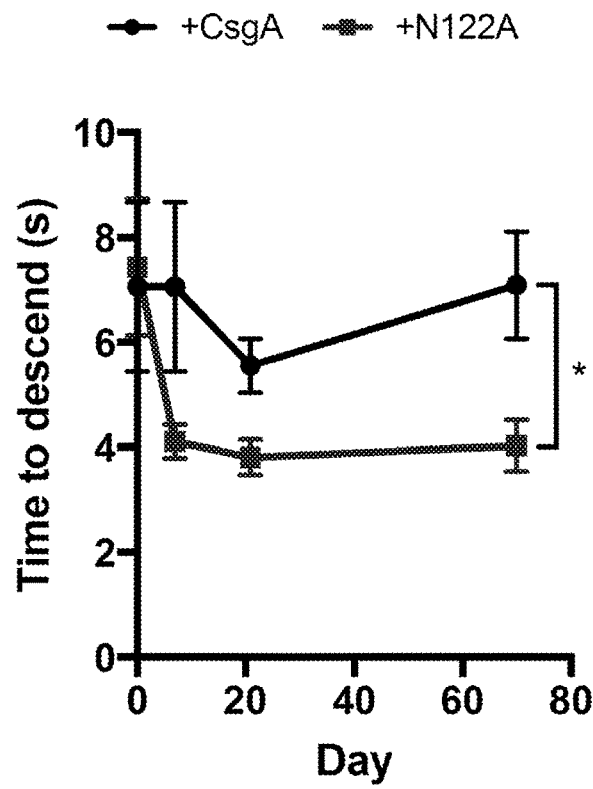
Figure 3C:
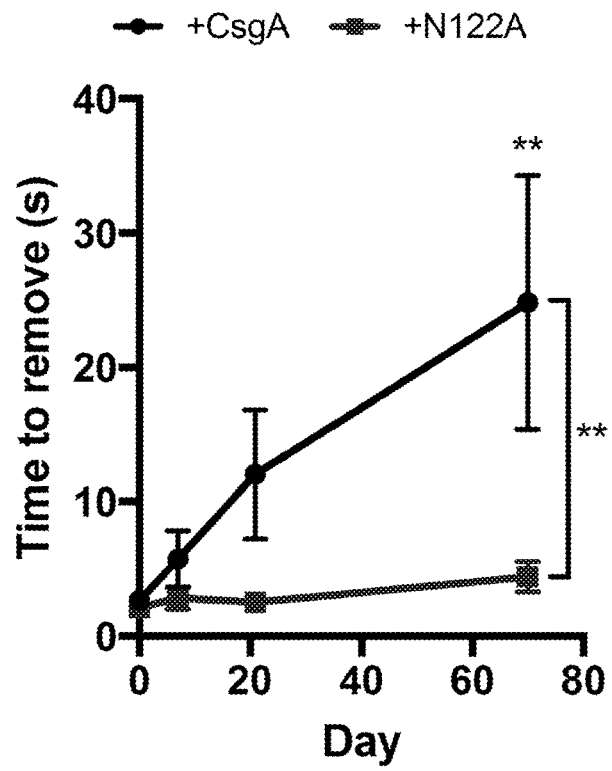
Figure 3D:
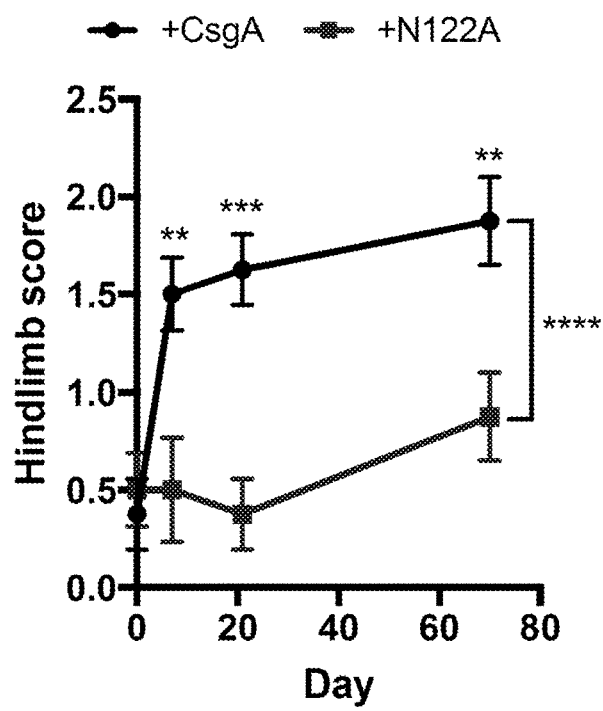
Figure 3E:
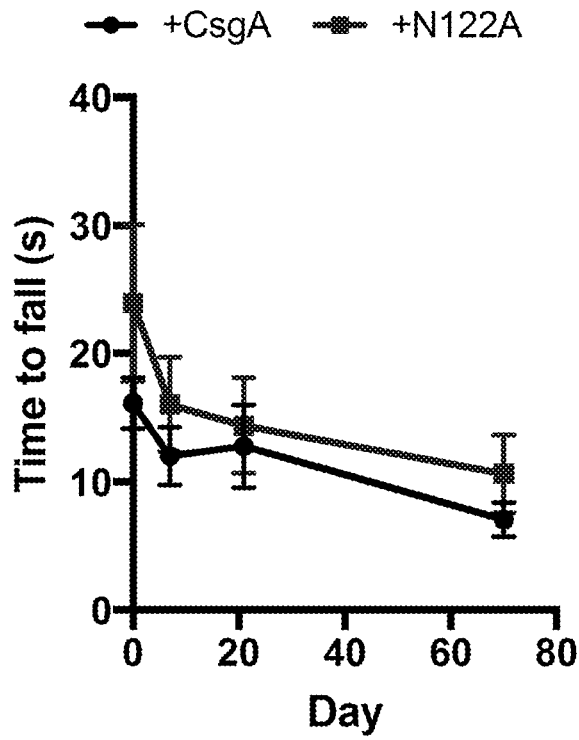
Figure 3F:
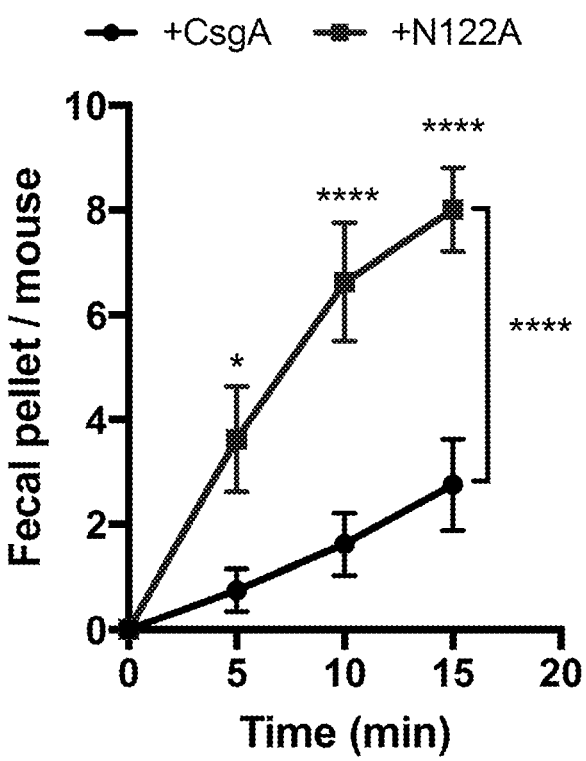
Figure 3G:
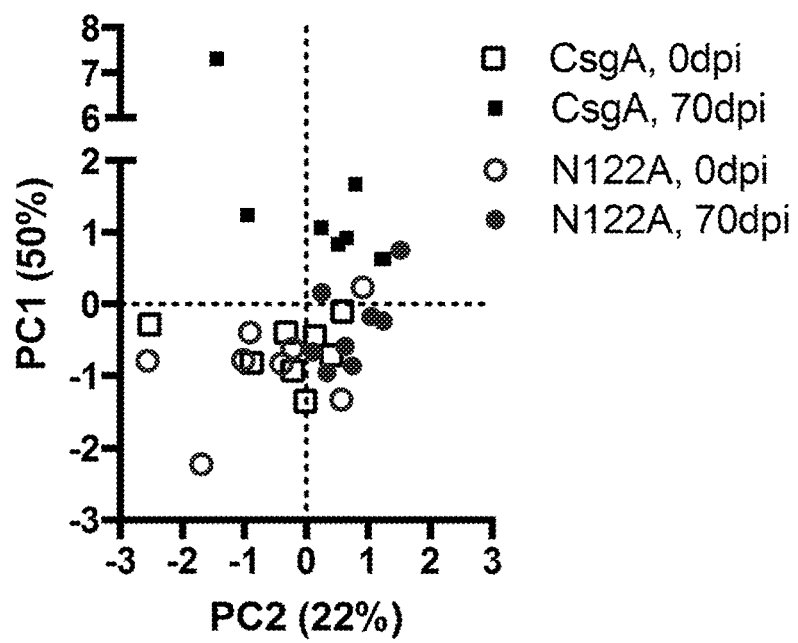
Figure 3H:
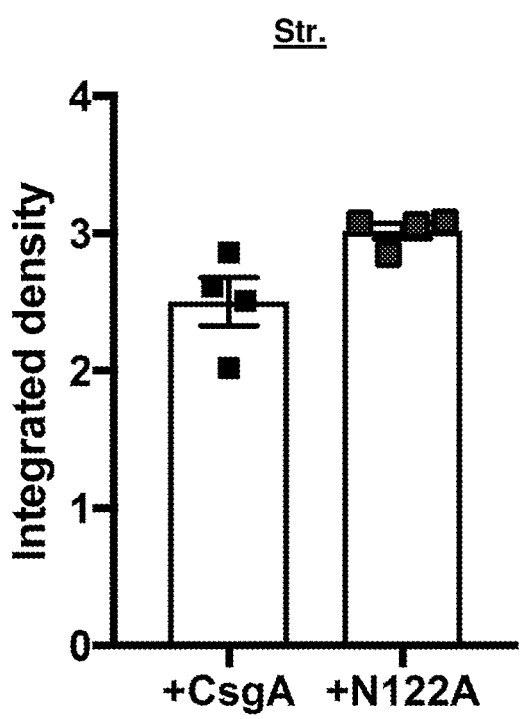
Figure 3I:
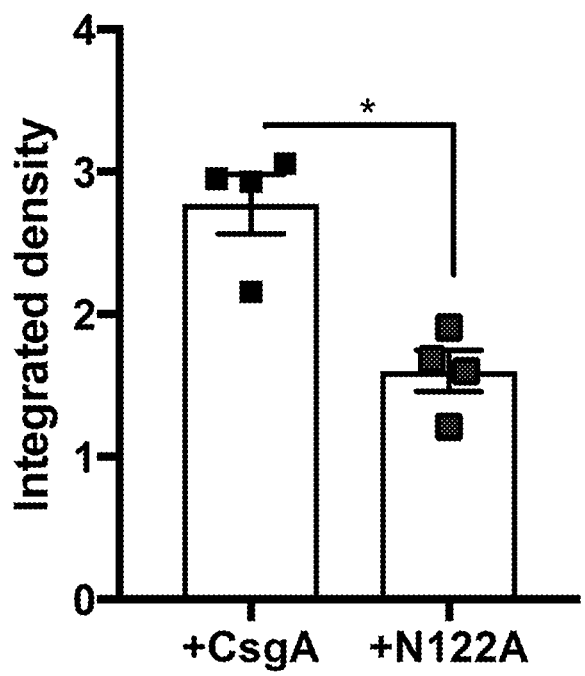

Additional experiments show that that intestinal curli promotes progressive synuclein-dependent pathophysiology. Conventionally-raised Thy1-αSyn (ASO) animals were injected intestinally with 30 μg of synthetic CsgA hexamer (CsgA; N-QYGGNN-C) or non-amyloidogenic peptide (N122A; N-QYGGNA-C). Each peptide spanned the aggregation domain of CsgA. Motor and GI function tested over time at 0, 7, 21, and 70 days post-injection in the beam traversal (FIG. 3A), pole descent (FIG. 3B), adhesive removal (FIG. 3C), hindlimb clasping score (FIG. 3D), wire hang (FIG. 3E), fecal output (at day 70) (FIG. 3F). FIG. 3G is a graph depicting principal component analysis of compiled motor scores of FIGS. 3A-F. FIGS. 3H-I depict quantification of insoluble αSyn fibrils in the striatum (FIG. 3H) and ventral midbrain (FIG. 3I) by dot blot assay. n=8 (FIGS. 3A-G), n=4 (FIG. 3H). Points represent individuals, bars represent the mean and standard error. Time courses analyzed by two-way ANOVA, with Sidak post-hoc test for between group comparisons indicated above individual time points, and brackets indicating significance between treatments. Data in FIG. 3H were analyzed by two-tailed Mann-Whitney test. For FIGS. 3A-I, *p≤0.05; p≤0.01; *p≤0.001; ****p≤0.0001. Compilation of motor performance by PCA indicates a symptomatic shift in mice injected with the CsgA peptide compared to controls, demonstrating that the overall motor function of these animals has been impaired (FIG. 3G). Furthermore, increased αSyn fibrils are detected in the midbrains of amyloidogenic CsgA-injected animals (FIG. 3H), demonstrating alterations to central nervous system (CNS) pathology following amyloid administration directly to the GI tract. Thus, gut exposure to a CsgA peptide capable of forming amyloids is sufficient to exacerbate long-lasting motor deficits in αSyn over-expressing mice.

Thus, it was shown herein that intestinal curli increased time to cross, time to descend, time to remove, and hindlimb score, and decreased time to fall and fecal pellets per mouse. The increases in time to cross, time to descend, and hindlimb score, and decrease in fecal pellets per mouse were statistically significant at the noted levels (See FIGS. 3B-D and 3F). Accordingly, it is contemplated that intestinal curli can induce symptoms of amyloid disorders in vivo.

Example 9

Figure 4A:
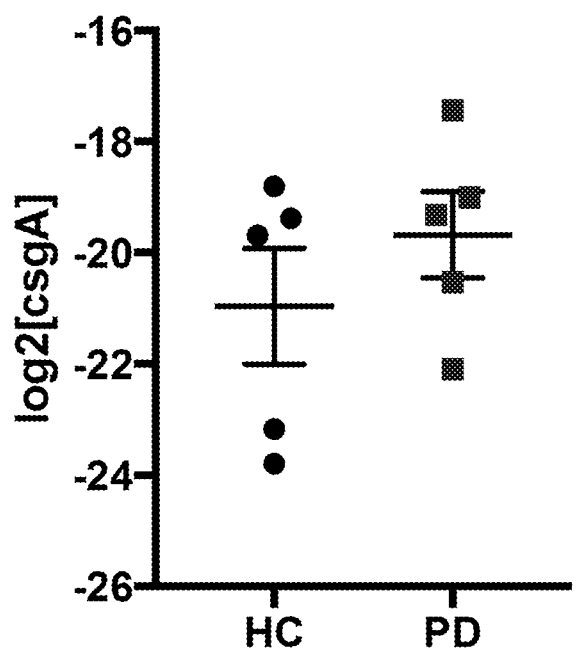
FIGS. 4A-C are a series of graphs depicting fecal abundance of amyloid-producing bacteria in humanized animals. Human samples from previous cohort (ENA Accession: PRJEB17694) were analyzed by PICRUSt to infer abundance of csgA encoded within each population (FIG. 4A). Fecal pellets of Thy1-αSyn (ASO) mice receiving healthy-human derived fecal microbes enriched with either wild-type, curli-sufficient E. coli (WT) or curli-deficient E. coli (ΔcsgBAC) were analyzed by qPCR for rrsA abundance relative to 16s rRNA present in fecal bacterial DNA (FIG. 4B) and by qPCR analysis for csgA expression relative to rrsA in fecal bacterial RNA (FIG. 4C). n=5 (FIG. 4A), n=8 (FIGS. 4B-C). Points represent individuals, bars represent the mean and standard error. Data were analyzed by two-tailed Mann-Whitney test. ***p≤0.001.
Figure 4B:
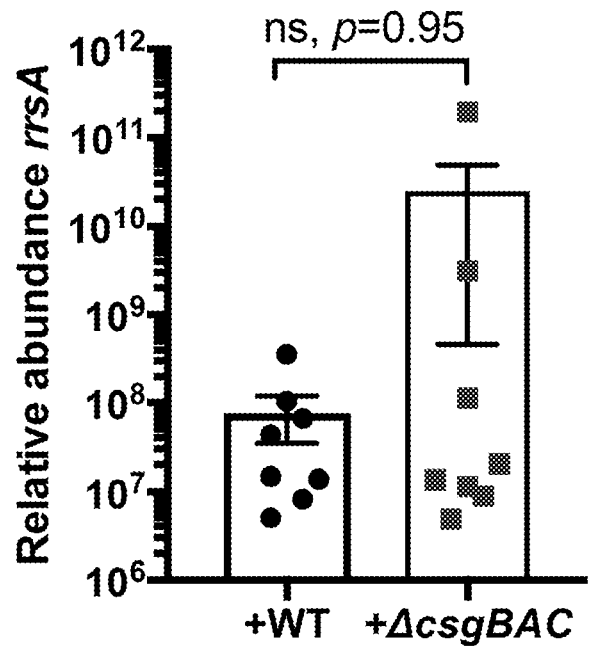
Figure 4C:
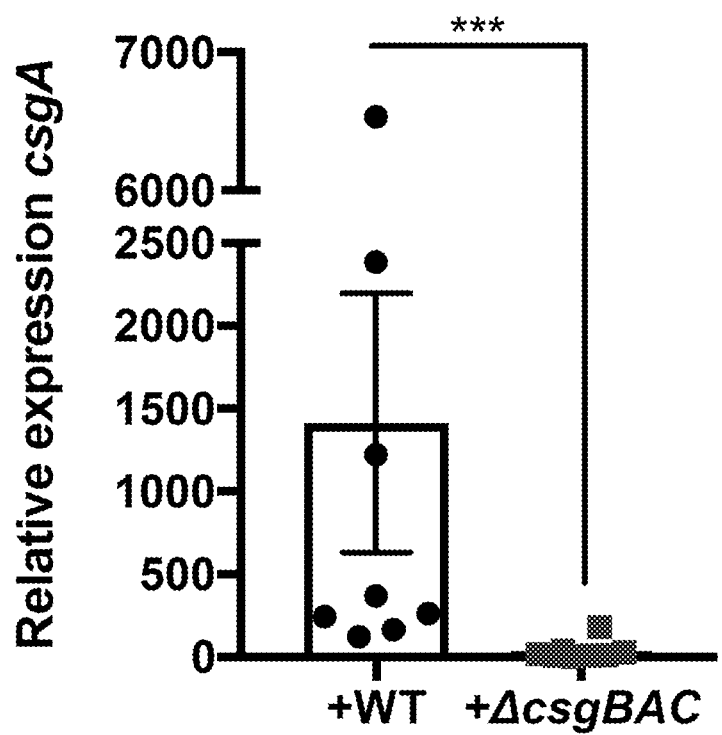

To further explore cause-and-effect relationships between the microbiome and PD, it was studied whether production of curli by an otherwise healthy human microbiome is sufficient to impair motor performance. GF ASO mice were transplanted with microbiota from a healthy human donor predicted to contain low levels of CsgA-producing bacteria, as indicated by PICRUSt analysis following 16S rRNA sequencing. Fecal abundance of amyloid-producing bacteria in these humanized animals was studied. Human samples from previous cohort (ENA Accession: PRJEB17694) were analyzed by PICRUSt to infer abundance of csgA encoded within each population (FIG. 4A). Fecal pellets of Thy1-αSyn (ASO) mice receiving healthy-human derived fecal microbes enriched with either wild-type, curli-sufficient *E. coli* (WT) or curli-deficient *E. coli* (ΔcsgBAC) were analyzed by b, qPCR for rrsA abundance relative to 16s rRNA present in fecal bacterial DNA and by c, qPCR analysis for csgA expression relative to rrsA in fecal bacterial RNA. n=5 (FIG. 4A), n=8 (FIGS. 4B-C). Points represent individuals, bars represent the mean and standard error. Data were analyzed by two-tailed Mann-Whitney test. ***p≤0.001.

Thus, it is shown that intestinal levels of amyloid-producing microbial organisms can be detected in samples in accordance with some embodiments herein, and moreover, intestinal levels of amyloid-producing microbial organisms have been shown differ in subjects having amyloid aggregates that model an amyloid disorder (compared to healthy controls).

Example 10

Figure 5A:
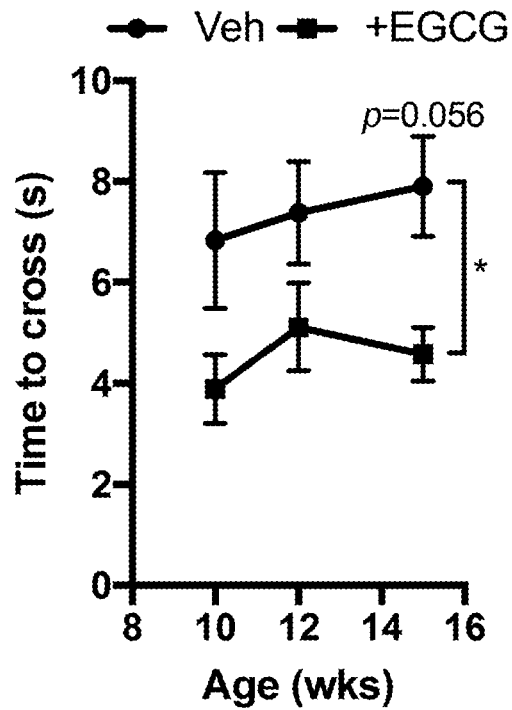
FIGS. 5A-J are a series of graphs depicting inhibition of functional amyloid formation in accordance with some embodiments herein dampens progressive motor deficits. Germ-free Thy1-αSyn mice (ASO) were monocolonized with wild-type E. coli and treated with water alone (Vehicle, Veh) or given EGCG ad lib in drinking water (+EGCG). Motor function was assessed at 10, 12, and 15 weeks of age by quantifying beam traversal time (FIG. 5A), pole descent time (FIG. 5B), nasal adhesive removal time (FIG. 5C), hindlimb clasping score (FIG. 5D), and wirehang tests (FIG. 5E).
Figure 5B:
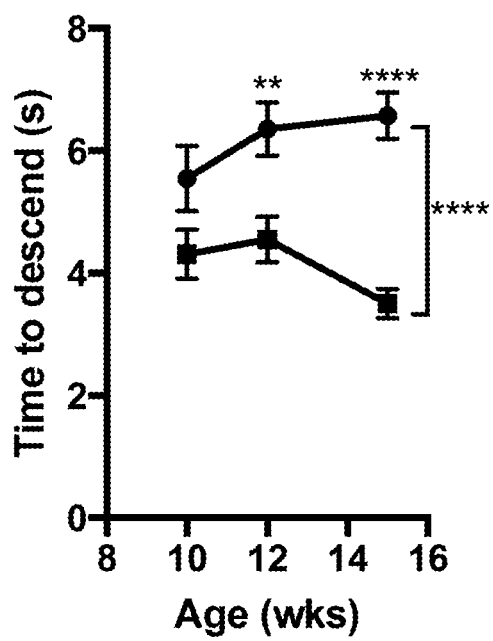
Figure 5C:
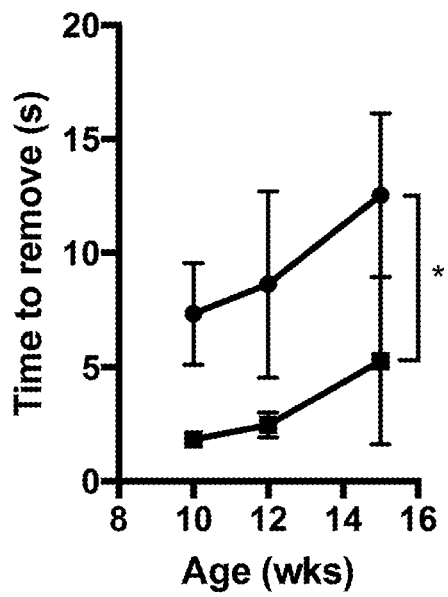
Figure 5D:
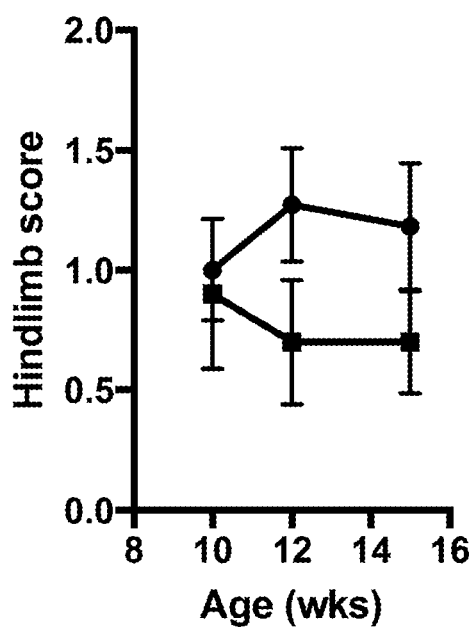
Figure 5E:
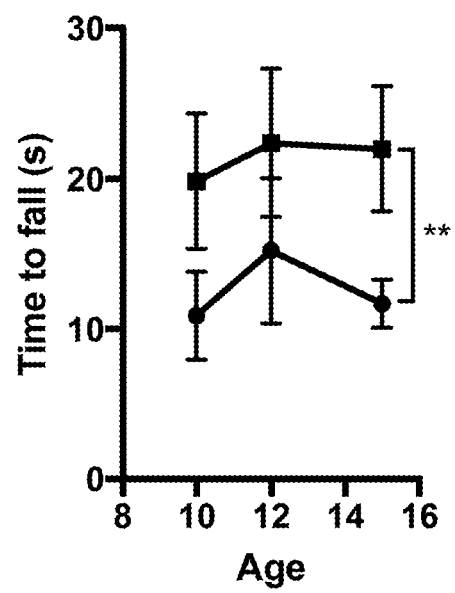
Figure 5F:
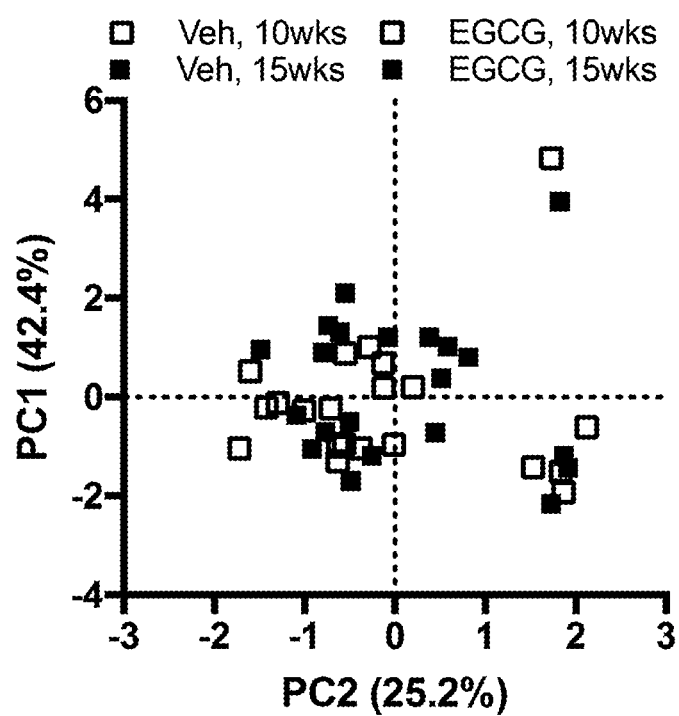
Figure 5G:
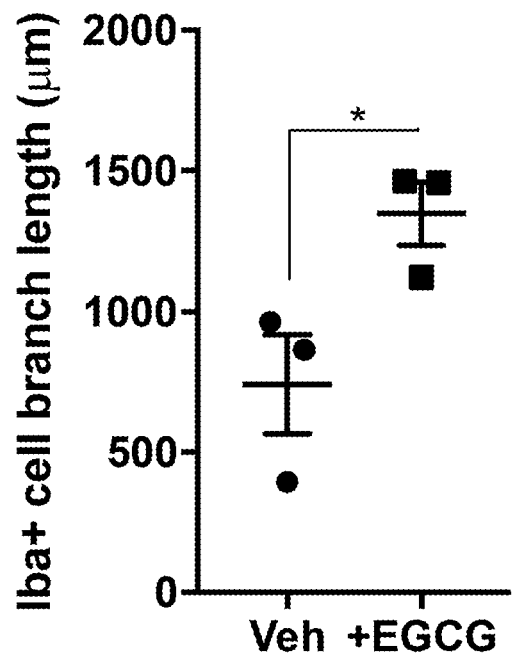
Figure 5H:
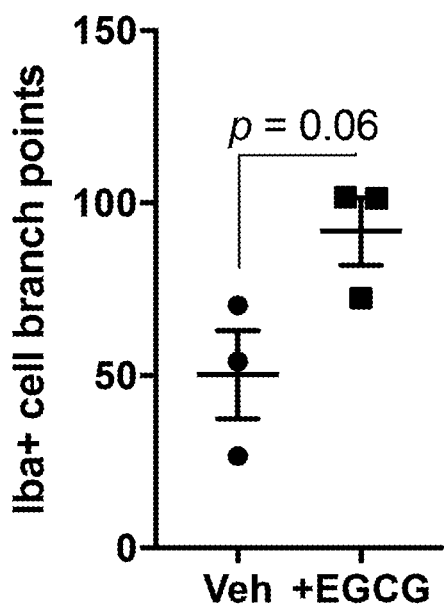
Figure 5I:
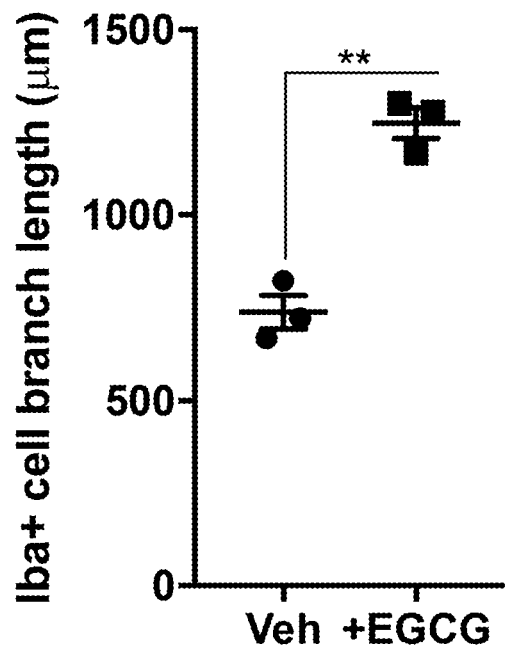
Figure 5J:
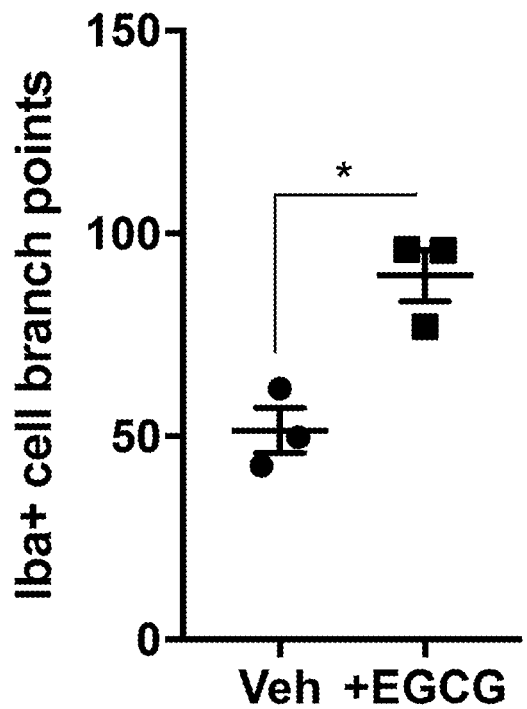

Inhibition of functional amyloid formation was studied. Germ-free Thy1-αSyn mice (ASO) were monocolonized with wild-type *E. coli* and treated with water alone (Vehicle, Veh) or given EGCG ad lib in drinking water (+EGCG). Motor function was assessed at 10, 12, and 15 weeks of age by quantifying beam traversal time (FIG. 5A), pole descent time (FIG. 5B), nasal adhesive removal time (FIG. 5C), hindlimb clasping score (FIG. 5D), and wire hang tests (FIG. 5E). FIG. 5F depicts principal component analysis of compiled motor scores from FIGS. 5A-D. Thin sections of brain were stained for Iba1 (microglia) and morphological characteristics quantified of microglia resident in the striatum (FIGS. 5G-H) and substantia nigra (FIGS. 5I-J). N=10-11 (FIGS. 5A-F), n=3 (FIGS. 5G-J) (averaged from 5-7 cells for branching). Bars represent the mean and standard error. Time courses analyzed by two-way ANOVA, with Sidak post-hoc test for between group comparisons indicated above individual time points, and brackets indicating significance between treatments. Data in (FIGS. 5G-J) analyzed by two-tailed t-test. *p≤0.05; p≤0.01; **p≤0.0001.

Accordingly, inhibition of functional amyloid formation in accordance with some embodiments herein dampens progressive motor deficits. Without being limited by theory, it is contemplated that curli produced by E. coli utilize an amyloid-dependent pathway to exacerbate hallmark motor deficits and pathologies of PD in this preclinical model. It is further contemplated that inhibition of bacterial amyloid production, formation and/or interaction with mammalian amyloids in accordance with some embodiments herein is a useful intervention of neurodegenerative conditions caused by protein aggregation, for example amyloid disorders as described herein.

Example 11

Effects of the bacterial amyloid protein, CsgA on the seeding of αSyn fibrilization were studied. In vitro biophysical analysis was conducted with purified αSyn and CsgA proteins. It was tested whether the major curli subunit, CsgA, is capable of cross-seeding the formation of αSyn aggregations. It was observed that addition of purified CsgA to monomeric αSyn in vitro results in significantly accelerated production of αSyn aggregates (FIGS. 6A-B). FIG. 6A shows aggregation as measured by Thioflavin T fluorescence over time during αSyn amyloid formation alone or in the presence of CsgA monomers (25:1 molar ratio, yellow). FIG. 6B shows time to reach exponential fibrilization, lag phase. FIGS. 6C-H are a series of representative transmission electron micrographs of αSyn alone (FIGS. 6C, 6F) or CsgA alone (FIGS. 6E, 6H), or in combination (FIGS. 6D, 6G), at 0 hours (FIGS. 6C-E) and 60 hours (FIGS. 6F-H) post-aggregation. FIGS. 6I-K are a series of graphs illustrating circular dichroism spectroscopic analysis of αSyn fibrilization alone or in the presence of CsgA at 0, 12.5, and 60 hours post-aggregation. For FIG. 6A and FIG. 6B, n=3. Bars represent the mean and standard error. Data are analyzed by two-tailed, t-test. **p≤0.01. Data are representative of 2 independent trials. Thus, the bacterial amyloid protein, CsgA, in accordance with some embodiments herein seeds αSyn fibrilization. Without being limited by theory, it is contemplated that CsgA not only accelerates the generation of αSyn aggregates in vitro, but these subsequent αSyn structures maintain pathogenic attributes, similar to observations with other amyloids that propagate in a prion-like manner.

Example 12

Effects of CsgA on seeding synuclein aggregation and propagation was studied through transient interactions.

FIG. 7A is a graph showing thioflavin T fluorescence during αSyn amyloid formation alone or in the presence of 5% seeds previously generated by addition of CsgA monomer to αSyn (as in FIG. 2A) or αSyn alone. FIGS. 7B-F are a series of transmission electron micrograph of fibril structures generated by the addition of above seeds and of seeds themselves. FIG. 7G is a graph showing surface plasmon resonance measurements of surface immobilized αSyn with additions of either CsgA monomer or seeds, or DOPS-DOPG cholesterol as positive control. Thus, it is shown that the final CsgA-induced synuclein fibrils purified from completed biochemical reactions maintain an ability to accelerate αSyn amyloid formation. Without being limited by theory, these results are consistent with transient interactions or interactions between oligomeric forms of the proteins at later stages in amyloidogenesis (FIG. 7G).

Accordingly, CsgA was shown to seed synuclein propagation through transient interactions.

Example 13

A library of potential amyloidogenesis inhibitors is obtained. Such libraries may be found in preexisting repositories, or may be generated de novo by, for example, combinatorial synthesis or by solid phase peptide synthesis utilizing such methods as are well known in the art. See, for example, Jensen, K. J. et al., eds, *Peptide Synthesis and Applications*, $2^{nd}$ Edition, 2913, which is incorporated by reference herein for its teachings of solid phase peptide synthesis, combinatorial peptide synthesis, and the generation of peptide libraries. Natural product libraries may also be utilized. In a multi-well assay plate, a bacterial amyloid initiator, such as E. coli CsgA is placed in varying concentrations in one dimension, while a host-derived amyloidogenic protein, such as α-synuclein, is placed in varying amounts in the second dimension, such that each well contains a different ratio of amyloid initiator and amyloid precursor. To each well, a constant amount of an indicator of amyloid formation, such as thioflavin (ThT), is added, as well as a constant amount of an individual test compound. Each tray is agitated to initiate amyloid formation, and thioflavin fluorescence is monitored. Compounds that show deviations in the rate of fluorescence development over time will be identified as candidates that enhance or inhibit amyloid formation.

Example 14

A suspected amyloidogenesis inhibitor is combined with a bacterial amyloid initiator and an amyloid precursor in the presence of Thioflavin T (ThT). Separately, as a control, bacterial amyloid initiator, amyloid precursor, and Thioflavin T are combined in the absence of the suspected amyloidogenesis inhibitor. Thioflavin T fluorescence is monitored over time. A reduction in the rate of increase in Thioflavin T fluorescence, and/or a reduction in the maximum level of Thioflavin T fluorescence in the sample containing the suspected inhibitor, relative to the control sample, confirms that the suspected amyloidogenesis inhibitor is in fact functioning to inhibit amyloid formation.

Example 15

A sample of tissue, fluid, feces, or intestinal contents is collected from a subject. Said sample is combined with a bacterial amyloid initiator, such as E. coli CsgA, a host-derived amyloidogenic protein, such as α-synuclein and an indicator of amyloid formation, such as Thioflavin T (ThT). Thioflavin T fluorescence is monitored. An increase in fluorescence consistent with an increase in the rate of formation of amyloid in the presence of said sample, relative to the rate of amyloid formation in the absence of said sample, indicates an increase in the risk of α-synucleinopathy, including Parkinson's disease and/or Lewy body dementia. This increased risk is further correlated with results from conventional neurological examinations in order to calculate a defined risk of commencement and/or progression of an α-synucleinopathy or other neurodegenerative disorder implicating amyloid formation.

Example 16

In non-binding, black plastic, 96-well plates, 50-100 μM α-synuclein is incubated in 0.01M Tris buffer (pH 7.4) or 0.05 M potassium phosphate buffer pH 7.3 in the presence of 12 μM of Thioflavin T (prepared in water). Purified CsgA monomer in 0.05 M potassium phosphate buffer, pH 7.3 is added to each well at a molar ratio of 1:10, 1:25, 1:50, or 1:100. Inhibitory compounds are prepared in appropriate buffered solutions based on solubility, such as 0.05 M potassium phosphate buffer, pH 7.3 or DMSO. Compounds and appropriate buffer controls are added to α-synuclein- and CsgA-containing wells, to a final volume of 150 μL per well. The concentration of each compound is dependent on the type of compound being screened but generally is expected to fall within the range of 1 μM to 200 μM in initial screens. Details regarding the addition of such compounds depend on the types of compounds available in the accessible small molecule libraries. Independent wells containing α-synuclein alone and CsgA alone serve as specificity controls, or in combination in the absence of potential inhibitors. A single, sterilized glass or Teflon bead with a ~1-2 mm diameter is added to each well. The plate is incubated within a fluorescent-capable microplate reader with continuous orbital shaking (~100-250 rpm) at 37° C. Fluorescence is measured every 1-2 hours with an excitation of 440±10 nm and emission of 490±10 nm. Measurements are taken over a 24-72 hour period. As α-synuclein amyloids form, emission spectra hit maximum intensity ~24-48 hours under these conditions following a sigmoidal curve. After this time, emission intensity can decrease as amyloids become insoluble and non-fluorescent.

Amyloid formation appears over 3 phases (See, e.g., FIG. 1B): (1) a lag phase whereby fluorescence intensity is low occurring over the first ~0-24 hrs; (2) A log phase whereby fluorescence intensity increases logarithmically from ~2-48 hrs; and (3) a plateau phase whereby fluorescence intensity hits a maximum and either remains unchanged for the remaining time period or begins to decrease due to insoluble α-synuclein precipitating out of solution. Maximum intensity occurs between 24-72 hours.

Aggregation kinetics, as measured by thioflavin fluorescence, in the presence of compounds can be normalized to the kinetics observed with α-synuclein and CsgA alone. Potential inhibitors may act to lengthen the lag phase, decrease the rate of change during the log phase, decrease the maximum intensity reached, or any combination thereof.

Once initial candidates are identified, dose responses over a wide-range of concentrations can be determined, as well as specificity against CsgA:synuclein aggregates, or CsgA and α-synuclein individually. In some variations of this screen, CsgA:synuclein aggregates can be monitored until the log phase, and potential inhibitory compounds introduced at this time. Subsequently, inhibitors which can act once amyloid formation is already in process can be identified (See, e.g., FIG. 1B).

Example 17

The assay is practiced as described in Example 16, in which full concentration curves are generated for each compound. This enables accurate determination of the EC50 for each compound and can expose certain compounds limitations (e.g., expose compounds that do not lead to complete inhibition of aggregation).

Example 18

The assay is practiced as described in Example 16, and is formatted for higher throughput screening in a variety of ways. For example, rather than a full concentration curve for each compound, a three-point concentration curve is used to distinguish compounds with a dose-response effect from those with a non-specific and concentration-independent effect. For even higher throughput screening, the assay is formatted in 96-well, 384-well or 1536-well plates and compounds are tested at a single concentration (e.g., 1 μM) and at a single timepoint (e.g., 24-72 hours). This enables the observer to distinguish potential candidates from compounds with no effect or with no effect at a relevant concentration.

Example 19

The assay is practiced as described in Example 16, in which full time course curves are generated for each compound. Time-course curves show whether a compound inhibits in a linear or sigmoidal fashion over time, and/or whether the complete inhibition can be achieved with a given compound.

Example 20

The assay is practiced as described in Example 16, and is further modified to assess mechanistic processes and compound activity in a more dynamic environment in which both α-synuclein (or other host amyloid protein) and curli (or other bacterial amyloid) are present in the assay. The observer then assesses the ability of compounds to inhibit aggregation of one or the other proteins in the presence of an aggregation template. For example, bacterial amyloid component CsgA is known to promote and/or accelerate α-synuclein aggregation. In an in vivo environment, a candidate compound with α-synuclein aggregation inhibition activity is exposed to an aggregation promoting or templating activity from bacterial amyloid. Thus, formatting the assay by inclusion of both monomeric α-synuclein (or other host amyloid) and aggregated bacterial amyloid allows assessment of drug candidates in a more physiologically relevant in vitro environment.

Example 21

The assay is practiced as described in Example 16, wherein the method further comprises combining a curli (bacterial amyloid) aggregation inhibitor with an α-synuclein aggregation inhibitor. This combination has the added benefit of blocking aggregation at two critical points simultaneously. The assay utilizes the monomeric forms of both α-synuclein and curli (CsgA), and measurements analogous to those shown in FIG. 1B are obtained.

Example 22

The assay is practiced as described in Example 16, wherein the method further comprises combining a curli (bacterial amyloid) dis-aggregation promoter with a promoter of α-synuclein dis-aggregation. This combination has the added advantage of effecting dis-aggregation at two critical points simultaneously. The assay utilizes the fully aggregated forms of both α-synuclein and curli, and measurements analogous to those shown in FIG. 1B are obtained.

Example 23

The assay is practiced as described in Example 16, wherein the method further comprises combining a curli (CsgA, bacterial amyloid) aggregation inhibitor with an α-synuclein dis-aggregation promoter. This combination has the added advantage of inhibiting the nucleation or origination of amyloid while simultaneously effecting dis-aggregation of an already initiated process. The assay utilizes the fully aggregated form of α-synuclein and the monomeric form of curli (CsgA), and measurements analogous to those shown in FIGS. 2A-3I are obtained.

Example 24

The assay is practiced as described in Example 16, wherein the method further comprises combining a curli (bacterial amyloid) dis-aggregation promoter with an α-synuclein aggregation inhibitor. This combination has the added advantage of destroying pathogenic bacterial amyloid while simultaneously inhibiting α-synuclein aggregation. The assay utilizes the monomeric form of α-synuclein and the fully aggregated form of curli, and measurements analogous to those shown in FIGS. 2A-3I are obtained.

Example 25

The assay is practiced as in any of Examples 16-24, except that a CsgA mutant that is incapable of aggregation is included. Compounds that rely on the presence of structured (aggregated) CsgA in these processes will show reduced effectiveness in this version of the assay.

Example 26

Human α-synuclein was expressed in E. coli BL21 (DE3) from a plasmid derived from pT7 or pET11a into which the full-length gene for untagged human α-synuclein was inserted. Cells were induced at OD600 0.6 with 0.8 mM IPTG for 4 hours, harvested by centrifugation and suspended in a volume of lysis buffer (10 mM Tris, pH 8.0, 1 mM EDTA, and 1 mM PMSF) equivalent to one-tenth the volume of culture, and lysed by boiling for 20 minutes. Cell debris was pelleted by centrifugation, clarified lysate was treated with 10% streptomycin sulfate at 136 µL/mL followed by glacial acetic acid at 228 µL/mL, lysate was centrifuged, supernatant was transferred to a fresh tube and protein was precipitated via addition of an equal volume of saturated (100%) ammonium sulfate and incubated at 4° C. on a rocking shaker for 1 hour. The protein was pelleted via centrifugation and washed with an equal volume of 100 mM ammonium acetate in chilled ethanol, pelleted via centrifugation, washed twice with chilled ethanol, dried overnight, resuspended in 50 mM potassium phosphate buffer pH 7.3 or 10 mM Tris pH 7.4, and passed through a 50 kDa cut-off column. Immediately prior to use, the purified α-synuclein was filtered with a 0.2 µm nylon filter. The α-synuclein concentration was determined using the absorption at 280 nm or BCA assay.

Example 27

Full length, recombinant CsgA monomers can be prepared as described from Zhou et al. (2012). *Journal of Biological Chemistry* 287(42). Briefly, CsgA is cloned into a pET11d vector containing a C-terminal 6× His tag. Following growth in rich media, CsgA production is induced at an OD600 of approximately 0.9 by 0.5 mM IPTG at 37° C. for 1 hr. Bacteria were lysed in 8M guanidine hydrochloride in 50 mM potassium phosphate buffer, pH 7.3 overnight or for approximately 1-2 hours at room temperature on a rocking platform. After centrifugation at 10,000×g for 20 minutes, the supernatant was sonicated on ice for 6 10 second intervals, incubated with nickel-nitrilotriacetic acid resin (Sigma) at room temperature for 1 h and then loaded onto a disposable polypropylene column (Thermo). The column was washed with 50 mM potassium phosphate buffer, pH 7.3 and 50 mM potassium phosphate buffer pH 7.3 containing 12.5 mM imidazole. Proteins were eluted with 50 mM potassium phosphate buffer, pH 7.3 containing 125 mM imidazole. To get monomeric CsgA, fractions containing the target protein were combined and loaded onto a 30-kDa centrifugal filter unit (Thermo) to remove dimers and other oligomers. Purified CsgA was passed through a pre-chilled desalting column (Zeba) to remove imidazole.

Alternatively, synthetic hexapeptides of CsgA consisting of the sequence: Nterm-QYGGNN-Cterm, are commercially available from Bio-synthesis, Inc.

Example 28

Another alternative is to utilize pre-formed CsgA amyloid seeds, by preparing purified curli extracts from biofilms as described in Collinson et al. (1991). *Journal of Bacteriology.* 173(15). Wild-type *Escherichia coli* is grown on YESCA media with or without Congo Red dye added, for 3-7 days at room temperature. The cultures are scraped into 10-30 mLs of 10 mM Tris, pH 8. Cells are lysed by sonication or by freeze-thaw. Cell lysates are treated with 0.1 mg RNase A, 0.1 mg DNase I and MgCl₂ added to 1 mM, and incubated for 20-30 min at 37 C. Lysozyme is added to 1 mg/mL and further incubated at 37° C. for 20-40 min. SDS is added to 1% and incubated at 37° C. for 20-40 min. Insoluble material is collected by centrifugation at 12,000×g for 15 min. Samples are re-suspended in 1-10 mL Tris buffer, boiled at 90° C. for 15 min, and the above processes are repeated (Digestion with RNase, DNase, Lysozyme, and SDS treatment). Samples are washed twice with Tris buffer, resuspended in Laemli buffer, boiled, and loaded onto an SDS-PAGE gel (4-20%). Samples are electrophoresed at 20 mA for 5 hrs. The remaining insoluble material in the stacking gel is collected, washed three times with water, washed twice with 95% ethanol, and dried. The sample is resuspended in 0.2M glycine pH 1.5 and boiled for 10-15 min. Insoluble material is collected by centrifuging at 16 k×g for 10 min. The insoluble material is washed five times with water, and resuspended in PBS. Finally, the sample is sonicated by electrode or water bath for 1 hour before protein content determined by BCA or absorbance at 280 nm.

Such alterations may change the kinetics of aggregation, the concentrations of compounds needed to inhibit aggregation, the ratios required to display CsgA-mediated synuclein aggregation, or combinations of the above.

Example 29

In other iterations of the protein purifications used in the assays of Examples 27 and 28, CsgA may be produced without a histidine tag or with an alternate tag, and it may contain a sequence to promote its excretion from the cell. α-synuclein may be engineered to contain a histidine tag or other tag to promote purification by affinity for example to immobilized metals such as nickel. CsgA and α-synuclein may be purified using alternate methods familiar to one skilled in the art, such as ammonium sulfate precipitation with alternate concentrations of ammonium sulfate in a single step or in multiple steps with increasing concentrations of ammonium sulfate; alternately, ammonium sulfate precipitation may be omitted. Alternate resins or materials to separate CsgA or α-synuclein from other proteins based on protein affinity, cation exchange, anion exchange, hydrophobic interactions, multiple modes or mixed modes may be used, as are familiar to one skilled in the art. Protein separation may be performed using batch purification, pre-packed columns, gravity flow, low pressure, high pressure, and high pressure liquid chromatography, using methods familiar to one skilled in the art, and the methods may be used individually or in combination. CsgA or α-synuclein may be separated from other proteins on the basis of size using methods familiar to one skilled in the art, such as size exclusion chromatography or high pressure liquid chromatography. CsgA and α-synuclein may be purified under denaturing conditions for all or part of the assay purification process, with alternate concentrations of guanidinium hydrochloride or with alternate denaturants at various concentrations known to one skilled, such as urea. Alternately, CsgA and α-synuclein may be purified under native conditions familiar to one skilled in the art; under native conditions or with steps using non-denaturing buffers, CsgA is generally purified rapidly to avoid aggregation during the purification process. His-tagged CsgA may be eluted from immobilized metal affinity materials such as Ni-NTA using alternate methods known to one skilled in the art, such as decreasing pH or addition of chelators such as ethylenediaminetetraacetic acid. In addition to or instead of immobilized metal affinity chromatography based on the affinity of histidine residues in the protein to immobilized nickel, alternate immobilized metal affinity chromatography or batch purification methods may be used, such as materials with immobilized copper, zinc, cobalt or nickel interacting with histidine or alternate amino acids in the protein, such as cysteine or tryptophan, as known to one skilled in the art. As known to one skilled in the art, alternate buffers may be used with Ni-NTA agarose, such as tris(hydroxymethyl)aminomethane, ("Tris"); 4-(2-hydroxyethyl)-1-piperazine ethanesulfonic acid, ("HEPES"); 3-(N-morpholino)propanesulfonic acid, ("MOPS"), optionally including sodium chloride, potassium chloride or other salts, and various detergents and reducing agents of compositions and concentrations compatible with Ni-NTA agarose chromatography or batch purification.

In the assays, alternate concentrations of dimethyl sulfoxide may be used, and concentrations of dimethyl sulfoxide significantly elevated above or decreased below 1% may affect the aggregation kinetics of CsgA and α-synuclein. Alternate concentrations of Thioflavin T may be used in the assay and may affect the fluorescent signal and sensitivity of the assay. Alternate concentrations of CsgA and α-synuclein may be used and such alterations may affect aggregation kinetics of α-synuclein and CsgA in the assay. Alternate concentrations of compounds may be tested in the assay, and dose-responses may be evaluated. Additional reagents may be added to the assay which may affect aggregation kinetics of α-synuclein and CsgA depending on their concentration, including detergents such as sodium dodecyl sulfate. Shaking may be included at alternate intervals in the assay and may affect CsgA and α-synuclein aggregation kinetics. 2 mm glass beads may be omitted from the assays including α-synuclein or may be included in the assays including CsgA, or other sizes or compositions of beads may be used, and these alterations may affect CsgA and α-synuclein aggregation kinetics. Alternate buffers, such as Tris, HEPES and MOPS, and alternate buffer concentrations may be used in the assay and may affect CsgA and α-synuclein aggregation kinetics. Any plate reader capable of fluorescent reads with excitation at 438 nM and emission at 495 nm with sufficiently narrow bandwidths, such as 10 nm, may be used. Alternate microplates may be used in the assay, such as black microplates with clear bottoms. Plates may be sealed with alternate coverings that do not absorb ThT fluorescence, or the coverings may be removed prior to reads. The fluorescence may be read at a single endpoint or at multiple points over various time intervals, and the time intervals at which the fluorescence is measured may be constant or may vary during the course of the assay. Other metrics may be used to determine the effects of the compounds on α-synuclein and CsgA expression, including examination of Thioflavin T signal over the course of a kinetic read to determine lag phase in Thioflavin T fluorescence, the shape of a curve produced by the fluorescent signal, and the slope of the curve.

Example 30

To assess the effects of compounds on aggregation of α-synuclein, a cell-free assay was performed using purified α-synuclein and Thioflavin T. In the assay, human α-synuclein was expressed in *E. coli* BL21 (DE3) from a plasmid derived from pT7 or pET11a into which the full-length gene for untagged human α-synuclein was inserted. Cells were induced at OD600 0.6 with 0.8 mM IPTG for 4 hours, harvested by centrifugation and suspended in a volume of lysis buffer (10 mM Tris, pH 8.0, 1 mM EDTA, and 1 mM PMSF) equivalent to one-tenth the volume of culture and lysed by boiling for 20 minutes. Cell debris was pelleted by centrifugation, clarified lysate was treated with 10% streptomycin sulfate at 136 μL/mL followed by glacial acetic acid at 228 μL/mL, lysate was centrifuged, supernatant was transferred to a fresh tube and protein was precipitated via addition of an equal volume of saturated (100%) ammonium sulfate and incubated at 4° C. on a rocking shaker for 1 hour. The protein was pelleted via centrifugation and washed with an equal volume of 100 mM ammonium acetate in chilled ethanol, pelleted via centrifugation, washed twice with chilled ethanol, dried overnight, resuspended in 50 mM potassium phosphate buffer pH 7.3 or 10 mM Tris pH 7.4, and passed through a 50 kDa cut-off column. Immediately prior to use, the purified α-synuclein was filtered with a 0.2 μm nylon filter. The assay was conducted in 96-well black microplates with a single 1-2 mm glass bead in each well, 20-40 μM ThioflavinT, 1% DMSO, α-synuclein at 50 μM and compounds at 20-50 μM. Plates were sealed with sealing tape (ThermoFisher 232701), incubated at 37° C. in a Tecan Nano F200 plate reader with excitation at 438 nm using a 439 nm filter with a bandwidth of 8 nm, and emission at 495 nm with a 490 nm filter with a bandwidth of 10 nm. During the assay, plates were shaken continuously or were shaken for 999 seconds every 18 minutes. Readings were performed for up to 72 hours. Readings were performed hourly for up to 73 hours. The effect of compounds on α-synuclein aggregation in the assay was determined with data from 36 hours. Fluorescence values for each compound with α-synuclein were first adjusted by subtracting the average fluorescence of the compound in the absence of α-synuclein. These adjusted values were normalized by dividing them by the average fluorescence in the no-compound (i.e., untreated) control wells containing α-synuclein, and the average normalized fluorescence with the compound was expressed as a percentage of the average fluorescence observed in untreated controls. Percent inhibition of α-synuclein aggregation by a compound was determined by subtracting the percent average fluorescence with the compound at 24 hours from 100%. Results are shown in Table 4. A higher positive percent inhibition reflects greater inhibition of α-synuclein aggregation, while a negative percent inhibition reflects potentiation of α-synuclein aggregation.

Example 32

In Vitro ThioflavinT Assay to Determine Effects of Compounds on CsgA Aggregation.

To assess the effects of compounds on aggregation of *E. coli* CsgA, a cell-free assay was performed using purified CsgA and Thioflavin T. In the assay, histidine-tagged CsgA was over-expressed in *E. coli* NEB 3016 slyD::kan cells harboring a pET11d vector containing csgA with the sequence for 6 histidine residues added to the C-terminus and without the Sec signal (amino acid 1-22) sequence. To induce over-expression of CsgA, 0.5 mM isopropyl β-D-1-thiogalactopyranoside ("IPTG") was added to cultures with an optical density at 600 nm ($OD_{600}$) of 0.8-1, and induced cells were cultured at 37° C. for 1 hour prior to harvest via centrifugation. Cells were lysed under denaturing conditions with 8 M guanidine hydrochloride in 50 mM potassium phosphate buffer pH 7.3, for 1-2 hours on a rocking platform at room temperature or at 4° C. overnight, and CsgA was purified via immobilized-metal affinity chromatography by batch purification with Nickel-NTA agarose and a combination of low pressure and gravity flow through a disposable polypropylene column, including washes under low pressure applied manually via application of a syringe plunger to the column with 50 mM potassium phosphate buffer pH 7.3 followed by 12.5 mM imidazole in 50 mM potassium phosphate buffer pH 7.3, and elution by gravity flow with 125 mM imidazole in 50 mM potassium phosphate buffer pH 7.3. Buffers with imidazole were freshly prepared prior to the protein purification. Purified CsgA was passed through a 30 kDa molecular weight cut-off filter and passed through a desalting column. All steps of the CsgA purification in the absence of guanidine hydrochloride were conducted in rapid succession with as little delay as possible. CsgA was quantified via BCA assay. The assay was conducted in 96-well black microplates with 20-40 µM ThioflavinT, 50 mM potassium phosphate buffer pH 7.3, 1% DMSO, CsgA at 6-20 µM, and compounds at 20 µM. Plates were incubated at 25° C. in a Tecan Nano F200 plate reader with excitation at 438 nm using a 439 nm filter with a bandwidth of 8 nm, and emission at 495 nm with a 490 nm filter with a bandwidth of 10 nm, or in a SpectraMax M5 or SpectraMax® i3× with excitation at 438 nM and emission at 495 nm. During the assay, plates were shaken initially for 5 seconds and subsequently for 3 seconds prior to fluorescent readings. Readings were performed every 20 minutes for up to 24 hours. The effect of compounds on CsgA aggregation in the assay was determined with data from 6-9 hours. Fluorescence values for each compound with CsgA were first adjusted by subtracting the average fluorescence of the compound in the absence of CsgA. These adjusted values were normalized by dividing them by the average fluorescence in the no-compound (i.e., untreated) control wells containing CsgA. The median normalized fluorescence from 6-6.5 hours or 8-9 hours with the compound was expressed as a percentage of the median fluorescence observed in untreated controls over the same time period. Percent inhibition of CsgA aggregation by a compound was determined by subtracting the percent average fluorescence with the compound rom 100%. Results are shown in Table 4. A higher positive percent inhibition reflects greater inhibition of CsgA aggregation, while a negative percent inhibition reflects potentiation of CsgA aggregation.

In Vitro Thioflavin T Assay to Determine the Effects of Compounds on CsgA-Seeded α-Synuclein Aggregation.

To assess the effects of compounds on aggregation of α-synuclein seeded by *E. coli* CsgA, a cell-free assay was performed using purified α-synuclein, purified CsgA and Thioflavin T. In the assay, histidine-tagged CsgA was over-expressed in *E. coli* NEB 3016 slyD::kan cells harboring a pET11d vector containing csgA with the sequence for 6 histidine residues added to the C-terminus and without the Sec signal (amino acid 1-22) sequence. To induce over-expression of CsgA, 0.5 mM IPTG was added to cultures with an optical density at 600 nm ($OD_{600}$) of 0.8-1, and induced cells were cultured at 37° C. for 1 hour prior to harvest via centrifugation. Cells were lysed under denaturing conditions with 8 M guanidine hydrochloride in 50 mM potassium phosphate buffer pH 7.3 for 1-2 hours on a rocking platform at room temperature or at 4° C. overnight, and CsgA was purified via immobilized-metal affinity chromatography by batch purification with Nickel-NTA agarose and a combination of low pressure and gravity flow through a disposable polypropylene column, including washes under low pressure applied manually via application of a syringe plunger to the column with 50 mM potassium phosphate buffer pH 7.3 followed by 12.5 mM imidazole in 50 mM potassium phosphate buffer pH 7.3, and elution with 125 mM imidazole in 50 mM potassium phosphate buffer pH 7.3. Buffers with imidazole were freshly prepared prior to the protein purification. Purified CsgA was passed through a 30 kDa molecular weight cut-off filter and through a desalting column. All steps of the CsgA purification in the absence of guanidine hydrochloride were conducted in rapid succession with as little delay as possible. CsgA was quantified using a BCA assay or absorbance at 280 nm with a nanodrop spectrophotometer. Human α-synuclein was expressed in *E. coli* BL21 (DE3) from a plasmid derived from pT7 or pET11a into which the full-length gene for untagged human α-synuclein was inserted. Cells were induced at OD600 0.6 with 0.8 mM IPTG for 4 hours. Cells were lysed by boiling for 20 minutes, cell debris was pelleted by centrifugation, clarified lysate was treated with 10% streptomycin sulfate at 136 µL/mL and glacial acetic acid at 228 µL/mL, lysate was centrifuged, supernatant was transferred to a fresh tube and protein was precipitated via addition of an equal volume of saturated (100%) ammonium sulfate. The ammonium sulfate pellet was washed with an equal volume of 100 mM ammonium acetate in ethanol, pelleted via centrifugation, washed twice with ethanol, dried overnight, resuspended in 10 mM Tris pH 7.4, and passed through a 50 kDa cut-off column. Immediately prior to use, the purified α-synuclein was filtered with a 0.2 µm nylon filter. The assay was conducted in 96-well black microplates with a single glass 1-2 mm bead per well, 20-40 µM ThioflavinT, 1% DMSO, 2 µM CsgA, 50-60 µM α-synuclein, 100 mM sodium chloride, 9.3 mM potassium phosphate pH 7.3, and compounds at 50 µM. Compounds were tested in triplicate. Plates were sealed with sealing tape (ThermoFisher 232701), incubated with continuous shaking at 37° C. in a Tecan Nano F200 plate reader, with excitation at 438 nm using a 439 nm filter with a bandwidth of 8 nm, and emission at 495 nm with a 490 nm filter with a bandwidth of 10 nm, or in a SpectraMax M5 or SpectraMax® i3× with excitation at 438 nM and emission at 495 nm., and readings were performed hourly for up to 73 hours. The effect of compounds on CsgA-seeded α-synuclein aggregation in the assay was determined with data from 17, 18 or 50-52 hours. Fluorescence values for each compound with CsgA and α-synuclein were first adjusted by subtracting the average fluorescence of the compound in the absence of CsgA and α-synuclein. These adjusted values were normalized by dividing them by the average fluorescence in the no-compound (i.e., untreated) control wells containing CsgA and α-synuclein, and the average or median normalized fluorescence with the compound at 17, 18 or 50-52 hours was expressed as a percentage of the average or median fluorescence observed in untreated controls at the same timepoints. Percent inhibition of CsgA-seeded α-synuclein aggregation by a compound was determined by subtracting the percent average or median fluorescence with the compound at from 100%. Results are shown in Table 4. A higher positive percent inhibition reflects greater inhibition of CsgA-seeded α-synuclein aggregation, while a negative percent inhibition reflects potentiation of CsgA-seeded α-synuclein aggregation.

TABLE 4

| Compound | Inhibition of Aggregation | | |
|---|---|---|---|
| | αSyn | CsgA-seeded αSyn | CsgA |
| 1 | | | 8% (−) |
| 2 | 93% (+++) | 63% (+++) | 45% (++) |
| 3 | | | −11% (−−) |
| 4 | | | 43% (++) |
| 5 | 22% (+) | | −4% (−) |
| 6 | 36% (++) | >90% (+++) | 40% (++) |
| 7 | | | 2% (−) |
| 8 | 18% (+) | | 13% (+) |
| 9 | | | −33% (−−) |
| 11 | | | −24% (−−) |
| 12 | | | −23% (−−) |
| 13 | | | −16% (−−) |
| 14 | 3% (−) | 74% (+++) | |
| 15 | | | 52% (++) |
| 16 | | | 31% (++) |
| 17 | | | 18% (+) |
| 18 | | | 16% (+) |
| 19 | 29% (+) | 14% (+) | 18% (+) |
| 20 | | 11% (+) | 61% (+++) |
| 21 | −1% (−) | | 4% (−) |
| 22 | | | 58% (++) |
| 23 | | −22% (−−) | −4% (−) |
| 24 | | −27% (−−) | −1% (−) |
| 25 | 17% (+) | | −150% (−−) |
| 26 | 24% (+) | <−50% (−−) | 8% (−) |
| 27 | 49% (++) | 79% (+++) | 44% (++) |
| 28 | 20% (+) | <−50% (−−) | −6% (−) |

TABLE 4-continued

| Compound | Inhibition of Aggregation | | |
|---|---|---|---|
| | αSyn | CsgA-seeded αSyn | CsgA |
| 29 | | | 9% (−) |
| 30 | | | −56% (−−) |
| 31 | | | −20% (−−) |
| 32 | 48% (++) | >90% (+++) | 53% (++) |
| 33 | 92% (+++) | | 59% (++) |
| 34 | | | −11% (−−) |
| 35 | | | −53% (−−) |
| 36 | | | −47% (−−) |
| 37 | | | −17% (−−) |
| 38 | 14% (+) | | |
| 39 | | | −4% (−) |
| 40 | −12% (−−) | | 15% (+) |
| 41 | 17% (+) | | 18% (+) |
| 42 | 98% (+++) | >90% (+++) | 114% (+++) |
| 43 | 63% (++) | | 90% (+++) |
| 44 | 98% (+++) | >90% (+++) | 64% (+++) |
| 45 | | | −18% (−−) |
| 46 | | | −7% (−) |
| 47 | | | 13% (+) |
| 48 | 37% (++) | >90% (+++) | −2% (−) |

Compound activity ranges presented are defined as follows: (−−) is less than −10% inhibition; (−) is between −10% to 10% inhibition; (+) is between 10% to 30% inhibition; (++) is between 30% to 60% inhibition; and (+++) is greater than 60% inhibition.

Results of Thioflavin T Assays of Compound Effects on Aggregation.

Compound activity ranges are defined below Table 4. Tested compounds demonstrated a variety of effects in the Thioflavin T assays of aggregation of α-synuclein, CsgA-seeded α-synuclein, and CsgA. Compounds of Table 4 demonstrated a range of activities. The inhibition of the various types of aggregation as described in Table 4 suggests that the compounds of the invention (e.g., compounds shown in Table 4) may be useful in preventing α-synuclein aggregation, the seeding of α-synuclein aggregation by CsgA or other microbial amyloids, and the formation of microbial amyloids that may seed α-synuclein aggregation in vivo, and these compounds may thereby be useful in preventing or treating Parkinson's Disease and other α-synucleinopathies. Oral administration of these compounds may allow relatively high concentrations to be achieved in the gut, where microbes producing amyloids may be abundant, and the compounds could inhibit their seeding of α-synuclein aggregation. Inhibition by these compounds of aggregation of α-synuclein on its own could be independently beneficial or may be synergistic with their inhibition of microbial amyloid-seeded α-synuclein aggregation. In keeping with Braak's hypothesis of prion-like propagation of α-synuclein from the enteric nervous system to the central nervous system (see, e.g., Rietdijk et al., "Exploring Braak's Hypothesis of Parkinson's Disease," *Front. Neurol.*, 13 Feb. 2017), these inhibitory effects could be beneficial in preventing propagation of α-synuclein aggregates in both the enteric and central nervous systems; furthermore, if orally administered compounds alleviate a continual seeding of α-synuclein aggregation by microbial amyloids or independent formation of α-synuclein aggregates, the processes by which subjects may clear α-synuclein aggregates may be able to have a greater net effect (i.e., the processed may be able to keep pace with the aggregates formed), and the compounds may thereby be efficacious in preventing or treating Parkinson's Disease and other microbial amyloid-seeded α-synucleinopathies. Without being limited by theory, oral administration may provide particular benefit in the gastrointestinal tract, potentially restoring gastrointestinal function in those patients in whom it is compromised or in preventing or slowing additional loss of gastrointestinal function and/or improving one or more symptoms of, e.g., dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof, in patients with α-synucleinopathies or in subjects at risk for developing α-synucleinopathies.

As shown in Table 4, some compounds demonstrated inhibition of only one or two types of aggregation in the assays, while other compounds appeared inactive or enhanced one or more types of aggregation, and some compounds inhibit three types of aggregation in the assays.

Example 33

Enteroendocrine cells (STC1 cell line cells) were treated with *E. coli* K12 or the ΔcsgBAC, curli-deficient strain at an MOI of 10:1 for 4 hours. Cells were lysed, and protein samples assessed by SDS-PAGE and western blot for alpha-synuclein (αSyn) and actin, as loading control. The western blot is shown in FIG. 9. These results indicate that CsgA affects αSyn aggregation in the gut, for example in enteroendocrine cells.

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

Example 34

Preparation of 2-(3,5-dihydroxybenzamido)-N-(3,4,5-trihydroxyphenyl)-4,5,6,7-tetrahydrobenzo[b]thiophene-3-carboxamide. (Compound 3)

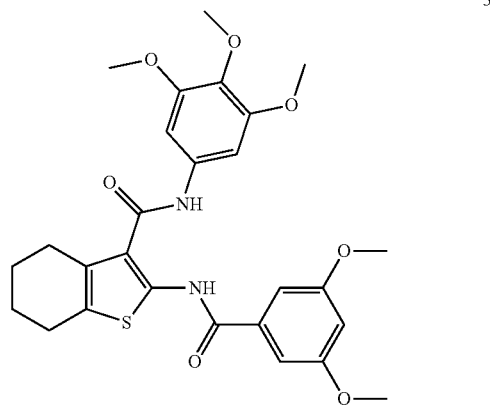

Step 1: Synthesis of ethyl 2-(3,5-dimethoxybenzamido)-4,5,6,7-tetrahydrobenzo[b]thiophene-3-carboxylate

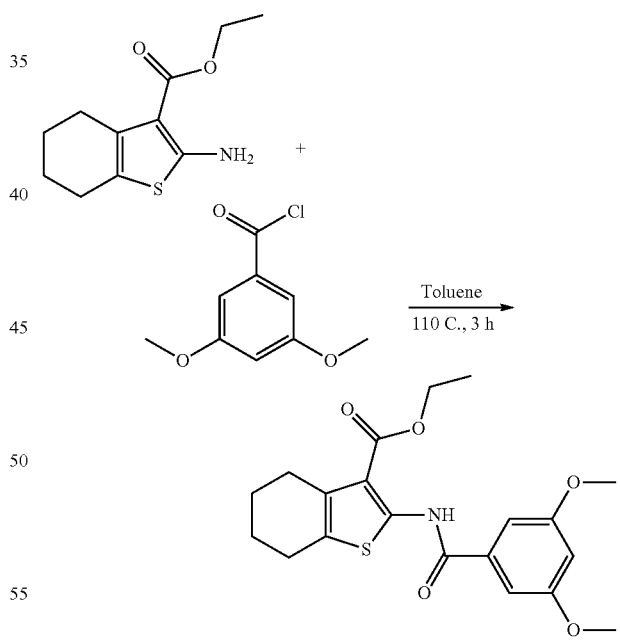

Ethyl 2-amino-4,5,6,7-tetrahydrobenzo[b]thiophene-3-carboxylate (1.0 g, 4.4 mmol) was dissolved in toluene and 3,5-trimethoxybenzoyl chloride (0.89 g, 4.4 mmol) was added. The reaction mixture was stirred for 30 min then heated at 110° C. for 3 hrs. The reaction mixture was cooled at 0° C. The solid was collected by filtration and washed with cold toluene (2×10 mL) to give ethyl 2-(3,5-dimethoxybenzamido)-4,5,6,7-tetrahydrobenzo[b]thiophene-3-carboxylate as an off white solid (1.5 g, 86.8%). Preparative High Pressure Liquid Chromatography (HPLC) Method H: Shimadzu LC-20AP, column X-Bridge C18 (250×19) mm, 5 micron, flow rate 15.0 mL/min, mobile phase A: 5 mM ammonium acetate in water, B: 100% acetonitrile. Liquid Chromatography Mass Spectrum (LCMS): 99.67% (RT: 2.412, 258 nm) (MS: ESI+ve 390.5 [M+H]).

Step 2: Synthesis of 2-(3,5-dimethoxybenzamido)-N-(3,4,5-trimethoxyphenyl)-4,5,6,7-tetrahydrobenzo[b]thiophene-3-carboxamide. (Compound 3)

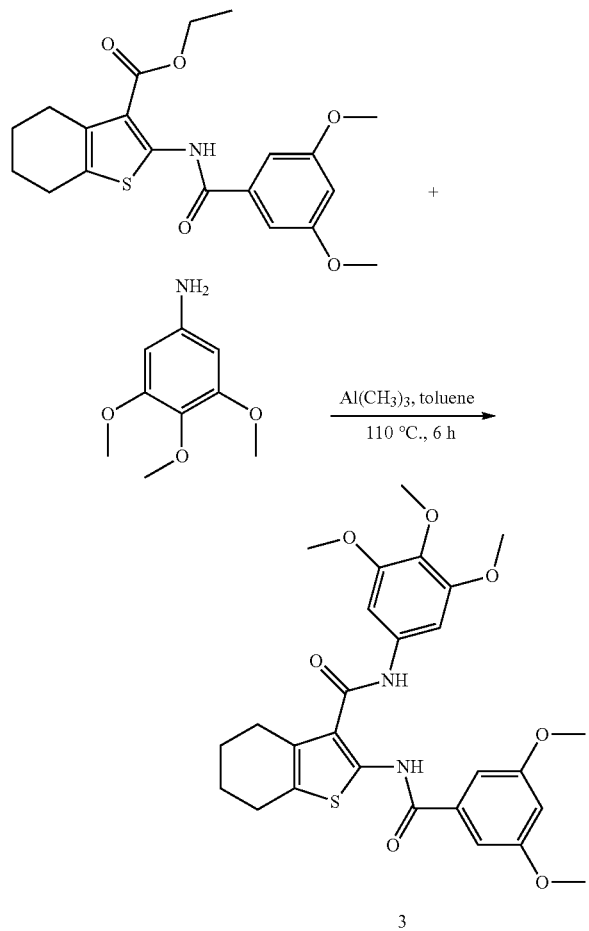

Ethyl 2-(3,5-dimethoxybenzamido)-4,5,6,7-tetrahydrobenzo[b]thiophene-3-carboxylate (0.20 g, 0.513 mmol) was dissolved in toluene (8.0 mL), The reaction mixture was cooled to 0° C. and a 2 M solution of trimethylaluminum in toluene (0.487 mL, 0.975 mmol) was added. After 30 min, 3,4,5-trimethoxyaniline (0.112 g, 0.616 mmol) was added and the mixture was heated at 110° C. for 4 hrs. After cooling to room temperature, the reaction was quenched with ice water (30 mL) and extracted with dichloromethane (3×30 mL). The organic layer was dried over sodium sulphate and concentrated. The crude residue was triturated with methanol (10 mL) to give 2-(3,5-dimethoxybenzamido)-N-(3,4,5-trimethoxyphenyl)-4,5,6,7-tetrahydrobenzo[b]thiophene-3-carboxamide (Compound 3) (79 mg, 29% yield) as an off white solid. LCMS: 100% (RT: 2.286, 254 nm) (MS: ESI+ve 526.83 [M+H]). $^1$H NMR: (400 MHz, DMSO-$d_6$) δ ppm: 1.970 (t, 2H, J=26.5), 2.811 (t, 2H, J=24.3) 2.939 (t, 2H J=24.3) 3.901 (s, 9H), 3.942 (s, 6H), 6.683 (s, 1H), 6.888 (s, 2H) 7.617 (s, 1H), 12.949 (s, 1H).

Example 35

Preparation of N-phenyl-2-(3,4,5-trimethoxybenzamido)-4,5,6,7-tetrahydrobenzo[b]thiophene-3-carboxamide. (Compound 9)

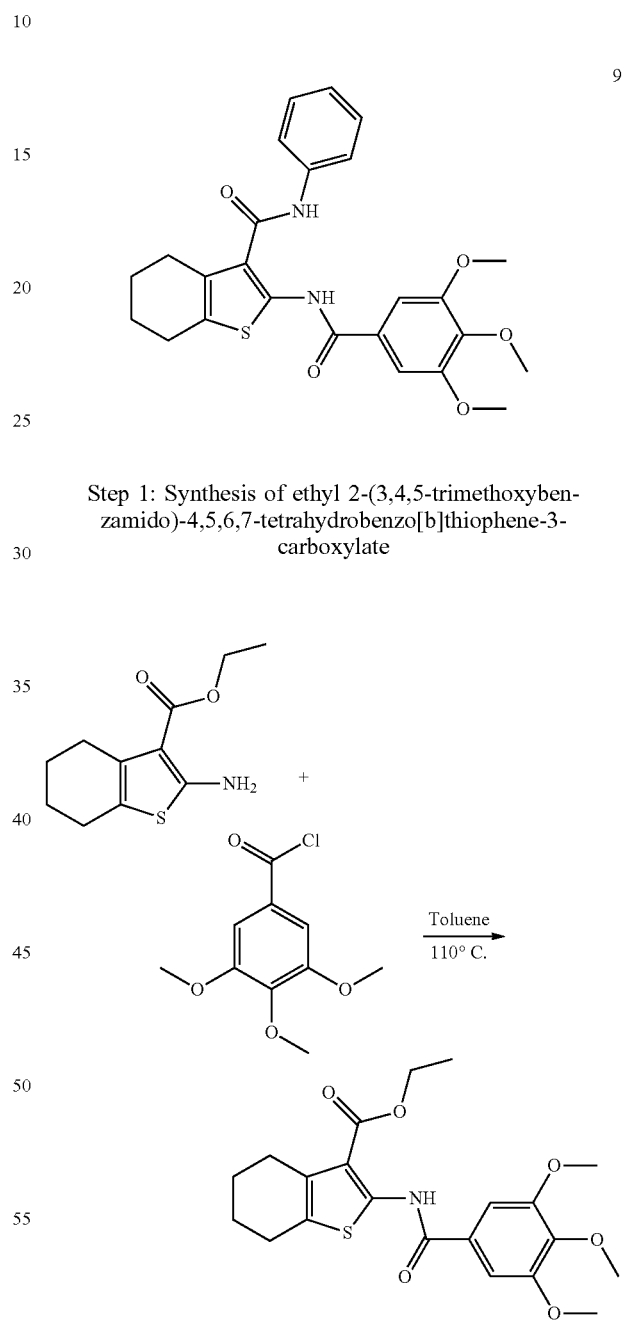

Step 1: Synthesis of ethyl 2-(3,4,5-trimethoxybenzamido)-4,5,6,7-tetrahydrobenzo[b]thiophene-3-carboxylate A mixture of ethyl 2-amino-4,5,6,7-tetrahydrobenzo[b]thiophene-3-carboxylate (10 g, 0.044 mol) and 3,4,5-trimethoxybenzoyl chloride (10.23 g, 0.0443 mol) in toluene was stirred for 30 min then heated to 110° C. for 3 hrs. The reaction mixture was cooled at 0° C. The resulting solid was collected by filtration and washed with cold toluene (2×50 mL) to obtain ethyl 2-(3,4,5-trimethoxybenzamido)-4,5,6,7-

85 tetrahydrobenzo[b]thiophene-3-carboxylate (10.5 g, 56.4% yield) as an off white solid. LCMS: 94.26% (RT: 2.345, 265 nm) (MS: ESI+ve 420.52 [M+H]).

Step 2: Synthesis of N-phenyl-2-(3,4,5-trimethoxy-benzamido)-4,5,6,7-tetrahydrobenzo[b]thiophene-3-carboxamide. (Compound 9)

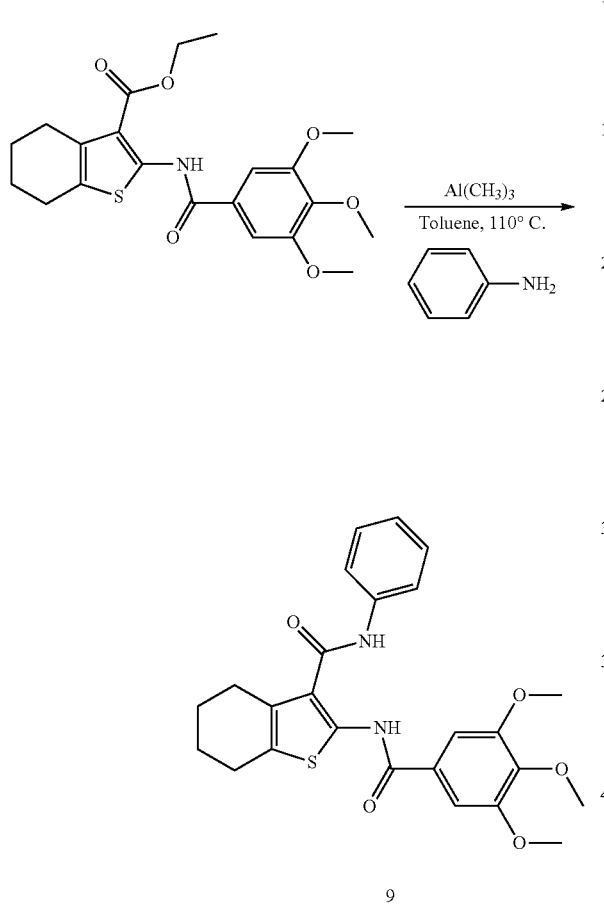

Ethyl 2-(3,4,5-trimethoxybenzamido)-4,5,6,7-tetrahydrobenzo[b]thiophene-3-carboxylate (0.3 g, 0.715 mmol) was dissolved in toluene (10 mL). The reaction mixture was cooled to 0° C. and a 2 M solution of trimethylaluminum in toluene (0.7 mL, 1.4 mmol) was added dropwise and stirring continued for 30 min. Aniline (0.086 g, 0.88 mmol) was added and the mixture was heated at 110° C. for 4 hrs. After cooling to room temperature, the reaction mixture was quenched with ice water (40 mL) and extracted with ethyl acetate (3×35 mL). The organic layer was dried over sodium sulphate and concentrated. The crude residue was triturated with methanol (10 mL) then further purified by reverse phase preparative HPLC to give N-phenyl-2-(3,4,5-trimethoxybenzamido)-4,5,6,7-tetrahydrobenzo[b]thiophene-3-carboxamide (Compound 9) (17 mg, 5.1% yield). Preparative HPLC Method B. LCMS: 98.49% (RT: 2.169, 340.0 nm) (MS: ESI+ve 467.2 [M+H]). $^1$H NMR (400 MHz, DMSO-$d_6$) δ ppm: 1.796 (m, 4H) 2.688 (t, 4H, J=22.42), 3.709 (s, 3H) 3.924 (s, 6H) 7.073 (s, 1H), 7.157 (s, 2H), 7.341-7.303 (t, 2H), 7.741-7.721 (d, 2H, J=8), 9.871 (s, 1H), 11.273 (s, 1H).

86

Example 36

Preparation of N-methyl-2-(3,4,5-trimethoxybenzamido)-N-(3,4,5-trimethoxyphenyl)-4,5,6,7-tetrahydrobenzo[b]thiophene-3-carboxamide (Compound 7)

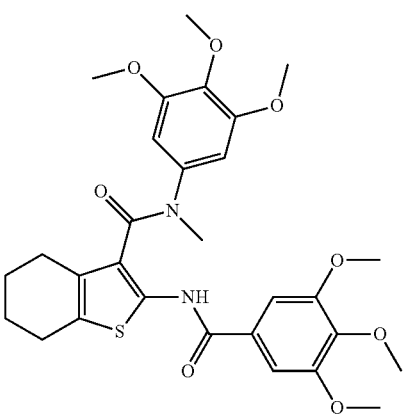

Prepared from ethyl 2-(3,4,5-trimethoxybenzamido)-4,5,6,7-tetrahydrobenzo[b]thiophene-3-carboxylate (300 mg, 0.715 mmol) and 3,4,5-trimethoxy-N-methylaniline (169 mg, 0.858 mmol) by a method similar to that described for N-phenyl-2-(3,4,5-trimethoxybenzamido)-4,5,6,7-tetrahydrobenzo[b]thiophene-3-carboxamide (Compound 9) to give N-methyl-2-(3,4,5-trimethoxybenzamido)-N-(3,4,5-trimethoxyphenyl)-4,5,6,7-tetrahydrobenzo[b]thiophene-3-carboxamide (Compound 7) (31 mg, 7.60% yield) as an off white solid. Preparative HPLC Method C. LCMS: 100% (RT: 1.720, 254.0 nm) (MS: ESI+ve 571.4 [M+H]). $^1$H NMR: (400 MHz, DMSO-$d_6$) δ ppm: 1.728 (m, 4H), 2.516-2.684 (t, 4H, J=33.4), 3.355 (s, 9H) 3.548 (s, 3H) 3.739 (s, 3H) 3.879 (s, 6H), 6.134 (s, 2H), 7.298 (s, 2H), 10.511 (s, 1H).

Example 37

Preparation of N-(3,5-dimethoxyphenyl)-2-(3,4,5-trimethoxybenzamido)-4,5,6,7-tetrahydrobenzo[b]thiophene-3-carboxamide. (Compound 5)

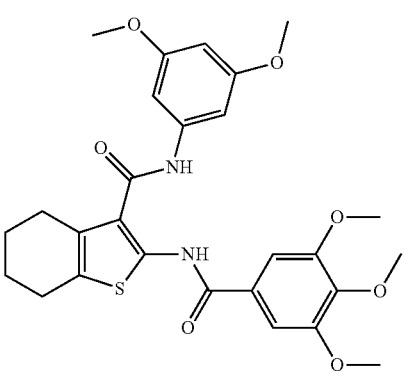

Prepared from ethyl 2-(3,4,5-trimethoxybenzamido)-4,5,6,7-tetrahydrobenzo[b]thiophene-3-carboxylate (0.20 g, 0.476 mmol) and 3,5-dimethoxyaniline (0.112 g, 0.572 mmol) by a method similar to that described for N-phenyl-2-(3,4,5-trimethoxybenzamido)-4,5,6,7-tetrahydrobenzo[b]thiophene-3-carboxamide (Compound 9) to give N-(3,5-dimethoxyphenyl)-2-(3,4,5-trimethoxybenzamido)-4,5,6,7-tetrahydrobenzo[b]thiophene-3-carboxamide (Compound 5) (128 mg, 51% yield) as an off white solid. LCMS: 100% (RT: 2.223, 225 nm) (MS: ESI-ve 525.5 [M–H]). $^1$H NMR: (400 MHz, DMSO-$d_6$) δ ppm: 1.963 (m, 4H), 2.806 (t, 2H, J=24.6), 2.932 (t, 2H, J=24.6), 3.854 (s, 6H), 3.938 (s, 3H), 3.978 (s, 6H) 6.341-6.336 (d, 1H, J=2.0), 6.879-6.873 (d, 1H, J=2.4), 7.333-7.304 (d, 1H, J=2.9), 7.698 (s, 1H), 13.102 (s, 1H).

Example 38

Preparation of 2-(3,4,5-trimethoxybenzamido)-N-(3,4,5-trimethoxyphenyl)-4,5,6,7-tetrahydrobenzo[b]thiophene-3-carboxamide. (Compound 1)

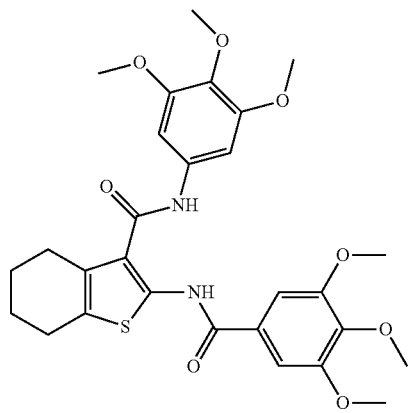

Prepared from ethyl 2-(3,4,5-trimethoxybenzamido)-4,5,6,7-tetrahydrobenzo[b]thiophene-3-carboxylate (0.2 g, 0.477 mmol) and 3,4,5-trimethoxyaniline (0.104 g, 0.572 mmol) by a method similar to that described for N-phenyl-2-(3,4,5-trimethoxybenzamido)-4,5,6,7-tetrahydrobenzo[b]thiophene-3-carboxamide (Compound 9) to give 2-(3,4,5-trimethoxybenzamido)-N-(3,4,5-trimethoxyphenyl)-4,5,6,7-tetrahydrobenzo[b]thiophene-3-carboxamide (Compound 1) (51 mg, 19.22%). LCMS: 98.99% (RT: 2.056, 275.0 nm) (MS: ESI+ve 557.6 [M+H]). $^1$H NMR (400 MHz, DMSO-$d_6$) δ ppm: 1.806 (m, 4H) 2.698 (t, 4H J=23.42) 3.642 (s, 3H) 3.736 (s, 15H) 7.161 (s, 2H) 7.207 (s, 2H) 9.713 (s, 1H) 11.372 (s, 1H)

Example 39

Preparation of 2-(3,4,5-trimethoxybenzamido)-4,5,6,7-tetrahydrobenzo[b]thiophene-3-carboxamide. (Compound 12)

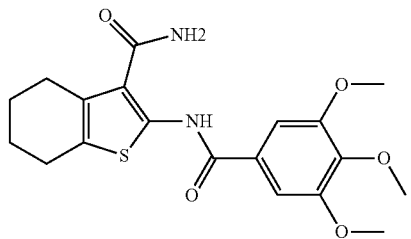 [SMILES: COc1cc(C(=O)Nc2sc3c(c2C(N)=O)CCCC3)cc(OC)c1OC]

Prepared from ethyl 2-(3,4,5-trimethoxybenzamido)-4,5,6,7-tetrahydrobenzo[b]thiophene-3 carboxylate (100 mg, 0.238 mmol) and ammonium carbonate (45 mg, 0.364 mmol) by a method similar to that described for N-phenyl-2-(3,4,5-trimethoxybenzamido)-4,5,6,7-tetrahydrobenzo[b]thiophene-3-carboxamide (Compound 9) to give 2-(3,4,5-trimethoxybenzamido)-4,5,6,7-tetrahydrobenzo[b]thiophene-3-carboxamide (Compound 12) (40 mg, 42.97% yield) as an off white solid. LCMS: 100.0% (RT: 1.692, 222 nm) (MS: ESI+ve 391.50 [M+H]). $^1$H NMR: (400 MHz, DMSO-$d_6$) 1.767 (s, 4H), 2.675-2.764 (m, 4H), 3.764 (s, 3H), 3.885 (s, 6H), 7.199 (s, 2H), 7.829 (s, 2H) 13.155 (s, 1H)

Example 40

Preparation of 2-benzamido-N-phenyl-4,5,6,7-tetrahydrobenzo[b]thiophene-3-carboxamide (Compound 10)

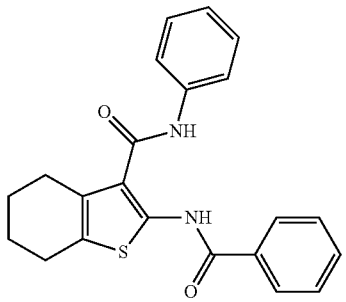

Step 1: Synthesis of Ethyl 2-benzamido-4,5,6,7-tetrahydrobenzo[b]thiophene-3-carboxylate

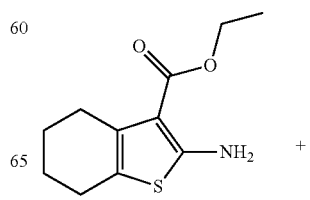

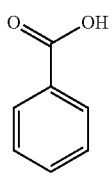

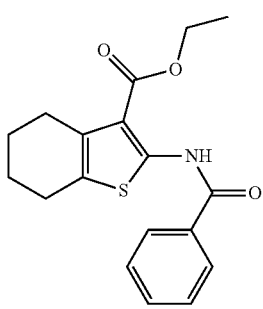

Pyridine (1.25 mL) and benzoic acid (542 mg, 4.438 mmol) were added to a solution of ethyl 2-amino-4,5,6,7-tetrahydrobenzo[b]thiophene-3-carboxylate (500 mg, 2.219 mmol) in dichloromethane (10 mL) at 0° C. After 10 min, phosphorus(V) oxychloride, (1.25 mL) was added. The mixture was allowed to slowly warm to room temperature and stirring continued for 16 h. Ice water (50 mL) was added and the crude mixture was extracted with dichloromethane (3×50 mL). The organic layer was dried over sodium sulphate and concentrated. The crude residue was purified by column chromatography eluting with ethyl acetate:hexane to give ethyl 2-benzamido-4,5,6,7-tetrahydrobenzo[b]thiophene-3-carboxylate (200 mg, 27.4% yield) as off white solid. LCMS: 57.85% (RT: 2.427, 230.0 nm) (MS: ESI+ve 330.08 [M+H])

Step 2: Synthesis of 2-benzamido-N-phenyl-4,5,6,7-tetrahydrobenzo[b]thiophene-3-carboxamide. (Compound 10)

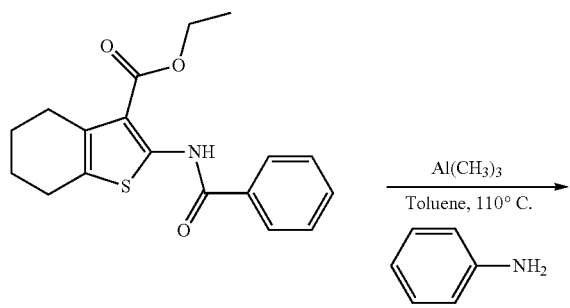

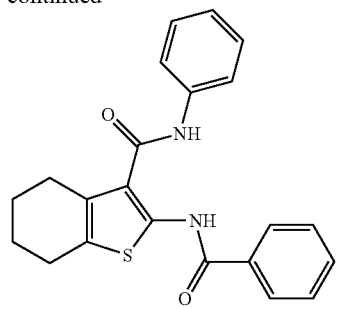

Ethyl 2-benzamido-4,5,6,7-tetrahydrobenzo[b]thiophene-3-carboxylate (100 mg, 0.303 mmol) was dissolved in toluene (3.0 mL), The reaction mixture was cooled to 0° C. and a 2 M solution of trimethylaluminum in toluene (0.3 mL) was added dropwise and stirring continued for 30 min. Aniline (33 mg, 0.364 mmol) was added and the mixture was heated at 110° C. for 4 hrs. After cooling to room temperature, the reaction mixture was quenched with ice water (30 mL) and extracted with dichloromethane (3×30 mL). The organic layer was dried over sodium sulphate and concentrated. The crude residue was purified by column chromatography eluting with ethyl acetate:hexane then further purified by reverse phase preparative HPLC to give 2-benzamido-N-phenyl-4,5,6,7-tetrahydrobenzo[b]thiophene-3-carboxamide (Compound 10) (7 mg, 6.1% yield) as an off white solid. LCMS: 100% (RT: 2.212, 202.0 nm) (MS: ESI+ve 377.1 [M+H]). $^1$H NMR: (400 MHz, DMSO-$d_6$) δ ppm: 1.800 (m, 4H), 2.682-2.887 (t, 4H), 7.10 (s, 1H), 7.332-7.368 (t, 2H, J=7.2), 7.558 (m, 3H), 7.702-7.722 (t, 2H, J=8), 7.901 (s, 2H), 9.689 (s, 1H), 11.627 (s, 1H).

Example 41

Preparation of 2-benzamido-N-(3,4,5-trimethoxyphenyl)-4,5,6,7-tetrahydrobenzo[b]thiophene-3-carboxamide (Compound 11)

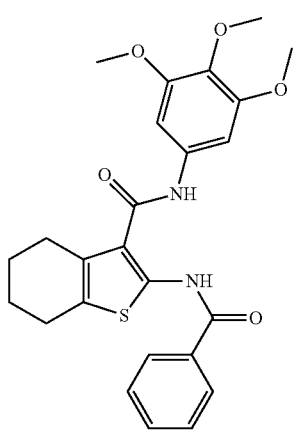

Prepared from ethyl 2-benzamido-4,5,6,7-tetrahydrobenzo[b]thiophene-3-carboxylate (100 mg, 0.303 mmol and 3,4,5-trimethoxyaniline (67 mg, 0.364 mmol)) by a method similar to that described for N-phenyl-2-(3,4,5-trimethoxybenzamido)-4,5,6,7-tetrahydrobenzo[b]thiophene-3-carboxamide (Compound 9) to give 2-benzamido-N-(3,4,5-trimethoxyphenyl)-4,5,6,7-tetrahydrobenzo[b]thiophene-3-carboxamide (Compound 11) (25 mg, 17.7% yield) as an off white solid. Preparative HPLC Method D. LCMS: 97.97% (RT: 2.082, 202.0 nm) (MS: ESI+ve 467.2 [M+H]). $^1$H NMR: (400 MHz, DMSO-$d_6$) δ ppm: 1.767 (m, 4H), 2.711-2.743 (t, 4H), 3.649 (s, 3H), 3.764 (s, 6H), 7.124 (s, 2H), 7.586 (m, 3H), 7.899-7.917 (d, 2H, J=7.2), 9.635 (s, 1H), 11.499 (s, 1H).

Example 42

Preparation of 2-(3,4,5-trimethoxy-N-methylbenzamido)-N-(3,4,5-trimethoxyphenyl)-4,5,6,7-tetrahydrobenzo[b]thiophene-3-carboxamide. (Compound 13)

13

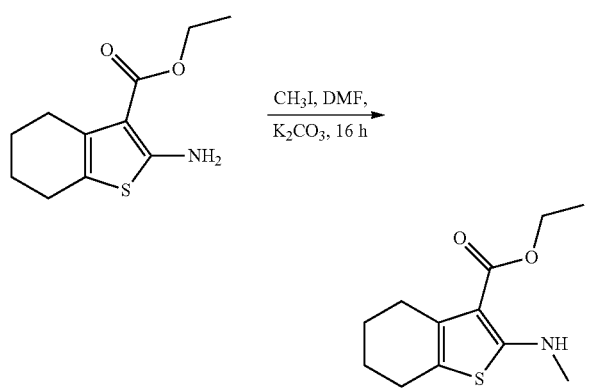

Step 1: Synthesis of ethyl 2-(methylamino)-4,5,6,7-tetrahydrobenzo[b]thiophene-3-carboxylate

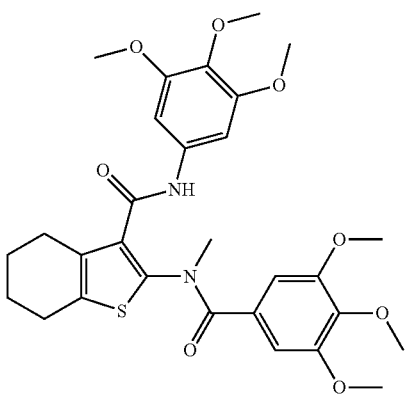 [SMILES: COc1cc(NC(=O)c2c(N(C)C(=O)c3cc(OC)c(OC)c(OC)c3)sc3c2CCCC3)cc(OC)c1OC]

A suspension of ethyl 2-amino-4,5,6,7-tetrahydrobenzo[b]thiophene-3-carboxylate (5 g, 22.19 mmol) and K$_2$CO$_3$ (4.6 g, 33.28 mmol) in dimethylformamide (30 mL) was stirred for 30 min at 0° C. Methyl iodide (1.53 mL, 24.40 mmol) was added and reaction mixture was warmed to room temperature and stirred for 16 h. The reaction mixture was quenched with water (200 mL), extracted with ethyl acetate (3×100 mL), dried over sodium sulfate and concentrated under reduce pressure. The crude residue was purified by flash chromatography eluting with ethyl acetate:hexane to give ethyl 2-(methylamino)-4,5,6,7-tetrahydrobenzo[b]thiophene-3-carboxylate (1.2 g, 22.6% yield) as brown solid. LCMS: 88.12%, (RT: 2.139) (MS: ESI+ve 240.2 [M+H]). $^1$H NMR: (400 MHz, DMSO-$d_6$) δ ppm: 1.24 (t, 3H, J=0.4), 1.6 8 (s, 4H), 2.63 (d, 2H, J=6), 2.86 (s, 3H), 4.12-4.19 (m, 2H), 7.63 (s, 1H).

Step 2: Synthesis of ethyl 2-(3,4,5-trimethoxy-N-methylbenzamido)-4,5,6,7 tetrahydrobenzo[b]thiophene-3-carboxylate

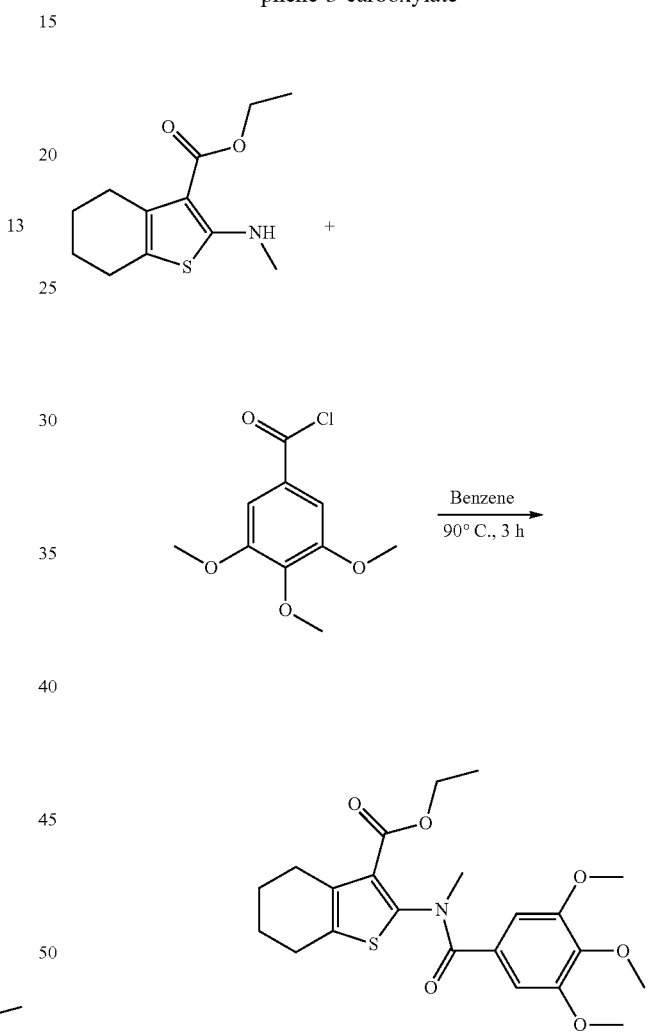

A mixture of ethyl 2-(methylamino)-4,5,6,7-tetrahydrobenzo[b]thiophene-3-carboxylate (1.0 g, 4.18 mmol) and 3,4,5-trimethoxybenzoyl chloride (1.93 g, 8.36 mmol) in benzene (20 mL) was heated at 90° C. for 3 h. The reaction mixture was quenched with water (200 mL), extracted with ethyl acetate (2×100 mL), dried over sodium sulfate and concentrated under reduce pressure. The crude residue was purified by flash chromatography eluting with ethyl acetate/hexane to give ethyl 2-(3,4,5-trimethoxy-N-methylbenzamido)-4,5,6,7 tetrahydrobenzo[b]thiophene-3-carboxylate (1.1 g, 60.7% yield) as yellow solid. LCMS: 80.52% (RT: 1.885) (MS: ESI+ve 434.4 [M+H]).

Step 3: 2-(3,4,5-trimethoxy-N-methylbenzamido)-N-(3,4,5-trimethoxyphenyl)-4,5,6,7-tetrahydrobenzo[b]thiophene-3-carboxamide. (Compound 13)

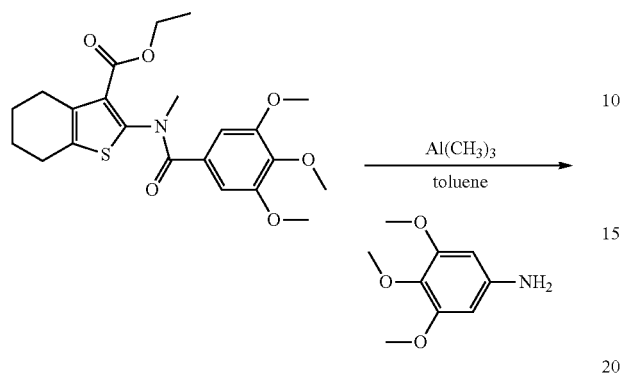

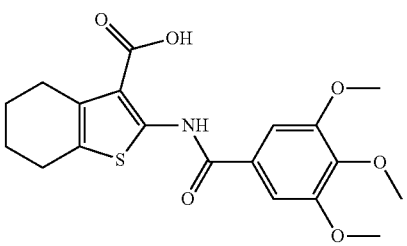

13

A 2 M solution of trimethylaluminum in toluene (2 mL, 4.0 mmol) was added dropwise to a solution of ethyl 2-(3,4,5-trimethoxy-N-methylbenzamido)-4,5,6,7 tetrahydrobenzo[b]thiophene-3-carboxylat (0.5 g, 1.15 mmol) in toluene (5 mL) at 0° C. The reaction mixture was stirred for 30 min. 3,4,5-trimethoxyaniline (0.317 g, 1.73 mmol) was added and the mixture was heated at 110° C. for 16 h. The reaction mixture was quenched with ice water (25 mL), extracted with ethyl acetate (2×25 mL), dried over sodium sulfate and concentrated under reduce pressure. The crude residue was purified by preparative HPLC to give 2-(3,4,5-trimethoxy-N-methylbenzamido)-N-(3,4,5-trimethoxyphenyl)-4,5,6,7-tetrahydrobenzo[b]thiophene-3-carboxamide (Compound 13) (0.05 g, 7.8% yield) as an off white solid. Preparative HPLC Method C. LCMS: 100%, (RT: 1.738) (MS: ESI+ve 571.5 [M+H]). $^1$H NMR: (400 MHz, DMSO-$d_6$) δ ppm: 1.75 (s, 5H), 2.64 (s, 3H), 3.18 (s, 3H), 3.45 (s, 6H), 3.63-3.66 (d, 6H, J=14.8), 3.74 (s, 6H), 6.74 (s, 2H), 7.03 (s, 2H).

Example 43

Preparation of 2-(3,4,5-trimethoxybenzamido)-4,5,6,7-tetrahydrobenzo[b]thiophene-3-carboxylic acid. (Compound 17)

Step 1: Synthesis of 2-(3,4,5-trimethoxybenzamido)-4,5,6,7-tetrahydrobenzo[b]thiophene-3-carboxylic acid. (Compound 17)

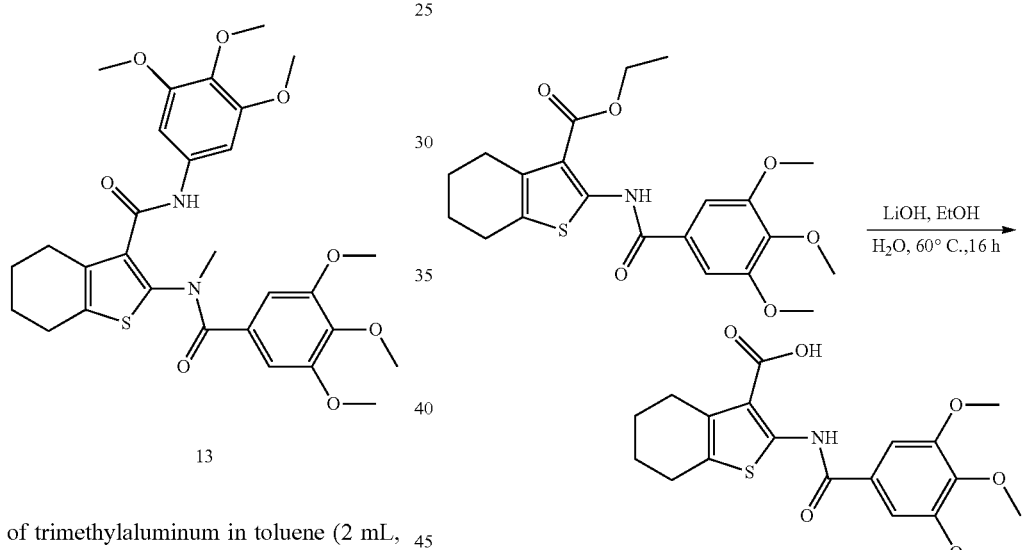

17

A solution of LiOH (599.6 mg, 14.290 mmol) in water (2 mL) was added to a solution of ethyl 2-(3,4,5-trimethoxybenzamido)-4,5,6,7-tetrahydrobenzo[b]thiophene-3-carboxylate (1.0 g, 2.383 mmol) in EtOH (24 mL). The mixture was stirred for 30 min then heated at 60° C. for 16 h. The reaction mixture was concentrated and diluted with ice water. 1N hydrochloric acid (5 mL) was added to adjust to pH 2 and stirring was continued for 30 min. The resulting ppt was collected by filtration and dried to give 970 mg crude of product. 100 mg of crude product was further purified by reverse phase preparative HPLC to give 2-(3,4,5-trimethoxybenzamido)-4,5,6,7-tetrahydrobenzo[b]thiophene-3-carboxylic acid (Compound 17) (21.75 mg, 23.3% yield) as an off white solid Preparative HPLC Method E: Shimadzu LC-20AP, column Kromasil Eternity XT-5 C18 (250×21.2) mm, 5 micron, flow rate 14.0 mL/min, mobile phase A: 0.1% trifluoroacetic acid in water and B: 100% acetonitrile. LCMS: 100.00% (RT: 1.914, 265.0 nm) (MS:

ESI-ve 390.41 [M−H]). ¹H NMR: (400 MHz, DMSO-d₆) δ ppm: 1.739-1.749 (m, 4H), 2.649-2.751 (m, 4H), 3.760 (s, 3H), 3.883 (s, 6H), 7.210 (s, 2H), 12.459 (s, 1H), 13.450 (s, 1H).

Example 44

Preparation of 2-amino-N-(3,4,5-trimethoxyphenyl)-4,5,6,7-tetrahydrobenzo[b]thiophene-3-carboxamide. (Compound 14)

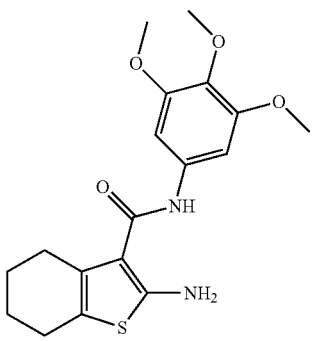 [SMILES: COc1cc(NC(=O)c2c(N)sc3c2CCCC3)cc(OC)c1OC]

Step 1: Synthesis of 2-amino-N-(3,4,5-trimethoxyphenyl)-4,5,6,7-tetrahydrobenzo[b]thiophene-3-carboxamide. (Compound 14)

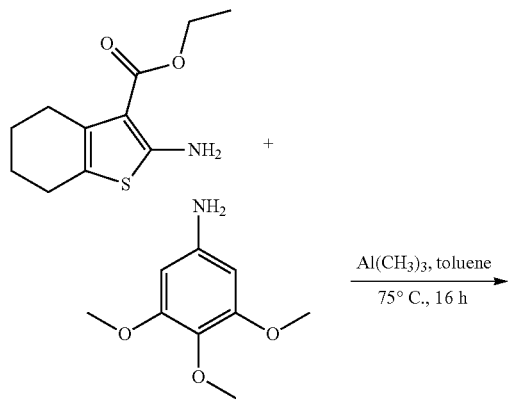

Step-1: 2 M trimethylaluminum in toluene (1.32 mL, 2.663 mmol) was added to a solution of 3,4,5-trimethoxyaniline (363.9 mg, 2.00 mmol) at 0° C. followed by ethyl 2-amino-4,5,6,7-tetrahydrobenzo[b]thiophene-3-carboxylate (300 mg, 1.331 mmol). The reaction mixture was stirred for 30 min then heated at 75° C. for 16 h. The mixture was quenched in ice water (30 mL), extracted with dichloromethane (3×30 mL), dried over sodium sulphate and concentrated. The crude residue was purified by column chromatography eluting with methanol:dichloromethane then further purified by reverse phase preparative HPLC to give 2-amino-N-(3,4,5-trimethoxyphenyl)-4,5,6,7-tetrahydrobenzo[b]thiophene-3-carboxamide (Compound 14) (10 mg, 2.1% yield) as an off white solid. Preparative HPLC Method D. LCMS: 98.26% (RT: 1.770, 230.0 nm) (MS: ESI+ve 363.13 [M+H]). ¹H NMR: (400 MHz, DMSO-d₆) δ ppm: 1.701-1.766 (m, 4H), 2.516-2.647 (m, 4H), 3.622-3.671 (s, 3H), 3.744-3.780 (s, 6H), 6.555 (s, 2H), 7.059 (s, 2H), 8.843 (s, 1H).

Example 45

Preparation of 2-(3,5-dihydroxybenzamido)-N-(3,4,5-trihydroxyphenyl)-4,5,6,7-tetrahydrobenzo[b]thiophene-3-carboxamide. (Compound 4)

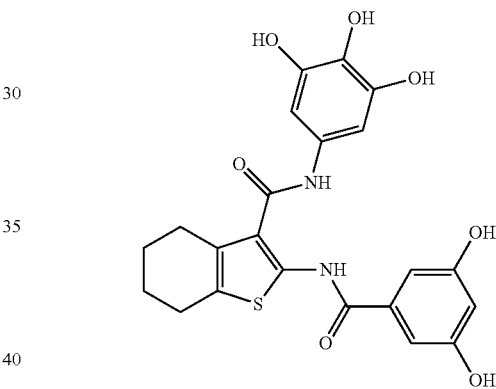

Step 1. Synthesis of 2-(3,5-dihydroxybenzamido)-N-(3,4,5-trihydroxyphenyl)-4,5,6,7-tetrahydrobenzo[b]thiophene-3-carboxamide. (Compound 4)

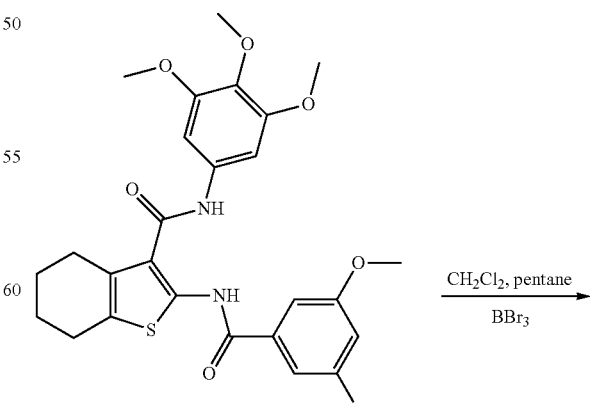

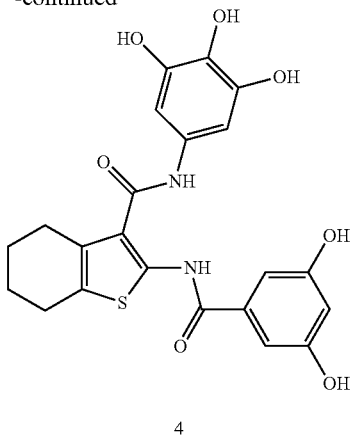

4

A mixture of 2-(3,5-dimethoxybenzamido)-N-(3,4,5-trimethoxyphenyl)-4,5,6,7-tetrahydrobenzo[b]thiophene-3-carboxamide (Compound 3) (100 mg, 0.189 mmol), dichloromethane (10 mL) and pentane (12 mL) was cooled at 0° C. Boron tribromide (1 M in dichloromethane) (2.27 mL, 2.278 mmol) was added dropwise and reaction mixture was warmed to room temperature and stirred for 16 h. After cooling to 0° C., methanol (3 mL) was added dropwise. The reaction mixture was concentrated and the crude residue was purified by reverse phase preparative HPLC to give 2-(3,5-dihydroxybenzamido)-N-(3,4,5-trihydroxyphenyl)-4,5,6,7-tetrahydrobenzo[b]thiophene-3-carboxamide (Compound 4) (17 mg, 19.6% yield) as an off white solid. Preparative HPLC Method A: Shimadzu LC-20AP; column: YMC Actus Triart C18 (250×20) mm, 5 micron, flow rate 16.0 mL/min, mobile phase A: 0.1% trifluoroacetic acid in water, B: 100% acetonitrile. LCMS: 100.00% (RT: 1.619, 202.0 nm) (MS: ESI-ve 455.5 [M−H]). $^1$H NMR: (400 MHz, DMSO-d$_6$) δ ppm: 1.748-1.786 (m, 4H), 2.337-2.755 (t, 4H, J=25.7), 6.449 (s, 1H), 6.702-6.723 (s, 3H), 7.951 (s, 1H), 8.899 (s, 2H), 9.070 (s, 1H), 9.780 (s, 2H), 11.674 (s, 1H).

Example 46

Preparation of N-phenyl-2-(3,4,5-trihydroxybenzamido)-4,5,6,7 tetrahydrobenzo[b]thiophene-3-carboxamide. (Compound 8)

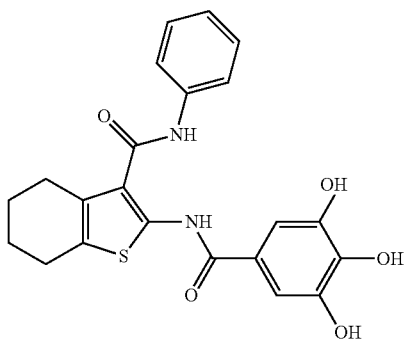

8

Prepared from N-phenyl-2-(3,4,5-trimethoxybenzamido)-4,5,6,7-tetrahydrobenzo[b]thiophene-3-carboxamide (Compound 9) (100 mg, 0.214 mmol) by a similar method to that described for (Compound 4) to give N-phenyl-2-(3,4,5-trihydroxybenzamido)-4,5,6,7-tetrahydrobenzo[b]thiophene-3-carboxamide (Compound 8) (5 mg, 5.50% yield Preparative HPLC Method B: Shimadzu LC-20AP; column YMC Actus Triart C18 (250×20) mm, 5 micron, flow rate 15.0 mL/min, mobile phase A: 0.1% formic acid in water, B: 100% acetonitrile. LCMS: 100% (RT: 1.739, 230.0 nm) (MS: ESI+ve 425.1 [M+H]). $^1$H NMR: (400 MHz, DMSO-d$_6$) δ ppm: 1.773 (m, 4H) 2.679 (t, 2H, J=23.4) 2.779 (t, 2H, J=23.4), 6.886 (s, 2H) 7.152-7.115 (t, 1H), 7.397-7.358 (t, 2H), 7.705-7.686 (d, 2H, J=8), 9.015 (s, 1H), 9.448 (s, 2H), 9.502 (s, 1H), 11.505 (s, 1H).

Example 47

Preparation of N-(3,5-dihydroxyphenyl)-2-(3,4,5-trihydroxybenzamido)-4,5,6,7-tetrahydrobenzo[b]thiophene-3-carboxamide. (Compound 6)

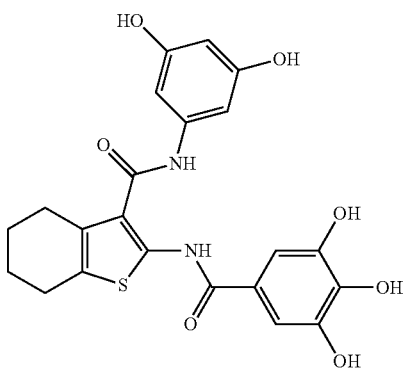

6

Prepared from N-(3,5-dimethoxyphenyl)-2-(3,4,5-trimethoxybenzamido)-4,5,6,7-tetrahydrobenzo[b]thiophene-3-carboxamide (Compound 5) (100 mg, 0.190 mmol) by a similar method to that described for (Compound 4) to give 5,7-dihydroxy-4-oxo-N-(3,4,5-trihydroxyphenyl)-1,4-dihydroquinoline-3-carboxamide (Compound 6) (49 mg, 56.5% yield) as an off white solid. Preparative HPLC Method C: Shimadzu LC-20AP; column Sunfire C18 (150×19) mm, 5 micron, flow rate 15.0 mL/min. mobile phase A: 0.1% formic acid in water, B: 100% acetonitrile. LCMS: 100% (RT: 1.491, 277.0 nm) (MS: ESI-ve 455.5 [M−H]). $^1$H NMR: (400 MHz, DMSO-d$_6$) δ ppm: 1.752 (m, 4H), 2.681 (t, 2H, J=25.6), 2.769 (t, 2H J=25.6), 5.981 (s, 1H), 6.664-6.644 (d, 1H, J=1.6), 6.874 (s, 2H), 9.220 (s, 3H), 9.251 (s, 2H), 11.480 (s, 1H).

Example 48

Preparation of 2-benzamido-N-(3,4,5-trihydroxyphenyl)-4,5,6,7-tetrahydrobenzo[b]thiophene-3-carboxamide. (Compound 18)

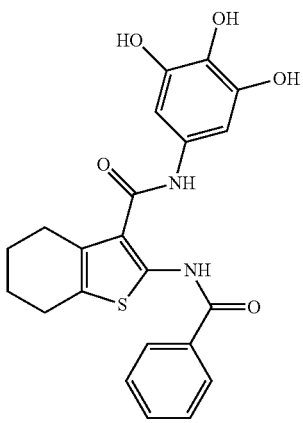

18

Prepared from 2-benzamido-N-(3,4,5-trimethoxyphenyl)-4,5,6,7-tetrahydrobenzo[b]thiophene-3-carboxamide (Compound 11) (100 mg, 0.214 mmol) by a similar method to that described for (Compound 4) to give 2-benzamido-N-(3,4,5-trihydroxyphenyl)-4,5,6,7-tetrahydrobenzo[b]thiophene-3-carboxamide (Compound 18) (10 mg, 11% yield) as a yellow solid. Preparative HPLC Method C. LCMS: 100% (RT: 1.679, 202.0 nm) (MS: ESI-ve 423.5 [M−H]). $^1$H NMR: (400 MHz, DMSO-d$_6$) δ ppm: 1.750-1.792 (m, 4H), 2.690-2.743 (t, 4H), 6.724 (s, 2H), 7.583-7.647 (m, 3H), 7.870-7.888 (d, 2H, J=7.2), 7.964 (s, 1H), 8.931 (s, 2H), 9.190 (s, 1H), 11.744 (s, 1H).

Example 49

Preparation of 2-(3,4,5-trihydroxybenzamido)-N-(3,4,5-trihydroxyphenyl)-4,5,6,7-tetrahydrobenzo[b]thiophene-3-carboxamide. (Compound 2)

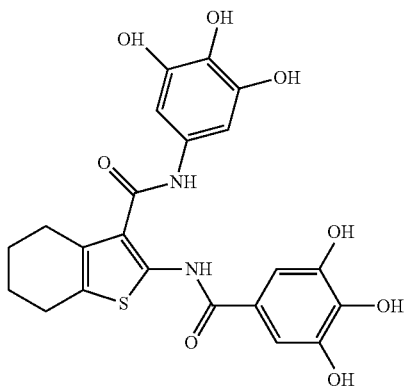

2

Prepared from 2-(3,4,5trimethoxybenzamido)-N-(3,4,5-trimethoxyphenyl)-4,5,6,7tetrahydrobenzo[b]thiophene-3-carboxamide (Compound 1) (100 mg, 0.179 mmol) by a similar method to that described for (Compound 4) to give 2-(3,4,5-trihydroxybenzamido)-N-(3,4,5-trihydroxyphenyl)-4,5,6,7-tetrahydrobenzo[b]thiophene-3-carboxamide (Compound 2) (11 mg, 12.96% Preparative HPLC Method D: Shimadzu LC-20AP, column X-Bridge C18 (150×19) mm, 5 micron, flow rate 15.0 mL/min. mobile phase A: 0.1% formic acid in water, B: 100% acetonitrile. LCMS: 100% (RT: 1.459, 232.0 nm) (MS: ESI-ve 471.5 [M−H]). $^1$H NMR: (400 MHz, DMSO-d$_6$) δ ppm: 1.773 (m, 4H) 2.679 (t, 2H, J=23.4) 2.779 (t, 2H, J=23.4) 6.761 (s, 2H) 6.886 (S, 2H) 7.966 (s, 1H) 9.006 (s, 4H) 9.445 (s, 2H) 11.632 (s, 1H).

Example 50

Preparation of 2-(3,4,5-trihydroxybenzamido)-4,5,6,7-tetrahydrobenzo[b]thiophene-3-carboxamide. (Compound 15)

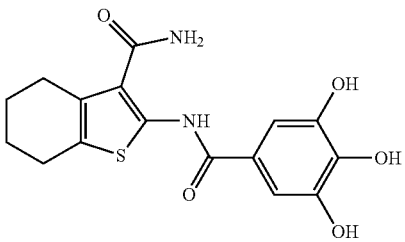 [SMILES: NC(=O)c1c(NC(=O)c2cc(O)c(O)c(O)c2)sc2c1CCCC2]

15

Prepared from 2-(3,4,5-trihydroxybenzamido)-4,5,6,7-tetrahydrobenzo[b]thiophene-3-carboxamide (Compound 12) (50 mg, 0.137 mmol) by a similar method to that described for (Compound 4) to give 2-(3,4,5-trihydroxybenzamido)-4,5,6,7-tetrahydrobenzo[b]thiophene-3-carboxamide (Compound 15) (9 mg, 18.83%) as an off white solid. Preparative HPLC Method C. LCMS: 100.00% (RT: 1.488, 223.0 nm) (MS: ESI+ve 349.26 [M+H]). $^1$H NMR: (400 MHz, DMSO-d$_6$) δ ppm: 1.759 (m, 4H), 2.651-2.758 (m, 4H), 6.896 (s, 2H), 7.693 (s, 1H), 9.412 (s, 3H), 12.750 (s, 1H).

Example 51

Preparation of 2-amino-N-(3,4,5-trihydroxyphenyl)-4,5,6,7-tetrahydrobenzo[b]thiophene-3-carboxamide. (Compound 16)

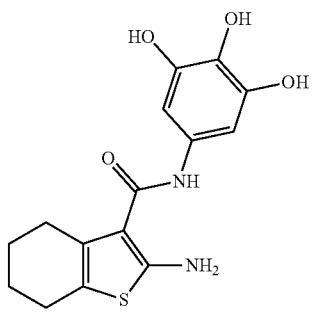

16

Prepared from 2-amino-N-(3,4,5-trimethoxyphenyl)-4,5,6,7-tetrahydrobenzo[b]thiophene-3-carboxamide (Compound 14) (80 mg, 0.220 mmol) by a similar method to that described for (Compound 4) to give 2-amino-N-(3,4,5-trihydroxyphenyl)-4,5,6,7-tetrahydrobenzo[b]thiophene-3-carboxamide (Compound 16) as an off white solid (8 mg, 11.31% yield). Preparative HPLC Method C. LCMS: 97.39% (RT: 1.469, 230.0 nm) (MS: ESI-ve 319.31 [M−H]). ¹H NMR: (400 MHz, DMSO-d$_6$) δ ppm: 1.682-1.733 (m, 4H), 2.547-2.676 (m, 4H), 6.399 (s, 2H), 6.366-6.735 (s, 2H), 7.787 (s, 1H), 8.533 (s, 1H), 8.755 (s, 2H).

Example 52

Preparation of 5,6,7-trimethoxy-4-oxo-2-(3,4,5-trimethoxyphenyl)-1,4-dihydroquinoline-3-carboxylic acid (Compound 36)

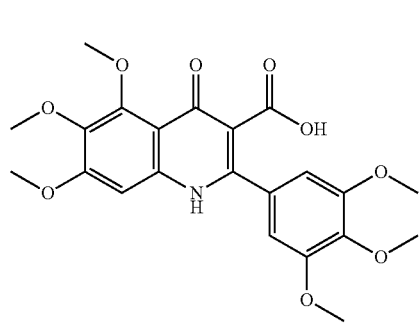

36

Step 1. Synthesis of 5,6,7-trimethoxy-2H-benzo[d][1,3]oxazine-2,4(1H)-dione

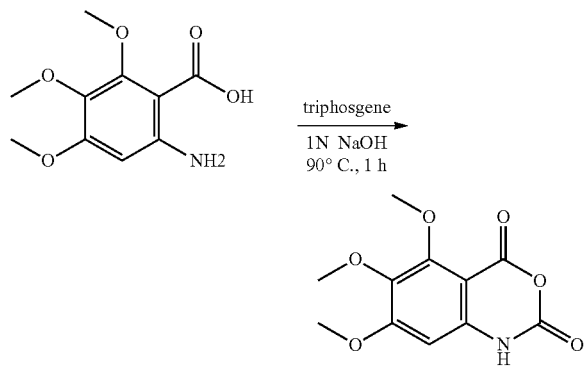

1N sodium hydroxide (31.5 mL) was added to a solution of 6-amino-3-hydroxy-2,4-dimethoxybenzoic acid (5 g 22.0 mmol) in toluene (60 mL) at 0° C. followed by triphosgene (14.36 g, 48.411 mmol). The reaction mixture warmed to room temperature over 1 h. The resulting ppt was collected by filtration and triturated with hexane (3×10 mL) to give 5,6,7-trimethoxy-2H-benzo[d][1,3]oxazine-2,4(1H)-dione (5.2 g, 87.6% yield) as an off white solid. LCMS: 91.49% (RT: 1.407, 254 nm) (MS: ESI+ve 254.32 [M+H]). ¹H NMR: (400 MHz, DMSO-d$_6$) δ ppm: 3.715 (s, 3H), 3.827 (s, 3H), 3.881 (s, 3H), 6.482 (s, 1H), 11.541 (s, 1H).

Step 2. Synthesis of ethyl 5,6,7-trimethoxy-4-oxo-2-(3,4,5-trimethoxyphenyl)-1,4-dihydro quinoline-3-carboxylate

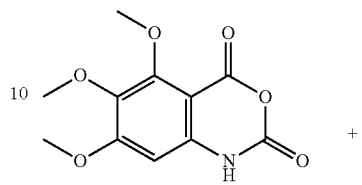

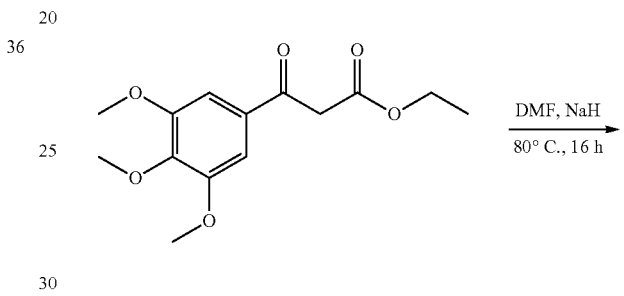

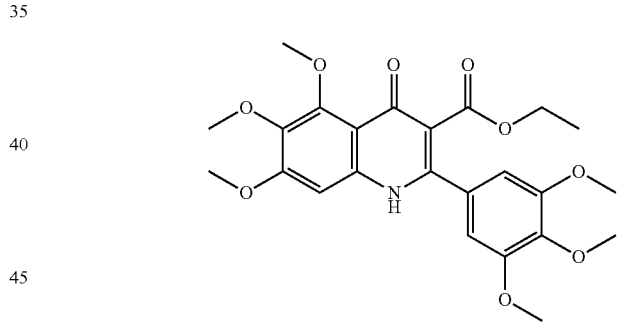

Ethyl 3-oxo-3-(3,4,5-trimethoxyphenyl)propanoate (2.9 g, 10.273 mmol) was dissolved in dry dimethylformamide (40 mL) and cooled to 0° C. Sodium hydride (60% in mineral oil) (1.23 g, 30.819 mmol) was added and the reaction mixture was stirred for 20 min. 5,6,7-trimethoxy-2H-benzo[d][1,3]oxazine-2,4(1H)-dione (5.2 g, 20.55 mmol) was added and the mixture was allowed to warm to room temperature then heated at 80° C. for 16 h. After cooling to room temperature, ice water (250 mL) was added and the pH was adjusted to 6 by the addition of 1N hydrochloric acid (10 mL). The mixture was extracted with ethyl acetate (3×100 mL), dried over sodium sulphate and concentrated. The crude product was purified by column chromatography eluting with methanol:dichloromethane to give ethyl 5,6,7-trimethoxy-4-oxo-2-(3,4,5-trimethoxyphenyl)-1,4-dihydroquinoline-3-carboxylate (1.7 g, 31.4% yield) as brown liquid. LCMS: 70.75% (RT: 1.517, 230.0 nm) (MS: ESI+ve 474.52 [M+H]).

Step 3. Synthesis of 5,6,7-trimethoxy-4-oxo-2-(3,4,5-trimethoxyphenyl)-1,4-dihydroquinoline-3-carboxylic acid. (Compound 36)

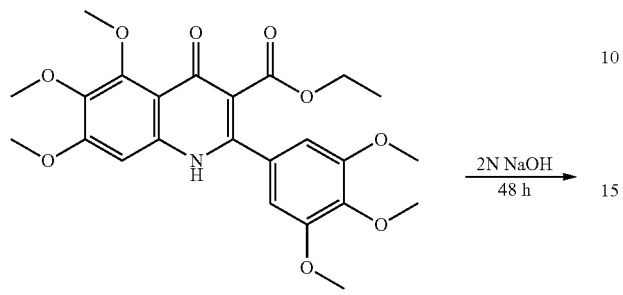

36

A mixture of ethyl 5,6,7-trimethoxy-4-oxo-2-(3,4,5-trimethoxyphenyl)-1,4-dihydroquinoline-3-carboxylate (700 mg 1.479 mmol) and 2N sodium hydroxide (14 mL) was heated at 90° C. for 48 h. The reaction mixture was cooled to room temperature and the pH was adjusted to 4 by the addition of 1N hydrochloric acid. The mixture was extracted with ethyl acetate (3×40 mL), dried over sodium sulphate and concentrated. The crude residue was purified by reverse phase preparative HPLC to give 5,6,7-trimethoxy-4-oxo-2-(3,4,5-trimethoxyphenyl)-1,4-dihydroquinoline-3-carboxylic acid (Compound 36) (26 mg, 4.0% yield). as an off white solid. Preparative HPLC Method F: Shimadzu LC-20AP, column X-Bridge C18 (250×19) mm, 5 micron, flow rate 14.0 mL/min, mobile phase A: 5 mM ammonium bicarbonate and 0.1% ammonia in water, B: 100% acetonitrile. LCMS: 99.81% (RT=1.908, 265 nm) (MS: ESI+ve 446.0 [M+H]). $^1$H NMR: (400 MHz, DMSO-$d_6$) δ ppm: 3.24 (s, 3H), 3.774 (s, 6H), 3.800 (s, 3H), 3.832 (s, 3H), 3.891 (s, 3H), 6.710 (s, 2H) 7.057 (s, 1H).

Example 53

Preparation of 5,6,7-trimethoxy-4-oxo-N,2-bis(3,4,5-trimethoxyphenyl)-1,4-dihydro quinoline-3-carboxamide. (Compound 40)

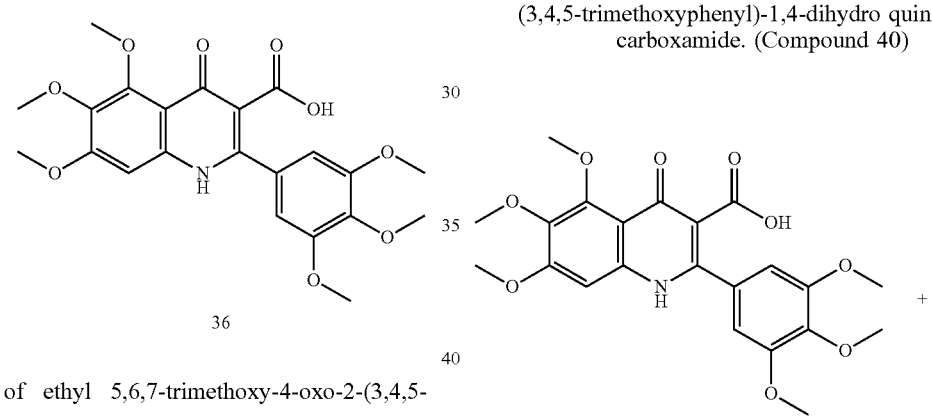

40

Step 1. Synthesis of 5,6,7-trimethoxy-4-oxo-N,2-bis(3,4,5-trimethoxyphenyl)-1,4-dihydro quinoline-3-carboxamide. (Compound 40)

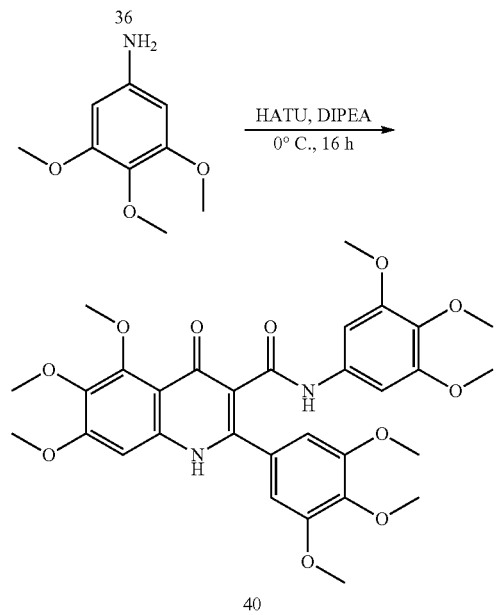

40

(1-[Bis(dimethylamino)methylene]-1H-1,2,3-triazolo[4,5-b]pyridinium 3-oxid hexafluorophosphate (HATU) (0.460 g, 1.212 mmol) was added to a solution of 5,6,7-trimethoxy-4-oxo-2-(3,4,5-trimethoxyphenyl)-1,4-dihydroquinoline-3-carboxylic acid (Compound 36) (0.36 g, 0.808 mmol) in dimethylformamide (4 mL), at 0° C. After 30 min, 3,4,5-trimethoxy aniline (0.161 g, 0.889 mmol) was added. After 15 min, N,N-diisopropylethylamine (0.40 mL, 2.424 mmol) was added and the mixture was stirred at room temperature for 16 h. Ice water (40 mL) was added and the mixture was extracted with ethyl acetate (3×40 mL), dried and concentrated. The crude residue was purified by reverse phase preparative HPLC to give 5,6,7-trimethoxy-4-oxo-N,2-bis(3,4,5-trimethoxyphenyl)-1,4-dihydroquinoline-3-carboxamide (Compound 40) (90 mg, 18.24% yield) as an off white solid. Preparative HPLC Method G: Shimadzu LC-20AP; column Sunfire C18 (250×19) mm, 5 micron, flow rate 15.0 mL/min, mobile phase A: 0.1% trifluoroacetic acid in water, B: 100% acetonitrile. LCMS: 99.80% (RT 1.463, 225 nm) (MS: ESI+ve 611.52 [M+H]). $^1$H NMR: (400 MHz, DMSO-$d_6$) δ ppm: 3.612-3.888 (m, 27H), 6.965-7.215 (m, 5H), 10.477 (s, 1H), 11.572 (s, 1H).

Example 54

Preparation of 5,6,7-trihydroxy-4-oxo-N,2-bis(3,4,5-trihydroxyphenyl)-1,4-dihydro quinoline-3-carboxamide. (Compound 44)

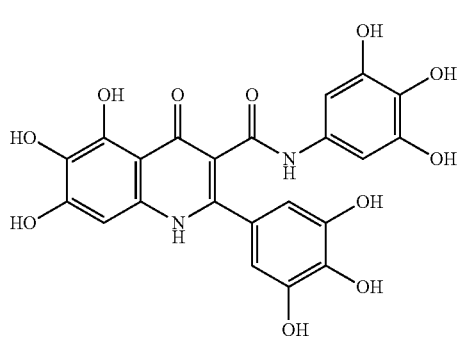

44

Step 1. Synthesis of 5,6,7-trihydroxy-4-oxo-N,2-bis(3,4,5-trihydroxyphenyl)-1,4-dihydro quinoline-3-carboxamide. (Compound 44)

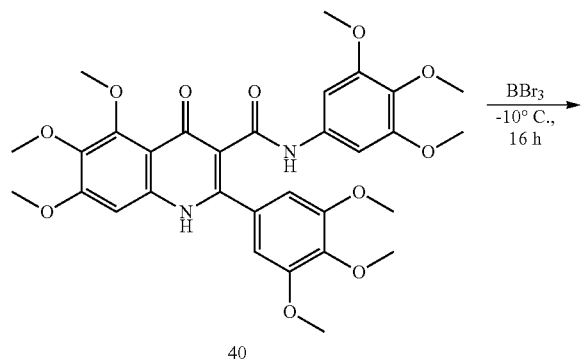

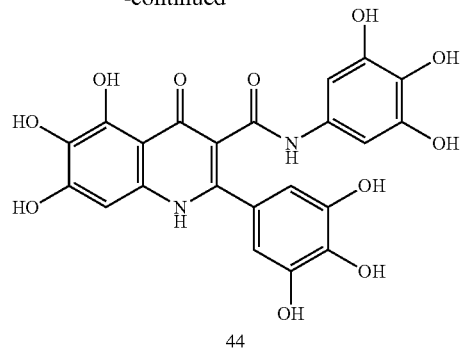

44

Borontribromide (1M in dichloromethane) (0.786 mL, 0.786 mmol) was added drop wise to a solution of 5,6,7-trimethoxy-4-oxo-N, 2-bis(3,4,5-trimethoxyphenyl)-1,4-dihydroquinoline-3-carboxamide (Compound 40) (40 mg, 0.0655 mmol) in dichloromethane at −10° C. The reaction mixture was allowed to slowly warm to room temperature and stirred for 16 h. The reaction mixture was cool to 0° C. and methanol (4 mL) was added dropwise. After 20 min, the mixture was concentrated and the resulting solid was triturated with MTBE (2×4 mL), then pentane (4×4 mL). Further purification by reverse phase preparative HPLC gave 5,6,7-trihydroxy-4-oxo-N,2-bis(3,4,5-trihydroxyphenyl)-1,4-dihydroquinoline-3-carboxamide (Compound 44) (2.27 mg, 7.0% yield) as a white solid. Preparative HPLC Method D. LCMS: 100% (RT 1.557, 202 nm) (MS: ESI+ve 485.0 [M+H]). $^1$H NMR: (400 MHz, DMSO-$d_6$) δ ppm: 6.533-6.601 (m, 5H), 7.900 (s, 2H), 8.526-8.830 (s, 4H), 8.894-9.179 (s, 2H), 9.759 (s, 1H) 11.667 (s, 1H) 14.439 (s, 1H).

Example 55

Preparation of 5,6,7-trimethoxy-4-oxo-N-(3,4,5-trimethoxyphenyl)-1,4-dihydroquinoline-3-carboxamide. (Compound 19)

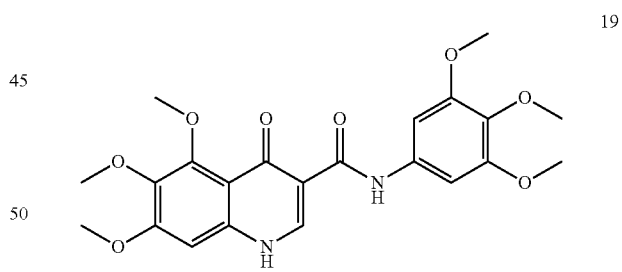

19

Step 1: Synthesis of diethyl 2-(((3,4,5-trimethoxyphenyl)amino)methylene)malonate

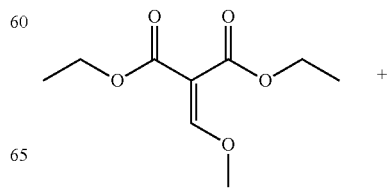

+

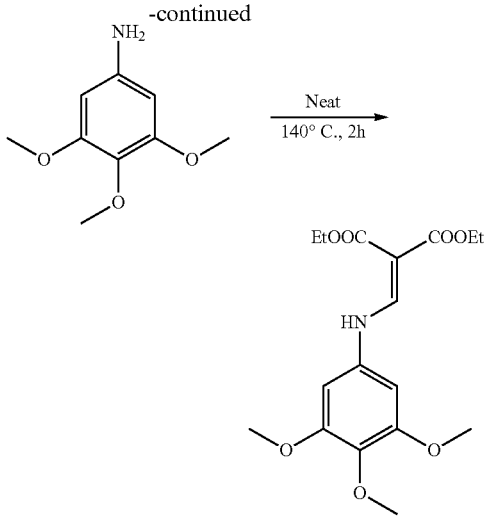

3,4,5-trimethoxy aniline (25 g, 0.136 mol) was dissolved in diethyl ethoxy methylene malonate (28 mL, 0.140 mol) and the mixture was heated at 140° C. for 2 hrs. The crude mixture was dissolved in dichloromethane (100 mL), concentrated then triturated with methanol (2×20 mL) to give diethyl 2-(((3,4,5-trimethoxyphenyl)amino)methylene)malonate (43.5 g, 99.6% yield) as brown solid. LCMS: 100% (RT: 2.286, 202 nm) (MS: ESI+ve 354.0 [M+H]). $^1$H NMR: (400 MHz, DMSO-$d_6$) δ ppm: 1.22-1.28 (m, 6H), 3.63-3.66 (d, 3H, J=13.6), 3.81 (s, 6H), 4.10-4.15 (m, 2H), 4.17-4.23 (m, 2H), 6.73 (s, 2H) 8.37-8.40 (d, 1H, J=12) 10.67-10.71 (d, 1H, J=16)

Step 2: Synthesis of ethyl 5,6,7-trimethoxy-4-oxo-1,4-dihydroquinoline-3-carboxylate

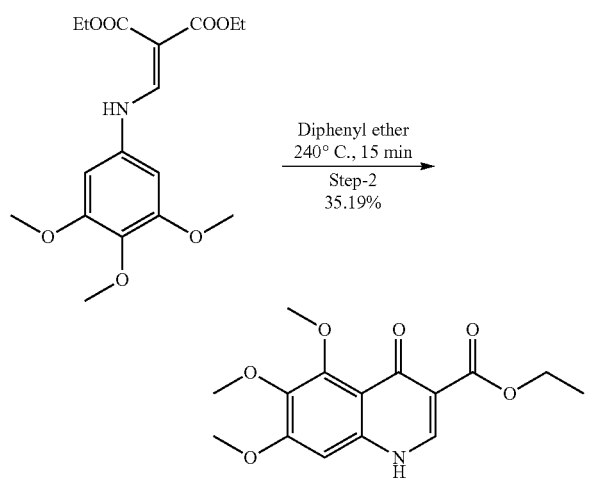

A solution of diethyl 2-(((3,4,5-trimethoxyphenyl)amino)methylene)malonate (5 g, 0.014 mol) in diphenyl ether (25 mL) was heated at 240° C. for 15 min. The reaction mixture was cooled to room temperature and the resulting ppt was collected by filtration and triturated with hexane (3×10 mL) to give ethyl 5,6,7-trimethoxy-4-oxo-1,4-dihydroquinoline-3-carboxylate (1.53 g, 35.2% yield) as a brown solid. LCMS: 84.53% (RT: 1.816, 254 nm) (MS: ESI+ve 308 [M+H]).

Step 3: Synthesis of 5,6,7-trimethoxy-4-oxo-1,4-dihydroquinoline-3-carboxylic acid

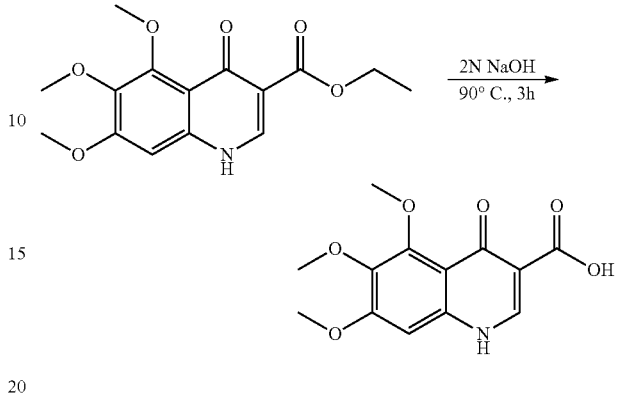

A mixture of ethyl 5,6,7-trimethoxy-4-oxo-1,4-dihydroquinoline-3-carboxylate (3 g, 0.009 mol) in 2N sodium hydroxide (150 mL) was heated at 90° C. for 3 h. After cooling to room temperature, the pH was adjusted to 4 by the addition of 2N hydrochloric acid. The resulting ppt was collected by filtration and triturated with methanol (5 mL) to give 5,6,7-trimethoxy-4-oxo-1,4-dihydroquinoline-3-carboxylic acid (2.2 g, 80.7% yield) as a pink solid. LCMS: 84.94% (RT: 1.348, 315 nm) (MS: ESI+ve 280.0 [M+H]).

Step 4: Synthesis of 5,6,7-trimethoxy-4-oxo-N-(3,4,5-trimethoxyphenyl)-1,4-dihydroquinoline-3-carboxamide. (Compound 19)

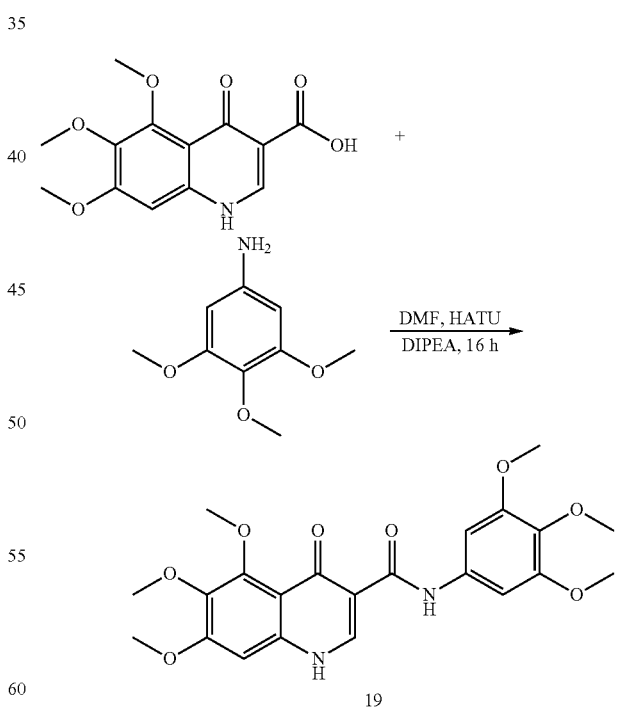

5,6,7-trimethoxy-4-oxo-1,4-dihydroquinoline-3-carboxylic acid (850 mg, 3.043 mmol) was dissolved in dimethylformamide (5 mL) and cooled to 0° C. HATU (1.7 g, 4.565 mmol) followed by 3,4,5-trimethoxy aniline (557.6 mg, 3.043 mmol) after 30 min. N,N-Diisopropylethylamine (1.56 mL, 9.145 mmol) was added and the mixture was allowed to slowly warm to room temperature and stirred for 16 h. The reaction mixture was quenched into ice water (50 mL), extracted with dichloromethane (3×50 mL), dried over sodium sulphate and concentrated. The crude residue was purified by column chromatography eluting with methanol: dichloromethane to give 350 mg which was further purified by reverse phase preparative HPLC to give 5,6,7-trimethoxy-4-oxo-N-(3,4,5-trimethoxyphenyl)-1,4-dihydroquinoline-3-carboxamide (Compound 19) (110 mg, 8.13% yield) as an off white solid. Preparative HPLC Method H: Shimadzu LC-20AP, column X-Bridge C18 (250×19) mm, 5 micron, flow rate 15.0 mL/min, mobile phase A: 5 mM ammonium acetate in water, B: 100% acetonitrile. LCMS: 99.86% (RT: 1.480, 254 nm) (MS: ESI+ve 445.4 [M+H]). $^1$H NMR: (400 MHz, DMSO-$d_6$) δ ppm: 3.65 (s, 3H), 3.79 (s, 3H), 3.81 (s, 6H), 3.86 (s, 3H), 3.92 (S, 3H), 6.97 (s, 1H), 7.11 (s, 2H), 8.71 (s, 1H), 12.74 (s, 1H).

Example 56

Preparation of 5,7-dimethoxy-4-oxo-N-(3,4,5-trimethoxyphenyl)-1,4-dihydroquinoline-3-carboxamide. (Compound 21)

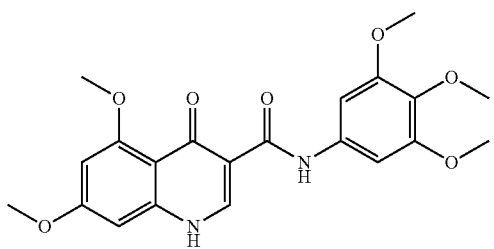

Prepared from 5,7-dimethoxy-4-oxo-1,4-dihydroquinoline-3-carboxylic acid (0.99 g, 3.97 mmol) and 3,4,5-trimethoxy aniline (0.73 g, 3.99 mmol) by a procedure similar to that described for 5,6,7-trimethoxy-4-oxo-N-(3,4,5-trimethoxyphenyl)-1,4-dihydroquinoline-3-carboxamide. (Compound 19) to give 5,7-dimethoxy-4-oxo-N-(3,4,5-trimethoxyphenyl)-1,4-dihydroquinoline-3-carboxamide (Compound 21) (612 mg, 37.0% yield) as an off white solid. Preparative HPLC Method H: LCMS: 100% (RT: 1.459, 235.0 nm) (MS: ESI+ve 415.3 [M+H]). $^1$H NMR: (400 MHz, CDCl$_3$) δ ppm: 3.749 (s, 3H), 3.862 (s, 9H), 4.066 (s, 3H), 6.441 (s, 2H), 7.109 (s, 1H), 7.543 (s, 1H), 8.983 (s, 1H), 12.640 (s, 1H)

Example 57

Preparation of 5,7-dimethoxy-4-oxo-N-phenyl-1,4-dihydroquinoline-3-carboxamide. (Compound 25)

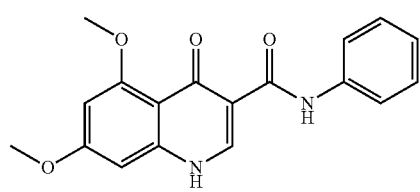

Prepared from 5,7-dimethoxy-4-oxo-1,4-dihydroquinoline-3-carboxylic acid (300 mg, 1.20 mmol) and aniline (0.11 mL, 1.20 mmol) by a procedure similar to that described for 5,6,7-trimethoxy-4-oxo-N-(3,4,5-trimethoxyphenyl)-1,4-dihydroquinoline-3-carboxamide. (Compound 19) to give 5,7-dimethoxy-4-oxo-N-phenyl-1,4-dihydroquinoline-3-carboxamide (Compound 25) (40 mg, 10.3% yield) as an off white solid. Preparative HPLC Method D. LCMS: 95.73% (RT: 1.466, 260.0 nm) (MS: ESI+ve 325.43 [M+H]). $^1$H NMR: (400 MHz, DMSO-$d_6$) δ ppm: 3.87 (s, 3H), 3.89 (s, 3H), 6.52 (d, 1H, J=2) 6.66-6.67 (d, 1H, J=2) 7.06-7.10 (t, 1H, J=7.2), 7.34-7.38 (t, 2H, J=8), 7.72-7.74 (d, 2H, J=7.6), 8.64-8.66 (d, 1H, J=6.4), 12.41-12.43 (d, 1H, J=6.8), 12.70 (s, 1H).

Example 58

Preparation of N-(3-hydroxyphenyl)-5,7-dimethoxy-4-oxo-1,4-dihydroquinoline-3-carboxamide. (Compound 26)

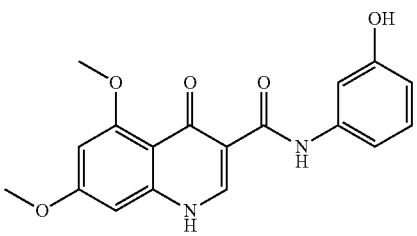

Prepared from 5,7-dimethoxy-4-oxo-1,4-dihydroquinoline-3-carboxylic acid (300 mg, 1.20 mmol) and 3-aminophenol (131.36, 1.20 mmol) by a procedure similar to that described for 5,6,7-trimethoxy-4-oxo-N-(3,4,5-trimethoxyphenyl)-1,4-dihydroquinoline-3-carboxamide. (Compound 19) to give N-(3-hydroxyphenyl)-5,7-dimethoxy-4-oxo-1,4-dihydroquinoline-3-carboxamide (Compound 26) (18 mg, 4.4% yield) as an off white solid. Preparative HPLC Method F. LCMS: 100.00% (RT: 1.399, 202 nm) (MS: ESI+ve 341.27 [M+H]). $^1$H NMR: (400 MHz, DMSO-$d_6$) (73043) δ ppm: 3.34 (s, 3H), 3.87 (s, 3H), 6.46-6.51 (t, 2H, J=9.2), 6.66 (s, 1H), 6.99-7.01 (d, 1H, J=8) 7.10-7.14 (t, 1H, J=8.2), 7.34 (s, 1H), 8.62 (s, 1H) 9.43 (s, 1H) 12.40-12.39 (d, 1H, J=4.8), 12.60 (s, 1H).

Example 59

Preparation of N-(3-hydroxyphenyl)-5,6,7-trimethoxy-4-oxo-1,4-dihydroquinoline-3-carboxamide. (Compound 28)

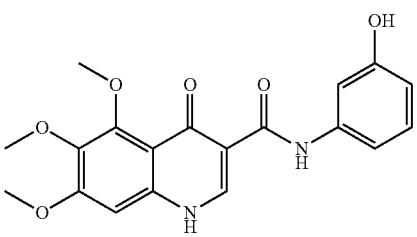

Prepared from 5,6,7-trimethoxy-4-oxo-1,4-dihydroquinoline-3-carboxylic acid (500 mg, 1.79 mol) and 3-aminophenol (195.3 mg, 1.79 mmol) by a procedure similar to that reported for 5,6,7-trimethoxy-4-oxo-N-(3,4,5-trimethoxyphenyl)-1,4-dihydroquinoline-3-carboxamide (Compound 19) to give N-(3-hydroxyphenyl)-5,6,7-trimethoxy-4-oxo-1,4-dihydroquinoline-3-carboxamide (Compound 28) (15 mg, 2.3% yield) as a white solid. Preparative HPLC Method D. LCMS: 99.36% (RT: 1.419, 317.0 nm) (MS: ESI+ve 371.47 [M+H]). $^1$H NMR: (400 MHz, DMSO-$d_6$) δ ppm: 3.784 (s, 3H), 3.844 (s, 3H), 3.922 (s, 3H), 6.469-6.493 (d, 1H, J=9.6), 7.008 (m, 2H), 7.125 (m, 1H), 7.325 (s, 1H), 8.693 (s, 1H), 9.444 (s, 1H), 12.546 (s, 1H), 12.626 (s, 1H).

Example 60

Preparation of 5,6,7-trimethoxy-4-oxo-N-phenyl-1,4-dihydroquinoline-3-carboxamide. (Compound 30)

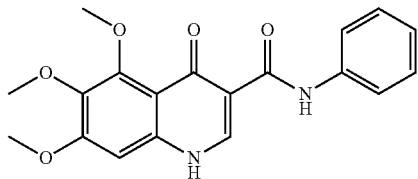

Prepared from 5,6,7-trimethoxy-4-oxo-1,4-dihydroquinoline-3-carboxylic acid (200 mg, 0.716 mmol) and aniline (66.6 mg, 0.716 mmol) by a procedure similar to that reported for 5,6,7-trimethoxy-4-oxo-N-(3,4,5-trimethoxyphenyl)-1,4-dihydroquinoline-3-carboxamide (Compound 19) to give 5,6,7-trimethoxy-4-oxo-N-phenyl-1,4-dihydroquinoline-3-carboxamide (Compound 30) (43.5 mg, 16.9% yield) as an off white solid. Preparative HPLC Method C. LCMS: 100.00% (RT: 1.520, 202.0 nm) (ESI+ve (M+1) 355.48). $^1$H NMR: (400 MHz, DMSO-$d_6$) δ ppm: 3.801 (s, 3H), 3.866 (s, 3H), 3.937 (s, 3H), 7.005 (s, 1H), 7.095 (m, 1H), 7.371 (m, 2H), 7.723-7.743 (d, 2H, J=8), 8.720 (s, 1H), 12.569 (s, 1H), 12.698 (s, 1H).

Example 61

Preparation of N-(4-hydroxyphenyl)-5,6,7-trimethoxy-4-oxo-1,4-dihydroquinoline-3-carboxamide. (Compound 29)

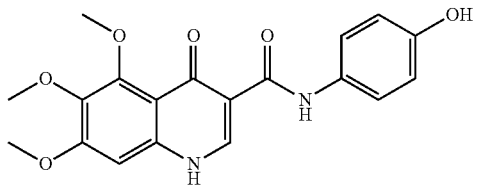 [SMILES: COc1cc2[nH]cc(C(=O)Nc3ccc(O)cc3)c(=O)c2c(OC)c1OC]

Prepared from 5,6,7-trimethoxy-4-oxo-1,4-dihydroquinoline-3-carboxylic acid (300 mg, 1.075 mmol) and 4-aminophenol (117 mg, 1.075 mmol) by a procedure similar to that reported for 5,6,7-trimethoxy-4-oxo-N-(3,4,5-trimethoxyphenyl)-1,4-dihydroquinoline-3-carboxamide (Compound 19) to give N-(4-hydroxyphenyl)-5,6,7-trimethoxy-4-oxo-1,4-dihydroquinoline-3-carboxamide (Compound 29) (34 mg, 8.55%) as a white solid. Preparative HPLC Method D. LCMS: 100.00% (RT: 1.393, 254.0 nm) (MS: ESI+ve 371.4 [M+H]). $^1$H NMR: (400 MHz, DMSO-$d_6$) δ ppm: 3.782 (s, 3H), 3.84 0 (s, 3H), 3.970 (s, 3H), 6.586 (s, 2H), 6.734-6.756 (d, 2H, J=8.8), 6.985 (s, 1H) 7.496-7.518 (d, 2H, J=9.2), 8.672 (s, 1H), 9.241 (s, 1H), 12.415 (s, 1H).

Example 62

Preparation of N-(4-hydroxyphenyl)-5,7-dimethoxy-4-oxo-1,4-dihydroquinoline-3-carboxamide. (Compound 31)

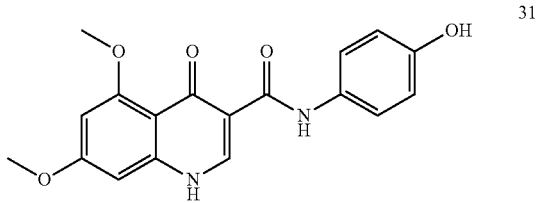

Prepared from 5,7-dimethoxy-4-oxo-1,4-dihydroquinoline-3-carboxylic acid (300 mg, 1.20 mmol) and 4-aminophenol (131.36, 1.20 mmol) by a procedure similar to that reported for 5,6,7-trimethoxy-4-oxo-N-(3,4,5-trimethoxyphenyl)-1,4-dihydroquinoline-3-carboxamide (Compound 19) to give N-(4-hydroxyphenyl)-5,7-dimethoxy-4-oxo-1,4-dihydroquinoline-3-carboxamide (Compound 31) (7.2 mg, 1.8% yield) as an off white solid. Preparative HPLC Method D. LCMS: 98.99% (RT: 1.365, 259 nm) (MS: ESI+ve 341.27 [M+H]). $^1$H NMR: (400 MHz, DMSO-$d_6$) δ ppm: 3.85 (s, 3H), 3.87 (s, 3H), 6.48-6.49 (d, 1H, J=2), 6.64-6.65 (d, 1H, J=2), 6.72-6.74 (d, 2H, J=8.8) 7.49-7.52 (d, 2H, J=8.8) 8.60 (s, 1H), 9.21 (s, 1H) 12.43 (s, 2H).

Example 63

Preparation of N-(3-fluoro-4-hydroxyphenyl)-5,6,7-trimethoxy-4-oxo-1,4-dihydroquinoline-3-carboxamide. (Compound 34)

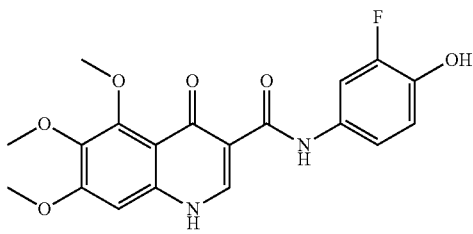

Prepared from 5,6,7-trimethoxy-4-oxo-1,4-dihydroquinoline-3-carboxylic acid (300 mg, 1.075 mmol) and 5-amino-2-fluorophenol (136 mg, 1.075 mmol) by a procedure similar to that reported for 5,6,7-trimethoxy-4-oxo-N-(3,4,5-trimethoxyphenyl)-1,4-dihydroquinoline-3-carboxamide (Compound 19) to give N-(3-fluoro-4-hydroxyphenyl)-5,6,7-trimethoxy-4-oxo-1,4-dihydroquinoline-3-carboxamide (Compound 34) (34 mg, 8.2% yield) as an off white solid. Preparative HPLC Method I: Shimadzu LC-20AP; column Sunfire C18 (150×19) mm, 5 micron, flow rate 15.0 mL/min, mobile phase A: 0.1% formic acid in water, B: acetonitrile:methanol (1:1). LCMS: 100.00% (RT: 1.414, 254.0 nm) (MS: ESI+ve 389.4 [M+H]). ¹H NMR: (400 MHz, DMSO-d₆) δ ppm: 3.783 (s, 3H), 3.840 (s, 3H), 3.922 (s, 3H), 6.901-6.947 (m, 1H), 6.986 (s, 1H), 7.118-7.140 (d, 1H, J=8.8), 7.762-7.801 (dd, 1H, J=2.4, 15.5) 8.683 (s, 1H), 9.623 (s, 1H) 12.430 (s, 1H), 12.575 (s, 1H).

Example 64

Preparation of 5,7-dimethoxy-N-methyl-4-oxo-N-(3,4,5-trimethoxyphenyl)-1,4-dihydroquinoline-3-carboxamide. (Compound 35)

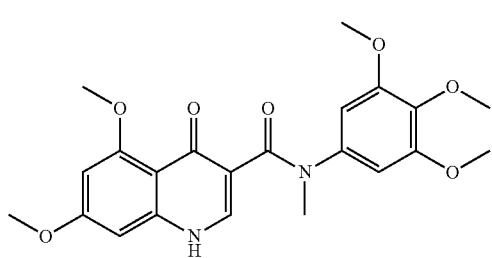

Prepared from 5,7-dimethoxy-4-oxo-1,4-dihydroquinoline-3-carboxylic acid (300 mg, 1.20 mmol) and 3,4,5-trimethoxy-N-methylaniline (237 mg, 1.20 mmol) by a procedure similar to that reported for 5,6,7-trimethoxy-4-oxo-N-(3,4,5-trimethoxyphenyl)-1,4-dihydroquinoline-3-carboxamide (Compound 19) to give 5,7-dimethoxy-N-methyl-4-oxo-N-(3,4,5-trimethoxyphenyl)-1,4-dihydroquinoline-3-carboxamide (Compound 35) (40 mg, 7.8% yield) as an off white solid. Preparative HPLC Method D. LCMS: 100.00% (RT: 1.344, 225 nm) (MS: ESI+ve 429.39 [M+H]). ¹H NMR: (400 MHz, DMSO-d₆) δ ppm: 3.279 (s, 3H), 3.569 (s, 3H), 3.661 (s, 6H), 3.743 (s, 3H), 3.795 (s, 3H), 6.301 (s, 1H), 6.390 (s, 1H), 6.640 (s, 2H), 7.622 (s, 1H), 11.347 (s, 1H).

Example 65

Preparation of N-(3-fluoro-4-hydroxyphenyl)-5,7-dimethoxy-4-oxo-1,4-dihydroquinoline-3-carboxamide. (Compound 37)

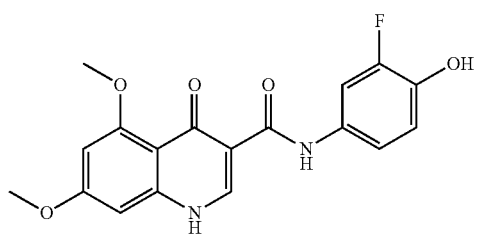

Prepared from 5,7-dimethoxy-4-oxo-1,4-dihydroquinoline-3-carboxylic acid (300 mg, 1.20 mmol) and 4-amino-2-fluorophenol (152 mg, 1.20 mmol) by a procedure similar to that reported for 5,6,7-trimethoxy-4-oxo-N-(3,4,5-trimethoxyphenyl)-1,4-dihydroquinoline-3-carboxamide (Compound 19) to give N-(3-fluoro-4-hydroxyphenyl)-5,7-dimethoxy-4-oxo-1,4-dihydroquinoline-3-carboxamide (Compound 37) (26 mg, 6.0% yield) as a white solid. Preparative HPLC Method A. LCMS: 100.0% (RT: 1.409, 260.0 nm) (MS: ESI+ve 359.08 [M+H]). ¹H NMR: (400 MHz, DMSO-d₆) δ ppm: 3.865 (s, 6H), 6.513-6.518 (d, 1H, J=2), 6.659-6.664 (d, 1H, J=2), 6.900-6.946 (t, 1H, J=9.2), 7.147-7.168 (d, 1H, J=8.4), 7.764-7.804 (q, 1H), 8.617-8.634 (d, 1H, J=6.8), 9.621 (s, 1H), 12.398-12.414 (d, 1H, J=6.4), 12.576 (s, 1H).

Example 66

Preparation of N-(2-hydroxyphenyl)-5,6,7-trimethoxy-4-oxo-1,4-dihydroquinoline-3-carboxamide. (Compound 39)

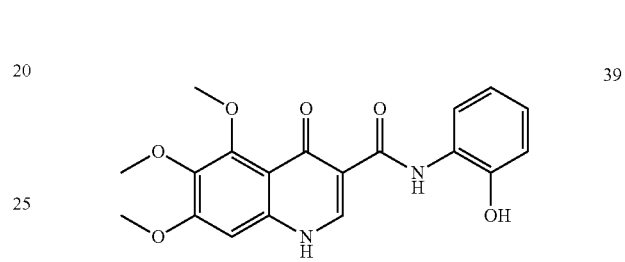

Prepared from 5,6,7-trimethoxy-4-oxo-1,4-dihydroquinoline-3-carboxylic acid (500 mg, 1.79 mmol) and 2-aminophenol (195.3 mg, 1.79 mmol) by a procedure similar to that reported for 5,6,7-trimethoxy-4-oxo-N-(3,4,5-trimethoxyphenyl)-1,4-dihydroquinoline-3-carboxamide (Compound 19) to give N-(2-hydroxyphenyl)-5,6,7-trimethoxy-4-oxo-1,4-dihydroquinoline-3-carboxamide (Compound 39) (40 mg, 6.0% yield) as a brown solid. Preparative HPLC Method B. LCMS: 98.57% (RT: 3.584, 254.0 nm) (MS: ESI+ve 371.4 [M+H]). ¹H NMR: (400 MHz, DMSO-d₆) δ ppm: 3.780-3.835 (s, 6H), 3.885-3.919 (s, 3H), 6.763-6.974 (m, 3H), 8.301-8.321 (d, 1H, J=8), 8.685

Example 67

Preparation of N-(2-hydroxyphenyl)-5,7-dimethoxy-4-oxo-1,4-dihydroquinoline-3-carboxamide. (Compound 41)

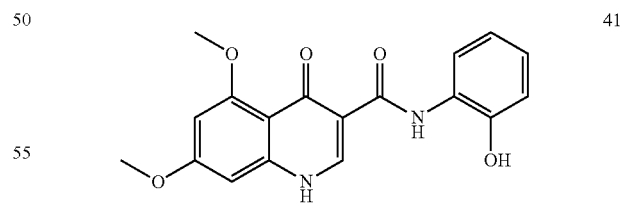

Prepared from 5,7-dimethoxy-4-oxo-1,4-dihydroquinoline-3-carboxylic acid (300 mg, 1.20 mmol) and 2-aminophenol (131.3 mg, 1.20 mmol)) by a procedure similar to that reported for 5,6,7-trimethoxy-4-oxo-N-(3,4,5-trimethoxyphenyl)-1,4-dihydroquinoline-3-carboxamide (Compound 19) to give N-(3-fluoro-4-hydroxyphenyl)-5,7-dimethoxy-4-oxo-1,4-dihydroquinoline-3-carboxamide (Compound 41) (4.0 mg, 1.0% yield) as a white solid. Preparative HPLC Method B. LCMS: 100.0% (RT: 1.477, 260.0 nm) (MS: ESI+ve 341.33 [M+H]). $^1$H NMR: (400 MHz, DMSO-$d_6$) δ ppm: 3.878 (s, 6H), 6.492-6.496 (d, 1H, J=1.6), 6.657-6.662 (d, 1H, J=2), 6.765-6.807 (m, 1H), 6.880-6.912 (t, 2H, J=6.4), 8.313-8.333 (d, 1H, J=8), 8.634 (s, 1H), 10.008 (s, 1H), 12.623 (s, 1H).

Example 68

Preparation of N-(3,5-dimethoxyphenyl)-5,7-dimethoxy-4-oxo-1,4-dihydroquinoline-3-carboxamide. (Compound 49)

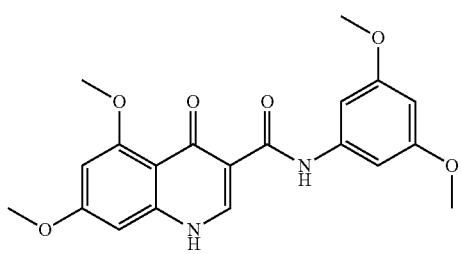

Prepared from 5,7-dimethoxy-4-oxo-1,4-dihydroquinoline-3-carboxylic acid (0.15 g, 0.602 mmol) and. 3,5-dimethoxy aniline (0.091 g, 0.602 mmol) by a procedure similar to that reported for 5,6,7-trimethoxy-4-oxo-N-(3,4,5-trimethoxyphenyl)-1,4-dihydroquinoline-3-carboxamide (Compound 19) to give N-(3,5-dimethoxyphenyl)-5,7-dimethoxy-4-oxo-1,4-dihydroquinoline-3-carboxamide (Compound 49) as an off white solid. Prep HPLC Method C. LCMS: 100% (RT 1.532, 260 nm) (MS: ESI+ve 385.41 [M+H]). $^1$H NMR: (400 MHz, DMSO-$d_6$) δ ppm: 3.776 (s, 6H), 3.885-3.870 (d, 6H, J=6), 6.240 (s, 1H), 6.523-6.518 (d, 1H J=2), 6.665-6.661 (s, 1H J=1.6), 6.968-6.963 (d, 2H, J=2) 8.648 (s, 1H) 12.499 (s, 1H), 12.695 (s, 1H).

Example 69

Preparation of 4-oxo-N-phenyl-1,4-dihydroquinoline-3-carboxamide. (Compound 45)

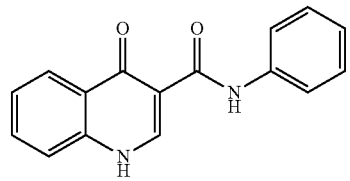

Prepared from 4-oxo-1,4-dihydroquinoline-3-carboxylic acid (150 mg, 0.7932 mmol) and aniline (73 mg, 0.7932 mmol) by a procedure similar to that reported for 5,6,7-trimethoxy-4-oxo-N-(3,4,5-trimethoxyphenyl)-1,4-dihydroquinoline-3-carboxamide (Compound 19) to give 4-oxo-N-phenyl-1,4-dihydroquinoline-3-carboxamide (Compound 45) (80.5 mg, 38.2% yield). Preparative HPLC Method C. LCMS: 100.00% (RT: 2.087, 226 nm) (MS: ESI+ve 265.3 [M+H]). $^1$H NMR: (400 MHz, DMSO-$d_6$) δ ppm: 7.092-7.128 (t, 1H, J=7.2) 7.366-7.405 (t, 2H, J=7.8), 7.540-7.577 (t, 1H, J=7.4), 7.745-7.854 (m, 4H), 8.340-8.358 (d, 1H, J=7.2), 8.907 (s, 1H), 12.52 (s, 1H), 12.98 (s, 1H).

Example 70

Preparation of N-(3-hydroxyphenyl)-4-oxo-1,4-dihydroquinoline-3-carboxamide. (Compound 46)

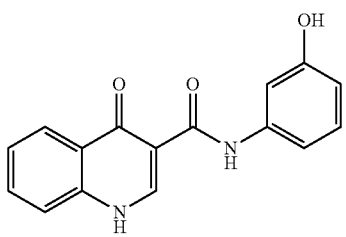

Step 1. Synthesis of N-(3-(benzyloxy)phenyl)-4-oxo-1,4-dihydroquinoline-3-carboxamide

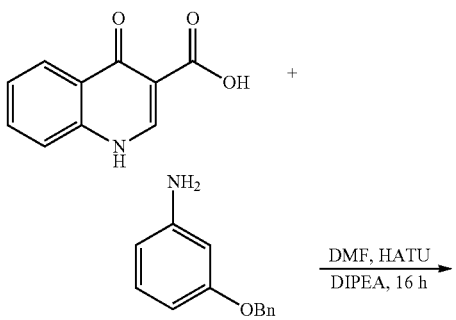

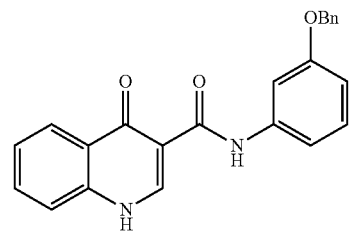

A mixture of 4-oxo-1,4-dihydroquinoline-3-carboxylic acid (150 mg, 0.7932 mmol) and HATU (452 mg, 1.1898 mmol) in dimethylformamide (10 mL) was cooled to 0° C. After 30 min, 3-(benzyloxy)aniline (158 mg, 0.7932 mmol) was added followed by N,N-diisopropylethylamine (0.75 mL, 3.966 mmol). The mixture slowly warmed to room temperature and was stirred for 16 h. The reaction mixture was quenched into ice water (25 mL), extracted with ethyl acetate (3×20 mL), dried over sodium sulphate and concentrated to give N-(3-(benzyloxy)phenyl)-4-oxo-1,4-dihydroquinoline-3-carboxamide as brown solid (250 mg, 85.12%). LCMS: 53.13% (RT: 1.855, 202.0 nm) (MS: ESI+ve 371.36 [M+H]).

117

Step 2. Synthesis of N-(3-hydroxyphenyl)-4-oxo-1,4-dihydroquinoline-3-carboxamide. (Compound 46)

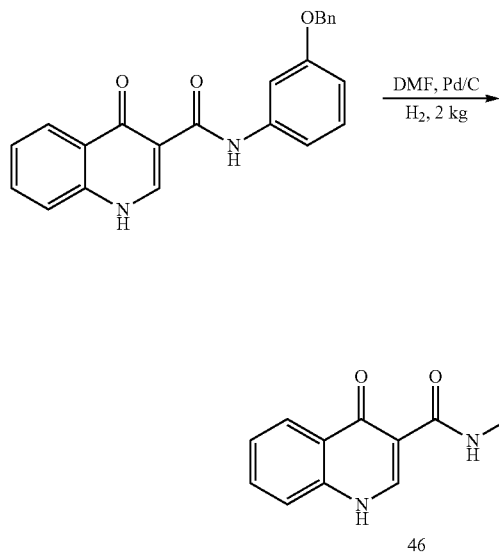

N-(3-(benzyloxy)phenyl)-4-oxo-1,4-dihydroquinoline-3-carboxamide (200 mg, 0.54025 mmol) was dissolved in dimethylformamide (15 mL) 10% palladium on carbon (50% moisture) (50 mg) was added and reaction mixture was stirred at room temperature under 2 kg pressure of hydrogen gas for 24 h in an autoclave. The catalyst was removed by filtration through a pad of celite and the filtrate concentrated. The crude product was purified by reverse phase preparative HPLC to give N-(3-hydroxyphenyl)-4-oxo-1,4-dihydroquinoline-3-carboxamide (Compound 46) (16.0 mg, 12.6% yield) as an off a white solid. Preparative HPLC Method D. LCMS: 100.00% (RT: 1.463, 202 nm) (MS: ESI+ve 281.3 [M+H]). $^1$H NMR: (400 MHz, DMSO-$d_6$) δ ppm: 6.502-6.522 (d, 1H, J=8), 7.025-7.045 (d, 1H, J=8), 7.131-7.171 (t, 1H, J=8), 7.370 (s, 1H), 7.530-7.567 (t, 1H, J=7.4), 7.757-7.846 (m, 2H), 8.33-8.353 (d, 1H, J=8), 8.890 (s, 1H), 9.492 (s, 1H), 12.46 (s, 1H), 13.0 (s, 1H).

Example 71

Preparation of 5,6,7-trihydroxy-4-oxo-N-(3,4,5-trihydroxyphenyl)-1,4-dihydroquinoline-3-carboxamide. (Compound 20)

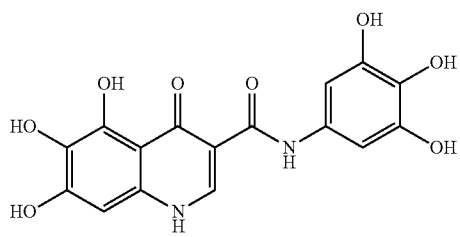

118

Step 1. Synthesis of 5,6,7-trihydroxy-4-oxo-N-(3,4,5-trihydroxyphenyl)-1,4-dihydroquinoline-3-carboxamide. (Compound 20)

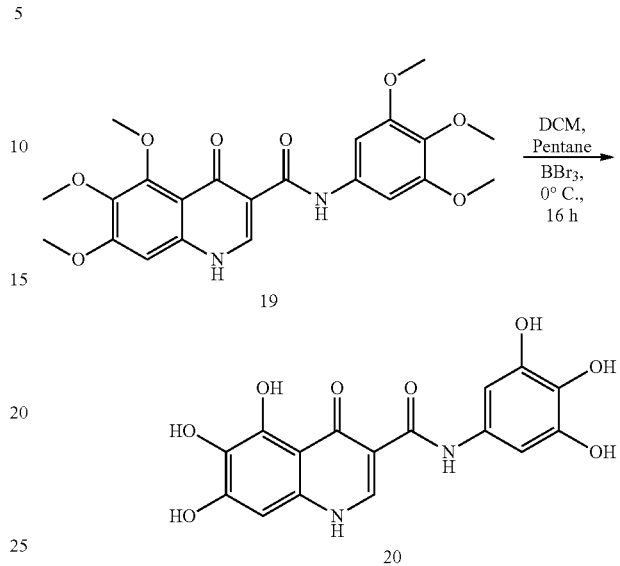

Step 1. 5,6,7-trimethoxy-4-oxo-N-(3,4,5-trimethoxyphenyl)-1,4-dihydroquinoline-3-carboxamide (Compound 19) (300 mg, 0.675 mmol) was dissolved in a mixture of dichloromethane (8 mL) and pentane (4 mL) and cooled to 0° C. Boron tribromide (1M in dichloromethane) (8.10 mL, 8.100 mmol) was added dropwise and the reaction mixture was allowed to slowly warm to room temperature and stirred for 16 h. After cooling to 0° C., methanol (8 mL) was added dropwise and the mixture was concentrated. The crude residue was purified by reverse phase preparative HPLC to give 5,6,7-trihydroxy-4-oxo-N-(3,4,5-trihydroxyphenyl)-1,4-dihydroquinoline-3-carboxamide (Compound 20) (30 mg, 12.3% yield) as an off white solid. Preparative HPLC Method A. LCMS: 99.24% (RT: 1.269, 270.0 nm) (MS: ESI-ve 359.4 [M–H]). $^1$H NMR: (400 MHz, DMSO-$d_6$) δ ppm: 6.605 (s, 1H), 6.709 (s, 2H), 7.894 (s, 1H), 8.611 (s, 1H), 8.780 (s, 1H), 8.913 (s, 2H), 10.409 (s, 1H), 11.414 (s, 1H), 12.807 (s, 1H), 13.567 (s, 1H).

Example 72

Preparation of Synthesis of 5,7-dihydroxy-4-oxo-N-(3,4,5-trihydroxyphenyl)-1,4-dihydroquinoline-3-carboxamide. (Compound 22)

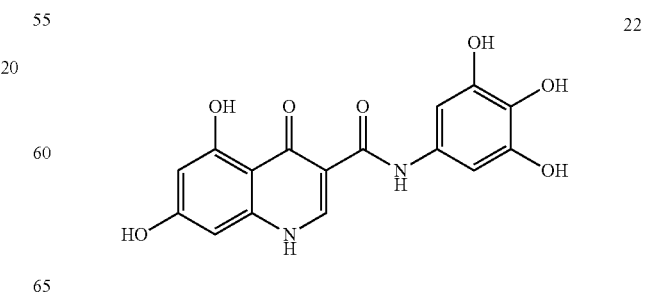

Prepared from 5,7-dimethoxy-4-oxo-N-(3,4,5-trimethoxyphenyl)-1,4-dihydroquinoline-3-carboxamide (Compound 21) (250 mg, 0.603 mmol) by a procedure similar to that described for 5,6,7-trihydroxy-4-oxo-N-(3,4,5-trihydroxyphenyl)-1,4-dihydroquinoline-3-carboxamide (Compound 20) to give 5,7-dihydroxy-4-oxo-N-(3,4,5-trihydroxyphenyl)-1,4-dihydroquinoline-3-carboxamide. (Compound 22) (30 mg, 14.4% yield) as an off white solid. Preparative HPLC Method A. LCMS: 98.98% (RT: 2.792, 260.0 nm) (MS: ESI+ve 345.5 [M+H]). $^1$H NMR: (400 MHz, DMSO-$d_6$) δ ppm: 6.204 (s, 1H), 6.482 (s, 1H), 6.688 (s, 2H), 7.918 (s, 1H), 8.660 (s, 1H), 8.934 (s, 2H), 10.667 (s, 1H), 11.270 (s, 1H), 12.832 (s, 1H), 13.670 (s, 1H).

Example 73

Preparation of 5,7-dihydroxy-4-oxo-N-phenyl-1,4-dihydroquinoline-3-carboxamide. (Compound 27)

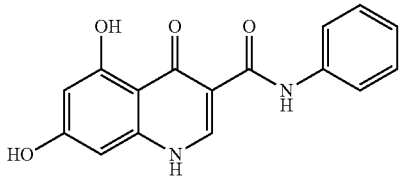

Prepared from 5,7-dimethoxy-4-oxo-N-phenyl-1,4-dihydroquinoline-3-carboxamide (Compound 25) (150 mg, 0.462 mmol) by a procedure similar to that described for 5,6,7-trihydroxy-4-oxo-N-(3,4,5-trihydroxyphenyl)-1,4-dihydroquinoline-3-carboxamide (Compound 20) to give 5,7-dihydroxy-4-oxo-N-phenyl-1,4-dihydroquinoline-3-carboxamide. (Compound 27) (15 mg, 3.3% yield) as an off white solid. Preparative HPLC Method D. LCMS: 95.66% (RT: 1.609, 272.0 nm) (MS: ESI+ve 297.21 [M'+H]). $^1$H NMR: (400 MHz, DMSO-$d_6$) δ ppm: 6.232 (s, 1H), 6.500 (s, 1H), 7.082-7.117 (t, 1H, J=7), 7.345-7.380 (t, 2H, J=7), 7.451 (s, 2H), 8.710 (s, 1H), 10.673 (s, 1H), 11.692 (s, 1H), 12.922 (s, 1H), 13.696 (s, 1H).

Example 74

Preparation of 5,6,7-trihydroxy-N-(3-hydroxyphenyl)-4-oxo-1,4-dihydroquinoline-3-carboxamide. (Compound 32)

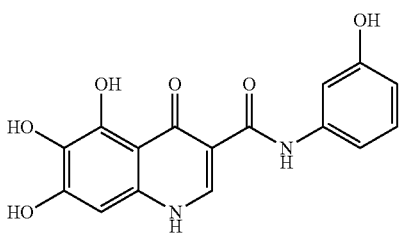 [SMILES: O=C(Nc1cccc(O)c1)c1c[nH]c2cc(O)c(O)c(O)c2c1=O]

Prepared from N-(3-hydroxyphenyl)-5,6,7-trimethoxy-4-oxo-1,4-dihydroquinoline-3-carboxamide (Compound 28) (150 mg, 0.405 mmol) by a procedure similar to that described for 5,6,7-trihydroxy-4-oxo-N-(3,4,5-trihydroxyphenyl)-1,4-dihydroquinoline-3-carboxamide (Compound 20) to give 5,6,7-trihydroxy-N-(3-hydroxyphenyl)-4-oxo-1,4-dihydroquinoline-3-carboxamide (Compound 32) (4 mg, 3.0% yield) as an off white solid. Preparative HPLC Method D. LCMS: 97.28% (RT: 1.828, 202 nm) (MS: ESI-ve 327.3 [M–H]). $^1$H NMR: (400 MHz, DMSO-$d_6$) δ ppm: 6.478-6.498 (d, 1H, J=8), 6.650 (s, 1H), 6.989-7.009 (d, 1H, J=8), 7.102-7.142 (t, 1H J=8), 7.333 (s, 1H), 8.230 (s, 1H), 8.625 (s, 1H), 9.472 (s, 1H), 11.744 (s, 1H) 13.537 (s, 1H).

Example 75

Preparation of 5,6,7-trihydroxy-4-oxo-N-phenyl-1,4-dihydroquinoline-3-carboxamide. (Compound 33)

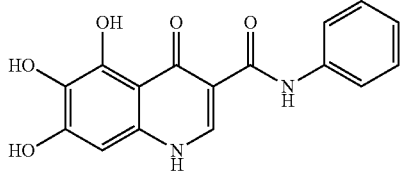 [SMILES: O=C(Nc1ccccc1)c1c[nH]c2cc(O)c(O)c(O)c2c1=O]

Prepared from 5,6,7-trimethoxy-4-oxo-N-phenyl-1,4-dihydroquinoline-3-carboxamide (500 mg, 1.412 mmol) (Compound 30) by a procedure similar to that described for 5,6,7-trihydroxy-4-oxo-N-(3,4,5-trihydroxyphenyl)-1,4-dihydroquinoline-3-carboxamide (Compound 20) to give 5,6,7-trihydroxy-4-oxo-N-phenyl-1,4-dihydroquinoline-3-carboxamide (Compound 33) (20 mg, 4.5% yield) as an off white solid. Preparative HPLC Method C. LCMS: 100.00% (RT: 1.481, 229.0 nm) (MS: ESI-ve 311.25 [M–H]). $^1$H NMR: (400 MHz, DMSO-$d_6$) δ ppm: 6.62 (s, 1H), 7.12-7.08 (t, 1H, J=8), 7.39-7.35 (t, 2H, J=8), 7.74-7.72 (d, 2H, J=8), 8.67 (s, 1H), 8.83 (s, 1H), 10.50 (s, 1H), 11.81 (s, 1H), 12.90 (s, 1H), 13.54 (s, 1H).

Example 76

Preparation of 5,6,7-trihydroxy-N-(4-hydroxyphenyl)-4-oxo-1,4-dihydroquinoline-3-carboxamide. (Compound 38)

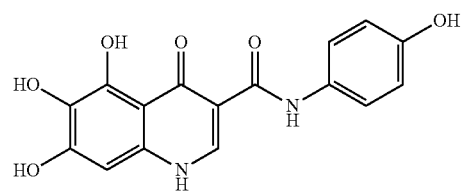 [SMILES: O=C(Nc1ccc(O)cc1)c1c[nH]c2cc(O)c(O)c(O)c2c1=O]

Prepared from N-(4-hydroxyphenyl)-5,6,7-trimethoxy-4-oxo-1,4-dihydroquinoline-3-carboxamide (Compound 29) (100 mg, 0.270 mmol) by a procedure similar to that described for 5,6,7-trihydroxy-4-oxo-N-(3,4,5-trihydroxyphenyl)-1,4-dihydroquinoline-3-carboxamide (Compound 20) to give 5,6,7-trihydroxy-N-(4-hydroxyphenyl)-4-oxo-1,4-dihydroquinoline-3-carboxamide (Compound 38) (7 mg, 7.9% yield) as an off white solid. Preparative HPLC Method C. LCMS: 95.95% (RT: 2.907, 278.0 nm) (MS: ESI+ve 329.43 [M+H]). $^1$H NMR: (400 MHz, DMSO-$d_6$) δ ppm: 6.593 (s, 1H), 6.732-6.754 (d, 2H J=8.8), 7.495-7.516 (d, 2H, J=8.4), 8.618 (s, 1H), 8.795 (s, 1H) 9.272, (s, 1H), 10.409 (s, 1H), 11.529 (s, 1H), 12.839 (s, 1H), 13.574 (s, 1H).

Example 77

Preparation of 5,7-dihydroxy-N-methyl-4-oxo-N-(3,4,5-trihydroxyphenyl)-1,4-dihydroquinoline-3-carboxamide. (Compound 42)

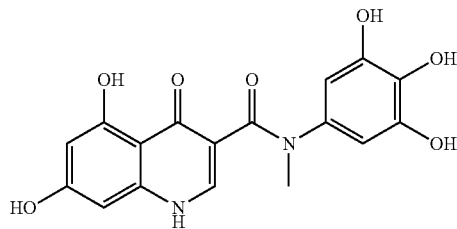 [SMILES: CN(C(=O)c1c[nH]c2cc(O)cc(O)c2c1=O)c1cc(O)c(O)c(O)c1]

Prepared from 5,7-dimethoxy-N-methyl-4-oxo-N-(3,4,5-trimethoxyphenyl)-1,4-dihydroquinoline-3-carboxamide (150 mg, 0.350 mmol) by a procedure similar to that described for 5,6,7-trihydroxy-4-oxo-N-(3,4,5-trihydroxyphenyl)-1,4-dihydroquinoline-3-carboxamide (Compound 20) to give 5,7-dihydroxy-N-methyl-4-oxo-N-(3,4,5-trihydroxyphenyl)-1,4-dihydroquinoline-3-carboxamide (Compound 42) (4 mg, 3.19%) as an off white solid. Preparative HPLC Method G. LCMS: 100.00% (RT: 1.252, 202 nm) (MS: ESI+ve 359.26 [M+H]). $^1$H NMR: (400 MHz, DMSO-$d_6$) δ ppm: 3.197 (s, 3H), 5.995 (s, 1H), 6.186 (s, 3H), 7.774 (s, 1H), 8.117 (s, 1H), 8.925 (s, 2H), 10.926 (s, 1H), 11.870 (s, 1H), 14.386 (s, 1H).

Example 78

Preparation of 5,7-dihydroxy-N-(3-hydroxyphenyl)-4-oxo-1,4-dihydroquinoline-3-carboxamide. (Compound 48)

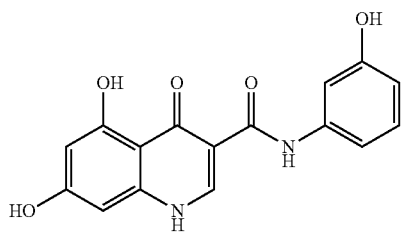

Prepared from N-(3-hydroxyphenyl)-5,7-dimethoxy-4-oxo-1,4-dihydroquinoline-3-carboxamide (Compound 26) (100 mg, 0.294 mmol) by a procedure similar to that described for 5,6,7-trihydroxy-4-oxo-N-(3,4,5-trihydroxyphenyl)-1,4-dihydroquinoline-3-carboxamide (Compound 20) to give 5,7-dihydroxy-N-(3-hydroxyphenyl)-4-oxo-1,4-dihydroquinoline-3-carboxamide (Compound 48) as an off white solid. Preparative HPLC Method G. LCMS: 98.54% (RT: 1.464, 263.0 nm) (MS: ESI ve 313.31 [M+H]). $^1$H NMR: (400 MHz, DMSO-$d_6$) δ ppm: 6.231 (s, 1H), 6.517-6.509 (d, 2H, J=3.2), 7.012-6.992 (d, 1H J=8.0), 7.157-7.137 (d, 1H, J=8.0), 7.137-7.117 (d, 1H, J=8.0), 7.340 (s, 1H), 8.721-8.704 (d, 1H, J=6.8), 9.481 (s, 1H), 10.704 (s, 1H), 11.587 (s, 1H), 12.920-12.905 (d, 1H, J=6.6), 13.650 (s, 1H).

Example 79

Preparation of 5,6,7-trihydroxy-N-(2-hydroxyphenyl)-4-oxo-1,4-dihydroquinoline-3-carboxamide. (Compound 43)

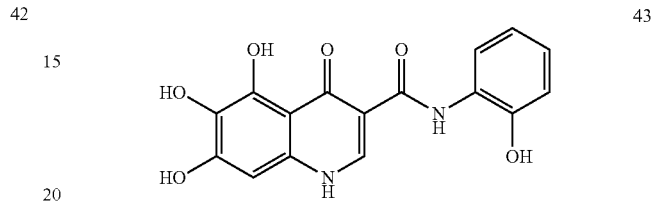

Prepared from N-(2-hydroxyphenyl)-5,6,7-trimethoxy-4-oxo-1,4-dihydroquinoline-3-carboxamide (100 mg, 0.270 mmol) (Compound 39) by a procedure similar to that described for 5,6,7-trihydroxy-4-oxo-N-(3,4,5-trihydroxyphenyl)-1,4-dihydroquinoline-3-carboxamide (Compound 20) to give 5,6,7-trihydroxy-N-(2-hydroxyphenyl)-4-oxo-1,4-dihydroquinoline-3-carboxamide (Compound 43) (7.0 mg, 7.1% yield) as an off white solid. Preparative HPLC Method D. LCMS: 100.00% (RT: 1.423, 278.0 nm) (MS: ESI-ve 327.4 [M−H]). $^1$H NMR: (400 MHz, DMSO-$d_6$) δ ppm: 6.600 (s, 1H), 6.802 (m, 1H), 6.903-6.913 (d, 2H, J=4), 8.380-8.400 (d, 1H, J=8), 8.651 (s, 2H), 9.998 (s, 2H), 11.823 (s, 1H) 12.800 (s, 1H), 13.752 (s, 1H).

Example 80

Preparation of N-(3,5-dihydroxyphenyl)-5,7-dihydroxy-4-oxo-1,4-dihydroquinoline-3-carboxamide. (Compound 47)

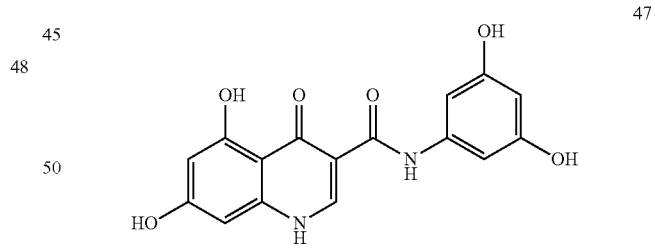

Prepared from N-(3,5-dimethoxyphenyl)-5,7-dimethoxy-4-oxo-1,4-dihydroquinoline-3-carboxamide (Compound 49) (0.15 mg, 0.39 mmol) by a procedure similar to that described for 5,6,7-trihydroxy-4-oxo-N-(3,4,5-trihydroxyphenyl)-1,4-dihydroquinoline-3-carboxamide (Compound 20) to give N-(3,5-dihydroxyphenyl)-5,7-dihydroxy-4-oxo-1,4-dihydroquinoline-3-carboxamide (Compound 47) (5 mg, 3.9% yield) as an off white solid. Prep HPLC Method C. LCMS: 98.10% (RT: 1.373, 230.0 nm) (MS: ESI+ve 329.31 [M+H]). $^1$H NMR: (400 MHz, DMSO-$d_6$) δ ppm: 5.96 (s, 1H), 6.20 (s, 1H), 6.49 (s, 1H), 6.63 (s, 2H), 8.69 (s, 1H), 9.28 (s, 2H) 10.61 (s, 1H) 11.52 (s, 1H) 12.84 (s, 1H) 13.73 (s, 1H).

Example 81

Preparation of 3,4,5-trimethoxyphenyl 5,6,7-trimethoxy-4-oxo-1,4-dihydroquinoline-3-carboxylate. (Compound 23)

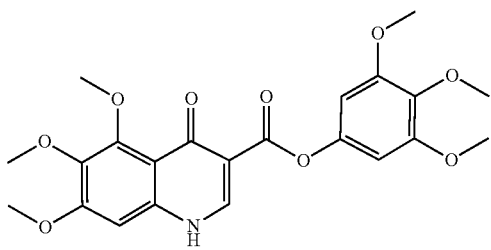

Step 1: Synthesis of 3,4,5-trimethoxyphenyl 5,6,7-trimethoxy-4-oxo-1,4-dihydroquinoline-3-carboxylate. (Compound 23)

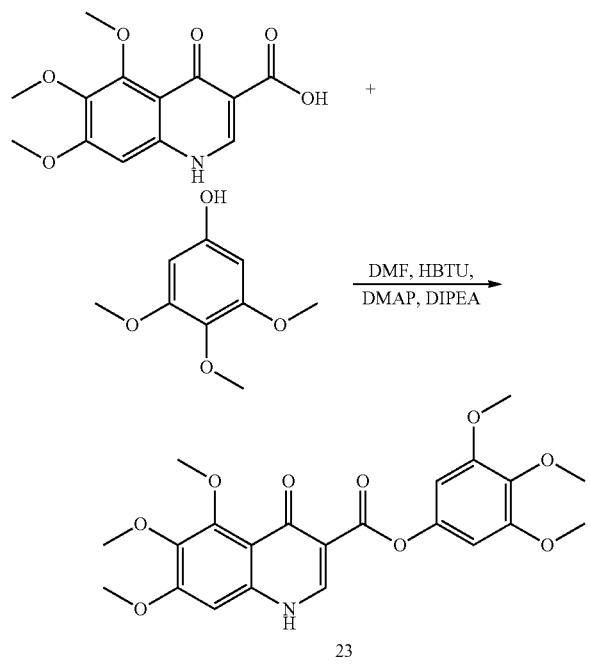

A mixture of 5,6,7-Trimethoxy-4-oxo-1,4-dihydroquinoline-3-carboxylic acid (500 mg, 1.790 mmol), N,N-dimethylpyridin-4-amine (218 mg, 1.790 mmol) and N,N-dimethylpyridin-4-amine (218 mg, 1.790 mmol) in dimethylformamide (25 mL) was cooled to 0° C. (2-(1H-benzotriazol-1-yl)-1,1,3,3-tetramethyluronium hexafluorophosphate (HBTU) (1.7 g, 4.476 mmol) was added and reaction the reaction mixture was stirred for 30 min. 3,4,5-trimethoxyphenol (329.7 mg, 1.790 mmol) was added followed by N,N-diisopropylethylamine (1.2 mL, 7.162 mmol). The mixture slowly warmed to room temperature and was stirred for 16 h. The reaction mixture was quenched into ice water (50 mL) and the resulting ppt was collected by filtration and triturated with methanol. The crude residue was purified by column chromatography eluting with methanol:dichloromethane to give 140 mg of product which was further purified by reverse phase preparative HPLC to give 3,4,5-trimethoxyphenyl 5,6,7-trimethoxy-4-oxo-1,4-dihydroquinoline-3-carboxylate (Compound 23) (35.8 mg, 4.49%) as white solid. Preparative HPLC Method C. LCMS: 97.85% (RT: 1.402, 259.0 nm) (MS: ESI+ve 446.46 [M+H]). $^1$H NMR: (400 MHz, DMSO-$d_6$) δ ppm: 3.36 (s, 3H), 3.78 (s, 12H), 3.91 (s, 3H), 6.55 (s, 2H), 6.94 (s, 1H), 8.60 (s, 1H), 12.10-12.12 (s, 1H).

Example 82

Preparation of 3,4,5-trimethoxyphenyl 5,7-dimethoxy-4-oxo-1,4-dihydroquinoline-3-carboxylate. (Compound 24)

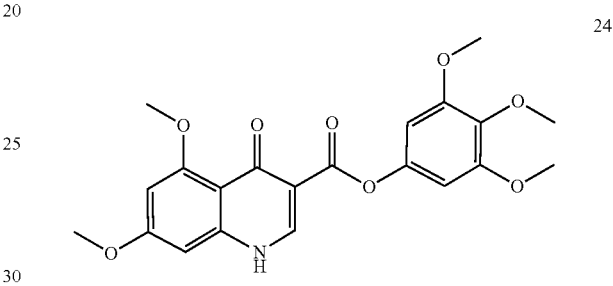

Prepared from 5,7-dimethoxy-4-oxo-1,4-dihydroquinoline-3-carboxylic acid (0.9 g, 3.61 mmol) and 3,4,5-trimethoxyphenol by a procedure similar to that described for 3,4,5-trimethoxyphenyl 5,6,7-trimethoxy-4-oxo-1,4-dihydroquinoline-3-carboxylate (Compound 23) give 5,7-dimethoxy-4-oxo-N-(3,4,5-trimethoxyphenyl)-1,4-dihydroquinoline-3-carboxamide f (40 mg, 2.7% yield) as off white solid. Preparative HPLC Method D. LCMS: 98.12% (RT: 1.495, 261.0 nm) (MS: ESI+ve 416.49 [M+H]). $^1$H NMR: (400 MHz, CDCl$_3$) (69274) δ ppm: 3.66 (s, 3H) 3.77 (s, 6H) 3.80 (s, 3H) 3.91 (s, 3H) 6.44-6.60 (m, 4H), 8.52 (s, 1H) 11.98 (s, 1H).

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method of using a composition (e.g., a method comprising administering a composition to a subject having an amyloid disorder) is disclosed herein, the corresponding composition for use is also expressly contemplated. For example, for the disclosure of a method of inhibiting, ameliorating, reducing the likelihood, delaying the onset of, treating, or preventing an amyloid disorder administering a composition to a subject, the corresponding composition for use in inhibiting, ameliorating, reducing the likelihood, delaying the onset of, treating, or preventing the amyloid disorder is also expressly contemplated.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A compound of Formula (II-a-1) or Formula (II-a-2):

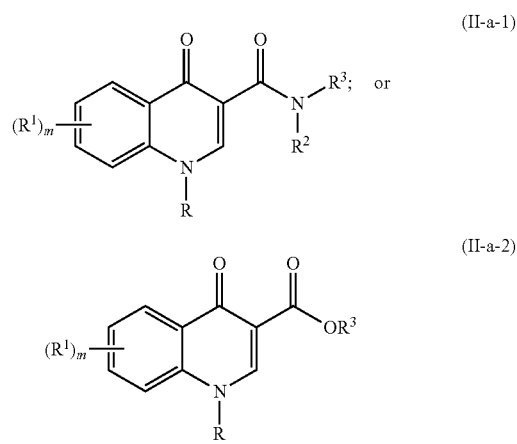

or a pharmaceutically acceptable salt thereof, wherein:

R is H or —CH$_3$;

R$^1$ is —OH;

R$^2$ is —H or —CH$_3$;

R$^3$ is phenyl substituted with n instances of R$^4$;

R$^4$ is —OH;

n is 0, 1, 2, 3, or 4;

m is 0, 1, 2, 3, or 4; and the sum of all instances of m and n is 2-9.

2. The compound of claim 1, wherein the sum of all instances of m and n is at least three.

3. A compound selected from:

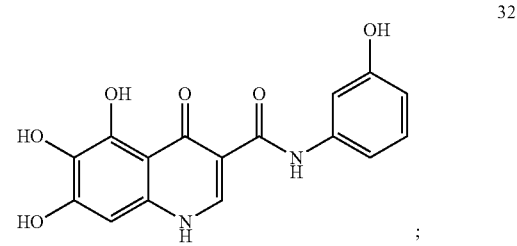

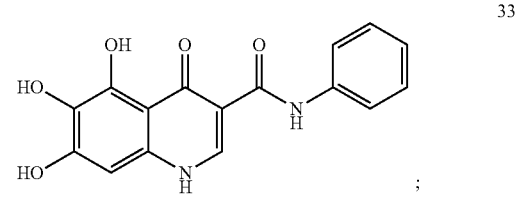

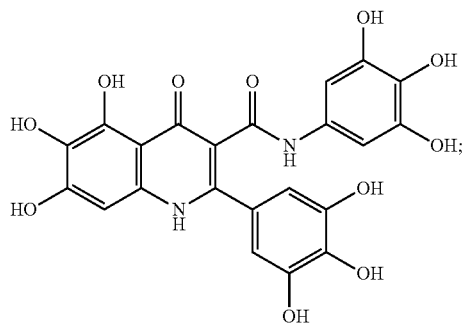
44
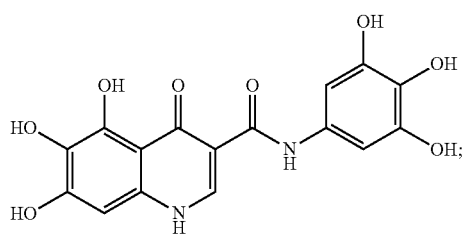
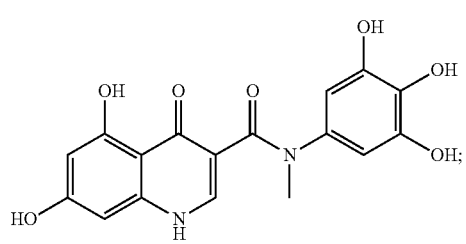
42
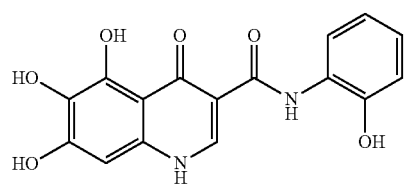 [SMILES: O=C(Nc1ccccc1O)c1c[nH]c2cc(O)c(O)c(O)c2c1=O]
43
and pharmaceutically acceptable salts thereof.
4. A pharmaceutical composition comprising a compound of claim 1, or a pharmaceutically acceptable salt thereof, and a pharmaceutically acceptable carrier.
5. The compound of claim 1, wherein R is H.
6. The compound of claim 1, wherein $R^2$ is —$CH_3$.
7. The compound of claim 1, wherein m is 1, 2, or 3.
* * * * *